United States Patent
Kurek et al.

(10) Patent No.: US 9,879,290 B2
(45) Date of Patent: Jan. 30, 2018

(54) INDUSTRIAL FATTY ACID ENGINEERING GENERAL SYSTEM FOR MODIFYING FATTY ACIDS

(71) Applicant: Kiverdi, Inc., Hayward, CA (US)

(72) Inventors: Itzhak Kurek, San Francisco, CA (US); Michael Siani-Rose, San Francisco, CA (US); Lisa Dyson, Berkeley, CA (US); Christer Jannson, Berkeley, CA (US); John S. Reed, Berkeley, CA (US)

(73) Assignee: KIVERDI, INC., Berkeley, CA (US)

(*) Notice: Subject to any disclaimer, the term of this patent is extended or adjusted under 35 U.S.C. 154(b) by 0 days.

(21) Appl. No.: 13/623,089

(22) Filed: Sep. 19, 2012

(65) Prior Publication Data

US 2013/0089899 A1    Apr. 11, 2013

Related U.S. Application Data

(63) Continuation-in-part of application No. PCT/US2011/034218, filed on Apr. 27, 2011, which is a continuation-in-part of application No. PCT/US2010/001402, filed on May 12, 2010, which is a continuation-in-part of application No. 12/613,550, filed on Nov. 6, 2009, now abandoned.

(60) Provisional application No. 61/536,056, filed on Sep. 19, 2011, provisional application No. 61/111,794, filed on Nov. 6, 2008, provisional application No. 61/542,823, filed on Oct. 4, 2011, provisional application No. 61/616,560, filed on Mar. 28, 2012.

(51) Int. Cl.
*C12P 7/40* (2006.01)
*C12P 5/00* (2006.01)
*C12N 1/20* (2006.01)
*C12P 1/04* (2006.01)
*C12P 3/00* (2006.01)
*C12P 5/02* (2006.01)
*C12P 7/06* (2006.01)
*C12P 7/54* (2006.01)
*C12P 7/64* (2006.01)
*C12N 9/02* (2006.01)
*C12N 9/16* (2006.01)
*C12N 15/88* (2006.01)
*C12N 9/88* (2006.01)

(52) U.S. Cl.
CPC .......... *C12P 7/40* (2013.01); *C12N 1/20* (2013.01); *C12N 9/0008* (2013.01); *C12N 9/16* (2013.01); *C12N 9/88* (2013.01); *C12P 1/04* (2013.01); *C12P 3/00* (2013.01); *C12P 5/00* (2013.01); *C12P 5/023* (2013.01); *C12P 7/065* (2013.01); *C12P 7/54* (2013.01); *C12P 7/649* (2013.01); *Y02E 50/13* (2013.01); *Y02E 50/17* (2013.01); *Y02E 50/343* (2013.01)

(58) Field of Classification Search
CPC ............. C12N 9/00; C12Y 102/0108; C12Y 401/99005; C12P 7/40; C12P 5/00
USPC ...................... 435/134, 166, 252.3
See application file for complete search history.

(56) References Cited

U.S. PATENT DOCUMENTS

| | | | |
|---|---|---|---|
| 5,326,702 A * | 7/1994 | Endo et al. ................. | 435/129 |
| 7,883,882 B2 | 2/2011 | Franklin et al. | |
| 2010/0120104 A1 | 5/2010 | Reed | |
| 2013/0078690 A1 | 3/2013 | Reed | |
| 2013/0149755 A1 | 6/2013 | Reed et al. | |
| 2013/0189763 A1 | 7/2013 | Dalla-Betta et al. | |

FOREIGN PATENT DOCUMENTS

| | | | |
|---|---|---|---|
| WO | WO 2009009391 A2 * | 1/2009 | |
| WO | WO 2009140695 A1 * | 11/2009 | |
| WO | WO 2009151342 A1 * | 12/2009 | |
| WO | WO 2010009348 A2 * | 1/2010 | |
| WO | 2011056183 A1 | 5/2011 | |
| WO | 2011139804 A2 | 11/2011 | |
| WO | 2013082309 A1 | 6/2013 | |
| WO | 2013090769 A2 | 6/2013 | |

OTHER PUBLICATIONS

Khaselev O et al. A Monolithic Photovoltaic-Photoelectrochemical Device for Hydrogen Production via Water Splitting. 1998. Science. 280:425-427.*
Thomas SM et al. Biocatalysis: applications and potentials for the chemical industry. 2002. Trends in Biotechnology. vol. 20 No. 6 p. 238-242.*
Grzeszik C et al. Genes encoding the NAD-reducing hydrogenase of Rhodococcus opacus MR11. 1997. Microbiology. 143,1271-1286.*
Ishizaki A et al. Production of Poly-b-hydroxybutyric Acid from Carbon Dioxide by Alcaligenes eutrophus ATCC 176797. Journal of Fermentation and Bioengineering. vol. 71, No. 4, 254-257. 1991.*
Taxonomy-Cupriavidus necator. Retrieved from Uniprot on Feb. 18, 2016. p. 1.*
ATCC 17697. Retrieved from http://www.atcc.org/products/all/17697.aspx[Feb. 16, 2016 11:11:36 AM]. p. 1-2.*
Jung Y et al. Metabolic engineering of Alcaligenes eutrophus through the transformation of cloned phbCAB genes for the invenstigation of the regulatory mechanism of polyhydroxyalkanoate biosynthesis. 2000. Enzyme and Microbial Technology. 26:201-208.*
Doan, T., et al., Functional expression of five *Arabidopsis* fatty acyl-CoA reductase genes in *Escherichia coli*, J Plant Phys, 2008; 166:787-96.
Kavanagh, KL, et al., The SDR superfannily: functional and structural diversity within a family of metabolic and regulatory enzymes, Cell Mol Life Sci, 2008; 65:3895-3906.

(Continued)

*Primary Examiner* — Paul J Holland
(74) *Attorney, Agent, or Firm* — Jill A. Jacobson

(57) ABSTRACT

Compositions and methods for a hybrid biological and chemical process utilizing chemotrophic microorganisms that converts syngas and/or gaseous CO2 and/or a mixture of CO2 gas and H2 gas into one or more desaturated hydrocarbons, unsaturated fatty acids, hydroxy acids, or diacids.

12 Claims, 27 Drawing Sheets

(56) References Cited

OTHER PUBLICATIONS

Labesse, G., et al., Structural comparisons lead to the definition of a new superfamily of NAD(P)(H)-accepting oxidoreductases: the single-domain reductases/epimerases/dehydrogenases (the 'RED' family), Biochem J, 1994; 304:95-99.
Paterson, P., et al., Genetic Analysis of the Mobilization and Leading Regions of the IncN plasmids pKM101 and pCU1, J. Bacteriol, 1999; 181:2572-2583.
Thauer, R. K., et al., R. Methanogenic archaea: ecologically relevant differences in energy conservation, Nat Rev Microbiol, Aug. 2008; 6(8):579-91.
Papoutsakis, Equations and calculations for fermentations of butyric acid bacteria, Biotechnol Bioeng., Feb. 1984; 26(2):174-87.
Heise R., et al., Sodium dependence of acetate formation by the acetogenic bacterium Acetobacterium woodii, Journal of Bacteriology, Oct. 1989; 171(10):5473-5478.
Fischer et al., Selection and optimization of microbial hosts for biofuels production, Metab Eng., 2008;10(6):295-304.
Ljungdahl, L., The Autotrophic Pathway of Acetate Synthesis in Acetogenic Bacteria, Annual Review of Microbiology, 1986; 40: 415-450.
Shively, J., et al., Something from almost nothing: carbon dioxide fixation in chemoautotrophs, Annu Rev Microbiol., 1998;52:191-230.
Smith, A., et al., Biochemical Basis of Obligate Autotrophy in Blue-Green Algae and Thiobacilli, J. Bacteriol., 1967; 94: 972-983.
Hugler, M., et al., Evidence for autotrophic CO2 fixation via the reductive tricarboxylic acid cycle by members of the epsilon subdivision of proteobacteria, J. Bacteriol., 2005; 187:3020-3027.
Scott, K., et al., CO2 Uptake and Fixation by Endosymbiotic Chemoautotrophs from the Bivalve Solemya velum, Appl. Environ. Microbiol., Feb. 2007; 73(4):1174-1179.
Henikoff, et al., Amino Acid Substitution Matrices From Protein Blocks, Proc. Natl. Acad. Sci. USA, 1992; 89, 10915-10919.
Karlin, et al., Applications and Sequences for Multiple High-scoring Segments in Molecular Sequences, Proc. Natl. Acad. Sci. USA, 1993; 90,5873-5877.
Altschul, S., et al., Basic Local Alignment Search Tool, J. Mol. Biol., 1990; 215:403-410.
Altschul, S., et al., Gapped BLAST and PSI-BLAST: a new generation of protein database search programs, Nuc. Acids Res., 1997; 25:33-89.
Caraballeira, N., et al., Unusual Fatty Acid Compositions of the hyperthermophilic Archaeon Pyrococcus furiosus and the Bacterium Thermotoga maritima., J. Bacteriol., 1997; 179(8):2766-68.
English, J., et al., The Wound Hormones of Plants. IV. Structure and Synthesis of a Traumatin, Science, 1939; 61:3434-36.
Krona K, Industrial Biotechnology Provides Opportunities for Commercial Production of New Long-Chain Dibasic Acids, Inform, 2004; 15(9):568-571.
Lee, S., et al., Fermentative Butanol Production by Clostridia, Biotechnology & Bioengineering, 2008; 101(2):209-228.
Bongers, L., Energy Generation and Utilization in Hydrogen Bacteria October, J. Bacteriology, 1970; 104(1):145-151.
Nishida, M., et al., Molecular Cloning and Site-directed Mutagenesis of Glutathione S-Transferase from *Escherichia coZi*, J. Biol Chem., 1994; 269 (51):32536-32541.
Piccolomini, R., et al., Glutathione Transferase in Bacteria: Subunit Composition and Antigenic Characterization J. Gen. Microbiol., 1989; 135:3119-3125.
Fukada, H. et al., Roles of Tral Protein With Activities of Cleaving and Rejoining the Single-stranded DNA in Both Initiation and Termination of Conjugal DNA Transfer, Genes to Cells, 1997; 2:735-751.
Na, K., et al., Development of a Genetic Transformation System for Benzene-Tolerant Rhodococcus opacus Strains, J Biosci Bioeng, 2005; 99 (4):408-414.
Kovach, M., et al., Four new derivatives of the broad-host-range cloning vector pBBR1MCS, carrying different antibiotic-resistance cassettes, Gene, 1995; 166:175-176.
Alton, N., et al., Nucleotide Sequence Analysis of the Chloramphenicol Resistance Transposon Tn9, Nature, 1979; 282:864-869.
Kandel, S., Enzyme Catalysis and Regulation: Cloning, Functional Expression, and Characterization of CYP709C1, the First Subterminal Hydroxylase of Long Chain Fatty Acid in Plants: Induction by Chbemicals and Methyl Jasmonate, J. Bio. Chem., 2005; 280:35881-35889.
Pompon, D., Yeast Expression of Animal and Plant P450s in Optimized Redox Environments, Methods in Enzymology, 1996; 272:51-64.
Rotani, J., et al., Visible light-induced oxidation of unsaturated components of cutins: a significant process during the senescence of higher plants, Phytohemistry, 2005; 66:313-321.
Sandoval-Basurto, E., Culture of *Escherichia coli* Under Dissolved Oxygen Gradients Simulated in a Two-Compartment Scale-Down System: Metabolic Response and Production of Recombinant Protein, Biotechnology and Bioengineering, 2005, 89(4):453-463.

* cited by examiner

Fig. 1

| DSM # | Name | Synonyms | Reference |
|---|---|---|---|
| 44193 | Rhodococcus opacus | Rhodococcus opacus PD 630 | 1 |
| 43205 | Rhodococcus opacus | Rhodococcus opacus ISO-5 | 2 |
| 3346 | Rhodococcus sp. | Nocardia opaca MR 22 | 3 |
| 531 | Cupriavidus necator | Ralstonia eutropha | 4 |

Fig. 3

| Definition | GenBank # | Length (bases) | Identity to NR_026186.1 (%) |
|---|---|---|---|
| Rhodococcus opacus strain DSM 43205 | NR_026186.1 | 1291 | 100 |
| Rhodococcus opacus GM14 | X89710.1 | 1271 | 98.4 |
| Rhodococcus opacus strain DSM43206T | X89710.1 | 1283 | 99.2 |
| Cupriavidus necator strain DSM 2839 | NR_043444.1 | 1291 | 73.7 |
| Ralstonia sp. HB1 | JN196539.1 | 1316 | 73.6 |
| Gordonia alkanivorans strain DSM 44187 | AY995556.1 | 1291 | 93.3 |
| Gordonia sp. CC-MJ-39a 16S ribosomal RNA gene, partial sequence | EU266488.1 | 1296 | 93.6 |
| Mycobacterium fortuitum subsp. Acetamidolyticum strain DSM44220T | FR733720.1 | 1297 | 92.7 |
| Mycobacterium parafortuitum strain DSM 43528 | NR_026285.1 | 1280 | 93.3 |
| Mycobacterium sphagni strain S32418 | AB649002.1 | 1301 | 93.5 |
| Nocardia farcinica strain DSM 43665 | AF430033.1 | 1281 | 94.3 |
| Nocardia sp. I7 | AY524861.1 | 1300 | 94.3 |
| Rhodococcus rhodochrous strain CG30 | AB562467.1 | 1303 | 95.0 |
| Rhodococcus coprophilus strain DSM43347T | X80626.1 | 1295 | 95.9 |
| Rhodococcus triatomae strain IMMIB RIV-085 | AJ854055.1 | 1272 | 94.8 |
| Nocardia coeliaca strain DSM44595T | FR733721.1 | 1296 | 95.6 |
| Nocardia globerula strain DSM 44596T | FR749915.1 | 1297 | 95.7 |
| Rhodococcus equi strain S32003 | AB649016.1 | 1300 | 95.9 |
| Rhodococcus sp. A2Y26 | AY512637.1 | 1288 | 96.4 |
| Rhodococcus sp. 871-AN040 | AF420421.1 | 1300 | 97.1 |
| Rhodococcus jostii | AB458522.1 | 1282 | 95.9 |
| Rhodococcus opacus strain 1CP | Y11893.1 | 1294 | 99.1 |
| Rhodococcus imtechensis strain RKJ300 | AY525785.2 | 1296 | 97.0 |
| Rhodococcus koreensis strain DNP505 | NR_024973.1 | 1280 | 97.8 |
| Rhodococcus opacus strainB-4 | AB192962.1 | 1308 | 96.4 |
| Rhodococcus sp. TCH14 | AB183440.1 | 292 | 97.0 |
| Rhodococcus opacus strain DNP14-5 | AY027585.1 | 1281 | 98.7 |
| Rhodococcus sp. pnp-5 | EF017807.1 | 1300 | 98.3 |
| Rhodococcus sp. Sulf-822 | AM922188.1 | 1270 | 97.0 |
| Rhodococcus wratislaviensis strain J7 | AY940038.1 | 1291 | 98.5 |

```
                         1501                                                           1560
R.opacus DSM 43205   (1446) GGGACGAAGTCGTAACAAGGTAGCCGTACCGGAAGG-----------------------  (SEQ ID NO:40)
     R. opacus GM14  (1426) GGGACGAAGTCGTAACAAGGTAGCCGTACCGGAAG------------------------  (SEQ ID NO:12)
R. opacus DSM 43206T (1438) GGGACGAAGTCGTAACAAGGTAGCCGTACCGGAAGG-----------------------  (SEQ ID NO:13)
   Cupriavidus necator (1442) GGGGTGAAGTCGTAACAAGGT------------------------------------  (SEQ ID NO:14)
     Ralstonia sp. HB1 (1467) GGGGTGAAGTCGT--------------------------------------------  (SEQ ID NO:15)
       G.alkanivorans  (1446) GGGACGAAGTCGTAACAAGGTAGCCGTACCGGAAGGTGCGG-----------------  (SEQ ID NO:16)
         G. CC-MJ-39a  (1451) GGGACGAAGTCGTAACAAGGTAGCCGTACCGGAAGGTGCGG-----------------  (SEQ ID NO:17)
         M. fortuitum  (1450) GGGACGAAGTCGTAACAAGGTAGCCGTACCGGAAGGTGCGGCTGGATCACCTCGTT---- (SEQ ID NO:18)
      M. parafortuitum (1435) GGGACGAAGTCGTAACAAGGTAGCCG--------------------------------  (SEQ ID NO:19)
           M. sphagni  (1456) GGGACGAAGTCGTAACAAGGTAGCC---------------------------------  (SEQ ID NO:20)
          N. farcinica (1436) GGGACGAAGTCGTAACAAGGTAGCCGTACCGGAAGGTGCGGCTGGATCACCTCCTTTCT- (SEQ ID NO:21)
              N. sp   (1455) GGGACGAAGTCGTAACAAGGTAGCCGTACCGGAAGGTGCGGCTGGATCACCTCCTTTCT- (SEQ ID NO:22)
      R.rhodochrous CG30 (1458) GGGACGAAGTCGTAACAAGGTAGCCGTACCGGA-------------------------  (SEQ ID NO:23)
         R.coprophilus (1450) GGGACGAAGTCGTAACAAGGTAGCCGTACCGG--------------------------  (SEQ ID NO:24)
          R. triatomae (1427) GGGACGAAGTCGTAACAAGGTAGCCGTACCGGAAGGTGCGGCTGGATCACTTCCTTTCTA (SEQ ID NO:25)

N. coeliaca (1451) GGGACGAAGTCGTAACAAGGTAGCCGTACCGGAAGGTGCGGCTGGATCACCTCCTTT---  (SEQ ID NO:26)
          N. globerula (1452) GGGACGAAGTCGTAACAAGGTAGCCGTACCGGAAGGTGCGGCTGGATCACCTCCTT----  (SEQ ID NO:27)
              R. equi (1453) GGGACGAAGTCGTAACAAGGTAGCCGTACCGGAAGGTGCGGCTGGATCACCTCCTT----  (SEQ ID NO:28)
            R. A2Y26  (1443) ------------------------------------------------------------  (SEQ ID NO:29)
         R. 871-AN040 (1455) GGGACGAAGTCGTAACAAGG----------------------------------------  (SEQ ID NO:30)
            R. jostii (1437) G-----------------------------------------------------------  (SEQ ID NO:31)
        R. opacus 1CP (1449) GGGACGAAGTCGTAACAAGGTAGCCGTACCGGAAGGT-----------------------  (SEQ ID NO:32)
  R. imtechensis RKJ300 (1451) GGGACGAAGTCGTAACAAGGTAGCCGTACCGGAAGGTGCGGCTGGAAACTGCCGAGGGGG (SEQ ID NO:33)
   R. koreensis DNP505  (1435) GGGACGAAGTCGTAACAAGGTAGCCGTACCGGAAGGTGC---------------------  (SEQ ID NO:34)
         R. opacus B-4 (1463) GGGACGAAGTCGTAACAAGGTAGCCGTACCGGAAGGTGCGGCTGGATCACCTCCTTTCT-  (SEQ ID NO:41)
              R. TCH14 (1447) GGGA--------------------------------------------------------  (SEQ ID NO:35)
      R. opacus DNP14-5 (1436) GGGACGAAGTCGTAACAAGGTAGCCGTACCGGAAGG-----------------------  (SEQ ID NO:36)
              R. pnp-5 (1455) GGGACGAAGTCGTAACAAGGTAGCCGTA--------------------------------  (SEQ ID NO:37)
           R. Sulf-822 (1425) GGGACGAAGTCGTAACAAGGTA--------------------------------------  (SEQ ID NO:38)
       R. wratislaviensis (1446) GGGACGAAGTCGTAACAAGGTAGCCGTACCGGAAGGTGCGGCTGGATCACCT--------  (SEQ ID NO:39)
```

Fig. 5

| Organism | Growth conditions | | |
|---|---|---|---|
| | Heterotrophic | Chemoautotrophic | Single carbon compound |
| R. opacus (DSM 44193) | 9.00 (6d) | 0.00 | ND |
| R. opacus (DSM 43205) | 9.00 (6d) | 1.00 (5d) | 2.70 (20d) |
| Rhodococcus sp. (DSM 3346) | 2.40 (3d) | 0.51 (9d) | ND |
| Cupriavidus necator (DSM 531) | 2.20 (3d) | 0.23 (3d) | ND |

Fig. 6

| Organism | Lipid content (% of CDM) | |
|---|---|---|
| | Heterotrophic | Chemoautotrophic |
| R. opacus (DSM 44193) | 49.3% | No growth |
| R. opacus (DSM 43205) | 61.2% | 10.3% |
| Rhodococcus sp. (DSM 3346) | 19% | 3.7% |
| Cupriavidus necator (DSM 531) | 0.5% | ND |

| Plasmid | Organisms | Backbone | Transformation method | Sequence ID |
|---|---|---|---|---|
| pSeqCo1 | E. coli Rhodococci | PUC18 | Electroporation | SEQ ID NO: 01 |
| pSeqCO2 | E. Coli Cupriavidus | pBBR1 | Bacterial conjugation Electroporation | SEQ ID NO: 02 |
| pVer1 | E. coli Rhodococci Cupriavidus | pBBR1MCS-2 | Bacterial conjugation Electroporation | SEQ ID NO: 03 |
| pVer2 | E. coli Rhodococci Cupriavidus | pBBR1MCS-2 | Bacterial conjugation Electroporation | SEQ ID NO: 04 |

B

| Plasmid | Replication gene | Mobilization gene | Antibiotic resistance | Direct selection gene | Cloning site |
|---|---|---|---|---|---|
| pSeqCo1 | Rep (pMB1)[1] RepAB (pKNR01)[2] | | Ampicillin Kanamycin | LacZ operon | MCS |
| pSeqCO2 | Rep (pBBR1)[3] | Mob[4] | Kanamycin | LacZ operon | MCS |
| pVer1 | Rep (pBBR1) RepAB (pKNR01) | Mob[4] | Kanamycin | LacZ operon | MCS |
| pVer2 | Rep (pBBR1) RepAB (pKNR01) | Mob[4] | Kanamycin Chloramphenicol | LacZ operon | MCS |

Fig. 12

| Organism | Plasmid | Transformation method | Kanamycin concentrations | Cultivation time | Number of Colonies |
| --- | --- | --- | --- | --- | --- |
| R. Opacus (44193) | pSeqCo1 | Electroporation[1] | 75 µg/ml | 4 days | 100 |
| R. opacus (44193) | pVer1 | Electroporation[1] | 75 µg/ml | 4 days | 50 |
| R. opacus (44193) | NC | Electroporation[1] | 75 µg/ml | 4 days | 0 |
| R. opacus (43205) | pSeqCo1 | Electroporation[1] | 75 µg/ml | 4 days | 20 |
| R. opacus (43205) | NC | Electroporation[1] | 75 µg/ml | 4 days | 0 |
| Cupriavidus necator (531) | pSeqCO2 | Electroporation[2] | 200 µg/ml | 2 days | 200 |
| Cupriavidus necator (531) | NC | Electroporation[2] | 200 µg/ml | 2 days | 0 |

Fig. 16

| Compound | Cn-FUEL 2.1 | Cn-FUEL 2.2 | Cn-P(1) | Cn-P(2) |
|---|---|---|---|---|
| Spiro[4.5]decane | 2.50% | 0.98% | - | - |
| 11-Hexacosyne | - | 0.41% | - | - |
| 9-Tricosene, (Z)- | 0.70% | 0.23% | - | - |
| Triacontyl acetate | 0.22% | - | - | - |
| 1-Heptacosanol | - | 0.18% | - | - |
| 5-Nonadecen-1-ol | - | 0.40% | - | - |
| Nonadecyl trifluoroacetate | 0.31% | 0.32% | - | - |
| Bicyclo[10.8.0]eicosane, (E)- | 33.09% | 40.34% | - | - |
| cis,cis-1,6-Dimethylspiro[4.5]decane | 3.55% | 3.63% | - | - |
| 1,19-Eicosadiene | 6.63% | 0.24% | - | - |
| Cyclododecene, 1-methyl- | 0.47% | - | - | - |
| Cyclooctacosane | 2.03% | 1.27% | - | - |
| Bicyclo[10.8.0]eicosane, cis- | 3.53% | 3.32% | - | - |
| 1-Pentadecyne | 0.48% | 6.97% | - | - |
| Heptacosyl acetate | 4.12% | 3.48 | - | - |
| Cyclotetracosane | 1.47% | 1.27 | - | - |
| 5-Cyclohexyl-1-pentene | 26.56% | 3.39% | - | - |
| Cyclododecene, 1-methyl- | 0.80% | - | - | - |
| 1-Hexadecyne | 10.41% | 18.95% | - | - |
| 1,21-Docosadiene | 1.64% | 1.78% | - | - |
| Cyclodecacyclotetradecene, -eicosahydro- | - | 10.87% | - | - |
| 17-Pentatriacontene | - | 0.28% | - | - |
| Squalene | - | - | X | X |

1-Hexadecyne ($C_{16}H_{30}$)
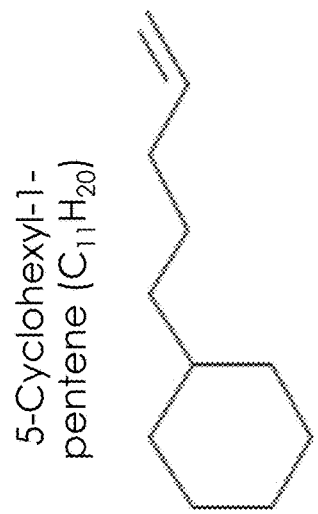
5-Cyclohexyl-1-pentene ($C_{11}H_{20}$)
Fig. 17

Fig. 21

| Definition | GenBank # | Length (amino acids) | (%) Identity to YP_002784058.1 |
|---|---|---|---|
| acyl-CoA thioesterase Rhodococcus opacus B4 | YP_002784058.1 | 590 | 100 |
| acyl-CoA thioesterase II Rhodococcus jostii RHA1 | YP_706811.1 | 563 | 100 |
| acyl-CoA thioesterase Rhodococcus erythropolis PR4 | YP_002766361.1 | 460 | 99 |
| acyl-CoA thioesterase II TesB2 Mycobacterium abscessus ATCC 19977 | YP_001703624.1 | 421 | 100 |
| acyl-CoA thioesterase II Rhodococcus equi 103S | YP_004006825.1 | 394 | 95 |
| acyl-CoA thioesterase II Nocardia farcinica IFM 10152 | YP_119916.1 | 390 | 95 |
| acyl-CoA thioesterase Gordonia neofelifaecis NRRL B-59395 | ZP_08203815.1 | 379 | 94 |
| acyl-CoA thioesterase II Amycolicicoccus subflavus DQS3-9A1 | YP_004493060.1 | 369 | 96 |
| acyl-CoA thioesterase II Dietzia cinnamea P4 | ZP_08021991.1 | 345 | 94 |
| Choloyl-CoA hydrolase Tsukamurella paurometabola DSM 20162 | YP_003646881.1 | 339 | 94 |
| acyl-coenzyme A thioesterase 8 Corynebacterium amycolatum SK46 | ZP_03394327.1 | 337 | 94 |
| acyl-CoA thioesterase II Mycobacterium smegmatis str. MC2 155 | YP_887257.1 | 333 | 95 |
| acyl-CoA thioesterase II Segniliparus rotundus DSM 44985 | YP_003659169.1 | 304 | 94 |
| acyl-CoA thioesterase II Polymorphum gilvum SL003B-26A1 | YP_004301843.1 | 269 | 95 |
| acyl-coa thioesterase ii protein Stappia aggregata IAM 12614 | ZP_015548795.1 | 264 | 93 |
| acyl-CoA thioesterase II Saccharomonospora viridis DSM 43017 | YP_003134297.1 | 263 | 92 |
| palmitoyl-CoA hydrolase Nocardioides sp. JS614 | YP_924040.1 | 261 | 92 |
| Palmitoyl-CoA hydrolase Catenulispora acidiphila DSM 44928 | YP_003115470.1 | 256 | 94 |
| acyl-CoA thioesterase II Actinosynnema mirum DSM 43827 | YP_003103347.1 | 258 | 92 |
| acyl-CoA thioesterase II Streptomyces bingchenggensis BCW-1 | ADI04815.1 | 249 | 92 |

INDUSTRIAL FATTY ACID ENGINEERING GENERAL SYSTEM FOR MODIFYING FATTY ACIDS

RELATED APPLICATIONS

This application claims priority under 35 U.S.C. §119(e) to U.S. Provisional Patent Application No. 61/536,056, filed Sep. 19, 2011 and entitled "INDUSTRIAL FATTY ACID ENGINEERING SYSTEM." This application is also a continuation-in-part of International Patent Application No. PCT/US2011/34218, filed Apr. 27, 2011, and entitled "USE OF OXYHYDROGEN MICROORGANISMS FOR NON-PHOTOSYNTHETIC CARBON CAPTURE AND CONVERSION OF INORGANIC AND/OR C1-CARBON SOURCES INTO USEFUL ORGANIC COMPOUNDS," which is a continuation-in-part of International Patent Application No. PCT/US2010/001402, filed May 12, 2010, and entitled "BIOLOGICAL AND CHEMICAL PROCESS UTILIZING CHEMOAUTOTROPHIC MICROORGANISMS FOR THE CHEMOSYNTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS," which is a continuation-in-part of U.S. patent application Ser. No. 12/613,550, filed Nov. 6, 2009, and entitled "BIOLOGICAL AND CHEMICAL PROCESS UTILIZING CHEMOAUTOTROPHIC MICROORGANISMS FOR THE CHEMOSYNTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS," which claims the benefit of U.S. Provisional Patent Application No. 61/111,794, filed Nov. 6, 2008, and entitled, "BIOLOGICAL AND CHEMICAL PROCESS UTILIZING CHEMOAUTOTROPHIC MICROORGANISMS FOR THE RECYCLING OF CARBON FROM CARBON DIOXIDE AND OTHER INORGANIC CARBON SOURCES THROUGH CHEMOSYNTHESIS INTO BIOFUEL AND ADDITIONAL USEFUL PRODUCTS." This application also claims priority under 35 U.S.C. §119(e) to U.S. Provisional Patent Application No. 61/542,823, filed Oct. 4, 2011 and entitled "ENGINEERED CO2-FIXING CHEMOTROPHIC MICROORGANISMS PRODUCING CARBON-BASED PRODUCTS AND METHODS OF USING THE SAME." This application also claims priority under 35 U.S.C. §119(e) to U.S. Provisional Patent Application No. 61/616,560, filed Mar. 28, 2012 and entitled "PROCESS FOR GENERATING HYDROXYLATED FATTY ACIDS." Each of these applications is incorporated herein by reference in its entirety for all purposes.

SEQUENCE LISTING

The instant application contains a Sequence Listing, which has been submitted electronically in ASCII format and is hereby incorporated by reference in its entirety. Said ASCII copy, created on Aug. 1, 2014, is named 164185.P001U1 SL.txt and is 146,662 bytes in size.

FIELD OF INVENTION

This disclosure relates to compositions capable of producing and methods of the producing oils, fuels, and oleochemicals through cultivating bacteria that grow on carbon-containing gas such as syngas, producer gas, CO2, carbon monoxide and mixtures of the same containing hydrogen gas. This disclosure further relates to methods of fixing carbon from gas input into useful organic molecules such as diacids, hydroxy fatty acids, unsaturated fatty acids. The bacteria of the invention can be genetically engineered for use in the methods or other aspects of the invention described herein.

BACKGROUND

Sustainable and renewable sources of organic molecules are needed to help reduce the amount of carbon dioxide emissions in the atmosphere, as well as to reduce global energy consumption based upon coal, oil, and natural gas economies. Increased demand in the global economy has placed increasing pressure on traditional hydrocarbon feedstocks for the production of organic molecules. Many industries, including plastics and chemical manufacturers, rely heavily on the availability of fossil hydrocarbon sources as a feedstock for their manufacturing processes. Cost-effective alternatives to current sources of supply could help mitigate the upward pressure on fossil resource demand and raw material costs.

Biologic systems that fix carbon through natural biochemical metabolic processes are known. Algal systems have been developed to create hydrocarbon or petroleum replacements through photosynthetic reactions, as well as heterotrophic reactions utilizing fixed carbon feedstocks such as sugar that indirectly depend upon photosynthesis, however insufficient yields limit the effectiveness, economic feasibility, practicality and commercial adoption of these algal technologies. Bacterial cells have also been genetically engineered to process sugar feedstocks into useful organic compounds in heterotrophic fermentation systems; however, there are significant drawbacks for these systems as well.

Heterotrophic fermentations are vulnerable to contamination because heterotrophic microorganisms that can grow on fixed carbon nutrients and compete with a production strain are far more ubiquitous in the surface environment. Heterotrophic technologies also generally suffer limitations in terms of food versus fuel conflict and negative environmental impacts.

Gas-to-liquid (GTL) technologies have the benefit of allowing the utilization of waste carbon sources—including highly lignocellulosic waste through the conversion to synthesis gas (syngas) via gasification, as well as waste CO2 through the provision of reduced hydrogen—in the production of organic chemicals. Syngas is a mix of gases that generally contains $H_2$, CO, and $CO_2$ as major components, which can be generated through steam reforming of methane and/or liquid petroleum gas or biogas or through gasification of any organic material, including but not limited to biomass, waste organic matter, various polymers, and coal. Many gasification processes are available for the production of syngas. A number of gasification processes subject the carbonaceous feedstock to partial oxidation at high temperatures (500-1500.degree. C.), with the oxygen supply restricted to prevent complete combustion, producing syngas with varying composition depending on feedstock and reaction conditions such that the ratio of $H_2$:CO can range from 0.5:1 to 3:1. The hydrogen component of syngas can be raised through the reaction of CO with steam in the water gas shift reaction with a concomitant increase in $CO_2$ in the syngas mix.

Some major technologies for syngas conversion to chemicals include chemical catalytic processes such as the Fischer-Tropsch (F-T) as well as processes for the synthesis of methanol or other mixed alcohols, and biological syngas fermentation processes. F-T has been worked on for almost one hundred years and relies on metal-based, inorganic catalysts for the conversion of syngas into longer chain hydrocarbons. Difficulties with F-T include: a wide chain length distribution of products resulting in the need to reprocess short chain length products such as methane and LPG and/or the need to perform additional costly post-processing steps on long chain waxes and tars such as hydrocracking; high catalyst sensitivity to syngas impurities such as sulfur containing compounds, tars, and particulates, generally necessitating multiple costly gas clean up steps; relatively low flexibility in terms of accommodating various ratios of syngas constituents i.e. H2:CO, and low tolerance of $CO_2$, often resulting in additional costly syngas conditioning steps such as water gas shift and $CO_2$ removal; the actual F-T step being relatively high temperature and pressure resulting in costly compression and heating requirements; the wide distribution of products generally necessitating the storage, handling, and transport of a wide array of products which is often uneconomic except for relatively large scale operations; F-T products (e.g. diesel, jet fuel, naphtha, waxes) being relatively low in value at current (2011) prices compared to many different higher value oils, lipids, and oleochemicals that can be produced biologically. The difficulties with F-T generally also apply to other chemical conversion processes such as methanol synthesis.

The gasification of biomass to generate syngas has a long history going back to World War II where biomass gasification was used for running modified automobiles, boats, buses, and trucks. Presently, a number of biomass gasification technologies are at, or near commercialization (able to gasify 10,000 or more tons of biomass per year), and are generally used for the production of heat and/or electricity. The synthesis of chemicals or fuels from syngas generated via biomass gasification is at an earlier stage of development, and is generally pre-commercial.

Using syngas and/or $CO_2$ and/or renewable $H_2$ in a gas bioprocess enables the utilization of cheaper and more flexible sources of energy and/or carbon for the biological synthesis of sustainable chemicals and fuels than is possible through heterotrophic or phototrophic synthesis. In a syngas bioprocess, syngas acts as both a carbon and energy source for the microbial culture. Some of the advantages of syngas bioprocesses include: the production of a relatively narrow range of carbon chain length distribution compared to F-T; lower sensitivity to syngas impurities; greater tolerance of varying ratios of H2:CO and the presence of CO2; ability to operate at much closer to ambient temperature and pressure; ability to produce various higher value oleochemical products.

A bioprocess based upon a gaseous feedstock such as syngas can allow for far lower negative environmental and food production impacts in the biological synthesis of liquid fuels and/or chemicals than the highly land and water intensive heterotrophic or phototrophic-based technologies. However, current biological GTL technologies generally yield relatively short chain alcohols, or other short chain organic compounds, as products, which have relatively low energy density and infrastructure compatibility and limited applications. The syngas-growing microorganisms used in current biological GTL technologies are generally inappropriate for the synthesis of mid- to long-carbon chain lipid-based chemicals. Furthermore the types of microorganisms used in current biological GTL technologies such as *Clostridia* have a relatively low tolerance for their short carbon chain gas fermentation products such as ethanol, butanol, or acetic acid, which limits titers and complicates product recovery, hurting the overall economics of the GTL process.

There is a need to identify a set of microorganisms that can grow in conventional and scalable contained reaction vessels and that produce commercially viable sets of organic carbon chains of at least eight carbon atoms long in a commercially feasible method. There is a need to identify microorganisms not limited metabolically by typical fixed carbon inputs such as sugar, and a microorganism that can additionally utilize syngas, producer gas, as well as a wide array of abiotic sources of carbon and energy for the synthesis of drop-in fuels and chemicals, leading to a feedstock flexibility that far exceeds comparable heterotrophic systems. There is a need to identify and use microorganisms that can utilize electron donors such as hydrogen, present in syngas, producer gas, as well as readily generated through a wide array of abiotic renewable energy technologies, for growth and carbon fixation.

The targeting of fatty acids produced through fatty acid biosynthesis to short chain lengths has been achieved in heterotrophic microorganisms. This has been accomplished through the use of thioesterases to change populations of fatty acids C8-C14 and the over-expression of thioesterases to increase shorter chain length fatty acids.

Examples in the prior art include C8-C14 thioesterase expression to produce shorter chain lengths in U.S. Pat. No. 7,883,882 Renewable chemical production from novel fatty acid feedstocks, Franklin et al. Solazyme, p. 58.

However there is a need to target the production of shorter chain length fatty acids in microorganisms that are capable of growing and producing lipids chemotrophically on syngas or $H_2/CO_2$ gas mixes to enable microbial GTL production of lipids with targeted, mid-length carbon chains.

Dicarboxylic acids (Diacids) such as dodecanedoic acid (n=10) are used in production of nylon (nylon-6,12), polyamides, coatings, adhesives, greases, polyesters, dyes, detergents, flame retardants and fragrances. Diacids can be produced by fermentation of long-chain alkanes by *candida tropicalis* (Kroha K, Infom 2004, 15, 568). Traumatic acid, monounsaturated dodecanedoic acid (10E-dodeca-1,12-dicarboxylic acid) has been produced from plant tissues English J et al., Science 1939, 90, 329. *Pyrococcus furiosus* produces an array of dicarboxylic acids (Carballeira, 1997). The total amount of dicarboxylic acids comprises only 3.4% of the total, however, this could be boosted by various literature methods.

There is a need for a biological, non-heterotrophic means of producing diacids from low-cost or sustainable syngas feedstocks.

Nutritionally important n-3 fatty acids include α-linolenic acid (ALA), eicosapentaenoic acid (EPA), and docosahexaenoic acid (DHA), all of which are polyunsaturated. N-3 fatty acids that are important in human physiology are α-linolenic acid (18:3, n-3; ALA), eicosapentaenoic acid (20:5, n-3; EPA), and docosahexaenoic acid (22:6, n-3; DHA). These three polyunsaturates have either 3, 5, or 6 double bonds in a carbon chain of 18, 20, or 22 carbon atoms, respectively. As with most naturally produced fatty acids, all double bonds are in the cis-configuration.

A fatty acid desaturase is an enzyme that removes two hydrogen atoms from a fatty acid, creating a carbon/carbon double bond. These desaturases are classified as delta— indicating that the double bond is created at a fixed position from the carboxyl group of a fatty acid (for example, $\Delta 9$ desaturase creates a double bond at the 9th position from the carboxyl end). omega (e.g. ω3desaturase)—indicating the double bond is created between the third and fourth carbon from the methyl end of the fatty acid. In the biosynthesis of essential fatty acids, an elongase alternates with different desaturases (for example, Δ6desaturase) repeatedly inserting an ethyl group, then forming a double bond.

Most polyunsaturated oils come from fish and there is a need for alternate, and particularly microbial sources of polyunsaturated fatty acids, given depleting fish stocks and increasing pollution in the oceans.

SUMMARY OF THE INVENTION

The present invention allows microorganisms to be engineered to convert $CO_2$ gas and/or syngas and/or producer gas to higher value mid- to long-carbon chain length oleochemicals or monomers. The present technology allows the development of new genetically enhanced strains of microorganisms that can be used for syngas bioprocessing within biological gas-to-liquid (GTL) processes to produce and/or secrete various relatively long chain organic compounds that are drop-in, and are currently only produced in bulk from petroleum or higher plants.

The present invention relates to the engineering of microorganisms, including but not limited to hydrogen oxidizing, carbon monoxide oxidizing, and knallgas microorganisms, with a natural capability to grow and synthesize biomass on gaseous carbon sources such as syngas and/or $CO_2$, such that the engineered microorganisms synthesize targeted products, including chemicals and fuels, under gas cultivation. The microorganisms and methods of the present invention enable low cost synthesis of chemicals and fuels, which can compete on price with petrochemicals and higher-plant derived oleochemicals and monomers, and which will generally have a substantially lower price than oleochemicals produced through heterotrophic or phototrophic synthesis.

The invention relates to a composition comprising a microorganism that converts syngas and/or gaseous CO2 and/or a mixture of CO2 gas and H2 gas into one or more lipids. In some embodiments, the composition comprises a microorganism, wherein the microorganism is a hydrogen-oxidizing chemotrophic microorganism. In some embodiments, the composition comprises a microorganism, wherein the microorganism is a carbon monoxide-oxidizing microorganism. In some embodiments, the composition comprises a microorganism, wherein the microorganism is a knallgas microorganism. In some embodiments, the composition comprises a microorganism, wherein the microorganism is chosen from the genera *Rhodococcus* or *Gordonia*. In some embodiments, the composition comprises a microorganism, wherein the microorganism is *Rhodococcus opacus*. In some embodiments, the composition comprises a microorganism, wherein the microorganism is *Rhodococcus opacus* (DSM 43205) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*.

In some embodiments, the composition comprises a microorganism wherein the microorganism can naturally grow on H2/CO2 and/or syngas, and wherein the microorganism can naturally accumulate lipid to 50% or more of the cell biomass by weight. In some embodiments the microorganisms have a native ability to send a high flux of carbon down the fatty acid biosynthesis pathway. In some embodiments the microorganism exhibiting these traits is *Rhodococcus opacus* (DSM 43205 or DSM 43206).

In some embodiments, the composition comprises a microorganism that can naturally grow on H2/CO2 and/or syngas, and wherein the microorganism can naturally accumulate polyhydroxybutyrate (PHB) or polyhydroxyalkanoate (PHA) to 50% or more of the cell biomass by weight. In some embodiments the microorganisms have a native ability to direct a high flux of carbon through the acetyl-CoA metabolic intermediate, which can lead into fatty acid biosynthesis, along with a number of other synthetic pathways including PHA and PHB synthesis. A microorganism is considered to direct a high flux of carbon through acetyl-CoA if a product of a synthesis pathway going through the acetyl-CoA metabolic intermediate, including but not limited to polyhydroxybutyrate (PHB) or polyhydroxyalkanoate (PHA), can represent 50% or more of the cell biomass by weight. In some embodiments the microorganism exhibiting these traits is *Cupriavidus necator* (DSM 531 or DSM 541).

In some embodiments, the invention relates to a non-naturally occurring microorganism capable of converting syngas or other gaseous carbon sources into targeted oleochemical and/or monomer products, where the wild-type microorganism is capable of growing on syngas or other gaseous carbon sources, but is either not capable of synthesizing said targeted oleochemical and/or monomer products, or is capable of synthesizing the targeted oleochemicals and/or monomers, but is not capable of synthesizing the targeted biochemical products at the concentration and/or efficiency of the non-natural microorganism. In such microorganisms, one or more proteins or enzymes are expressed in the microorganism, thereby modifying, extending, diverting, enhancing, promoting, or otherwise altering the lipid biosynthesis pathway or its regulation for the synthesis and/or enhanced synthesis of a targeted lipid-based product, oleochemical, monomer, or hydrocarbon.

In some embodiments, the invention relates to a non-naturally occurring microorganism capable of converting syngas or other gaseous carbon sources into targeted oleochemical and monomer products, where the wild-type microorganism is capable of growing on syngas or other gaseous carbon sources and is capable of synthesizing said targeted oleochemical and monomer products, but the non-naturally occurring microorganism is capable of synthesizing the targeted biochemical products at a higher concentration and/or efficiency than the wild-type microorganism due to the overexpression and/or underexpression of one or more proteins or enzymes.

In some embodiments, the invention relates to compositions comprising one or more bacterial cells that consist of one, two, or three exogenous nucleic acid sequences where said bacteria can grow using syngas and/or gaseous CO2 and/or a mixture of CO2 gas and H2 gas as a source of carbon and/or energy.

In some embodiments, the invention relates to compositions comprising one or more bacterial cells of *Rhodococcus opacus* (DSM 43205) that consist of zero, one, two, or three exogenous nucleic acid sequences.

In some embodiments one, two, or three exogenous nucleic acid sequences encode one or more thioesterase proteins.

In some embodiments the source of thioesterase is inherent to the production organisms. In some embodiments the source of thioesterase is *Rhodococcus opacus* B4. In some embodiments the thioesterase is derived from bacteria or plants other than the host microorganism.

In some embodiments, the invention relates to compositions comprising one or more bacterial cells that consist of two exogenous nucleic acid sequences that encode the following proteins: fatty acid acyl-ACP reductase, a fatty acid aldehyde decarbonylase, where said bacteria can grow using syngas and/or gaseous CO2 and/or a mixture of CO2 gas and H2 gas as a source of carbon and/or energy.

In some embodiments, the invention relates to compositions comprising one or more bacterial cells that consist of three exogenous nucleic acid sequences that encode the following proteins: fatty acid acyl-ACP reductase, a fatty acid aldehyde decarbonylase, and a thioesterase, where said bacteria can grow using syngas and/or gaseous CO2 and/or a mixture of CO2 gas and H2 gas as a source of carbon and/or energy.

In some embodiments, the bacterial cell produces and/or secretes one or more lipids in an amount that is greater than the amount of lipids produced and/or secreted by the same cell not comprising the exogenous nucleic acid sequence.

In some embodiments, the bacterial cell produces and/or secretes one or more lipids having a given carbon chain length, where the amount of said lipid produced and/or secreted is greater than the amount produced and/or secreted by the same cell not comprising the exogenous nucleic acid sequence.

In some embodiments, the bacterial cell produces and/or secretes one or more lipid molecules in an amount that is less than the amount of lipids produced and/or secreted by the same cell not comprising the exogenous nucleic acid sequence.

In some embodiments, the bacterial cell produces and/or secretes one or more hydrocarbons in an amount that is greater than the amount of hydrocarbons produced and/or secreted by the same cell not comprising the exogenous nucleic acid sequence.

In some embodiments, the bacterial cell or compositions comprising the bacterial cell comprise at least one exogenous nucleic acid sequence that is integrated into the genome of the cell.

In some embodiments, the invention relates to a composition comprising a microorganism that converts syngas and/or gaseous CO2 and/or a mixture of CO2 gas and H2 gas into one or more unsaturated hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase. In some embodiments the microorganism is *Rhodococcus opacus*.

In some embodiments the invention relates to a method of producing a lipid or mixture of lipids in a microorganism population comprising the cell or the composition described herein, wherein the method comprises: culturing a population of microorganisms comprising the cell or the composition described herein in a feedstock comprising syngas and/or gaseous CO2 and/or a mixture of CO2 gas and H2 gas.

In some embodiments, the invention relates to a method of producing a lipid or mixture of lipids, wherein the method comprises: culturing a population of bacterial cells comprising the cell or the composition described herein in a feedstock comprising syngas and/or gaseous CO2 and/or a mixture of CO2 gas and H2 gas. In some embodiments, the microorganism population comprises a bacterial strain of *Rhodococcus opacus*. In some embodiments, the microorganism population comprises a bacterial strain of *Rhodococcus opacus* (DSM 43205 or 43206).

In some embodiments, the invention relates to a method of producing a lipid or mixture of lipids, wherein the method comprises: culturing a population of bacterial cells comprising the cell or the composition described herein in a feedstock comprising methanol, a common impurity of syngas, with or without the addition of syngas and/or gaseous CO2 and/or a mixture of CO2 gas and H2 gas. In some embodiments, the microorganism population comprises a bacterial strain of *Rhodococcus opacus*. In some embodiments, the microorganism population comprises a bacterial strain of *Rhodococcus opacus* (DSM 43205).

In some embodiments, the invention relates to a method of producing a lipid or mixture of lipids, wherein the method comprises: culturing a population of bacterial cells comprising the cell or the composition described herein in a feedstock comprising syngas and/or gaseous CO2 and/or a mixture of CO2 gas and H2 gas. In some embodiments, the microorganism population comprises a bacterial strain of *Cupriavidus necator*.

In some embodiments, the molecule is chosen from one or more alkene, alkyne, unsaturated fatty acid, hydroxyacid and/or dicarboxylic acid (diacid). In some embodiments, the method produces a lipid or mixture of lipids at a quantity higher than the quantity of lipid or mixture of lipids in the same bacterial cell population not comprising the exogenous nucleic acids described herein. In some embodiments the one or more lipids comprise a quantity of at least one alkene, alkyne, unsaturated fatty acid, hydroxyacid and/or diacid at a level higher than the quantity of the alkene, alkyne, unsaturated fatty acid, hydroxyacid and/or diacid in the same microorganism not comprising the exogenous nucleic acid sequences.

In some embodiments of the invention, the invention relates to a method of producing and/or secreting a lipid or mixture of lipids by culturing a population of microorganisms comprising a bacterial cell described herein, wherein the exogenous nucleic acid sequences are operably linked to a promoter that is inducible in response to a first stimulus, and wherein the method further comprises: culturing the population of bacterial cells for a first period of time in the presence of a first stimulus to produce one or more lipids chosen from an alkene, alkyne, unsaturated fatty acid, hydroxyacid and/or diacid.

In some embodiments, the invention relates to a method of producing one or more diacids, comprising exposing a bacterial cell to syngas and/or gaseous CO2 or a mixture of gaseous CO2 and gaseous H2; wherein the bacterial cell is capable of fixing gaseous CO2 into one or more diacids, and wherein the microorganism comprises at least a first exogenous nucleic acid and a second exogenous nucleic acid, wherein the first exogenous nucleic acid encodes cytochrome P450 enzyme and the second exogenous nucleic acid encodes NADPH cytochrome P450 reductase or NADH cytochrome P450 reductase. In some embodiments, the first and second exogenous nucleic acids are heterologous nucleic acid sequences. In some embodiments, the bacterial cell comprises at least a first, a second, and a third exogenous nucleic acid sequence, wherein the first exogenous nucleic acid sequence encodes a cytochrome P450 enzyme, the second exogenous nucleic acid sequence encodes a NADPH cytochrome P450 reductase, and the third exogenous nucleic acid sequence encodes a thioesterase. In some embodiments, the bacterial cell comprises at least a first exogenous nucleic acid sequence, wherein the first exogenous nucleic acid sequence encodes a thioesterase. In some embodiments, the bacterial cell comprises no more than five exogenous nucleic acid sequences that encode a lipid pathway enzyme. In some embodiments, the composition comprises a microorganism, wherein the microorganism is *Rhodococcus opacus* (DSM 43205 or 43206) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*. In some embodiments the microorganism is from the suborder corynebacterineae or the family burkholderiaceae. In some embodiments the microorganism through its native machinery produces a complement of fatty acids described in the Fatty Acid Output section below.

In some embodiments, the invention relates to a method of producing one or more hydroxyacid, diacid, or unsaturated fatty acid, or any combination thereof comprising exposing a bacterial cell to syngas and/or gaseous CO2 or a mixture of gaseous CO2 and gaseous H2; wherein the bacterial cell is capable of fixing gaseous CO2 into one or more lipids; wherein the lipids are recovered from the bioreactor and fed to a second bioreactor wherein the lipids are postprocessed to generate hydroxyacid, diacid, and/or unsaturated fatty acids via a second microorganism such as but not limited to *Candida tropicalis*. In some embodiments, the bacterial cell comprises at least a first exogenous nucleic acid sequence, wherein the first exogenous nucleic acid sequence encodes a thioesterase. In some embodiments, the composition comprises a bacterial cell, wherein the bacteria is *Rhodococcus opacus* (DSM 43205 or 43206) or *Rhodococcus* sp (DSM 3346). In some embodiments, the bacterial cell is chosen from the genera *Ralstonia* or *Cupriavidus*. In some embodiments, the bacterial cell is *Cupriavidus necator*. In some embodiments the bacterial cell is from the suborder corynebacterineae or the family burkholderiaceae. In some embodiments the bacterial cell through its native machinery produces a complement of fatty acids described in the Fatty Acid Output section below.

In some embodiments, the invention relates to a method of producing one or more unsaturated fatty acids, comprising exposing a bacterial cell to syngas and/or gaseous CO2 or a mixture of gaseous CO2 and gaseous H2; wherein the bacterial cell is capable of fixing gaseous CO2 into one or more unsaturated fatty acids and wherein the microorganism comprises at least a first exogenous nucleic acid, wherein the first exogenous nucleic acid encodes a desaturase that introduces double bonds to fatty acids. In some embodiments, the first exogenous nucleic acids is a heterologous nucleic acid sequence. In some embodiments, the bacterial cell comprises at least a first, and a second exogenous nucleic acid sequence, wherein the first exogenous nucleic acid sequence encodes a desaturase, the second exogenous nucleic acid sequence encodes a thioesterase. In some embodiments, the composition comprises a microorganism, wherein the microorganism is *Rhodococcus opacus* (DSM 43205 or 43206) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*. In some embodiments the microorganism is from the suborder corynebacterineae or the family burkholderiaceae. In some embodiments the microorganism through its native machinery produces a complement of fatty acids described in the Fatty Acid Output section below.

In some embodiments, the invention relates to a method of producing one or more hydroxy fatty acids (hydroxy acids), comprising exposing a bacterial cell to syngas and/or gaseous CO2 or a mixture of gaseous CO2 and gaseous H2; wherein the bacterial cell is capable of fixing gaseous CO2 into one or more hydroxy acids and wherein the microorganism comprises at least a first exogenous nucleic acid, wherein the first exogenous nucleic acid encodes a P450-dependent fatty acid hydroxylase that introduces hydroxyl groups at positions along the fatty acid chain. In some embodiments, the first exogenous nucleic acids is a heterologous nucleic acid sequence. In some embodiments, the bacterial cell comprises at least a first, and a second exogenous nucleic acid sequence, wherein the first exogenous nucleic acid sequence encodes a P450-dependent fatty acid hydroxylase, the second exogenous nucleic acid sequence encodes a thioesterase. In some embodiments, the composition comprises a microorganism, wherein the microorganism is *Rhodococcus opacus* (DSM 43205 or 43206) or *Rhodococcus* sp (DSM 3346). In some embodiments, the composition comprises a microorganism, wherein the microorganism is chosen from the genera *Ralstonia* or *Cupriavidus*. In some embodiments, the composition comprises a microorganism, wherein the microorganism is *Cupriavidus necator*. In some embodiments the microorganism is from the suborder corynebacterineae or the family burkholderiaceae. In some embodiments the microorganism through its native machinery produces a complement of fatty acids described in the Fatty Acid Output section below.

In some embodiments, the invention relates to a method of manufacturing one or more lipids, comprising (a) culturing a cell described herein in a reaction vessel or bioreactor in the presence of syngas and/or gaseous CO2 or a mixture of gaseous CO2 and gaseous H2, wherein the cell produces and/or secretes one or more lipids in an quantity equal to or greater than at least 10% of the cell's total dry cellular mass; and (b) separating the one or more lipids from reaction vessel. In some embodiments, the method further comprises purifying the one or more lipids after separation from the reaction vessel or bioreactor.

In some embodiments, the invention relates to a method of producing a alkene or alkyne in a bacterial cell comprising at least a first and a second exogenous nucleic acid sequence, wherein the first exogenous nucleic acid sequence encodes a fatty acid acyl-ACP reductase and the second exogenous nucleic acid encodes a fatty acid aldehyde decarbonylase.

In some embodiments, the bacterial cell producing a alkene or alkyne comprises at least a first, a second, and a third exogenous nucleic acid sequences, wherein the first exogenous nucleic acid sequence encodes a fatty acid acyl-ACP reductase and the second exogenous nucleic acid encodes a fatty acid aldehyde decarbonylase, and the third exogenous nucleic acid encodes a thioesterase.

In some embodiments, the invention relates to a bioreactor comprising the composition or bacterial cells described herein.

In some embodiments, the invention relates to a system for the production of one or more lipids or mixture of lipids, comprising a bioreactor, which comprises: (a) a microorganism population comprising a cell described herein; and (b) an inlet connected to a feedstock source allowing delivery of a feedstock comprising syngas and/or gaseous CO2 or a mixture of gaseous CO2 and gaseous H2.

In some embodiments, the invention relates to the population of fatty acids being modified to produce molecules of desired carbon chain length by incorporation of one or more thioesterases.

In some embodiments, the invention relates to the population of fatty acids being modified to add additional carboxylic acid (—COOH) groups using exogenous enzymes.

In some embodiments, the invention relates to the population of fatty acids being modified to add hydroxyl groups (—OH) using the exogenous enzymes (hydroxylases).

In some embodiments, the invention relates to the population of fatty acids being modified to add desaturation through the incorporation of one or more double bonds, using the exogenous enzymes (desaturases).

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention. In the figures:

FIG. 1 describes the taxonomic names afforded to the chemoautotrophic and oleaginous microorganisms used in selected embodiments of the invention.

Bar, 0.01% estimated sequence divergence.

FIG. 3 shows the sequence similarity of *Rhodococcus opacus* (DSM 43205) 16S rRNA gene (NR_026186.1) to members of the family gordoniaceae, mycobacteriaceae, nocardiaceae and burkholderiaceae. The Genbank accession numbers, DNA length and % identity of analyzed genes are indicated.

FIG. 4 describes the nucleotide sequence alignment of the 16S rRNA genes. Alignment discloses SEQ ID Nos 40, 12-34, 41, and 3539, respectively, in order of appearance.

FIG. 5 demonstrates the growth of chemotrophic and oleaginous microorganisms on different carbon sources. Bacterial growth was measured using optical density (OD) detection at 650 nm after the indicated days (in parentheses). Media and growth conditions described in the Examples section below. ND, not done.

FIG. 6 describes the measured lipid content of microorganisms on heterotrophic and chemoautotrophic growth conditions as a percentage of total cellular dry matter (CDM). Cells were grown under conditions described in FIG. 5, harvested after 72 hr (unless otherwise indicated) and analyzed by gas chromatography. For CDM, total dry weight was determined gravimetrically.

Figure 7:
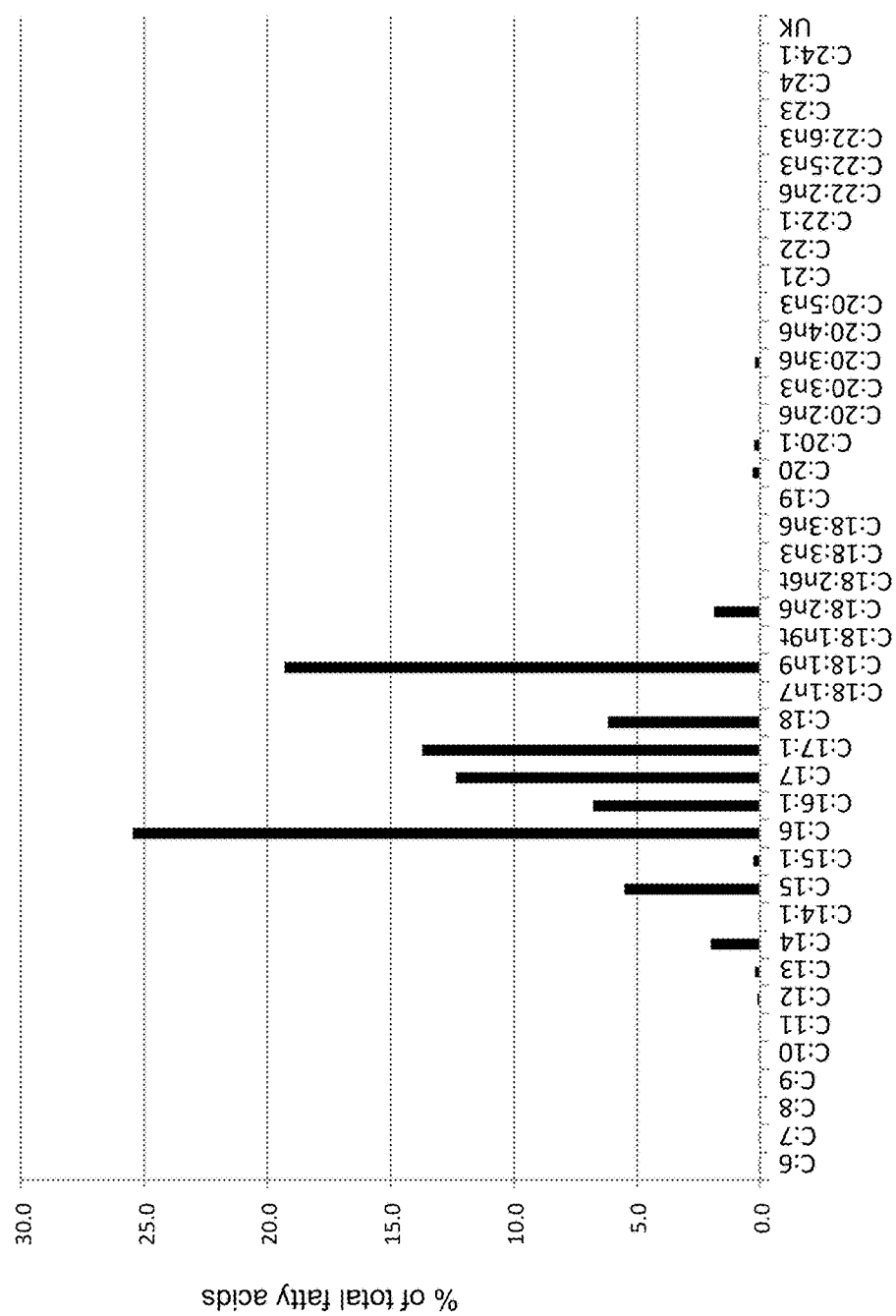

FIG. 7 describes the fatty acid profile of *R. opacus* (DSM 44193) under heterotrophic growth conditions. Cells were harvested after 72 hr and analyzed by gas chromatography.

Figure 8:
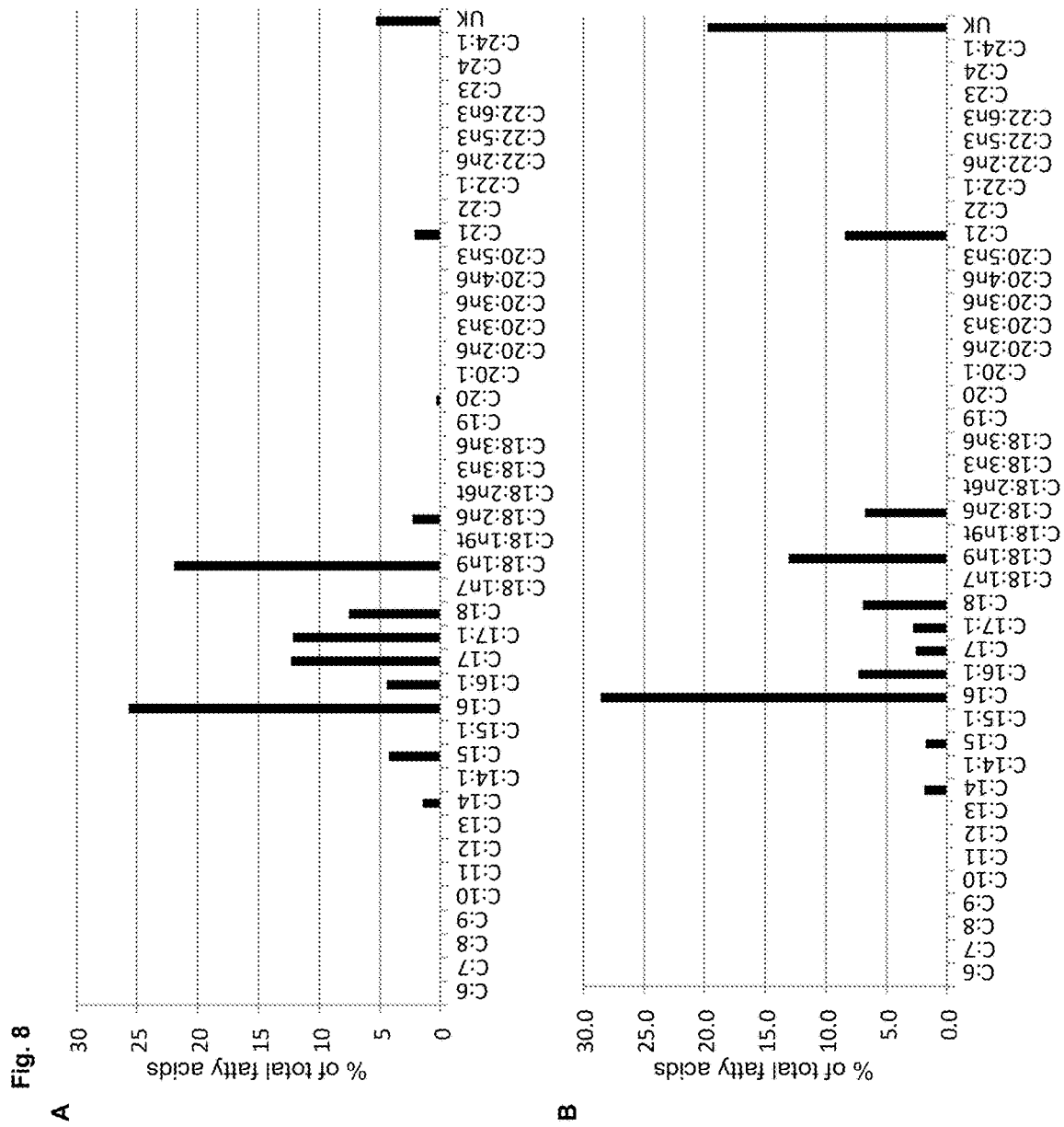

FIG. 8 describes the fatty acid profile *R. opacus* (DSM43205) under heterotrophic (A) and chemoautotrophic (B) growth conditions. Cells were harvested after 72 hours of growth and analyzed by gas chromatography.

Figure 9:
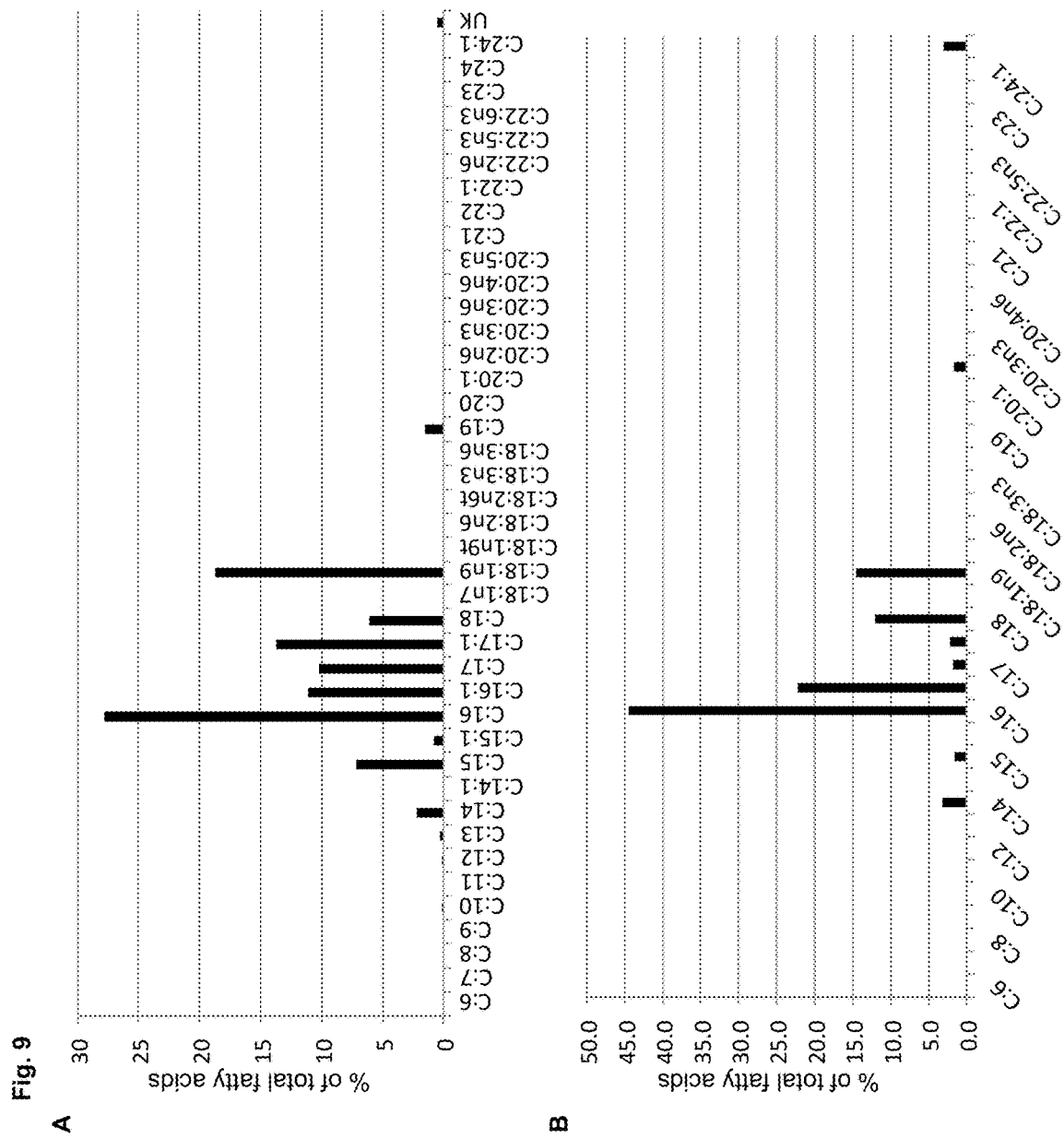

FIG. 9 describes the fatty acid profile *Rhodococcus* sp. (DSM 3346) under heterotrophic (A) chemoautotrophic (B) growth conditions. Cells were harvested after 72 hr and analyzed by gas chromatography.

FIG. 10 describes shuttle vectors (A) and genetic elements (B) for transformation and gene expression of in chemoautotrophic and oleaginous microorganisms. MCS: multiple cloning site.

Figure 11:
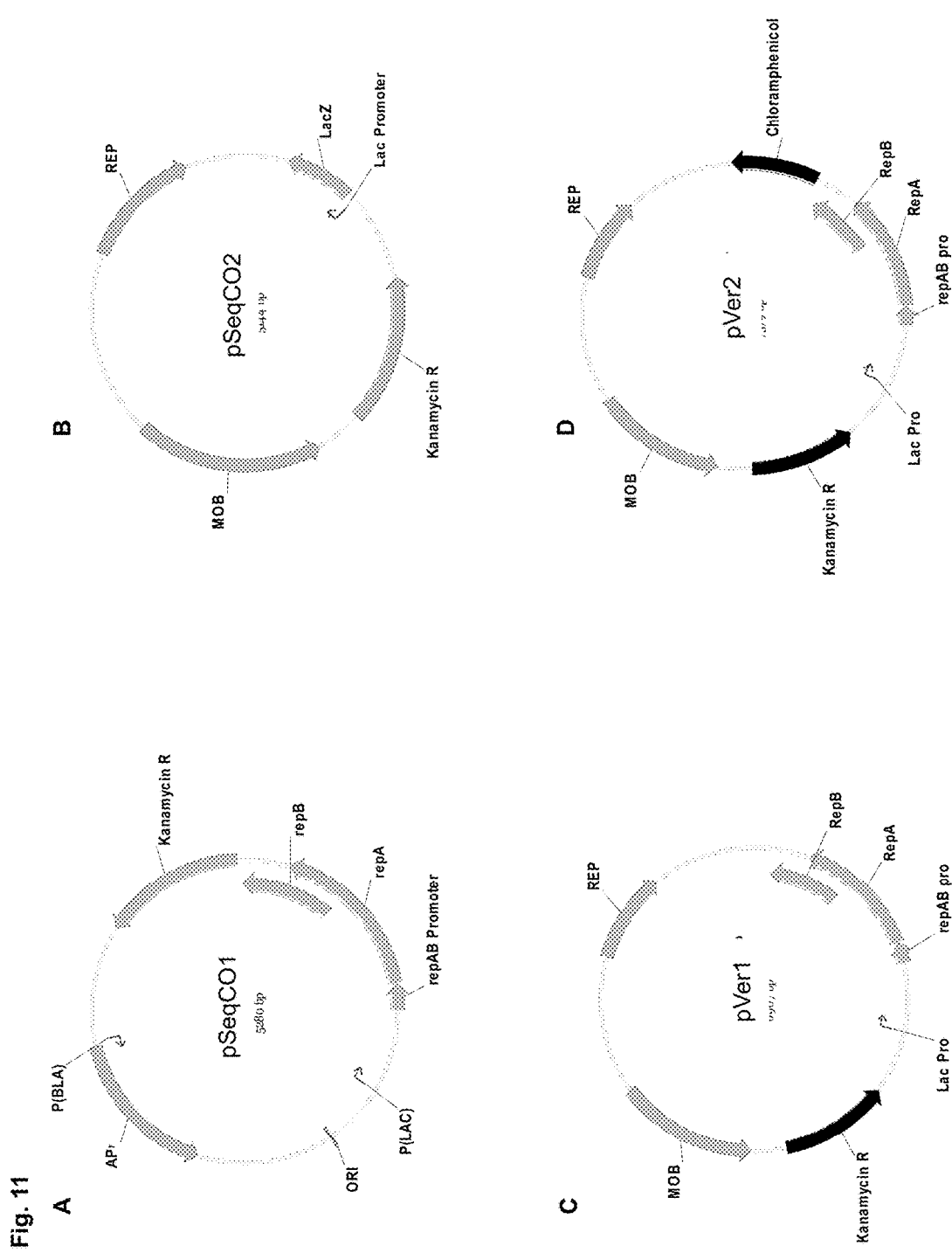

FIG. 11 describes the map of the plasmids pSeqCO1 (A; SEQ ID: 01), pSeqCO2 (B; SEQ ID: 02), pVer1 (C; SEQ ID: 03) and pVer2 (D; SEQ ID: 04) described in FIG. 10. The genetic elements are indicated.

FIG. 12 describes the transformation of chemoautotrophic and oleaginous microorganisms with shuttle vectors described in FIG. 10.

Figure 13:
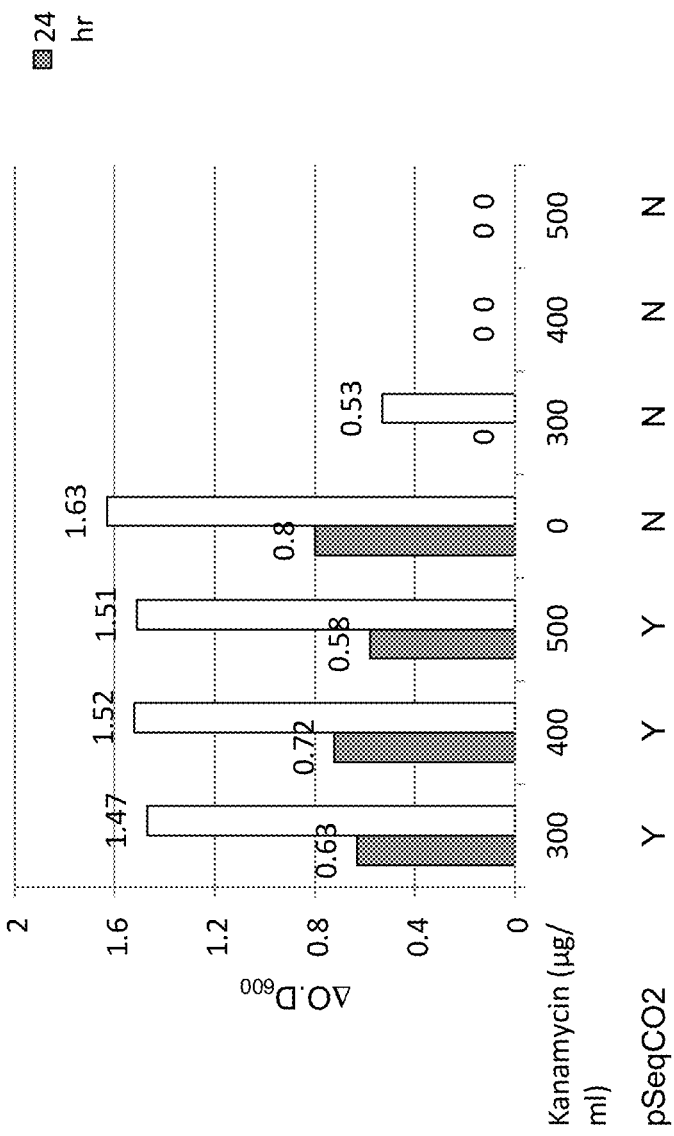

FIG. 13 describes the growth of *Cupriavidus necator* (DSM531) transformed with the plasmid (Y) pSeqCO2 (SEQ ID:2) and untransformed (N) on different kanamycin concentrations. Single colony of transformants and control were grown LB medium (per 1 L: 10 g Bacto-tryptone, 5 g yeast extract, 10 g NaCl pH=7.0) at 30° C. in the indicated kanamycin concentrations. The growth was measured using O.D650 after the indicated number of days.

Figure 14:
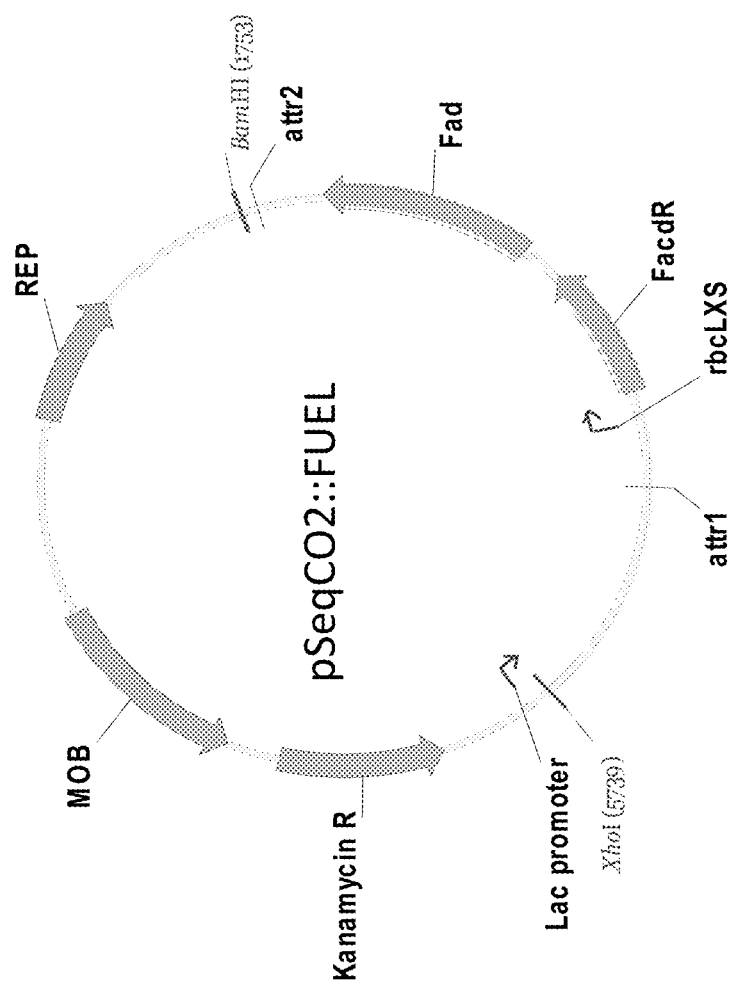

FIG. 14 describes the restriction map related to the cloning strategy of FadDR and Fad genes into pSeqCO2 plasmid transformed for the experiment. Genes from the cyanobacterium (*Synechocystis* sp. PCC 6803) used in the experiment were FadR (SEQ ID: 08) and FAD (SEQ ID: 09) driven by the *Synechocystis* sp. Rubisco large subunit promoter (SEQ ID: 10) were cloned into pSeqCO2 plasmid using the indicated restriction sites to give pSeqCO2::FUEL.

Figure 15:
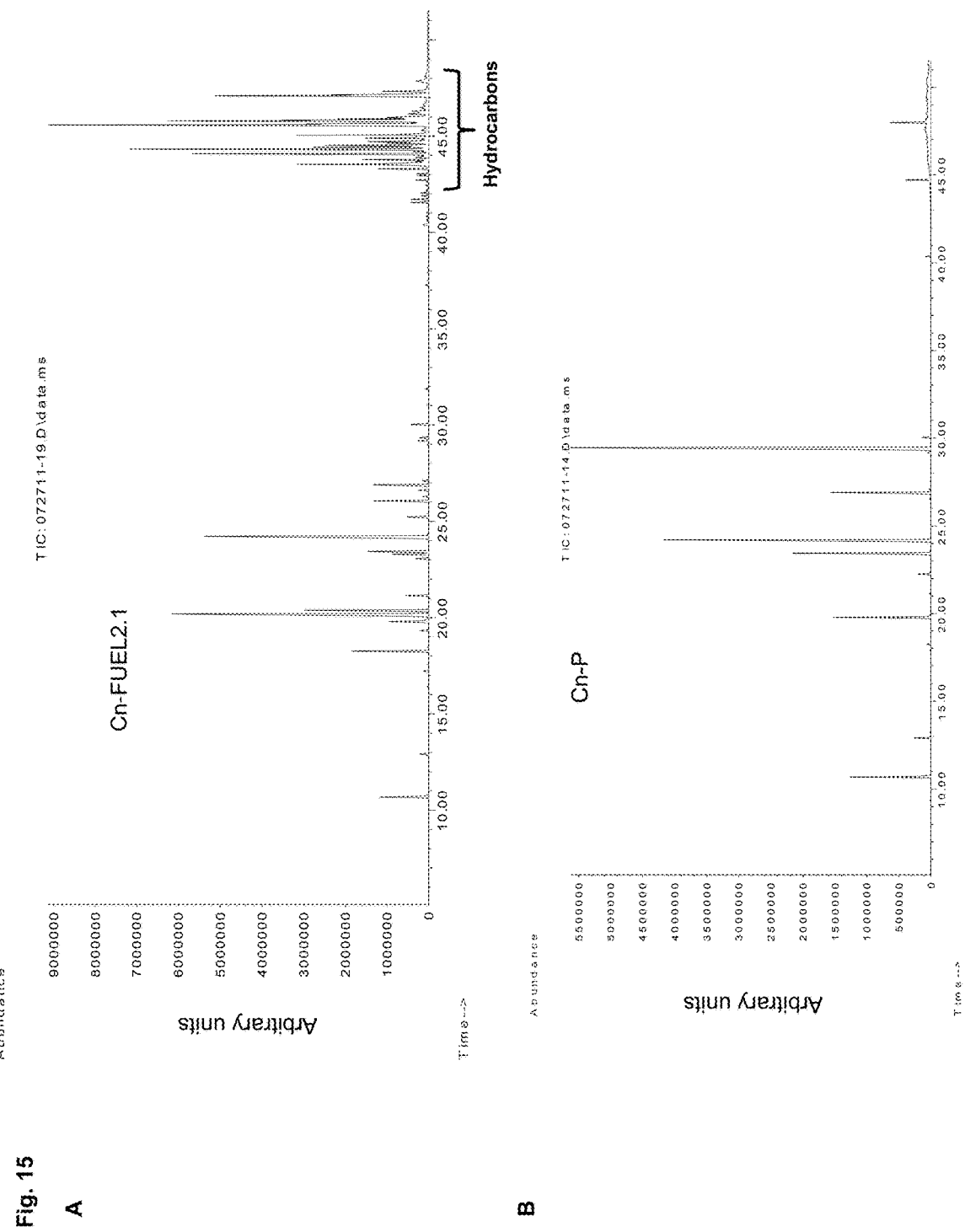

FIG. 15 describes the production of hydrocarbons in *Cupriavidus necator* transformed with pSeqCO2::FUEL (Cn_FUEL2.1) and empty vector (Cn-P). GC chromatogram of hydrocarbon (indicated in red) extracted from transformants grown in 50 ml LB media under previously identified conditions.

FIG. 16 describes the hydrocarbons specific products and distribution (percentage in parentheses) from *Cupriavidus necator* transformed with pSeqCO2::FUEL (Cn_FUEL2.1 and Cn_FUEL2.2) and empty vector (Cn-P).

FIG. 17 shows the molecular structure of two hydrocarbons that were produced in relative abundance in the *Cupriavidus necator* transformed with pSeqCO2::FUEL (Cn_FUEL2.1 and Cn_FUEL2.2).

Figure 18:
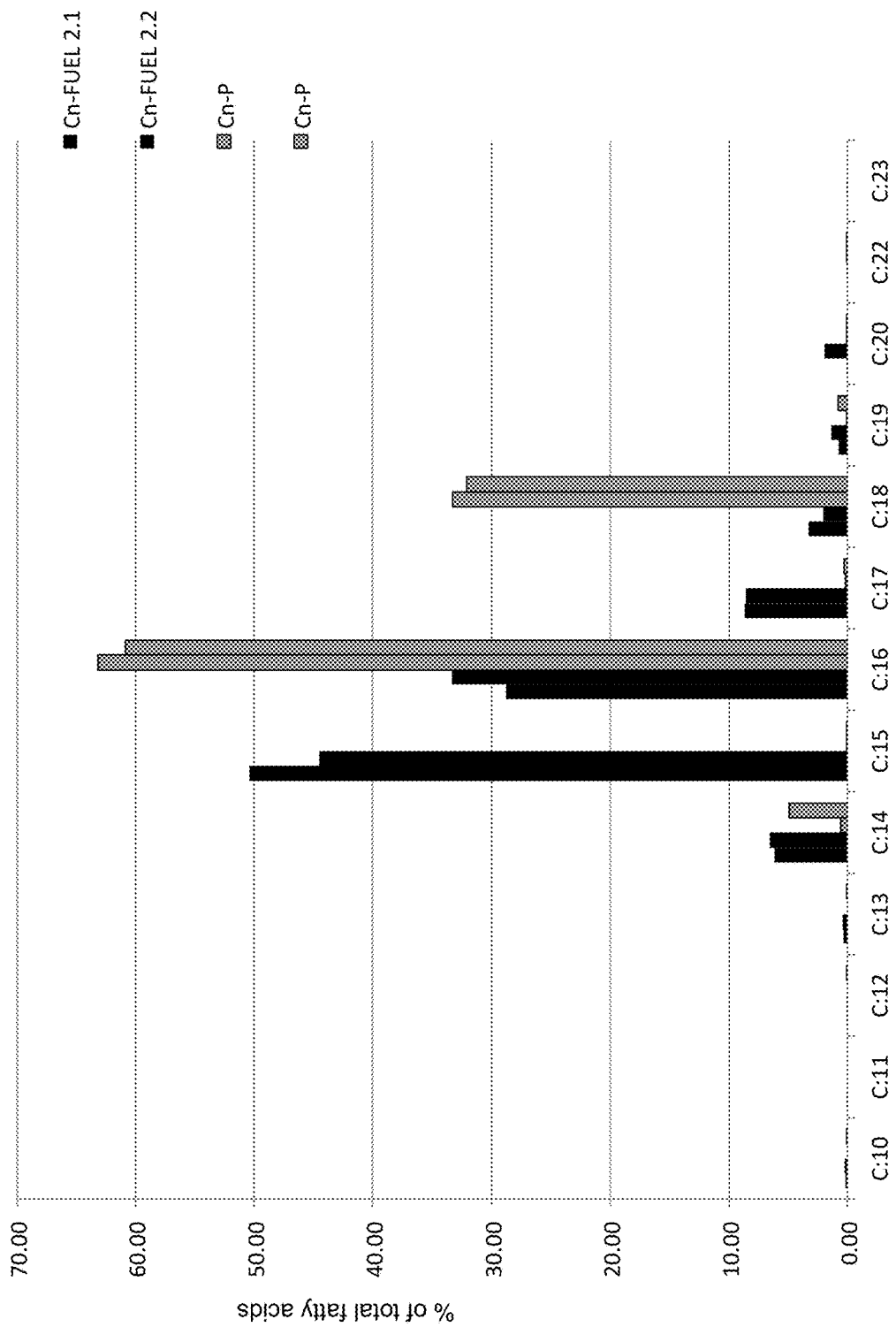

FIG. 18 describes the effect of pSeqCO2::FUEL (Cn_FUEL2.1 and 2.2) and empty vector (Cn-P) on the fatty acids distribution under the experimental conditions described previously.

Figure 19:
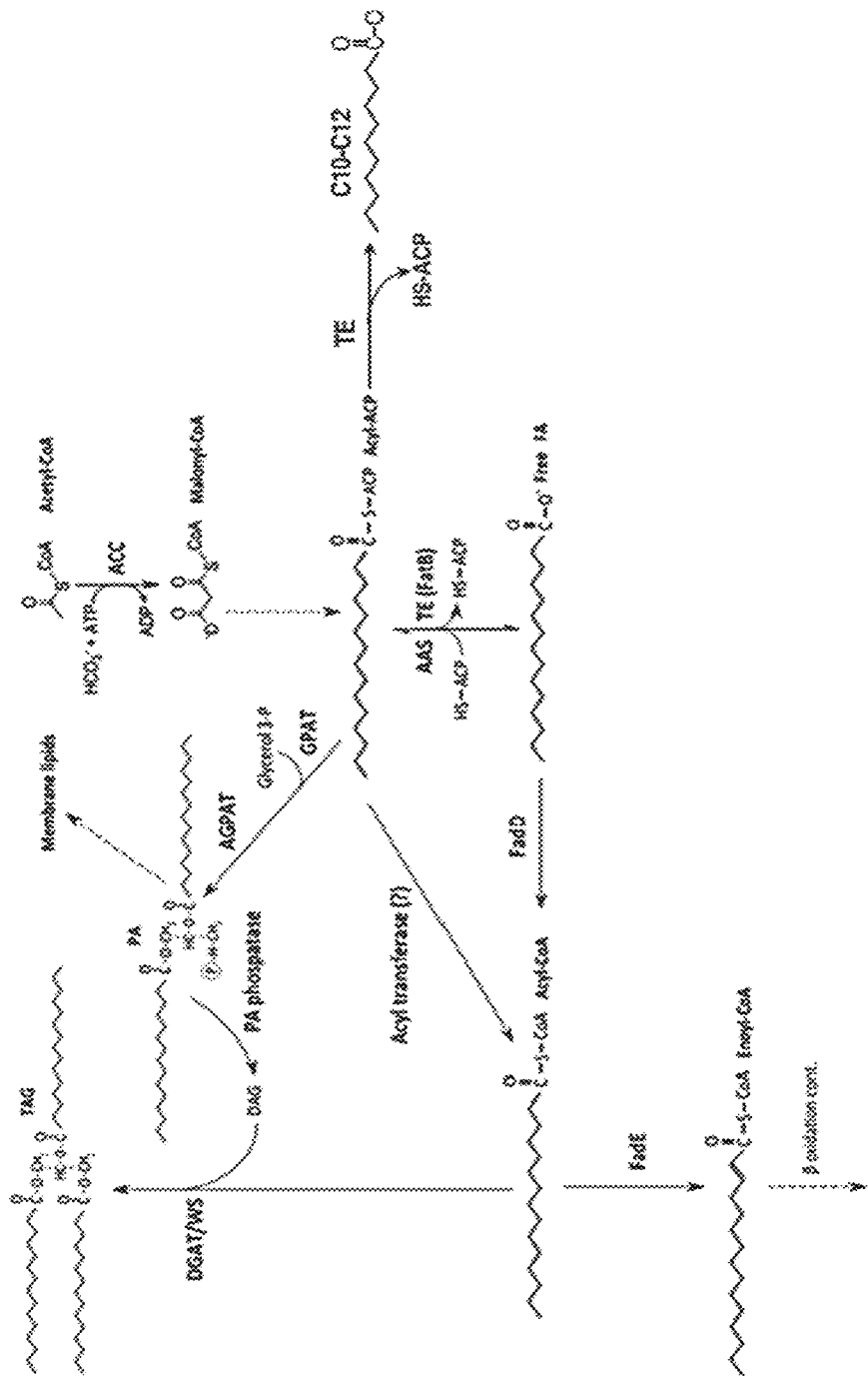

FIG. 19 describes the modification of the fatty acid chain length by the enzymatic action of thioesterase (TE) in oleaginous bacteria.

Figure 20:
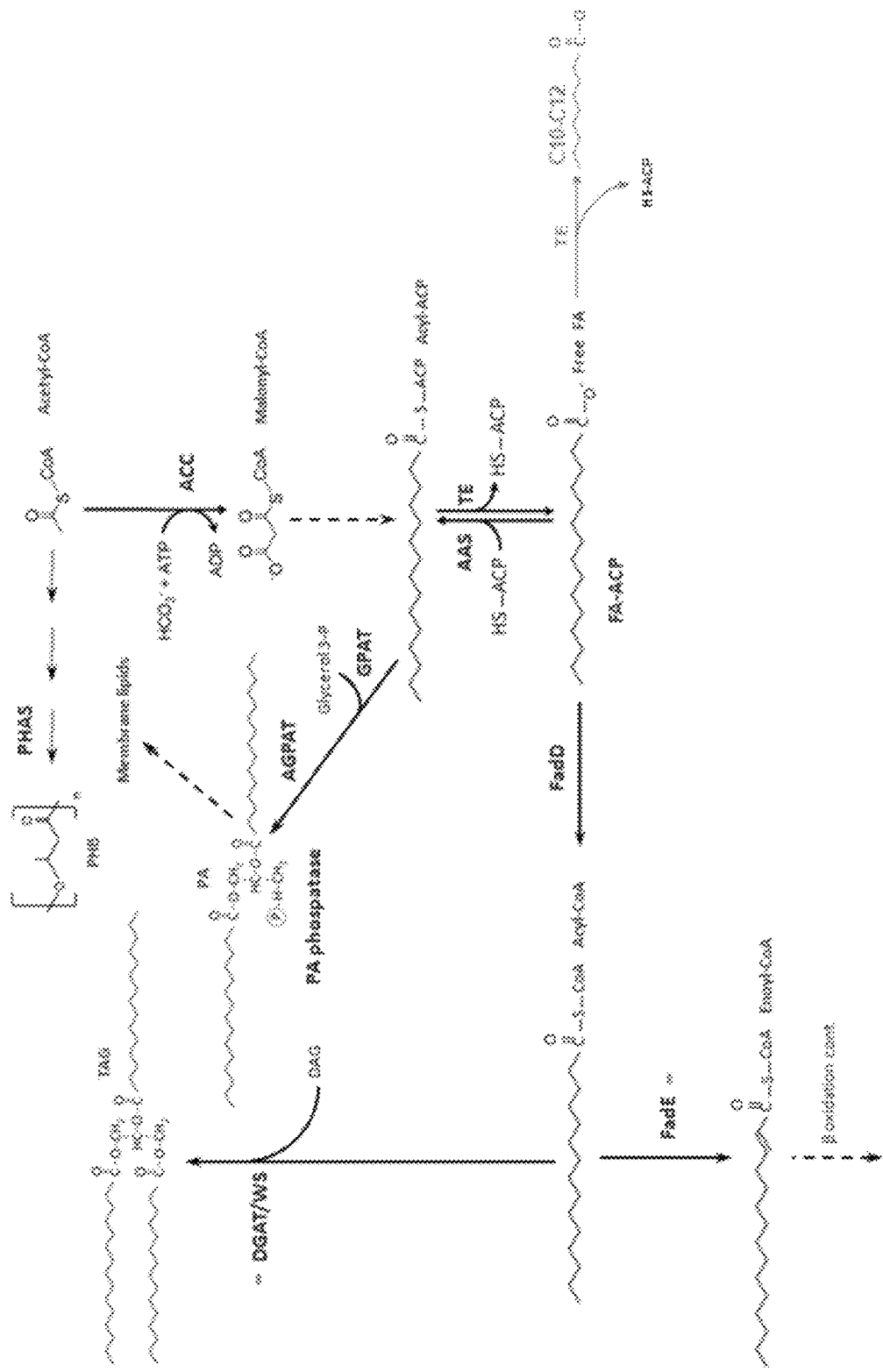

FIG. 20 describes the modification of the fatty acid chain length by the enzymatic action of fatty acyl-ACP thioesterase (TE) in burkholderiaceae.

FIG. 21 describes the similarity of *Rhodococcus opacus* (B4) thioesterases protein sequence (YP_002784058.1) to other organisms. The Genbank accession numbers, amino acid length and % identity of analyzed proteins are indicated.

Figure 22:
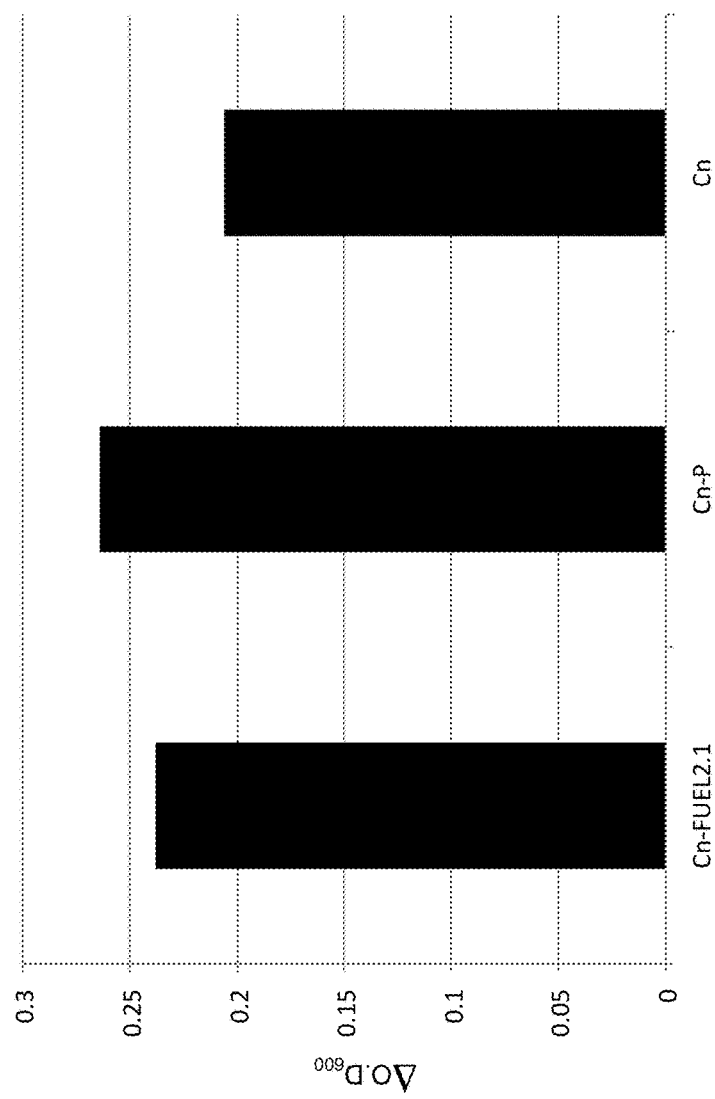

FIG. 22 describes the chemoautotrophic growth of *Cupriavidus necator* transformed with pSeqCO2::FUEL (Cn-FUEL2.1), empty vector (Cn-P) and untransformed (Cn). Bacterial growth was measured at O.D650 after 12 days.

DETAILED DESCRIPTION

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The terms "amino acid" refer to a molecule containing both an amine group and a carboxyl group that are bound to a carbon, which is, designated the α-carbon. Suitable amino acids include, without limitation, both the D- and L-isomers of the naturally occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

The term "biomass" refers to a material produced by growth and/or propagation of cells. Biomass may contain cells and/or intracellular contents as well as extracellular material, includes, but is not limited to, compounds secreted by a cell.

The term "bioreactor" or "fermentor" refers to a closed or partially closed vessel in which cells are grown and maintained. The cells may be, but are not necessarily held in liquid suspension. In some embodiments rather than being held in liquid suspension, cells may alternatively be growing and/or maintained in contact with, on, or within another non-liquid substrate including but not limited to a solid growth support material.

The term "catalyst" refers to a chemical actor, such as a molecule or macromolecular structure, which accelerates the speed at which a chemical reaction occurs where a reactant or reactants is converted into a product or products, while the catalyst is not turned into a product itself, or otherwise changed or consumed at the completion of the chemical reaction. After a catalyst participates in one chemical reaction, because it is unchanged, it may participate in further chemical reactions, acting on additional reactants to create additional products. To accelerate a chemical reaction a catalyst decreases the activation energy barrier across the reaction path allowing it to occur at a colder temperature, or faster at a given temperature. In this way a more rapid approach of the system to chemical equilibrium may be achieved. Catalysts subsume enzymes, which are protein catalysts.

The term "cellulosic material" refers to any material with a high amount of cellulose, which is a polysaccharide having the formula (C6H10O5)n, that generally consists of a linear chain of hundreds to thousands of β(1→4) linked D-glucose monomers. Sources of cellulosic material include but are not limited to cardboard, cotton, corn stover, paper, lumber chips, sawdust, sugar beet pulp, sugar cane bagasses, and switchgrass.

The term "CoA" or "coenzyme A" refers to an organic cofactor for condensing enzymes involved in fatty acid synthesis and oxidation, pyruvate oxidation, acetyl or other acyl group transfer, and in other acetylation.

The term "cofactor" subsumes all molecules needed by an enzyme to perform its catalytic activity. In some embodiments, the cofactor is any molecule apart from the substrate.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C, H), nonpolar side chains (e.g., G, A, V, L, I, P, F, M, W), beta-branched side chains (e.g., T, V, I) and aromatic side chains (e.g., Y, F, W, H). Thus, a predicted nonessential amino acid residue in an amino acid sequence encoded by an exogenous nucleic acid sequence, for example, is replaced with another amino acid residue from the same side chain family. Other examples of acceptable substitutions are substitutions based on isosteric considerations (e.g. norleucine for methionine) or other biochemical properties (e.g. 2-thienylalanine for phenylalanine).

As used herein, "enzyme fragment" is meant to refer to a fragment of an enzyme that includes the sequences sufficient to function substantially similar to the function of the wild-type enzyme upon which the fragment sequence is based. Fragments are generally 10 or more amino acids in length. Some preferred lengths of fatty acid reductase are at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, at least 420, at least 425, or at least 430. Some preferred lengths of fatty acid reductase fragments are 15 or fewer, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer, 260 or fewer, 265 or fewer, 270 or fewer, 275 or fewer, 280 or fewer, 285 or fewer, 290 or fewer, 295 or fewer, 300 or fewer, 305 or fewer, 310 or fewer, 315 or fewer, 320 or fewer, 325 or fewer, 330 or fewer, 335 or fewer, 340 or fewer, 345 or fewer, 350 or fewer, 355 or fewer, 360 or fewer, 365 or fewer, 370 or fewer, 375 or fewer, 380 or fewer, 385 or fewer, 390 or fewer, 395 or fewer, 400 or fewer, 415 or fewer, 420 or fewer, 425 or fewer, 430 or fewer, or 435 or fewer. Some preferred lengths of fatty acid decarbonylase are at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, at least 400, at least 405, at least 410, at least 415, or at least 420 amino acids long. In some embodiments, the lengths of the fatty acid decarbonylase fragments are 15 or fewer, amino acids, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer, 260 or fewer, 265 or fewer, 270 or fewer, 275 or fewer, 280 or fewer, 285 or fewer, 290 or fewer, 295 or fewer, 300 or fewer, 305 or fewer, 310 or fewer, 315 or fewer, 320 or fewer, 325 or fewer, 330 or fewer, 335 or fewer, 340 or fewer, 345 or fewer, 350 or fewer, 355 or fewer, 360 or fewer, 365 or fewer, 370 or fewer, 375 or fewer, 380 or fewer, 385 or fewer, 390 or fewer, 395 or fewer, 400 or fewer, 415 or fewer, 422 or fewer. Some preferred lengths of thioesterase fragments are at least 10 amino acids, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210 at least 215, at least 220, at least 225, least 230 at least 235, at least 240, at least 245, at least 250 or at least 255. Some preferred lengths of thioesterase fragments are 15 or fewer, 20 or fewer, 25 or fewer, 30 or fewer, 35 or fewer, 40 or fewer, 45 or fewer, 50 or fewer, 55 or fewer, 60 or fewer, 65 or fewer, 70 or fewer, 75 or fewer, 80 or fewer, 85 or fewer, 90 or fewer, 95 or fewer, 100 or fewer, 105 or fewer, 110 or fewer, 115 or fewer, 120 or fewer, 125 or fewer, 130 or fewer, 135 or fewer, 140 or fewer, 145 or fewer, 150 or fewer, 155 or fewer, 160 or fewer, 165 or fewer, 170 or fewer, 175 or fewer, 180 or fewer, 185 or fewer, 190 or fewer, 195 or fewer, 200 or fewer, 205 or fewer, 210 or fewer, 215 or fewer, 220 or fewer, 225 or fewer, 230 or fewer, 235 or fewer, 240 or fewer, 245 or fewer, 250 or fewer, 255 or fewer or 260 or fewer. As used in the paragraph herein reference to preferred fragment sizes are intended to refer to all permutation of ranges between at least and less than such as ranges may be any number set forth as an "at least" size to any number set forth as an "less than t" size in order to provide a range of sizes such as 20-400, 20-30, 40-100, etc.

The terms "exogenous gene" means a nucleic acid that has been recombinantly introduced into a cell, which encodes the synthesis of RNA and/or protein. In some embodiments, the exogenous gene is introduced by transformation. In some embodiments, the exogenous gene is introduced into the cell by electroporation. A transformed cell may be referred to as a recombinant cell, into which additional exogenous gene(s) may be introduced. The exogenous gene put into the host species may be taken from a different species (this is called heterologous), or it may naturally occur within the same species (this is homologous as defined below). Therefore, exogenous genes subsume homologous genes that are integrated within or introduced to regions of the genome, episome, or plasmid that differ from the locations where the gene naturally occurs. Multiple copies of the exogenous gene may be introduced into the cell. An exogenous gene may be present in more than one copy within the host cell or transformed cell. In some embodiments, the microorganism comprises between and including 1 and 10,000 copies of the nucleic acid that encodes an exogenous protein. In some embodiments, the microorganism comprises between and including 1 and 1,000 copies of the nucleic acid that encodes an exogenous protein. In some embodiments, the microorganism comprises between and including 1 and 10,000 copies of the nucleic acid that encodes an exogenous protein. In some embodiments, the microorganism comprises between and including 1 and 1,000 copies of the nucleic acid that encodes an exogenous protein. In some embodiments, the microorganism comprises between and including 1 and 500 copies of the nucleic acid that encodes an exogenous protein. In some embodiments, the exogenous gene is maintained by a cell as an insertion into the genome or as an episomal molecule. In some embodiments, the microorganism comprises no more than 1, 2, 3, 4, 5, 6, 7, 8, 9, 10, 20, 30, 40, 50, 60, 70, 80, 90, 100, or 1000 copies of the one or more nucleic acids that encode one or more exogenous proteins.

As used herein, the term "expressible form" refers to gene constructs that contain the necessary regulatory elements operably linked to a coding sequence that encodes an enzyme or fragment thereof capable of conferring enzymatic activity to a cell, such that when present in the cell, the coding sequence will be expressed. In some embodiments of the invention, the composition comprising the microorganisms or bacterial cells of the present invention comprise no more than ten expressible forms of exogenous nucleic acid sequences. In some embodiments of the invention, the composition comprising the microorganisms or bacterial cells of the present invention comprise no more than nine expressible forms of exogenous nucleic acid sequences. In some embodiments of the invention, the composition comprising the microorganisms or bacterial cells of the present invention comprise no more than eight expressible forms of exogenous nucleic acid sequences. In some embodiments of the invention, the composition comprising the microorganisms or bacterial cells of the present invention comprise no more than seven expressible forms of exogenous nucleic acid sequences. In some embodiments of the invention, the composition comprising the microorganisms or bacterial cells of the present invention comprise no more than six expressible forms of exogenous nucleic acid sequences. In some embodiments of the invention, the composition comprising the microorganisms or bacterial cells of the present invention comprise no more than five expressible forms of exogenous nucleic acid sequences. In some embodiments of the invention, the composition comprising the microorganisms or bacterial cells of the present invention comprise no more than four expressible forms of exogenous nucleic acid sequences. In some embodiments of the invention, the composition comprising the microorganisms or bacterial cells of the present invention comprise no more than three expressible forms of exogenous nucleic acid sequences. In some embodiments of the invention, the composition comprising the microorganisms or bacterial cells of the present invention comprise no more than two expressible forms of exogenous nucleic acid sequences. In some embodiments of the invention, the composition comprising the microorganisms or bacterial cells of the present invention comprise no more than one expressible form of an exogenous nucleic acid sequences.

SEQ ID NO:1 refers to Sequesco plasmid sequence 1.

SEQ ID NO:2 refers to Sequesco plasmid sequence 2.

SEQ ID NO: 3 refers to Sequesco plasmid Ver1 plasmid sequence.

SEQ ID NO:4 refers to Sequesco plasmid Ver2 plasmid sequence.

SEQ ID NO:5 refers to cyanobacterium FadR.

SEQ ID NO:6 refers to cyanobacterium FAD.

SEQ ID NO:7 refers to cyanobacterium Rubisco large subunit promoter

SEQ ID NO:8, refers to the 16S rRNA sequence from the genus *Rhodococcus opacus* DSM43205

SEQ ID NO:9 refers to the 16S rRNA sequence from the genus *Rhodococcus opacus* B4.

SEQ ID NO:10 refers to the 16S rRNA sequence from the genus *Ralstonia*.

SEQ ID NO:11 refers to *Rhodococcus opacus* TE

The terms "fatty acyl-ACP thioesterase" (TE) mean an enzyme that catalyzes the cleavage of a fatty acid from an acyl carrier protein (ACP) during lipid synthesis.

The terms "fatty acyl-ACP/acyl-CoA reductase" (FadR) refers to an enzyme catalyzing the reaction that produces a fatty aldehyde from an acyl-ACP or acyl-CoA molecule by reduction.

The terms "fatty aldehyde decarbonylase" (FAD) refers to an enzyme catalyzing the reaction that produces an alkane from a fatty aldehyde molecule by decarbonylization.

As used herein, the term "functional fragment" is meant to refer to a fragment of any polypeptide or amino acid sequence that is encoded by an exogenous nucleic acid sequence of the present invention which retains its ability to function like the amino acid sequence to which the fragment is homologous. Functional fragments of enzymes are at least about 5 amino acids in length derived from enzyme and may comprise non-wild-type amino acid sequences. One having ordinary skill in the art can readily determine whether a protein or peptide is a functional fragment of a particular amino acid sequence by examining its sequence and testing its ability to function in a fashion similar to that function of the amino acid sequence upon which the fragment is based. Truncated versions of exogenous proteins may be prepared and tested using routine methods and readily available starting material. As used herein, the term "functional fragment" is also meant to refer to peptides, polypeptides, amino acid sequence linked by non-peptidal bonds, or proteins which comprise an amino acid sequence that is identical or substantially homologous to at least a portion of the exogenous amino acid sequence and which are capable of functioning in a similar function to the exogenous amino acid sequence to which the fragment is homologous. The term "substantially homologous" refers to an amino acid sequence that has conservative substitutions. One having ordinary skill in the art can produce functional fragments of the FadD, FAD, thioesterase, cytochrome P450 enzyme, desaturase, and hydroxylase amino acid sequences following the disclosure provided herein and well known techniques. The functional fragments thus identified may be used and formulated in place of full length FadD, FAD, thioesterase, cytochrome P450 enzyme, desaturase, and hydroxylase without undue experimentation.

The term "gasification" refers to a generally high temperature (>700° C.) process that converts carbonaceous materials into a mixture of gases including hydrogen, carbon monoxide, and carbon dioxide called syngas or producer gas. The process generally involves partial combustion and/or the application of externally generated heat along with the controlled addition of oxygen and/or steam.

As used herein, "homologous" refers to the sequences homology between two nucleic acid sequences or two amino acid sequences. Two nucleic acid sequences or two amino acid sequences that are sufficiently homologous to retain immunogenic function are "homologues." Sequence homology for nucleotides and amino acids may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). "Percentage of similarity" is calculated using PAUP* 4.0b10 software (D. L. Swofford, Sinauer Associates, Massachusetts). The average similarity of the enzymatic sequence or 16S rRNA sequence is calculated compared to all sequences in the phylogenic tree. Briefly, the BLAST algorithm, which stands for Basic Local Alignment Search Tool is suitable for determining sequence similarity (Altschul et al., J. Mol. Biol., 1990, 215, 403410, which is incorporated herein by reference in its entirety). Software for performing BLAST analyses is publicly available though the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extension for the word hits in each direction are halted when: 1) the cumulative alignment score falls off by the quantity X from its maximum achieved value; 2) the cumulative score goes to zero or below, due to the accumulation of one or more negative-scoring residue alignments; or 3) the end of either sequence is reached. The Blast algorithm parameters W, T and X determine the sensitivity and speed of the alignment. The Blast program uses as defaults a word length (W) of 11, the BLOSUM62 scoring matrix (see Henikoff et al., Proc. Natl. Acad. Sci. USA, 1992, 89, 10915-10919, which is incorporated herein by reference in its entirety) alignments (B) of 50, expectation (E) of 10, M=5, N=4, and a comparison of both strands. The BLAST algorithm (Karlin et al., Proc. Natl. Acad. Sci. USA, 1993, 90, 5873-5787, which is incorporated herein by reference in its entirety) and Gapped BLAST perform a statistical analysis of the similarity between two sequences. One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001.

The term "hydrocarbon" refers to a molecule composed exclusively of carbon and hydrogen atoms with the carbons bonded covalently in a branched, cyclic, linear, or partially cyclic chain and with hydrogen atoms covalently bonded to the carbons such that the chemical octet rule for the carbons is generally satisfied. In some hydrocarbons there may occur some number of double or triple bonds between adjacent carbon atoms in the chain. Thus, the label hydrocarbon subsumes branched, cyclic, linear, branched, or partially cyclic alkanes (also called paraffins), alkenes (also called olefins), and alkynes. The structure of hydrocarbon molecules range from the smallest, methane (CH4), a primary component of natural gas, to high molecular weight complex molecules including asphaltenes present in bitumens crude oil, and petroleum. Other examples include dodecane (C12), hexadecane (C16), or octadecane (C18) etc. Hydrocarbons of the present invention may be in gaseous, liquid, or solid phases, either as singly or in multiply coexisting phases. In some embodiments, the hydrocarbons are selected from one or more of the following: linear, branched, cyclic, or partially cyclic alkanes, alkenes, alkynes, lipids, and paraffin. In some embodiments the hydrocarbon are selected from one or more of the following: octane, squalene Spiro[4.5]decane, Bicyclo[10.8.0]eicosane, cis,cis-1,6-Dimethylspiro[4.5]decane, 1,19-Eicosadiene, Cyclooctacosane, Bicyclo[10.8.0] eicosane, 1-Pentadecyne, 1-Pentadecyne, Heptacosyl acetate, 5-Cyclohexyl-1-pentene, 1-Hexadecyne and Cyclodecacyclotetradecene, -eicosahydro.

The term "hydrophobic fraction" gives the fraction of matter that has low solubility in water and greater solubility in a hydrophobic phase than in an aqueous phase. In some embodiments, the hydrophobic fraction is non-polar. In some embodiments, the genetically modified bacterial cells described herein increase the hydrophobic fraction of hydrocarbons in a cell as compared to the same cell that is not genetically modified.

The term "improve lipid yield" refers to an increase in the lipid production of an organism through any means. In some embodiments, the increase is caused by raising the cell dry weight density of a microbial culture and/or raising the fraction of cell mass that is composed of lipid and/or reducing the cell doubling time and/or the biomass doubling time, resulting in an overall increase in the lipid production rate per unit volume.

The term "knallgas" refers to the mixture of molecular hydrogen and oxygen gas. A "knallgas microorganism" is a microbe that can use hydrogen as an electron donor and oxygen as an electron acceptor in the generation of intracellular energy carriers such as Adenosine-5'-triphosphate (ATP). The terms "oxyhydrogen" and "oxyhydrogen microorganism" can be used synonymously with "knallgas" and "knallgas microorganism" respectively.

The term "lignocellulosic material" is any material composed of cellulose, hemicellulose, and lignin where the carbohydrate polymers (cellulose and hemicelluloses) are tightly bound to lignin. Lignocellulosic materials subsume agricultural residues (including corn stover and sugarcane bagasse), most biomass energy crops, wood residues (including sawmill and paper mill discards), and a substantial fraction of municipal waste.

The terms "lipids" refers to category of molecules that can be dissolved in nonpolar solvents (such as chloroform and/or ether) and which also have low or no solubility in water. The hydrophobic character of lipids molecules typically results from the presence of long chain hydrocarbon sections within the molecule. Lipids subsume the following molecule types: hydrocarbons, fatty acids (saturated and unsaturated), fatty alcohols, fatty aldehydes, hydroxy acids, diacids, monoglycerides, diglycerides, triglycerides, phospholipids, sphingolipids, sterols such as cholesterol and steroid hormones, fat-soluble vitamins (such as vitamins A, D, E and K), polyketides, terpenoids, and waxes.

The term "lipid modification enzyme" corresponds to an enzyme that catalyzes a reaction changing a lipid's covalent bonds such as TE, FAR, FadR, FAD, fatty aldehyde reductase, lipase, cytochrome P450 enzyme, desaturase, or hydroxylase. Any enzyme that catalyzes a reaction step or steps in lipid synthesis, catabolism, or modification, including carrier proteins, is called a "lipid pathway enzyme".

The term "lysate" refers to the liquid containing a mixture and/or a solution of cell contents that result from cell lysis. In some embodiments, the methods of the present invention comprise a purification of hydrocarbons or mixture of hydrocarbons in a cellular lysate. In some embodiments, the methods of the present invention comprise a purification of lipids and/or hydrocarbons and/or a mixture of hydrocarbons in a cellular lysate.

The term "lysis" refers to the rupture of the plasma membrane and if present the cell wall of a cell such that a significant amount of intracellular material escapes to the extracellular space. Lysis can be performed using electrochemical, mechanical, osmotic, thermal, or viral means. In some embodiments, the methods of the present invention comprise performing a lysis of cells or microorganisms described herein in order to separate a hydrocarbon or mixture of hydrocarbons from the contents of a bioreactor. In some embodiments, the methods of the present invention comprise performing a lysis of cells or microorganisms described herein in order to separate a lipid or mixture of lipids from the contents of a bioreactor.

The terms "microorganism" and "microbe" mean microscopic single celled life forms.

The term "molecule" means any distinct or distinguishable structural unit of matter comprising one or more atoms, and includes for example hydrocarbons, lipids, polypeptides and polynucleotides.

The term "oleaginous" refers to something that is rich in oil or produces oil in high quantities.

The term "organic compound" refers to any gaseous, liquid, or solid chemical compounds which contain carbon atoms with the following exceptions that are consider inorganic: carbides, carbonates, simple oxides of carbon, cyanides, and allotropes of pure carbon such as diamond and graphite.

"Promoter" is a control DNA sequence that regulates transcription. For purposes of the invention, a promoter may includes nucleic acid sequences near the start site of transcription that are required for proper function of the promoter, as for example, a TATA element for a promoter of polymerase II type. Promoters of the present invention can include distal enhancer or repressor elements that may lie in positions up to many thousands of base pairs away from the start site of transcription. The term "inducible promoter" refers to an operable linkage between a promoter and a nucleic acid where the promoter's mediation of nucleic acid transcription is sensitive to a specific stimulus. In some embodiments, the inducible promoter requires a cofactor which can be added to the environment of the composition comprising the nucleic acid sequence that contains the inducible promoter. An "operable linkage" refers to an operative connection between nucleic acid sequences, such as for example between a control sequence (e.g. a promoter) and another sequence that codes for a protein i.e. a coding sequence. If a promoter can regulate transcription of an exogenous gene then it is in operable linkage with the gene.

The term "syngas" (from synthetic gas or synthesis gas) refers to a gas mixture that contains various proportions of hydrogen, carbon monoxide, and carbon dioxide, and which typically also includes a variety of impurities such as methane, hydrogen sulfide, condensable gases, and tars. "Producer gas" is a related term that generally refers to gas mixes similar to syngas except for the presence of a large N2 component that results from using air directly in the gasification process.

Bacterial Species

The invention relates to chemotrophic bacterial strains that comprise one or more exogenous nucleic acid sequences. The present invention results from the discovery that chemotrophic bacteria and particular related microorganisms provide unforeseen advantages in the economic and large scale production of chemicals, oils, fuels, and other hydrocarbon or lipid substances from gaseous and waste carbon feedstocks, and also from the discovery of genetic techniques and systems for modifying these microorganisms for improved performance in these applications. The lipids and other biochemicals synthesized by the microorganisms of the present invention can be applied to uses including but not limited to petrochemical substitutes, monomers, feedstock for the production of polymers, lubricants, as ingredients in animal feed, food, personal care, and cosmetic products. In some embodiments of the present invention enzymatic and chemical processes can be utilized to produce alkenes, alkynes, hydroxy acids, diacids, and unsaturated fatty acids. Some embodiments enable the production of renewable hydrocarbons. In addition, the present invention gives methods for culturing and/or modifying chemotrophic bacteria for improved lipid yield and/or lower production costs. In some embodiments the genetically modified bacteria produce more of a certain type or types of lipid molecules as compared to the same bacteria that is not genetically modified.

The present invention relates to compositions comprising and methods of using genetically modified microorganisms to produce and/or secrete carbon-based products from conversion of gaseous carbon feedstocks including but not limited to syngas or producer gas. The present invention relates to methods and mechanisms to confer production and/or secretion of carbon-based products of interest including but not limited to ethylene, chemicals, monomers, polymers, alkenes, alkynes, hydroxy acids, diacids, unsaturated fatty acids, hydrocarbons, isoprenoids, proteins, polysaccharides, nutraceutical or pharmaceutical products or intermediates thereof in obligate or facultative chemotrophic organisms such that these organisms convert carbon dioxide and/or other forms of inorganic carbon and/or syngas and/or other C1 compounds such as methanol and/or the liquid, gaseous, and solid products of pyrolytic reactions such as pyrolysis oil, into carbon-based products of interest, and in particular the use of such organisms for the commercial production of ethylene, chemicals, monomers, polymers, alkenes, alkynes, hydroxy acids, diacids, unsaturated fatty acids, hydrocarbons, isoprenoids, proteins, polysaccharides, nutraceutical or pharmaceutical products or intermediates thereof.

Chemoautotrophs are capable of performing chemosynthetic reactions that fix CO2, and/or other forms of inorganic carbon, to organic compounds, using the potential energy stored in inorganic chemicals to drive the reaction, rather than radiant energy from light as in microorganisms performing photosynthesis [Shively et al, 1998; Smith et al, 1967; Hugler et al, 2005; Hugker et al., 2005; Scott and Cavanaugh, 2007]. Carbon fixing biochemical pathways that occur in chemoautotrophs include the reductive tricarboxylic acid cycle, the Calvin-Benson-Bassham cycle [Jessup Shively, Geertje van Kaulen, Wim Meijer, Annu Rev. Microbiol., 1998, 191-230], and the Wood-Ljungdahl pathway [Ljungdahl, 1986; Gottschalk, 1989; Lee, 2008; Fischer, 2008].

The invention relates to compositions comprising and methods of using chemoautotrophic metabolism to produce ATP for the support of ATP consuming synthetic reactions and cellular maintenance, without the co-production of methane or short chain organic acids such as acetic or butyric acid, by means of energy conserving reactions for the production of ATP using inorganic electron donors, including but not limited to the oxyhydrogen reaction.

The production of hydrocarbons or other lipids with carbon chain lengths longer than C4 is most commonly and efficiently accomplished biologically through fatty acid biosynthesis [Fischer, Klein-Marcuschamer, Stephanolpoulos, Metabolic Engineering (2008) 10, 295-304]. The initial molecule entering into the fatty acid biosynthesis pathway is acetyl-coenzyme A (acetyl-CoA), a central metabolite from which many high value biochemicals can be derived. In some embodiments, the invention utilizes microorganisms with a naturally occurring pathway for the conversion of CO, CO.sub.2 and/or H.sub.2 to acetyl-CoA. In some embodiments, the invention utilizes microorganisms that can fix CO and/or CO.sub.2 through the reductive tricarboxylic acid cycle, the Calvin-Benson-Bassham cycle, and/or the Wood-Ljungdahl pathway. In some embodiments the invention utilizes microorganisms the fix C1 compounds through a methanotropic pathway. In some embodiments the microorganisms naturally produce enzymes that catalyze the fixation of gaseous inorganic carbon to produce acetyl-CoA, utilizing gaseous electron donors such as are present in syngas as reducing agents, with such enzymatic proteins including but not limited to acetyl-CoA synthase, acetyl-CoA synthase disulfide reductase, cobalamide corrinoid/iron-sulfur protein, carbon monoxide dehydrogenase, hydrogenase, and methyltransferase.

Unlike methanogenic, acetogenic and solventogenic pathways, present in methanogens and acetogens respectively, which can produce short chain organic compounds (C1-C4) with net ATP production or zero net consumption, fatty acid synthesis involves net ATP consumption. For example the following gives the net reaction for synthesis of Palmitic acid (C16) starting from Acetyl-CoA:

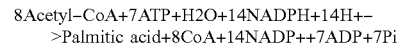

8Acetyl–CoA+7ATP+H2O+14NADPH+14H+–>Palmitic acid+8CoA+14NADP++7ADP+7Pi

A drawback with using an obligate methanogen or acetogen in a GTL process for the production of lipids, is the obligate use of CO2 as an electron acceptor for the production of ATP that is needed for fatty acid synthesis. If H2 is the electron donor, the ATP produced per H2 consumed in an acetogen or methanogen is relatively low: one ATP per 4H2 for methane [Thauer, R. K., Kaster, A. K., Seedorf, H., Buckel, W. & Hedderich, R. Methanogenic archaea: ecologically relevant differences in energy conservation. Nat Rev Microbiol 6, 579-591, doi:nrmicro1931 [pii]] or acetic acid production, and one ATP per 10H2 for butyric acid production [Papoutsakis, Biotechnology & Bioengineering (1984) 26, 174-187; Heise, Muller, Gottschalk, J. of Bacteriology (1989) 5473-5478; Lee, Park, Jong, Nielsen, Kim, Jung, Biotechnology & Bioengineering (2008) 101, 2, 209-228]. In some embodiments, the invention relates to a microorganism or compositions comprising a microorganism, wherein the microorganism produces ATP from an inorganic electron donor such as but not limited to H2 without synthesis of methane or short chain organic acids.

Hydrogen-oxidizing microorganisms that use more electronegative electron acceptors in energy conserving reactions for ATP production, such as but not limited to hydrogenotrophic oxyhydrogen or knallgas microbes that link the oxyhydrogen reaction, 2 H2+O2->2 H2 O, to ATP production, can produce more ATP per H2 consumed than acetogens or methanogens. For example knallgas microorganisms can produce up to two ATP per H2 consumed [Bongers, J. Bacteriology, (October 1970) 145-151], which is eight times more ATP produced per H2 consumed than what can be produced in microorganisms undergoing methanogenesis or acetogenesis. For this reason using microorganisms that can utilize more electronegative electron acceptors in the production of ATP, such as but not limited to knallgas microbes, in fatty acid biosynthesis from syngas or H2, can be more efficient for supporting fatty acid biosynthesis than using the acetogens or methanogens that are currently used in biological GTL technologies. In some embodiments, the invention relates to a microorganism or compositions comprising a microorganism, wherein the microorganism is a knallgas microbe and comprises at least one or more exogenous nucleic acid sequences that encodes one or more enzymes to enable fixation of a carbon-containing gas feedstock, including but not limited to syngas or producer gas, into useful carbon-based products of interest including but not limited to ethylene, chemicals, monomers, polymers, alkenes, alkynes, hydroxy acids, diacids, unsaturated fatty acids, hydrocarbons, isoprenoids, proteins, polysaccharides, nutraceutical or pharmaceutical products or intermediates thereof. The invention relates to a genetically modified microorganism and compositions comprising such a microorganism, wherein the microorganism comprises one or more exogenous genes and wherein the microorganism grows on carbon-containing gas or utilizes a gaseous feedstock selected from syngas, CO2, H2, CO, or mixtures of gas comprising one or more gases selected from syngas, CO2, H2, or CO.

The invention relates to a cell and compositions comprising a cell of the class Actinobacteria comprising at least one exogenous gene. The invention also relates to cells and compositions comprising cells of the family of Nocardiaceae comprising at least one exogenous gene. The invention relates to cells and compositions comprising cells of *Corynebacterium, Gordonia, Rhodococcus, Mycobacterium* and *Tsukamurella* comprising at least one exogenous gene. In some embodiments, the invention relate to cells of the family of Nocardiaceae comprising an exogenous gene, wherein the cell is not a cell of the genus *Mycobacterium*. In some embodiments, the invention provides a cell and compositions comprising a cell of the genus *Rhodococcus* comprising an exogenous gene, and in some embodiments the cell is a strain of the species *Rhodococcus* sp., *Rhodococcus opacus, Rhodococcus aurantiacus; Rhodococcus baikonurensis; Rhodococcus boritolerans; Rhodococcus equi; Rhodococcus coprophilus; Rhodococcus corynebacterioides; Nocardia corynebacterioides* (synonym: *Nocardia corynebacterioides*); *Rhodococcus erythropolis; Rhodococcus fascians; Rhodococcus globerulus; Rhodococcus gordoniae; Rhodococcus jostii Rhodococcus koreensis; Rhodococcus kroppenstedtii; Rhodococcus maanshanensis; Rhodococcus marinonascens; Rhodococcus opacus; Rhodococcus percolatus; Rhodococcus phenolicus; Rhodococcus polyvorum; Rhodococcus pyridinivorans; Rhodococcus rhodochrous; Rhodococcus rhodnii;* (synonym: *Nocardia rhodnii*); *Rhodococcus ruber* (synonym: *Streptothrix rubra*); *Rhodococcus* sp. RHA1; *Rhodococcus triatomae; Rhodococcus tukisamuensis; Rhodococcus wratislaviensis* (synonym: *Tsukamurella wratislaviensis*); *Rhodococcus yunnanensis; Rhodococcus zopfii*. In some embodiments the cell comprising one or more exogenous genes is strain *Rhodococcus opacus* DSM number 43205 or 43206. In some embodiments the cell comprising one or more exogenous genes is strain *Rhodococcus* sp. DSM number 3346. In some embodiments, the invention provides cells and compositions comprising a cell of the genus *Rhodococcus* comprising an exogenous gene, wherein the cell or composition comprising a cell of *Rhodococcus* is non-infectious to animals and/or plants. In some embodiments, the invention provides cells and compositions comprising a cell of the genus *Rhodococcus* comprising an exogenous gene, wherein the *Rhodococcus* cell or composition comprising a *Rhodococcus* cell is non-infectious to humans. In some embodiments, the invention provides cells and compositions comprising a cell of the genus *Rhodococcus* comprising an exogenous gene, wherein the *Rhodococcus* cell or composition comprising a *Rhodococcus* cell is non-infectious to plants. In some embodiments, the invention provides cells and compositions comprising cells of the genus *Rhodococcus* comprising an exogenous gene, wherein, if the cell is from *Rhodococcus equi* or *Rhodococcus fascians* species, the species is non-infectious to animals and/or plants. In some embodiments, the invention relates to a *Rhodococcus* cell or composition comprising a *Rhodococcus* cell, wherein the cell is not a species selected from *Rhodococcus equi* or *Rhodococcus fascians*.

In some embodiments, the invention relates to a *Rhodococcus* cell or composition comprising a *Rhodococcus* cell, wherein the cell is incapable of producing any acrylic acid or acrylamide. In some embodiments, the invention relates to a *Rhodococcus* cell or composition comprising a *Rhodococcus* cell, wherein the cell produces less than 10, 9, 8, 7, 6, 5, 4, 3, 2, or 1% of its weight of total dry cellular matter in acrylamide or acrylic/methylacrylic acid. In some embodiments, the invention relates to a *Rhodococcus* cell or composition comprising a *Rhodococcus* cell, wherein the cell is not from the species *Rhodococcus rhodochrous*. In some embodiments, the invention relates to *Rhodococcus* cell or composition comprising a *Rhodococcus* cell, wherein the cell is incapable of producing 10-hydroxy-12-octadecenoic acid. In some embodiments, the invention relates to a *Rhodococcus* cell or composition comprising a *Rhodococcus* cell, wherein the cell is unable to produce more than 10, 9, 8, 7, 6, 5, 4, 3, 2, or 1% of its weight of total dry cellular matter in 10-hydroxy-12-octadecenoic acid. In some embodiments, the invention relates to *Rhodococcus* cell or composition comprising a *Rhodococcus* cell, wherein the cell is incapable of producing optically-active 4-amino-3-hydroxybutyric acid. In some embodiments, the invention relates to a *Rhodococcus* cell or composition comprising a *Rhodococcus* cell, wherein the cell is unable to produce more than 10, 9, 8, 7, 6, 5, 4, 3, 2, or 1% of its weight of total dry cellular matter in optically-active 4-amino-3-hydroxybutyric acid.

In some embodiments, the cell or compositions comprising one of more cells is not *E. coli*. In some embodiments, the cell or compositions comprising one of more cells is from the genus *Rhodococcus* but is not for the species *equi*. In some embodiments, the cell of the present invention is not pathogenic to animals or plants. In some embodiments, the cell of the present invention is not pathogenic to humans. In some embodiments, the cell or compositions comprising one of more cells is from the genus *Ralstonia*. In some embodiments, the cell or compositions comprising one of more cells is from the species *Ralstonia eutropha*. In some embodiments the cell comprising one or more exogenous genes is strain *Cupriavidus necator* DSM number 531 or 541.

In some embodiments, the cell or compositions comprising the one or more cells have a 16S rRNA sequence with at least 50, 60, 70, 75, 80, 85, 90, 91, 92, 93, 94, 95, 96, 97, 98 or 99% nucleotide homology to one or more of SEQ ID NOs: 11 or 12. In some embodiments, the cell or compositions comprising the one or more cells have a 16S rRNA sequence with at least 70, 75, 80, 85, 90, 91, 92, 93, 94, 95, 96, 97, 98 or 99% nucleotide homology to one or more of SEQ ID NOs: 11. In some embodiments, the cell or compositions comprising the one or more cells have a 16S rRNA sequence with at least 70, 75, 80, 85, 90, 91, 92, 93, 94, 95, 96, 97, 98 or 99% nucleotide homology to one or more of SEQ ID NOs: 12. In some embodiments, the cell or compositions comprising the one or more cells have a 16S rRNA sequence with at least 70, 75, 80, 85, 90, 91, 92, 93, 94, 95, 96, 97, 98 or 99% nucleotide homology to one or more of SEQ ID NOs: 13.

In some embodiments the microorganism of the claimed invention is not dependent upon light to grow and/or metabolize and/or synthesize lipid molecules. In some embodiments, the microorganism of the claimed invention does not require any type of sugar to grow and/or metabolize and/or synthesize lipid molecules. In some embodiments, the microorganism of the claimed invention does not require any type of organic compound to grow and/or metabolize and/or synthesize lipid molecules. In some embodiments, the microorganism of the claimed invention does not require any type of fixed carbon to grow and/or metabolize and/or synthesize lipid molecules. In some embodiments, the microorganism can grow and/or metabolize lipids in a slightly anaerobic or extremely anaerobic environment. In some embodiments, the microorganism of the claimed invention is a facultative microorganism Microbial culturing in the present invention is performed both for the sake of implementing genetic modifications, and for production of organic compounds, and specifically lipids and/or hydrocarbons (e.g., alkenes, alkynes, unsaturated fatty acids, or triacylglycerols, hydroxy acids, diacids). Microbial culturing with the aim of genetic manipulation is generally performed at a small benchtop scale and often under conditions that select for genetically modified traits. Microbial culturing aimed at the commercial production of organic compounds and specifically lipids and/or hydrocarbons is typically performed in bioreactors at much greater scale (e.g., 500 L, 1,000 L 5,000 L, 10,000 L, 50,000 L, 100,000 L, 1,000,000 L bioreactor volumes and higher). In certain embodiments the chemoautotrophs of the present invention are grown in a liquid media inside a bioreactor using the methods of the invention. In some embodiments, the bioreactor containing the microorganisms is constructed of opaque materials that keep the culture in darkness. Bioreactors constructed out of opaque materials such as steel or reinforced concrete can be designed to have extremely big working volumes. In some embodiments of the present invention steel fermenters 50,000 liter and greater in volume are utilized. In some embodiments of the present invention egg-shape or cylindrical digesters 3,000,000 liters and greater in volume are utilized. In some embodiments, the bioreactor comprising the microorganism does not allow light to penetrate its interior.

The bioreactor or fermentor is used to culture cells through the various phases of their physiological cycle. A bioreactor is utilized for the cultivation of cells, which may be maintained at particular phases in their growth curve. The use of bioreactors is advantageous in many ways for culti-vating chemoautotrophic growth. For certain embodiments, oleaginous cell mass, which is used to produce oleochemicals, is grown to high densities in liquid suspension. Generally the control of growth conditions including control of dissolved carbon dioxide, oxygen, and other gases such as hydrogen, as well as other dissolved nutrients, trace elements, temperature and pH, is facilitated in a bioreactor.

Nutrient media as well as gases can be added to the bioreactor as either a batch addition, or periodically, or in response to a detected depletion or programmed set point, or continuously over the period the culture is grown and/or maintained. For certain embodiments, the bioreactor at inoculation is filled with a starting batch of nutrient media and/or gases at the beginning of growth, and no additional nutrient media and/or gases are added after inoculation. For certain embodiments, nutrient media and/or gases are added periodically after inoculation. For certain embodiments, nutrient media and/or gas is added after inoculation in response to a detected depletion of nutrient and/or gas. For certain embodiments, nutrient media and/or gas is added continuously after inoculation.

For certain embodiments the bioreactors have mechanisms to enable mixing of the nutrient media that include but are not limited to spinning stir bars, blades, impellers, or turbines, spinning, rocking, or turning vessels, gas lifts and sparging. The culture media may be mixed continuously or intermittently.

The ports that are standard in bioreactors may be utilized to deliver, or withdraw, gases, liquids, solids, and/or slurries, into the bioreactor vessel enclosing the microbes of the present invention. Many bioreactors have multiple ports for different purposes (e.g. ports for media addition, gas addition, probes for pH and DO, sampling), and a given port may be used for various purposes during the course of a fermentation run. As an example, a port might be used to add nutrient media to the bioreactor at one point in time and at another time might be used for sampling. Preferably, the multiple use of a sampling port can be performed without introducing contamination or invasive species into the growth environment. A valve or other actuator enabling control of the sample flow or continuous sampling can be provided to a sampling port. For certain embodiments the bioreactors are equipped with at least one port suitable for culture inoculation that can additionally serve other uses including the addition of media or gas. Bioreactors ports enable control of the gas composition and flow rate into the culture environment. For example the ports can be used as gas inlets into the bioreactor through which gases are pumped. For some embodiments gases that may be pumped into a bioreactor include syngas, producer gas, hydrogen gas, $CO_2$, air, air/$CO_2$ mixtures, ammonia, nitrogen, noble gases, such as argon, as well as other gases. In some embodiments that $CO_2$ may come from sources including but are not limited to: $CO_2$ from the gasification of organic matter; $CO_2$ from the calcination of limestone, $CaCO_3$, to produce quicklime, $CaO$; $CO_2$ from methane steam reforming, such as the $CO_2$ byproduct from ammonia or hydrogen production; combustion; $CO_2$ byproduct of sugar fermentation; $CO_2$ byproduct from sodium phosphate production; geologically or geothermally produced $CO_2$. Raising the gas flow rate into a bioreactor can enhance mixing of the culture and produce turbulence if the gas inlet is positioned under the surface of the liquid media such that gas bubbles or sparges up through the media. In some embodiments, a bioreactor comprises gas outlet ports for gas escape and pressure release. In some embodiments, gas inlets and outlets are preferably equipped with check valves to prevent gas backflow.

The present invention relates to bioreactors that comprise a cell, which comprises at least one exogenous nucleic acid sequences that encodes a lipid pathway enzyme. The present invention relates to a system of at least one bioreactor that comprise a cell, which comprises at least one exogenous nucleic acid sequences that encodes a lipid pathway enzyme. In some embodiments, the system comprises two or more, three or more, or four or more bioreactors, at least one of which comprise a cell, which comprises at least one exogenous nucleic acid sequences that encodes a lipid pathway enzyme. In some embodiments, the system of bioreactors comprises at least a first and second bioreactor, wherein the first bioreactor comprises a cell, which comprises at least one exogenous nucleic acid sequences that encodes a lipid pathway enzyme; and wherein the second bioreactor comprises a microorganism derived from a different species, wherein the microorganism from a different species comprises at least one exogenous nucleic acid sequence that encodes a lipid pathway enzyme. In some embodiments, the system of bioreactors comprises a first bioreactor that comprises the cell of the present invention and a second bioreactor comprising a microalgal, yeast, or bacterial cell.

In some embodiments, the cells of the present invention are capable of producing desaturated alkanes between 8 and 18 carbon atoms long at greater than 18 grams per liter volume of culture per three day period. In some embodiments, the cells of the present invention are capable of producing desaturated hydrocarbons between 8 and 18 carbon atoms long at greater than or equal to 18 grams per liter volume of culture per three day period, wherein the desatruated hydrocarbons are desatuated at a carbon position other than carbon-9.

Genetic Modifications

The present invention relates to methods of modifying a bacterial cell to express one or more exogenous nucleic acid sequences that encodes one or more enzymes to enable fixation of a carbon-containing gas feedstock into useful carbon-based products of interest in an amount greater than an amount of carbon-based products produced by the same bacterial cell that does not express the exogenous nucleic acid sequences. Methods of selecting and manufacturing nucleic acid sequences for modification of bacterial cells are known and can be performed by transformation, electroporation, phage infection of bacteria, or other techniques for nucleic acid transfer generally known in the art. Standard recombinant DNA and molecular cloning techniques useful for the invention are well known in the art and are described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987), all of which are incorporated by reference in their entireties.

The invention relates to genetic constructs comprising one or more exogenous genes that encode one or more amino acid sequences to enable fixation of a carbon-containing gas feedstock, including but not limited to syngas or producer gas, into useful carbon-based products of interest in an amount greater than an amount of carbon-based products produced by the same bacterial cell that does not express the exogenous nucleic acid sequence or sequences. Another aspect of the present invention relates to compositions that comprise at least one bacterial cell, which comprises at least one nucleic acid sequence that encodes at least one exogenous amino acid sequence that functions as a fatty acid acyl-ACP reductase, a fatty acid aldehyde decarbonylase and/or a thioesterase. In some embodiments, the bacterial cell is transformed with one or more, two or more, three or more, four or more, or five or more exogenous nucleic acid sequences that encode one or more amino acid sequences to enable fixation of a carbon-containing gas feedstock, including but not limited to syngas or producer gas, into useful carbon-based products of interest in an amount greater than an amount of carbon-based products produced by the same bacterial cell that does not express the exogenous nucleic acid sequence or sequences. According to the present invention, genetic material that encodes the enzyme is delivered to a bacterial cell in an expressible form. The genetic material, DNA or RNA, is taken up by the cells of the invention and expressed. The enzyme or enzymes that are thereby produced can biochemically modify lipid molecules to remove or add hydroxyl groups, remove or add carbonyl groups, remove or add carbon-carbon double bonds, remove or add carbon-carbon triple bonds, remove or add aldehyde groups, remove or add hydroxy groups, remove or add carboxylic acid groups, or remove or add ester groups to lipid molecules in lipid.

In some embodiments, the genetic constructs of the present invention comprise DNA, RNA, or combinations of both DNA and RNA. In some embodiments, the genetic construct of the present invention is a plasmid. It will be appreciated that, in some embodiments, the plasmid contains a variety of open reading frames (ORFs) encoding proteins of many diverse functions, including those enzymes that enable hydrocarbon or lipid modification, glutathione-S transferase (GST) activity, origins of replication, multiple cloning sites, promoters, and/or termination sequences. It is contemplated therefore that a host cell transformed with the plasmid will demonstrate the ability to modify a variety of lipids as well as maintain its copy number in the cytoplasm of the cell. The glutathione-S transferases (GSTs) represent a large group of detoxification enzymes. GSTs catalyze the conjugation of glutathione, homoglutathione and other glutathione-like analog via sulfhydryl group, to a large range of hydrophobic, electrophilic compounds. The conjugation can result in detoxification of these compounds. GST genes are found in both prokaryotic (e.g., $E.$ $coli$) and eukaryotic organisms (e.g., yeast, plant and human). Although the homologies between the GSTs from prokaryotes and eukaryotes were low, many of the residues assigned to be important for the enzymatic function or structure in the eukaryotes were found to be conserved in prokaryotic GSTs (Nishida et al., J. Biol Chem 269:32536-32541 (1994)). It has been suggested that bacterial GST may represent a defense against the effects of antibiotics (Piccolomini et al., J Gen Microbiol 135:3119-3125 (1989)). Accordingly it is contemplated that a host strain transformed with the plasmid will have the ability detoxify harmful compounds via conjugation of those compounds to glutathione.

In some embodiments, the instant plasmid additionally encodes a variety of maintenance proteins, useful for maintaining, stabilizing and replicating the plasmid. It is contemplated that these genes may be used in conjunction with other bacterial plasmids deficient in these functions for the increased stabilization or robust maintenance of the plasmid. In some embodiments, the plasmid comprises maintenance proteins of particular interest including the REP origin of replication (encoded by ORF 38) the TRA proteins (TRAI, TRAJ and TRAK, encoded by ORF's 23, 24 and 25 respectively) and the VAG proteins (VAGD and VAGC, encoded by ORF's 33 and 34 respectively). The tra gene family is known to be involved in plasmid conjugation, a process that promotes DNA transfer from a donor to a recipient cell mediated by physical contact (Firth et al, *Escherichia coli* and *Salmonella*: Cellular and Molecular Biology, ASM press (1996)). Among tra gene products, TraI and TraK proteins are reported to be required for efficient plasmid site-specific recombination (Paterson et al. J. Bacteriol 181:2572-2583 (1999)). Furthermore, TraI is required for conjugal DNA transfer. Fukuda and Ohtsubo (Genes Cells 2:735-751 (1997)) reported that TraI has the activity of site- and strand-specific nicking of the supercoiled plasmid DNA. TraJ, traJ gene product, regulates transcription originating at the tra operon promoter P.sub.traY. (Firth et al., *Escherichia coli* and *Salmonella*: Cellular and Molecular Biology, ASM press (1996)). The stabilization proteins VAGC and VAGD encoded by vagC and vagD are involved in the maintaining the plasmid as an autonomous replicating unit. Bacterial maintenance proteins of particular interest on the pSeq and pVer plasmids include.

SEQ ID: 01

```
TCGCGCGTTT CGGTGATGAC GGTGAAAACC TCTGACACAT
GCAGCTCCCG GAGACGGTCA CAGCTTGTCT GTAAGCGGAT
GCCGGGAGCA GACAAGCCCG AGCGCGCAAA GCCACTACTG
CCACTTTTGG AGACTGTGTA CGTCGAGGGC CTCTGCCAGT
GTCGAACAGA CATTCGCCTA CGGCCCTCGT CTGTTCGGGC
TCAGGGCGCG TCAGCGGGTG TTGGCGGGTG TCGGGGCTGG
CTTAACTATG CGGCATCAGA GCAGATTGTA CTGAGAGTGC
ACCATATGCG GTGTGAAATA AGTCCCGCGC AGTCGCCCAC
AACCGCCCAC AGCCCCGACC GAATTGATAC GCCGTAGTCT
CGTCTAACAT GACTCTCACG TGGTATACGC CACACTTTAT
CCGCACAGAT GCGTAAGGAG AAAATACCGC ATCAGGCGCC
ATTCGCCATT CAGGCTGCGC AACTGTTGGG AAGGGCGATC
GGTGCGGGCC TCTTCGCTAT GGCGTGTCTA CGCATTCCTC
TTTTATGGCG TAGTCCGCGG TAAGCGGTAA GTCCGACGCG
TTGACAACCC TTCCCGCTAG CCACGCCCGG AGAAGCGATA
TACGCCAGCT GGCGAAAGGG GGATGTGCTG CAAGGCGATT
AAGTTGGGTA ACGCCAGGGT TTTCCCAGTC ACGACGTTGT
AAAACGACGG CCAGTGCCAA ATGCGGTCGA CCGCTTTCCC
CCTACACGAC GTTCCGCTAA TTCAACCCAT TGCGGTCCCA
AAAGGGTCAG TGCTGCAACA TTTTGCTGCC GGTCACGGTT
GCTTGCATGC CTGCAGGTCG ACGGGCCCGG GATCCGATGC
TCTTCCGCTA AGATCTGCCG CGGCCGCGTC CTCAGAAGAA
CTCGTCAAGA AGGCGATAGA CGAACGTACG GACGTCCAGC
TGCCCGGGCC CTAGGCTACG AGAAGGCGAT TCTAGACGGC
GCCGGCGCAG GAGTCTTCTT GAGCAGTTCT TCCGCTATCT
AGGCGATGCG CTGCGAATCG GGAGCGGCGA TACCGTAAAG
CACGAGGAAG CGGTCAGCCC ATTCGCCGCC AAGCTCTTCA
GCAATATCAC GGGTAGCCAA TCCGCTACGC GACGCTTAGC
CCTCGCCGCT ATGGCATTTC GTGCTCCTTC GCCAGTCGGG
TAAGCGGCGG TTCGAGAAGT CGTTATAGTG CCCATCGGTT
CGCTATGTCC TGATAGCGGT CCGCCACACC CAGCCGGCCA
CAGTCGATGA ATCCAGAAAA GCGGCCATTT TCCACCATGA
TATTCGGCAA GCAGGCATCG GCGATACAGG ACTATCGCCA
GGCGGTGTGG GTCGGCCGGT GTCAGCTACT TAGGTCTTTT
CGCCGGTAAA AGGTGGTACT ATAAGCCGTT CGTCCGTAGC
CCATGGGTCA CGACGAGATC CTCGCCGTCG GGCATGCGCG
CCTTGAGCCT GGCGAACAGT TCGGCTGGCG CGAGCCCCTG
ATGCTCTTCG TCCAGATCAT GGTACCCAGT GCTGCTCTAG
GAGCGGCAGC CCGTACGCGC GGAACTCGGA CCGCTTGTCA
AGCCGACCGC GCTCGGGGAC TACGAGAAGC AGGTCTAGTA
CCTGATCGAC AAGACCGGCT TCCATCCGAG TACGTGCTCG
CTCGATGCGA TGTTTCGCTT GGTGGTCGAA TGGGCAGGTA
GCCGGATCAA GCGTATGCAG GGACTAGCTG TTCTGGCCGA
AGGTAGGCTC ATGCACGAGC GAGCTACGCT ACAAAGCGAA
CCACCAGCTT ACCCGTCCAT CGGCCTAGTT CGCATACGTC
CCGCCGCATT GCATCAGCCA TGATGGATAC TTTCTCGGCA
GGAGCAAGGT GGGATGACAG GAGATCCTGC CCCGGCACTT
CGCCCAATAG CAGCCAGTCC GGCGGCGTAA CGTAGTCGGT
ACTACCTATG AAAGAGCCGT CCTCGTTCCA CCCTACTGTC
CTCTAGGACG GGGCCGTGAA GCGGGTTATC GTCGGTCAGG
CTTCCCGCTT CAGTGACAAC GTCGAGCACA GCTGCGCAAG
GAACGCCCGT CGTGGCCAGC CACGATAGCC GCGCTGCCTC
GTCCTGCAGT TCATTCAGGG GAAGGGCGAA GTCACTGTTG
CAGCTCGTGT CGACGCGTTC CTTGCGGGCA GCACCGGTCG
GTGCTATCGG CGCGACGGAG CAGGACGTCA AGTAAGTCCC
CACCGGACAG GTCGGTCTTG ACAAAAAGAA CCGGGCGCCC
CTGCGCTGAC AGCCGGAACA CGGCGGCATC AGAGCAGCCG
ATTGTCTGTT GTGCCCAGTC GTGGCCTGTC CAGCCAGAAC
TGTTTTTCTT GGCCCGCGGG GACGCGACTG TCGGCCTTGT
GCCGCCGTAG TCTCGTCGGC TAACAGACAA CACGGGTCAG
ATAGCCGAAT AGCCTCTCCA CCCAAGCGGC CGGAGAACCT
GCGTGCAATC CATCTTGTTC AATCATGATA TCCCTTAATT
AACCGTTAAC ACTAGTTCAG TATCGGCTTA TCGGAGAGGT
GGGTTCGCCG GCCTCTTGGA CGCACGTTAG GTAGAACAAG
TTAGTACTAT AGGGAATTAA TTGGCAATTG TGATCAAGTC
TCCATCTCGC CGTGTATGCG GGCCTGACGG ATCAACGTTC
```

```
CCACCGAGCC AGTCGAGATG TTCATCTGGT CGGCGATCTG
CCGGTACTTC AAACCTTGTT AGGTAGAGCG GCACATACGC
CCGGACTGCC TAGTTGCAAG GGTGGCTCGG TCAGCTCTAC
AAGTAGACCA GCCGCTAGAC GGCCATGAAG TTTGGAACAA
TGCGCAGTTC CACAGCCTTC TTGCGGCGTT CCTGCGCACG
AGCGATGTAG TCGCCTCGGT CTTCGGCGAC GAGCCGTTTG
ATGGTGCTTT TCGAGACGCC ACGCGTCAAG GTGTCGGAAG
AACGCCGCAA GGACGCGTGC TCGCTACATC AGCGGAGCCA
GAAGCCGCTG CTCGGCAAAC TACCACGAAA AGCTCTGCGG
GAACTTGTCA GCCAACTCCT GCGCGGTCTG CGTGCGACGC
ATCACGCGTT CTGCAGCACC CATCAGTCCG TCCCCTCTGC
TGCTGCGAAC AGTGCCGATC CTTGAACAGT CGGTTGAGGA
CGCGCCAGAC GCACGCTGCG TAGTGCGCAA GACGTCGTGG
GTAGTCAGGC AGGGGAGACG ACGACGCTTG TCACGGCTAG
GATCGACCTT CTTGAGCTTC GGCCGCGGCG CGGTGGCGTT
CTTCCGTACC GCTTCCGTTT TTGCGCTGCT GCTCACTTTG
CCGCGGCGTG CCTGGATTTT CTAGCTGGAA GAACTCGAAG
CCGGCGCCGC GCCACCGCAA GAAGGCATGG CGAAGGCAAA
AACGCGACGA CGAGTGAAAC GGCGCCGCAC GGACCTAAAA
CGAGAACTCG GCGGCGGTGA AGGTGCGGTG GGTCCAGTGG
GCGACTGATT TGCCGATCTG CTCGGCCTCG GCCCGACTCA
TGGGGCCGAT CCCGTCGTTG GCTCTTGAGC CGCCGCCACT
TCCACGCCAC CCAGGTCACC CGCTGACTAA ACGGCTAGAC
GAGCCGGAGC CGGGCTGAGT ACCCCGGCTA GGGCAGCAAC
GCGTCGAGGG TGAAGTTGGT CAGGGCGGTG AAGTCGGTGA
CCATCTGCCG CCACACAGTG ATCGACGGGT AGTTCTGTTT
CCGGATCTCG CGGTAGGCCC CGCAGCTCCC ACTTCAACCA
GTCCCGCCAC TTCAGCCACT GGTAGACGGC GGTGTGTCAC
TAGCTGCCCA TCAAGACAAA GGCCTAGAGC GCCATCCGGG
ATTCCCGGGT GCGGTCGAAC AGTTCGACGT TCCGGCCCGT
TTCGGTCCTG ACCTGTGTCT TGCGGCCGTA GTCCGGTGGG
GCGGGAAAC GGTCACCGAG TAAGGGCCCA CGCCAGCTTG
TCAAGCTGCA AGGCCGGGCA AAGCCAGGAC TGGACACAGA
ACGCCGGCAT CAGGCCACCC CGCCCCTTTG CCAGTGGCTC
CGCTTTTGCG AGGCCTTTGA GCGAGTACGG ATCCGAGGGA
CCCCAGACCG TCGTCCAGTG CGGGTGGATC GGGTTCTGGG
TGAGCTGCTG CGCGTAGCCC GCGAAAACGC TCCGGAAACT
CGCTCATGCC TAGGCTCCCT GGGGTCTGGC AGCAGGTCAC
GCCCACCTAG CCCAAGACCC ACTCGACGAC GCGCATCGGG
TGATCGGCGC CGACCACCGA GGCGATCAGC CCCTGGTTCA

CCCGGTCGTA GAGCCGCAGC GGGCCCTGTC GGGCTGCCTG
GAGGGTGTAG ACCGGGCTTT ACTAGCCGCG GCTGGTGGCT
CCGCTAGTCG GGGACCAAGT GGGCCAGCAT CTCGGCGTCG
CCCGGGACAG CCCGACGGAC CTCCCACATC TGGCCCGAAA
CGAGCAGCCA CCACAGGTGC GCGTGCTCGG TCGCGGGATT
GATCGTCATC ACGGTCGGAT CGGGCAGATC CGCGTTACGT
GCGGCCCACT GCGCCTGGTC GCTCGTCGGT GGTGTCCACG
CGCACGAGCC AGCGCCCTAA CTAGCAGTAG TGCCAGCCTA
GCCCGTCTAG GCGCAATGCA CGCCGGGTGA CGCGGACCAG
GTCGTCCACG TCGAGCACCA AGCCCAACCT GATCGACGGG
GTGCGGGCCG CAATGTAGCG GCGGGTGAGC GCCTCCGCGC
GCGGCTGCGG CCACTGCCCG CAGCAGGTGC AGCTCGTGGT
TCGGGTTGGA CTAGCTGCCC CACGCCCGGC GTTACATCGC
CGCCCACTCG CGGAGGCGCG CGCCGACGCC GGTGACGGGC
TCCCGGACGT AGTCATCCGT CGCGTGCGGG TATTTGAACC
GCCAGCGGTC CAACCAGGCG TCAACAGCAG CGGTCATGAC
CGCCAAGCTA GGGCCGGATC AGGGCCTGCA TCAGTAGGCA
GCGCACGCCC ATAAACTTGG CGGTCGCCAG GTTGGTCCGC
AGTTGTCGTC GCCAGTACTG GCGGTTCGAT CCCGGCCTAG
TGTACCGATC GGGGGAGGCG CGCCGCAAAT TATTTAAGAG
TCTCGCTAGC AAACCATGTC AGGTGTTGCG GTGGGTTCCG
GGTAAACCTC CACCCGAATT ACATGGCTAG CCCCCTCCGC
GCGGCGTTTA ATAAATTCTC AGAGCGATCG TTTGGTACAG
TCCACAACGC CACCCAAGGC CCATTTGGAG GTGGGCTTAA
ATTTAAGAGT CTCGCTAGCT AAGCCCTATC TGATGCTGCG
CGGGGGGTCC TTCGCACTGA ATCTCAAAGG TGGCCGGCTG
AATTTCGTCG CGCGAAAACC TAAATTCTCA GAGCGATCGA
TTCGGGATAG ACTACGACGC GCCCCCCAGG AAGCGTGACT
TAGAGTTTCC ACCGGCCGAC TTAAAGCAGC GCGCTTTTGG
TCCCTGGACA GTTCTGGAAT TCAGCAAGAG GTGTGTCTGA
ACTTCGGTGT TTTTTTGGGG GGTGACTCCA GCGGGGTGGG
CACAACGCGA ACAGAGACCT AGGGACCTGT CAAGACCTTA
AGTCGTTCTC CACACAGACT TGAAGCCACA AAAAAACCCC
CCACTGAGGT CGCCCCACCC GTGTTGCGCT TGTCTCTGGA
TGTGTGTACG ACGGCGGGAG GTAAGTCGGG TACGGCTCGG
ACTGCGGTAG AGCAACCGTC GAATCGATTT CGAGCAGAGC
GAGCAGAGCA AGATATTCCA ACACACATGC TGCCGCCCTC
CATTCAGCCC ATGCCGAGCC TGACGCCATC TCGTTGGCAG
CTTAGCTAAA GCTCGTCTCG CTCGTCTCGT TCTATAAGGT
AAACTCCGGG GTTCCTCGGC GGCCTCCCCC GTCTGTTTGC
```

```
TCAACCGAGG GAGACCTGGC GGTCCCGCGT TTCCGGACGC
GCGGGACCGC CTACCGCTCG TTTGAGGCCC AAGGAGCCG
CCGGAGGGGG CAGACAAACG AGTTGGCTCC CTCTGGACCG
CCAGGGCGCA AAGGCCTGCG CGCCCTGGCG GATGGCGAGC
AGAGCGGAAG AGCATCTAGA TGCATTCGCG AGGTACCGAG
CTCGAATTCG TAATCATGGT CATAGCTGTT TCCTGTGTGA
AATTGTTATC CGCTCACAAT TCTCGCCTTC TCGTAGATCT
ACGTAAGCGC TCCATGGCTC GAGCTTAAGC ATTAGTACCA
GTATCGACAA AGGACACACT TTAACAATAG GCGAGTGTTA
TCCACACAAC ATACGAGCCG GAAGCATAAA GTGTAAAGCC
ATGGGGTGCC TATGAGTGAG CTAACTCACA TTAATTGCGT
TGCGCTCACT GCCCGCTTTC AGGTGTGTTG TATGCTCGGC
CTTCGTATTT CACATTTCGG ACCCCACGGA TTACTCACTC
GATTGAGTGT AATTAACGCA ACGCGAGTGA CGGGCGAAAG
CAGTCGGGAA ACCTGTCGTG CCAGCTGCAT TAATGAATCG
GCCAACGCGC GGGGAGAGGC GGTTTGCGTA TTGGGCGCTC
TTCCGCTTCC TCGCTCACTG GTCAGCCCTT TGGACAGCAC
GGTCGACGTA ATTACTTAGC CGGTTGCGCG CCCCTCTCCG
CCAAACGCAT AACCCGCGAG AAGGCGAAGG AGCGAGTGAC
ACTCGCTGCG CTCGGTCGTT CGGCTGCGGC GAGCGGTATC
AGCTCACTCA AAGGCGGTAA TACGGTTATC CACAGAATCA
GGGGATAACG CAGGAAAGAA TGAGCGCACG GAGCCAGCAA
GCCGACGCCG CTCGCCATAG TCGAGTGAGT TTCCGCCATT
ATGCCAATAG GTGTCTTAGT CCCCTATTGC GTCCTTTCTT
CATGTGAGCA AAAGGCCAGC AAAAGGCCAG GAACCGTAAA
AAGGCCGCGT TGCTGGCGTT TTTCCATAGG CTCCGCCCCC
CTGACGAGCA TCACAAAAAT GTACACTCGT TTTCCGGTCG
TTTTCCGGTC CTTGGCATTT TTCCGGCGCA ACGACCGCAA
AAAGGTATCC GAGGCGGGGG GACTGCTCGT AGTGTTTTTA
CGACGCTCAA GTCAGAGGTG GCGAAACCCG ACAGGACTAT
AAAGATACCA GGCGTTTCCC CCTGGAAGCT CCCTCGTGCG
CTCTCCTGTT CCGACCCTGC GCTGCGAGTT CAGTCTCCAC
CGCTTTGGGC TGTCCTGATA TTTCTATGGT CCGCAAAGGG
GGACCTTCGA GGGAGCACGC GAGAGGACAA GGCTGGGACG
CGCTTACCGG ATACCTGTCC GCCTTTCTCC CTTCGGGAAG
CGTGGCGCTT TCTCATAGCT CACGCTGTAG GTATCTCAGT
TCGGTGTAGG TCGTTCGCTC GCGAATGGCC TATGGACAGG
CGGAAAGAGG GAAGCCCTTC GCACCGCGAA AGAGTATCGA
GTGCGACATC CATAGAGTCA AGCCACATCC AGCAAGCGAG
CAAGCTGGGC TGTGTGCACG AACCCCCCGT TCAGCCCGAC
CGCTGCGCCT TATCCGGTAA CTATCGTCTT GAGTCCAACC
CGGTAAGACA CGACTTATCG GTTCGACCCG ACACACGTGC
TTGGGGGGCA AGTCGGGCTG GCGACGCGGA ATAGGCCATT
GATAGCAGAA CTCAGGTTGG GCCATTCTGT GCTGAATAGC
CCACTGGCAG CAGCCACTGG TAACAGGATT AGCAGAGCGA
GGTATGTAGG CGGTGCTACA GAGTTCTTGA AGTGGTGGCC
TAACTACGGC TACACTAGAA GGTGACCGTC GTCGGTGACC
ATTGTCCTAA TCGTCTCGCT CCATACATCG GCCACGATGT
CTCAAGAACT TCACCACCGG ATTGATGCCG ATGTGATCTT
GGACAGTATT TGGTATCTGC GCTCTGCTGA AGCCAGTTAC
CTTCGGAAAA AGAGTTGGTA GCTCTTGATC CGGCAAACAA
ACCACCGCTG GTAGCGGTGG CCTGTCATAA ACCATAGACG
CGAGACGACT TCGGTCAATG GAAGCCTTTT TCTCAACCAT
CGAGAACTAG GCCGTTTGTT TGGTGGCGAC CATCGCCACC
TTTTTTTGTT TGCAAGCAGC AGATTACGCG CAGAAAAAAA
GGATCTCAAG AAGATCCTTT GATCTTTTCT ACGGGGTCTG
ACGCTCAGTG GAACGAAAAC AAAAAAACAA ACGTTCGTCG
TCTAATGCGC GTCTTTTTTT CCTAGAGTTC TTCTAGGAAA
CTAGAAAAGA TGCCCCAGAC TGCGAGTCAC CTTGCTTTTG
TCACGTTAAG GGATTTTGGT CATGAGATTA TCAAAAAGGA
TCTTCACCTA GATCCTTTTA AATTAAAAAT GAAGTTTTAA
ATCAATCTAA AGTATATATG AGTGCAATTC CCTAAAACCA
GTACTCTAAT AGTTTTTCCT AGAAGTGGAT CTAGGAAAAT
TTAATTTTTA CTTCAAAATT TAGTTAGATT TCATATATAC
AGTAAACTTG GTCTGACAGT TACCAATGCT TAATCAGTGA
GGCACCTATC TCAGCGATCT GTCTATTTCG TTCATCCATA
GTTGCCTGAC TCCCCGTCGT TCATTTGAAC CAGACTGTCA
ATGGTTACGA ATTAGTCACT CCGTGGATAG AGTCGCTAGA
CAGATAAAGC AAGTAGGTAT CAACGGACTG AGGGGCAGCA
GTAGATAACT ACGATACGGG AGGGCTTACC ATCTGGCCCC
AGTGCTGCAA TGATACCGCG AGACCCACGC TCACCGGCTC
CAGATTTATC AGCAATAAAC CATCTATTGA TGCTATGCCC
TCCCGAATGG TAGACCGGGG TCACGACGTT ACTATGGCGC
TCTGGGTGCG AGTGGCCGAG GTCTAAATAG TCGTTATTTG
CAGCCAGCCG GAAGGGCCGA GCGCAGAAGT GGTCCTGCAA
CTTTATCCGC CTCCATCCAG TCTATTAATT GTTGCCGGGA
AGCTAGAGTA AGTAGTTCGC GTCGGTCGGC CTTCCCGGCT
CGCGTCTTCA CCAGGACGTT GAAATAGGCG GAGGTAGGTC
AGATAATTAA CAACGGCCCT TCGATCTCAT TCATCAAGCG
CAGTTAATAG TTTGCGCAAC GTTGTTGCCA TTGCTACAGG
```

```
CATCGTGGTG TCACGCTCGT CGTTTGGTAT GGCTTCATTC
AGCTCCGGTT CCCAACGATC GTCAATTATC AAACGCGTTG
CAACAACGGT AACGATGTCC GTAGCACCAC AGTGCGAGCA
GCAAACCATA CCGAAGTAAG TCGAGGCCAA GGGTTGCTAG
AAGGCGAGTT ACATGATCCC CCATGTTGTG CAAAAAGCG
GTTAGCTCCT TCGGTCCTCC GATCGTTGTC AGAAGTAAGT
TGGCCGCAGT GTTATCACTC TTCCGCTCAA TGTACTAGGG
GGTACAACAC GTTTTTTCGC CAATCGAGGA AGCCAGGAGG
CTAGCAACAG TCTTCATTCA ACCGGCGTCA CAATAGTGAG
ATGGTTATGG CAGCACTGCA TAATTCTCTT ACTGTCATGC
CATCCGTAAG ATGCTTTTCT GTGACTGGTG AGTACTCAAC
CAAGTCATTC TGAGAATAGT TACCAATACC GTCGTGACGT
ATTAAGAGAA TGACAGTACG GTAGGCATTC TACGAAAAGA
CACTGACCAC TCATGAGTTG GTTCAGTAAG ACTCTTATCA
GTATGCGGCG ACCGAGTTGC TCTTGCCCGG CGTCAATACG
GGATAATACC GCGCCACATA GCAGAACTTT AAAAGTGCTC
ATCATTGGAA AACGTTCTTC CATACGCCGC TGGCTCAACG
AGAACGGGCC GCAGTTATGC CCTATTATGG CGCGGTGTAT
CGTCTTGAAA TTTTCACGAG TAGTAACCTT TTGCAAGAAG
GGGGCGAAAA CTCTCAAGGA TCTTACCGCT GTTGAGATCC
AGTTCGATGT AACCCACTCG TGCACCCAAC TGATCTTCAG
CATCTTTTAC TTTCACCAGC CCCCGCTTTT GAGAGTTCCT
AGAATGGCGA CAACTCTAGG TCAAGCTACA TTGGGTGAGC
ACGTGGGTTG ACTAGAAGTC GTAGAAAATG AAAGTGGTCG
GTTTCTGGGT GAGCAAAAAC AGGAAGGCAA AATGCCGCAA
AAAAGGGAAT AAGGGCGACA CGGAAATGTT GAATACTCAT
ACTCTTCCTT TTTCAATATT CAAAGACCCA CTCGTTTTTG
TCCTTCCGTT TTACGGCGTT TTTTCCCTTA TTCCCGCTGT
GCCTTTACAA CTTATGAGTA TGAGAAGGAA AAAGTTATAA
ATTGAAGCAT TTATCAGGGT TATTGTCTCA TGAGCGGATA
CATATTTGAA TGTATTTAGA AAAATAAACA AATAGGGGTT
CCGCGCACAT TTCCCCGAAA TAACTTCGTA AATAGTCCCA
ATAACAGAGT ACTCGCCTAT GTATAAACTT ACATAAATCT
TTTTATTTGT TTATCCCCAA GGCGCGTGTA AAGGGGCTTT
AGTGCCACCT GACGTCTAAG AAACCATTAT TATCATGACA
TTAACCTATA AAAATAGGCG TATCACGAGG CCCTTTCGTC
TCACGGTGGA CTGCAGATTC TTTGGTAATA ATAGTACTGT
AATTGGATAT TTTTATCCGC ATAGTGCTCC GGGAAAGCAG
                                      SEQ ID: 02
GGGGAGCCGC GCCGAAGGCG TGGGGGAACC CCGCAGGGGT
GCCCTTCTTT GGGCACCAAA GAACTAGATA TAGGGCGAAA
TGCGAAAGAC TTAAAAATCA CCCCTCGGCG CGGCTTCCGC
ACCCCCTTGG GGCGTCCCCA CGGGAAGAAA CCCGTGGTTT
CTTGATCTAT ATCCCGCTTT ACGCTTTCTG AATTTTTAGT
ACAACTTAAA AAAGGGGGGT ACGCAACAGC TCATTGCGGC
ACCCCCCGCA ATAGCTCATT GCGTAGGTTA AGAAAATCT
GTAATTGACT GCCACTTTTA TGTTGAATTT TTTCCCCCA
TGCGTTGTCG AGTAACGCCG TGGGGGGCGT TATCGAGTAA
CGCATCCAAT TTCTTTTAGA CATTAACTGA CGGTGAAAAT
CGCAACGCAT AATTGTTGTC GCGCTGCCGA AAAGTTGCAG
CTGATTGCGC ATGGTGCCGC AACCGTGCGG CACCCTACCG
CATGGAGATA AGCATGGCCA GCGTTGCGTA TTAACAACAG
CGCGACGGCT TTTCAACGTC GACTAACGCG TACCACGGCG
TTGGCACGCC GTGGGATGGC GTACCTCTAT TCGTACCGGT
CGCAGTCCAG AGAAATCGGC ATTCAAGCCA AGAACAAGCC
CGGTCACTGG GTGCAAACGG AACGCAAAGC GCATGAGGCG
TGGGCCGGGC TTATTGCGAG GCGTCAGGTC TCTTTAGCCG
TAAGTTCGGT TCTTGTTCGG GCCAGTGACC CACGTTTGCC
TTGCGTTTCG CGTACTCCGC ACCCGGCCCA ATAACGCTC
GAAACCCACG GCGGCAATGC TGCTGCATCA CCTCGTGGCG
CAGATGGGCC ACCAGAACGC CGTGGTGGTC AGCCAGAAGA
CACTTTCCAA GCTCATCGGA CTTTGGGTGC GCCGTTACG
ACGACGTAGT GGAGCACCGC GTCTACCCGG TGGTCTTGCG
GCACCACCAG TCGGTCTTCT GTGAAAGGTT CGAGTAGCCT
CGTTCTTTGC GGACGGTCCA ATACGCAGTC AAGGACTTGG
TGGCCGAGCG CTGGATCTCC GTCGTGAAGC TCAACGGCCC
CGGCACCGTG TCGGCCTACG GCAAGAAACG CCTGCCAGGT
TATGCGTCAG TTCCTGAACC ACCGGCTCGC GACCTAGAGG
CAGCACTTCG AGTTGCCGGG GCCGTGGCAC AGCCGGATGC
TGGTCAATGA CCGCGTGGCG TGGGGCCAGC CCCGCGACCA
GTTGCGCCTG TCGGTGTTCA GTGCCGCCGT GGTGGTTGAT
CACGACGACC AGGACGAATC ACCAGTTACT GGCGCACCGC
ACCCCGGTCG GGGCGCTGGT CAACGCGGAC AGCCACAAGT
CACGGCGGCA CCACCAACTA GTGCTGCTGG TCCTGCTTAG
GCTGTTGGGG CATGGCGACC TGCGCCGCAT CCCGACCCTG
TATCCGGGCG AGCAGCAACT ACCGACCGGC CCCGGCGAGG
AGCCGCCCAG CCAGCCCGGC CGACAACCCC GTACCGCTGG
ACGCGGCGTA GGGCTGGGAC ATAGGCCCGC TCGTCGTTGA
TGGCTGGCCG GGGCCGCTCC TCGGCGGGTC GGTCGGGCCG
ATTCCGGGCA TGGAACCAGA CCTGCCAGCC TTGACCGAAA
CGGAGGAATG GGAACGGCGC GGGCAGCAGC GCCTGCCGAT
```

```
GCCCGATGAG CCGTGTTTTC TAAGGCCCGT ACCTTGGTCT
GGACGGTCGG AACTGGCTTT GCCTCCTTAC CCTTGCCGCG
CCCGTCGTCG CGGACGGCTA CGGGCTACTC GGCACAAAAG
TGGACGATGG CGAGCCGTTG GAGCCGCCGA CACGGGTCAC
GCTGCCGCGC CGGTAGCACT TGGGTTGCGC AGCAACCCGT
AAGTGCGCTG TTCCAGACTA ACCTGCTACC GCTCGGCAAC
CTCGGCGGCT GTGCCCAGTG CGACGGCGCG GCCATCGTGA
ACCCAACGCG TCGTTGGGCA TTCACGCGAC AAGGTCTGAT
TCGGCTGTAG CCGCCTCGCC GCCCTATACC TTGTCTGCCT
CCCCGCGTTG CGTCGCGGTG CATGGAGCCG GGCCACCTCG
ACCTGAATGG AAGCCGGCGG AGCCGACATC GGCGGAGCGG
CGGGATATGG AACAGACGGA GGGGCGCAAC GCAGCGCCAC
GTACCTCGGC CCGGTGGAGC TGGACTTACC TTCGGCCGCC
CACCTCGCTA ACGGATTCAC CGTTTTTATC AGGCTCTGGG
AGGCAGAATA AATGATCATA TCGTCAATTA TTACCTCCAC
GGGGAGAGCC TGAGCAAACT GTGGAGCGAT GCCTAAGTG
GCAAAAATAG TCCGAGACCC TCCGTCTTAT TTACTAGTAT
AGCAGTTAAT AATGGAGGTG CCCCTCTCGG ACTCGTTTGA
GGCCTCAGGC ATTTGAGAAG CACACGGTCA CACTGCTTCC
GGTAGTCAAT AAACCGGTAA ACCAGCAATA GACATAAGCG
GCTATTTAAC GACCCTGCCC CCGGAGTCCG TAAACTCTTC
GTGTGCCAGT GTGACGAAGG CCATCAGTTA TTTTGGCCATT
TGGTCGTTAT CTGTATTCGC CGATAAATTG CTGGGACGGG
TGAACCGACG ACCGGGTCGA ATTTGCTTTC GAATTTCTGC
CATTCATCCG CTTATTATCA CTTATTCAGG CGTAGCACCA
GGCGTTTAAG GGCACCAATA ACTTGGCTGC TGGCCCAGCT
TAAACGAAAG CTTAAAGACG GTAAGTAGGC GAATAATAGT
GAATAAGTCC GCATCGTGGT CCGCAAATTC CCGTGGTTAT
ACTGCCTTAA AAAATTACG CCCCGCCCTG CCACTCATCG
CAGTCGGCCT ATTGGTTAAA AAATGAGCTG ATTTAACAAA
AATTTAACGC GAATTTTAAC TGACGGAATT TTTTTAATGC
GGGGCGGGAC GGTGAGTAGC GTCAGCCGGA TAACCAATTT
TTTACTCGAC TAAATTGTTT TTAAATTGCG CTTAAAATTG
AAAATATTAA CGCTTACAAT TTCCATTCGC CATTCAGGCT
GCGCAACTGT TGGGAAGGGC GATCGGTGCG GGCCTCTTCG
CTATTACGCC AGCTGGCGAA TTTTATAATT GCGAATGTTA
AAGGTAAGCG GTAAGTCCGA CGCGTTGACA ACCCTTCCCG
CTAGCCACGC CCGGAGAAGC GATAATGCGG TCGACCGCTT
AGGGGGATGT GCTGCAAGGC GATTAAGTTG GGTAACGCCA
GGGTTTTCCC AGTCACGACG TTGTAAAACG ACGGCCAGTG

AGCGCGCGTA ATACGACTCA TCCCCCTACA CGACGTTCCG
CTAATTCAAC CCATTGCGGT CCCAAAAGGG TCAGTGCTGC
AACATTTTGC TGCCGGTCAC TCGCGCGCAT TATGCTGAGT
CTATAGGGCG AATTGGAGCT CCACCGCGGT GGCGGCCGCT
CTAGAACTAG TGGATCCCCC GGGCTGCAGG AATTCGATAT
CAAGCTTATC GATACCGTCG GATATCCCGC TTAACCTCGA
GGTGGCGCCA CCGCCGGCGA GATCTTGATC ACCTAGGGGG
CCCGACGTCC TTAAGCTATA GTTCGAATAG CTATGGCAGC
ACCTCGAGGG GGGGCCCGGT ACCCAGCTTT TGTTCCCTTT
AGTGAGGGTT AATTGCGCGC TTGGCGTAAT CATGGTCATA
GCTGTTTCCT GTGTGAAATT TGGAGCTCCC CCCCGGGCCA
TGGGTCGAAA ACAAGGGAAA TCACTCCCAA TTAACGCGCG
AACCGCATTA GTACCAGTAT CGACAAAGGA CACACTTTAA
GTTATCCGCT CACAATTCCA CACAACATAC GAGCCGGAAG
CATAAAGTGT AAAGCCTGGG GTGCCTAATG AGTGAGCTAA
CTCACATTAA TTGCGTTGCG CAATAGGCGA GTGTTAAGGT
GTGTTGTATG CTCGGCCTTC GTATTTCACA TTTCGGACCC
CACGGATTAC TCACTCGATT GAGTGTAATT AACGCAACGC
CTCACTGCCC GCTTTCCAGT CGGGAAACCT GTCGTGCCAG
CTGCATTAAT GAATCGGCCA ACGCGCGGGG AGAGGCGGTT
TGCGTATTGG GCGCATGCAT GAGTGACGGG CGAAAGGTCA
GCCCTTTGGA CAGCACGGTC GACGTAATTA CTTAGCCGGT
TGCGCGCCCC TCTCCGCCAA ACGCATAACC CGCGTACGTA
AAAAACTGTT GTAATTCATT AAGCATTCTG CCGACATGGA
AGCCATCACA AACGGCATGA TGAACCTGAA TCGCCAGCGG
CATCAGCACC TTGTCGCCTT TTTTTGACAA CATTAAGTAA
TTCGTAAGAC GGCTGTACCT TCGGTAGTGT TTGCCGTACT
ACTTGGACTT AGCGGTCGCC GTAGTCGTGG AACAGCGGAA
GCGTATAATA TTTGCCCATG GGGGTGGGCG AAGAACTCCA
GCATGAGATC CCCGCGCTGG AGGATCATCC AGCCGGCGTC
CCGGAAAACG ATTCCGAAGC CGCATATTAT AAACGGGTAC
CCCCACCCGC TTCTTGAGGT CGTACTCTAG GGGCGCGACC
TCCTAGTAGG TCGGCCGCAG GGCCTTTTGC TAAGGCTTCG
CCAACCTTTC ATAGAAGGCG GCGGTGGAAT CGAAATCTCG
TGATGGCAGG TTGGGCGTCG CTTGGTCGGT CATTTCGAAC
CCCAGAGTCC CGCTCAGAAG GGTTGGAAAG TATCTTCCGC
CGCCACCTTA GCTTTAGAGC ACTACCGTCC AACCCGCAGC
GAACCAGCCA GTAAAGCTTG GGTCTCAGG GCGAGTCTTC
AACTCGTCAA GAAGGCGATA GAAGGCGATG CGCTGCGAAT
CGGGAGCGGC GATACCGTAA AGCACGAGGA AGCGGTCAGC
```

```
CCATTCGCCG CCAAGCTCTT TTGAGCAGTT CTTCCGCTAT
CTTCCGCTAC GCGACGCTTA GCCCTCGCCG CTATGGCATT
TCGTGCTCCT TCGCCAGTCG GGTAAGCGGC GGTTCGAGAA
CAGCAATATC ACGGGTAGCC AACGCTATGT CCTGATAGCG
GTCCGCCACA CCCAGCCGGC CACAGTCGAT GAATCCAGAA
AAGCGGCCAT TTTCCACCAT GTCGTTATAG TGCCCATCGG
TTGCGATACA GGACTATCGC CAGGCGGTGT GGGTCGGCCG
GTGTCAGCTA CTTAGGTCTT TTCGCCGGTA AAAGGTGGTA
GATATTCGGC AAGCAGGCAT CGCCATGGGT CACGACGAGA
TCCTCGCCGT CGGGCATGCG CGCCTTGAGC CTGGCGAACA
GTTCGGCTGG CGCGAGCCCC CTATAAGCCG TTCGTCCGTA
GCGGTACCCA GTGCTGCTCT AGGAGCGGCA GCCCGTACGC
GCGGAACTCG GACCGCTTGT CAAGCCGACC GCGCTCGGGG
TGATGCTCTT CGTCCAGATC ATCCTGATCG ACAAGACCGG
CTTCCATCCG AGTACGTGCT CGCTCGATGC GATGTTTCGC
TTGGTGGTCG AATGGGCAGG ACTACGAGAA GCAGGTCTAG
TAGGACTAGC TGTTCTGGCC GAAGGTAGGC TCATGCACGA
GCGAGCTACG CTACAAAGCG AACCACCAGC TTACCCGTCC
TAGCCGGATC AAGCGTATGC AGCCGCCGCA TTGCATCAGC
CATGATGGAT ACTTTCTCGG CAGGAGCAAG GTGAGATGAC
AGGAGATCCT GCCCCGGCAC ATCGGCCTAG TTCGCATACG
TCGGCGGCGT AACGTAGTCG GTACTACCTA TGAAAGAGCC
GTCCTCGTTC CACTCTACTG TCCTCTAGGA CGGGGCCGTG
TTCGCCCAAT AGCAGCCAGT CCCTTCCCGC TTCAGTGACA
ACGTCGAGCA CAGCTGCGCA AGGAACGCCC GTCGTGGCCA
GCCACGATAG CCGCGCTGCC AAGCGGGTTA TCGTCGGTCA
GGGAAGGGCG AAGTCACTGT TGCAGCTCGT GTCGACGCGT
TCCTTGCGGG CAGCACCGGT CGGTGCTATC GGCGCGACGG
TCGTCCTGCA GTTCATTCAG GGCACCGGAC AGGTCGGTCT
TGACAAAAAG AACCGGGCGC CCCTGCGCTG ACAGCCGGAA
CACGGCGGCA TCAGAGCAGC AGCAGGACGT CAAGTAAGTC
CCGTGGCCTG TCCAGCCAGA ACTGTTTTTC TTGGCCCGCG
GGGACGCGAC TGTCGGCCTT GTGCCGCCGT AGTCTCGTCG
CGATTGTCTG TTGTGCCCAG TCATAGCCGA ATAGCCTCTC
CACCCAAGCG GCCGGAGAAC CTGCGTGCAA TCCATCTTGT
TCAATCATGC GAAACGATCC GCTAACAGAC AACACGGGTC
AGTATCGGCT TATCGGAGAG GTGGGTTCGC CGGCCTCTTG
GACGCACGTT AGGTAGAACA AGTTAGTACG CTTTGCTAGG
TCATCCTGTC TCTTGATCAG ATCTTGATCC CCTGCGCCAT
CAGATCCTTG GCGGCAAGAA AGCCATCCAG TTTACTTTGC
AGGGCTTCCC AACCTTACCA AGTAGGACAG AGAACTAGTC
TAGAACTAGG GGACGCGGTA GTCTAGGAAC CGCCGTTCTT
TCGGTAGGTC AAATGAAACG TCCCGAAGGG TTGGAATGGT
GAGGGCGCCC CAGCTGGCAA TTCCGGTTCG CTTGCTGTCC
ATAAAACCGC CCAGTCTAGC TATCGCCATG TAAGCCCACT
GCAAGCTACC TGCTTTCTCT CTCCCGCGGG GTCGACCGTT
AAGGCCAAGC GAACGACAGG TATTTTGGCG GGTCAGATCG
ATAGCGGTAC ATTCGGGTGA CGTTCGATGG ACGAAAGAGA
TTGCGCTTGC GTTTTCCCTT GTCCAGATAG CCCAGTAGCT
GACATTCATC CCAGGTGGCA CTTTTCGGGG AAATGTGCGC
GCCCGCGTTC CTGCTGGCGC AACGCGAACG CAAAAGGGAA
CAGGTCTATC GGGTCATCGA CTGTAAGTAG GGTCCACCGT
GAAAAGCCCC TTTACACGCG CGGGCGCAAG GACGACCGCG
TGGGCCTGTT TCTGGCGCTG GACTTCCCGC TGTTCCGTCA
GCAGCTTTTC GCCCACGGCC TTGATGATCG CGGCGGCCTT
GGCCTGCATA TCCCGATTCA ACCCGGACAA AGACCGCGAC
CTGAAGGGCG ACAAGGCAGT CGTCGAAAAG CGGGTGCCGG
AACTACTAGC GCCGCCGGAA CCGGACGTAT AGGGCTAAGT
ACGGCCCCAG GGCGTCCAGA ACGGGCTTCA GGCGCTCCCG
AAGGTCTCGG GCCGTCTCTT GGGCTTGATC GGCCTTCTTG
CGCATCTCAC GCGCTCCTGC TGCCGGGGTC CCGCAGGTCT
TGCCCGAAGT CCGCGAGGGC TTCCAGAGCC CGGCAGAGAA
CCCGAACTAG CCGGAAGAAC GCGTAGAGTG CGCGAGGACG
GGCGGCCTGT AGGGCAGGCT CATACCCCTG CCGAACCGCT
TTTGTCAGCC GGTCGGCCAC GGCTTCCGGC GTCTCAACGC
GCTTTGAGAT TCCCAGCTTT CCGCCGGACA TCCCGTCCGA
GTATGGGAC GGCTTGGCGA AAACAGTCGG CCAGCCGGTG
CCGAAGGCCG CAGAGTTGCG CGAAACTCTA AGGGTCGAAA
TCGGCCAATC CCTGCGGTGC ATAGGCGCGT GGCTCGACCG
CTTGCGGGCT GATGGTGACG TGGCCCACTG GTGGCCGCTC
CAGGGCCTCG TAGAACGCCT AGCCGGTTAG GGACGCCACG
TATCCGCGCA CCGAGCTGGC GAACGCCCGA CTACCACTGC
ACCGGGTGAC CACCGGCGAG GTCCGGAGC ATCTTGCGGA
GAATGCGCGT GTGACGTGCC TTGCTGCCCT CGATGCCCCG
TTGCAGCCCT AGATCGGCCA CAGCGGCCGC AAACGTGGTC
TGGTCGCGGG TCATCTGCGC CTTACGCGCA CACTGCACGG
AACGACGGGA GCTACGGGGC AACGTCGGGA TCTAGCCGGT
GTCGCCGGCG TTTGCACCAG ACCAGCGCCC AGTAGACGCG
TTTGTTGCCG ATGAACTCCT TGGCCGACAG CCTGCCGTCC
TGCGTCAGCG GCACCACGAA CGCGGTCATG TGCGGGCTGG
```

```
TTTCGTCACG GTGGATGCTG AAACAACGGC TACTTGAGGA
ACCGGCTGTC GGACGGCAGG ACGCAGTCGC CGTGGTGCTT
GCGCCAGTAC ACGCCCGACC AAAGCAGTGC CACCTACGAC
GCCGTCACGA TGCGATCCGC CCCGTACTTG TCCGCCAGCC
ACTTGTGCGC CTTCTCGAAG AACGCCGCCT GCTGTTCTTG
GCTGGCCGAC TTCCACCATT CGGCAGTGCT ACGCTAGGCG
GGGCATGAAC AGGCGGTCGG TGAACACGCG GAAGAGCTTC
TTGCGGCGGA CGACAAGAAC CGACCGGCTG AAGGTGGTAA
CCGGGCTGGC CGTCATGACG TACTCGACCG CCAACACAGC
GTCCTTGCGC CGCTTCTCTG GCAGCAACTC GCGCAGTCGG
CCCATCGCTT CATCGGTGCT GGCCCGACCG GCAGTACTGC
ATGAGCTGGC GGTTGTGTCG CAGGAACGCG GCGAAGAGAC
CGTCGTTGAG CGCGTCAGCC GGGTAGCGAA GTAGCCACGA
GCTGGCCGCC CAGTGCTCGT TCTCTGGCGT CCTGCTGGCG
TCAGCGTTGG GCGTCTCGCG CTCGCGGTAG GCGTGCTTGA
GACTGGCCGC CACGTTGCCC CGACCGGCGG GTCACGAGCA
AGAGACCGCA GGACGACCGC AGTCGCAACC CGCAGAGCGC
GAGCGCCATC CGCACGAACT CTGACCGGCG GTGCAACGGG
ATTTTCGCCA GCTTCTTGCA TCGCATGATC GCGTATGCCG
CCATGCCTGC CCCTCCCTTT TGGTGTCCAA CCGGCTCGAC
GGGGGCAGCG CAAGGCGGTG TAAAAGCGGT CGAAGAACGT
AGCGTACTAG CGCATACGGC GGTACGGACG GGGAGGGAAA
ACCACAGGTT GGCCGAGCTG CCCCCGTCGC GTTCCGCCAC
CCTCCGGCGG GCCACTCAAT GCTTGAGTAT ACTCACTAGA
CTTTGCTTCG CAAAGTCGTG ACCGCCTACG GCGGCTGCGG
CGCCCTACGG GCTTGCTCTC GGAGGCCGCC CGGTGAGTTA
CGAACTCATA TGAGTGATCT GAAACGAAGC GTTTCAGCAC
TGGCGGATGC CGCCGACGCC GCGGGATGCC CGAACGAGAG
CGGGCTTCGC CCTGCGCGGT CGCTGCGCTC CCTTGCCAGC
CCGTGGATAT GTGGACGATG GCCGCGAGCG GCCACCGGCT
GGCTCGCTTC GCTCGGCCCG GCCCGAAGCG GGACGCGCCA
GCGACGCGAG GGAACGGTCG GGCACCTATA CACCTGCTAC
CGGCGCTCGC CGGTGGCCGA CCGAGCGAAG CGAGCCGGGC
TGGACAACCC TGCTGGACAA GCTGATGGAC AGGCTGCGCC
TGCCCACGAG CTTGACCACA GGGATTGCCC ACCGGCTACC
CAGCCTTCGA CCACATACCC ACCTGTTGGG ACGACCTGTT
CGACTACCTG TCCGACGCGG ACGGGTGCTC GAACTGGTGT
CCCTAACGGG TGGCCGATGG GTCGGAAGCT GGTGTATGGG
ACCGGCTCCA ACTGCGCGGC CTGCGGCCTT GCCCCATCAA
TTTTTTTAAT TTTCTCTGGG GAAAAGCCTC CGGCCTGCGG
CCTGCGCGCT TCGCTTGCCG TGGCCGAGGT TGACGCGCCG
GACGCCGGAA CGGGGTAGTT AAAAAAATTA AAAGAGACCC
CTTTTCGGAG GCCGGACGCC GGACGCGCGA AGCGAACGGC
GTTGGACACC AAGTGGAAGG CGGGTCAAGG CTCGCGCAGC
GACCGCGCAG CGGCTTGGCC TTGACGCGCC TGGAACGACC
CAAGCCTATG CGAGTGGGGG CAACCTGTGG TTCACCTTCC
GCCCAGTTCC GAGCGCGTCG CTGGCGCGTC GCCGAACCGG
AACTGCGCGG ACCTTGCTGG GTTCGGATAC GCTCACCCCC
CAGTCGAAGG CGAAGCCCGC CCGCCTGCCC CCGAGCCTC
ACGGCGGCGA GTGCGGGGGT TCCAAGGGGG CAGCGCCACC
TTGGGCAAGG CCGAAGGCCG GTCAGCTTCC GCTTCGGGCG
GGCGGACGGG GGGCTCGGAG TGCCGCCGCT CACGCCCCCA
AGGTTCCCCC GTCGCGGTGG AACCCGTTCC GGCTTCCGGC
CGCAGTCGAT CAACAAGCCC GGAGGGGCC ACTTTTTGCC
GGAGGCGTCA GCTAGTTGTT CGGGGCCTCC CCGGTGAAAA
ACGGCCTC
```

SEQ ID: 03
```
GGGGAGCCGC GCCGAAGGCG TGGGGGAACC CCGCAGGGGT
GCCCTTCTTT GGGCACCAAA GAACTAGATA TAGGGCGAAA
TGCGAAAGAC TTAAAAATCA CCCCTCGGCG CGGCTTCCGC
ACCCCCTTGG GGCGTCCCCA CGGGAAGAAA CCCGTGGTTT
CTTGATCTAT ATCCCGCTTT ACGCTTTCTG AATTTTTAGT
ACAACTTAAA AAAGGGGGGT ACGCAACAGC TCATTGCGGC
ACCCCCCGCA ATAGCTCATT GCGTAGGTTA AAGAAAATCT
GTAATTGACT GCCACTTTTA TGTTGAATTT TTTCCCCCCA
TGCGTTGTCG AGTAACGCCG TGGGGGGCGT TATCGAGTAA
CGCATCCAAT TTCTTTTAGA CATTAACTGA CGGTGAAAAT
CGCAACGCAT AATTGTTGTC GCGCTGCCGA AAAGTTGCAG
CTGATTGCGC ATGGTGCCGC AACCGTGCGG CACCCTACCG
CATGGAGATA AGCATGGCCA GCGTTGCGTA TTAACAACAG
CGCGACGGCT TTTCAACGTC GACTAACGCG TACCACGGCG
TTGGCACGCC GTGGGATGGC GTACCTCTAT TCGTACCGGT
CGCAGTCCAG AGAAATCGGC ATTCAAGCCA AGAACAAGCC
CGGTCACTGG GTGCAAACGG AACGCAAAGC GCATGAGGCG
TGGGCCGGGC TTATTGCGAG CGTCAGGTC TCTTTAGCCG
TAAGTTCGGT TCTTGTTCGG GCCAGTGACC CACGTTTGCC
TTGCGTTTCG CGTACTCCGC ACCCGGCCCG AATAACGCTC
GAAACCCACG GCGGCAATGC TGCTGCATCA CCTCGTGGCG
CAGATGGGCC ACCAGAACGC CGTGGTGGTC AGCCAGAAGA
CACTTTCCAA GCTCATCGGA CTTTGGGTGC GCGCCGTTACG
ACGACGTAGT GGAGCACCGC GTCTACCCGG TGGTCTTGCG
```

```
GCACCACCAG TCGGTCTTCT GTGAAAGGTT CGAGTAGCCT
CGTTCTTTGC GGACGGTCCA ATACGCAGTC AAGGACTTGG
TGGCCGAGCG CTGGATCTCC GTCGTGAAGC TCAACGGCCC
CGGCACCGTG TCGGCCTACG GCAAGAAACG CCTGCCAGGT
TATGCGTCAG TTCCTGAACC ACCGGCTCGC GACCTAGAGG
CAGCACTTCG AGTTGCCGGG GCCGTGGCAC AGCCGGATGC
TGGTCAATGA CCGCGTGGCG TGGGGCCAGC CCCGCGACCA
GTTGCGCCTG TCGGTGTTCA GTGCCGCCGT GGTGGTTGAT
CACGACGACC AGGACGAATC ACCAGTTACT GGCGCACCGC
ACCCCGGTCG GGGCGCTGGT CAACGCGGAC AGCCACAAGT
CACGGCGGCA CCACCAACTA GTGCTGCTGG TCCTGCTTAG
GCTGTTGGGG CATGGCGACC TGCGCCGCAT CCCGACCCTG
TATCCGGGCG AGCAGCAACT ACCGACCGGC CCCGGCGAGG
AGCCGCCCAG CCAGCCCGGC CGACAACCCC GTACCGCTGG
ACGCGGCGTA GGGCTGGGAC ATAGGCCCGC TCGTCGTTGA
TGGCTGGCCG GGGCCGCTCC TCGGCGGGTC GGTCGGGCCG
ATTCCGGGCA TGGAACCAGA CCTGCCAGCC TTGACCGAAA
CGGAGGAATG GGAACGGCGC GGGCAGCAGC GCCTGCCGAT
GCCCGATGAG CCGTGTTTTC TAAGGCCCGT ACCTTGGTCT
GGACGGTCGG AACTGGCTTT GCCTCCTTAC CCTTGCCGCG
CCCGTCGTCG CGGACGGCTA CGGGCTACTC GGCACAAAAG
TGGACGATGG CGAGCCGTTG GAGCCGCCGA CACGGGTCAC
GCTGCCGCGC CGGTAGCACT TGGGTTGCGC AGCAACCCGT
AAGTGCGCTG TTCCAGACTA ACCTGCTACC GCTCGGCAAC
CTCGGCGGCT GTGCCCAGTG CGACGGCGCG GCCATCGTGA
ACCCAACGCG TCGTTGGGCA TTCACGCGAC AAGGTCTGAT
TCGGCTGTAG CCGCCTCGCC GCCCTATACC TTGTCTGCCT
CCCCGCGTTG CGTCGCGGTG CATGGAGCCG GGCCACCTCG
ACCTGAATGG AAGCCGGCGG AGCCGACATC GGCGGAGCGG
CGGGATATGG AACAGACGGA GGGGCGCAAC GCAGCGCCAC
GTACCTCGGC CCGGTGGAGC TGGACTTACC TTCGGCCGCC
CACCTCGCTA ACGGATTCAC CGTTTTTATC AGGCTCTGGG
AGGCAGAATA AATGATCATA TCGTCAATTA TTACCTCCAC
GGGGAGAGCC TGAGCAAACT GTGGAGCGAT TGCCTAAGTG
GCAAAAATAG TCCGAGACCC TCCGTCTTAT TTACTAGTAT
AGCAGTTAAT AATGGAGGTG CCCCTCTCGG ACTCGTTTGA
GGCCTCAGGC ATTTGAGAAG CACACGGTCA CACTGCTTCC
GGTAGTCAAT AAACCGGTAA ACCAGCAATA GACATAAGCG
GCTATTTAAC GACCCTGCCC CCGGAGTCCG TAAACTCTTC
GTGTGCCAGT GTGACGAAGG CCATCAGTTA TTTGGCCATT
TGGTCGTTAT CTGTATTCGC CGATAAATTG CTGGGACGGG
TGAACCGACG ACCGGGTCGA ATTTGCTTTC GAATTTCTGC
CATTCATCCG CTTATTATCA CTTATTCAGG CGTAGCACCA
GGCGTTTAAG GGCACCAATA ACTTGGCTGC TGGCCCAGCT
TAAACGAAAG CTTAAAGACG GTAAGTAGGC GAATAATAGT
GAATAAGTCC GCATCGTGGT CCGCAAATTC CCGTGGTTAT
ACTGCCTTAA AAAAATTACG CCCCGCCCTG CCACTCATCG
CAGTCGGCCT ATTGGTTAAA AAATGAGCTG ATTTAACAAA
AATTTAACGC GAATTTTAAC TGACGGAATT TTTTTAATGC
GGGGCGGGAC GGTGAGTAGC GTCAGCCGGA TAACCAATTT
TTTACTCGAC TAAATTGTTT TTAAATTGCG CTTAAAATTG
AAAATATTAA CGCTTACAAT TTCCATTCGC CATTCAGGCT
GCGCAACTGT TGGGAAGGGC GATCGGTGCG GGCCTCTTCG
CTATTACGCC AGCTGGCGAA TTTTATAATT GCGAATGTTA
AAGGTAAGCG GTAAGTCCGA CGCGTTGACA ACCCTTCCCG
CTAGCCACGC CCGGAGAAGC GATAATGCGG TCGACCGCTT
AGGGGGATGT GCTGCAAGGC GATTAAGTTG GGTAACGCCA
GGGTTTTCCC AGTCACGACG TTGTAAAACG ACGGCCAGTG
AGCGCGCGTA ATACGACTCA TCCCCCTACA CGACGTTCCG
CTAATTCAAC CCATTGCGGT CCCAAAAGGG TCAGTGCTGC
AACATTTTGC TGCCGGTCAC TCGCGCGCAT TATGCTGAGT
CTATAGGGCG AATTGGAGCT CCACCGCGGT GGCGGCCGCT
CTAGAACTAG TGGATCCCCC GGGCTGCAGG AATTCGATAT
CAAGCTTATC GATACCGTCG GATATCCCGC TTAACCTCGA
GGTGGCGCCA CCGCCGGCGA GATCTTGATC ACCTAGGGGG
CCCGACGTCC TTAAGCTATA GTTCGAATAG CTATGGCAGC
ACGGGCCCGG GATCCGATGC TCTTCCGCTA AGATCTTTTA
CTAGTTCAGT CCATCTCGCC GTGTATGCGG GCCTGACGGA
TCAACGTTCC CACCGAGCCA TGCCCGGGCC CTAGGCTACG
AGAAGGCGAT TCTAGAAAAT GATCAAGTCA GGTAGAGCGG
CACATACGCC CGGACTGCCT AGTTGCAAGG GTGGCTCGGT
GTCGAGATGT TCATCTGGTC GGCGATCTGC CGGTACTTCA
AACCTTGTTT GCGCAGTTCC ACAGCCTTCT TGCGGCGTTC
CTGCGCACGA GCGATGTAGT CAGCTCTACA AGTAGACCAG
CCGCTAGACG GCCATGAAGT TTGGAACAAA CGCGTCAAGG
TGTCGGAAGA ACGCCGCAAG GACGCGTGCT CGCTACATCA
CGCCTCGGTC TTCGGCGACG AGCCGTTTGA TGGTGCTTTT
CGAGACGCCG AACTTGTCAG CCAACTCCTG CGCGGTCTGC
GTGCGACGCA TCACGCGTTC GCGGAGCCAG AAGCCGCTGC
TCGGCAAACT ACCACGAAAA GCTCTGCGGC TTGAACAGTC
```

-continued

```
GGTTGAGGAC GCGCCAGACG CACGCTGCGT AGTGCGCAAG
TGCAGCACCC ATCAGTCCGT CCCCTCTGCT GCTGCGAACA
GTGCCGATCG ATCGACCTTC TTGAGCTTCG GCCGCGGCGC
GGTGGCGTTC TTCCGTACCG ACGTCGTGGG TAGTCAGGCA
GGGGAGACGA CGACGCTTGT CACGGCTAGC TAGCTGGAAG
AACTCGAAGC CGGCGCCGCG CCACCGCAAG AAGGCATGGC
CTTCCGTTTT TGCGCTGCTG CTCACTTTGC CGCGGCGTGC
CTGGATTTTC GAGAACTCGG CGGCGGTGAA GGTGCGGTGG
GTCCAGTGGG CGACTGATTT GAAGGCAAAA ACGCGACGAC
GAGTGAAACG GCGCCGCACG GACCTAAAAG CTCTTGAGCC
GCCGCCACTT CCACGCCACC CAGGTCACCC GCTGACTAAA
GCCGATCTGC TCGGCCTCGG CCCGACTCAT GGGGCCGATC
CCGTCGTTGG CGTCGAGGGT GAAGTTGGTC AGGGCGGTGA
AGTCGGTGAC CATCTGCCGC CGGCTAGACG AGCCGGAGCC
GGGCTGAGTA CCCCGGCTAG GGCAGCAACC GCAGCTCCCA
CTTCAACCAG TCCCGCCACT TCAGCCACTG GTAGACGGCG
CACACAGTGA TCGACGGGTA GTTCTGTTTC CGGATCTCGC
GGTAGGCCCA TTCCCGGGTG CGGTCGAACA GTTCGACGTT
CCGGCCCGTT TCGGTCCTGA GTGTGTCACT AGCTGCCCAT
CAAGACAAAG GCCTAGAGCG CCATCCGGGT AAGGGCCCAC
GCCAGCTTGT CAAGCTGCAA GGCCGGGCAA AGCCAGGACT
CCTGTGTCTT GCGGCCGTAG TCCGGTGGGG CGGGGAAACG
GTCACCGAGC GCTTTTGCGA GGCCTTTGAG CGAGTACGGA
TCCGAGGGAC CCCAGACCGT GGACACAGAA CGCCGGCATC
AGGCCACCCC GCCCCTTTGC CAGTGGCTCG CGAAAACGCT
CCGGAAACTC GCTCATGCCT AGGCTCCCTG GGGTCTGGCA
CGTCCAGTGC GGGTGGATCG GGTTCTGGGT GAGCTGCTGC
GCGTAGCCCT GATCGGCGCC GACCACCGAG GCGATCAGCC
CCTGGTTCAC CCGGTCGTAG GCAGGTCACG CCCCACCTAGC
CCAAGACCCA CTCGACGACG CGCATCGGGA CTAGCCGCGG
CTGGTGGCTC CGCTAGTCGG GGACCAAGTG GGCCAGCATC
AGCCGCAGCG GGCCCTGTCG GGCTGCCTGG AGGGTGTAGA
CCGGGCTTTC GAGCAGCCAC ACAGGTGCG CGTGCTCGGT
CGCGGGATTG ATCGTCATCA TCGGCGTCGC CCGGGACAGC
CCGACGGACC TCCCACATCT GGCCCGAAAG CTCGTCGGTG
GTGTCCACGC GCACGAGCCA GCGCCCTAAC TAGCAGTAGT
CGGTCGGATC GGGCAGATCC GCGTTACGTG CGGCCCACTG
CGCCTGGTCG TCGTCCACGT CGAGCACCAA GCCCAACCTG
ATCGACGGGG TGCGGGCCGC GCCAGCCTAG CCCGTCTAGG
CGCAATGCAC GCCGGGTGAC GCGGACCAGC AGCAGGTGCA
GCTCGTGGTT CGGGTTGGAC TAGCTGCCCC ACGCCCGGCG
AATGTAGCGG CGGGTGAGCG CCTCCGCGCG CGGCTGCGGC
CACTGCCCGT CCCGGACGTA GTCATCCGTC GCGTGCGGGT
ATTTGAACCG CCAGCGGTCC TTACATCGCC GCCCACTCGC
GGAGGCGCGC GCCGACGCCG GTGACGGGCA GGGCCTGCAT
CAGTAGGCAG CGCACGCCCA TAAACTTGGC GGTCGCCAGG
AACCAGGCGT CAACAGCAGC GGTCATGACC GCCAAGCTAG
GGCCGGATCT GTACCGATCG GGGGAGGCGC GCCGCAAATT
ATTTAAGAGT CTCGCTAGCA TTGGTCCGCA GTTGTCGTCG
CCAGTACTGG CGGTTCGATC CCGGCCTAGA CATGGCTAGC
CCCCTCCGCG CGGCGTTTAA TAAATTCTCA GAGCGATCGT
AACCATGTCA GGTGTTGCGG TGGGTTCCGG GTAAACCTCC
ACCCGAATTA TTTAAGAGTC TCGCTAGCTA AGCCCTATCT
GATGCTGCGC GGGGGGTCCT TTGGTACAGT CCACAACGCC
ACCCAAGGCC CATTTGGAGG TGGGCTTAAT AAATTCTCAG
AGCGATCGAT TCGGGATAGA CTACGACGCG CCCCCCAGGA
TCGCACTGAA TCTCAAAGGT GGCCGGCTGA ATTTCGTCGC
GCGAAAACCT CCCTGGACAG TTCTGGAATT CAGCAAGAGG
TGTGTCTGAA CTTCGGTGTT AGCGTGACTT AGAGTTTCCA
CCGGCCGACT TAAAGCAGCG CGCTTTTGGA GGGACCTGTC
AAGACCTTAA GTCGTTCTCC ACACAGACTT GAAGCCACAA
TTTTTGGGGG GTGACTCCAG CGGGGTGGGC ACAACGCGAA
CAGAGACCTT GTGTGTACGA CGGCGGGAGG TAAGTCGGGT
ACGGCTCGGA CTGCGGTAGA AAAAACCCCC CACTGAGGTC
GCCCCACCCG TGTTGCGCTT GTCTCTGGAA CACACATGCT
GCCGCCCTCC ATTCAGCCCA TGCCGAGCCT GACGCCATCT
GCAACCGTCG AATCGATTTC GAGCAGAGCG AGCAGAGCAA
GATATTCCAA AACTCCGGGG TTCCTCGGCG GCCTCCCCCG
TCTGTTTGCT CAACCGAGGG CGTTGGCAGC TTAGCTAAAG
CTCGTCTCGC TCGTCTCGTT CTATAAGGTT TTGAGGCCCC
AAGGAGCCGC CGGAGGGGGC AGACAAACGA GTTGGCTCCC
AGACCTGGCG GTCCCGCGTT TCCGGACGCG CGGGACCGCC
TACCGCTCGA GAGCGGAAGA GCATCTAGAT GCATTCGCGA
GGTACCCAGC TTTTGTTCCC TCTGGACCGC CAGGGCGCAA
AGGCCTGCGC GCCCTGGCGG ATGGCGAGCT CTCGCCTTCT
CGTAGATCTA CGTAAGCGCT CCATGGGTCA AAAACAAGGG
TTTAGTGAGG GTTAATTGCG CGCTTGGCGT AATCATGGTC
ATAGCTGTTT CCTGTGTGAA ATTGTTATCC GCTCACAATT
CCACACAACA TACGAGCCGG AAATCACTCC CAATTAACGC
GCGAACCGCA TTAGTACCAG TATCGACAAA GGACACACTT
```

```
TAACAATAGG CGAGTGTTAA GGTGTGTTGT ATGCTCGGCC
AAGCATAAAG TGTAAAGCCT GGGGTGCCTA ATGAGTGAGC
TAACTCACAT TAATTGCGTT GCGCTCACTG CCCGCTTTCC
AGTCGGGAAA CCTGTCGTGC TTCGTATTTC ACATTTCGGA
CCCCACGGAT TACTCACTCG ATTGAGTGTA ATTAACGCAA
CGCGAGTGAC GGGCGAAAGG TCAGCCCTTT GGACAGCACG
CAGCTGCATT AATGAATCGG CCAACGCGCG GGGAGAGGCG
GTTTGCGTAT TGGGCGCATG CATAAAAACT GTTGTAATTC
ATTAAGCATT CTGCCGACAT GTCGACGTAA TTACTTAGCC
GGTTGCGCGC CCCTCTCCGC CAAACGCATA ACCCGCGTAC
GGAAGCCATC ACAAACGGCA TGATGAACCT GAATCGCCAG
CGGCATCAGC ACCTTGTCGC CTTGCGTATA ATATTTGCCC
ATGGGGGTGG GCGAAGAACT CCTTCGGTAG TGTTTGCCGT
ACTACTTGGA CTTAGCGGTC GCCGTAGTCG TGGAACAGCG
GAACGCATAT TATAAACGGG TACCCCCACC CGCTTCTTGA
CCAGCATGAG ATCCCCGCGC TGGAGGATCA TCCAGCCGGC
GTCCCGGAAA ACGATTCCGA AGCCCAACCT TTCATAGAAG
GCGGCGGTGG AATCGAAATC GGTCGTACTC TAGGGGCGCG
ACCTCCTAGT AGGTCGGCCG CAGGGCCTTT TGCTAAGGCT
TCGGGTTGGA AAGTATCTTC CGCCGCCACC TTAGCTTTAG
TCGTGATGGC AGGTTGGGCG TCGCTTGGTC GGTCATTTCG
AACCCCAGAG TCCCGCTCAG AAGAACTCGT CAAGAAGGCG
ATAGAAGGCG ATGCGCTGCG AGCACTACCG TCCAACCCGC
AGCGAACCAG CCAGTAAAGC TTGGGGTCTC AGGGCGAGTC
TTCTTGAGCA GTTCTTCCGC TATCTTCCGC TACGCGACGC
AATCGGGAGC GGCGATACCG TAAAGCACGA GGAAGCGGTC
AGCCCATTCG CCGCCAAGCT CTTCAGCAAT ATCACGGGTA
GCCAACGCTA TGTCCTGATA TTAGCCCTCG CCGCTATGGC
ATTTCGTGCT CCTTCGCCAG TCGGGTAAGC GGCGGTTCGA
GAAGTCGTTA TAGTGCCCAT CGGTTGCGAT ACAGGACTAT
GCGGTCCGCC ACACCCAGCC GGCCACAGTC GATGAATCCA
GAAAAGCGGC CATTTTCCAC CATGATATTC GGCAAGCAGG
CATCGCCATG GGTCACGACG CGCCAGGCGG TGTGGGTCGG
CCGGTGTCAG CTACTTAGGT CTTTTCGCCG GTAAAGGTG
GTACTATAAG CCGTTCGTCC GTAGCGGTAC CCAGTGCTGC
AGATCCTCGC CGTCGGGCAT GCGCGCCTTG AGCCTGGCGA
ACAGTTCGGC TGGCGCGAGC CCCTGATGCT CTTCGTCCAG
ATCATCCTGA TCGACAAGAC TCTAGGAGCG CAGCCCGTA
CGCGCGGAAC TCGGACCGCT TGTCAAGCCG ACCGCGCTCG
GGGACTACGA GAAGCAGGTC TAGTAGGACT AGCTGTTCTG
CGGCTTCCAT CCGAGTACGT GCTCGCTCGA TGCGATGTTT
CGCTTGGTGG TCGAATGGGC AGGTAGCCGA ATCAAGCGTA
TGCAGCCGCC GCATTGCATC GCCGAAGGTA GGCTCATGCA
CGAGCGAGCT ACGCTACAAA GCGAACCACC AGCTTACCCG
TCCATCGGCC TAGTTCGCAT ACGTCGGCGG CGTAACGTAG
AGCCATGATG GATACTTTCT CGGCAGGAGC AAGGTGAGAT
GACAGGAGAT CCTGCCCCGG CACTTCGCCC AATAGCAGCC
AGTCCCTTCC CGCTTCAGT TCGGTACTAC CTATGAAAGA
GCCGTCCTCG TTCCACTCTA CTGTCCTCTA GGACGGGGCC
GTGAAGCGGG TTATCGTCGG TCAGGGAAGG GCGAAGTCAC
ACAACGTCGA GCACAGCTGC GCAAGGAACG CCCGTCGTGG
CCAGCCACGA TAGCCGCGCT GCCTCGTCCT GCAGTTCATT
CAGGGCACCG GACAGGTCGG TGTTGCAGCT CGTGTCGACG
CGTTCCTTGC GGGCAGCACC GGTCGGTGCT ATCGGCGCGA
CGGAGCAGGA CGTCAAGTAA GTCCCGTGGC CTGTCCAGCC
TCTTGACAAA AGAACCGGG CGCCCCTGCG CTGACAGCCG
GAACACGGCG GCATCAGAGC AGCCGATTGT CTGTTGTGCC
CAGTCATAGC CGAATAGCCT AGAACTGTTT TTCTTGGCCC
GCGGGGACGC GACTGTCGGC CTTGTGCCGC CGTAGTCTCG
TCGGCTAACA GACAACACGG GTCAGTATCG GCTTATCGGA
CTCCACCCAA GCGGCCGGAG AACCTGCGTG CAATCCATCT
TGTTCAATCA TGCGAAACGA TCCTCATCCT GTCTCTTGAT
CAGATCTTGA TCCCCTGCGC GAGGTGGGTT CGCCGGCCTC
TTGGACGCAC GTTAGGTAGA ACAAGTTAGT ACGCTTTGCT
AGGAGTAGGA CAGAGAACTA GTCTAGAACT AGGGGACGCG
CATCAGATCC TTGGCGGCAA GAAAGCCATC CAGTTTACTT
TGCAGGGCTT CCCAACCTTA CCAGAGGGCC CCCCAGCTGG
CAATTCCGGT TCGCTTGCTG GTAGTCTAGG AACCGCCGTT
CTTTCGGTAG GTCAAATGAA ACGTCCCGAA GGGTTGGAAT
GGTCTCCCGC GGGGTCGACC GTTAAGGCCA AGCGAACGAC
TCCATAAAAC CGCCCAGTCT AGCTATCGCC ATGTAAGCCC
ACTGCAAGCT ACCTGCTTTC TCTTTGCGCT TGCGTTTTCC
CTTGTCCAGA TAGCCCAGTA AGGTATTTTG GCGGGTCAGA
TCGATAGCGG TACATTCGGG TGACGTTCGA TGGACGAAAG
AGAAACGCGA ACGCAAAAGG GAACAGGTCT ATCGGGTCAT
GCTGACATTC ATCCCAGGTG GCACTTTTCG GGGAAATGTG
CGCGCCCGCG TTCCTGCTGG CGCTGGGCCT GTTTCTGGCG
CTGGACTTCC CGCTGTTCCG CGACTGTAAG TAGGGTCCAC
CGTGAAAAGC CCCTTTACAC GCGCGGGCGC AAGGACGACC
GCGACCCGGA CAAAGACCGC GACCTGAAGG GCGACAAGGC
```

```
TCAGCAGCTT TTCGCCCACG GCCTTGATGA TCGCGGCGGC
CTTGGCCTGC ATATCCCGAT TCAACGGCCC CAGGGCGTCC
AGAACGGGCT TCAGGCGCTC AGTCGTCGAA AAGCGGGTGC
CGGAACTACT AGCGCCGCCG GAACCGGACG TATAGGGCTA
AGTTGCCGGG GTCCCGCAGG TCTTGCCCGA AGTCCGCGA
CCGAAGGTCT CGGGCCGTCT CTTGGGCTTG ATCGGCCTTC
TTGCGCATCT CACGCGCTCC TGCGGCGGCC TGTAGGGCAG
GCTCATACCC CTGCCGAACC GGCTTCCAGA GCCCGGCAGA
GAACCCGAAC TAGCCGGAAG AACGCGTAGA GTGCGCGAGG
ACGCCGCCGG ACATCCCGTC CGAGTATGGG ACGGCTTGG
GCTTTTGTCA GCCGGTCGGC ACGGCTTCC GGCGTCTCAA
CGCGCTTTGA GATTCCCAGC TTTTCGGCCA ATCCCTGCGG
TGCATAGGCG CGTGGCTCGA CGAAAACAGT CGGCCAGCCG
GTGCCGAAGG CCGCAGAGTT GCGCGAAACT CTAAGGGTCG
AAAAGCCGGT TAGGGACGCC ACGTATCCGC GCACCGAGCT
CCGCTTGCGG GCTGATGGTG ACGTGGCCCA CTGGTGGCCG
CTCCAGGGCC TCGTAGAACG CCTGAATGCG CGTGTGACGT
GCCTTGCTGC CCTCGATGCC GGCGAACGCC CGACTACCAC
TGCACCGGGT GACCACCGGC GAGGTCCCGG AGCATCTTGC
GGACTTACGC GCACACTGCA CGGAACGACG GGAGCTACGG
CCGTTGCAGC CCTAGATCGG CCACAGCGGC CGCAAACGTG
GTCTGGTCGC GGGTCATCTG CGCTTTGTTG CCGATGAACT
CCTTGGCCGA CAGCCTGCCG GGCAACGTCG GGATCTAGCC
GGTGTCGCCG GCGTTTGCAC CAGACCAGCG CCCAGTAGAC
GCGAAACAAC GGCTACTTGA GGAACCGGCT GTCGGACGGC
TCCTGCGTCA GCGGCACCAC GAACGCGGTC ATGTGCGGGC
TGGTTTCGTC ACGGTGGATG CTGGCCGTCA CGATGCGATC
CGCCCCGTAC TTGTCCGCCA AGGACGCAGT CGCCGTGGTG
CTTGCGCCAG TACACGCCCG ACCAAAGCAG TGCCACCTAC
GACCGGCAGT GCTACGCTAG GCGGGGCATG AACAGGCGGT
GCCACTTGTG CGCCTTCTCG AAGAACGCCG CCTGCTGTTC
TTGGCTGGCC GACTTCCACC ATTCCGGGCT GGCCGTCATG
ACGTACTCGA CCGCCAACAC CGGTGAACAC GCGGAAGAGC
TTCTTGCGGC GGACGACAAG AACCGACCGG CTGAAGGTGG
TAAGGCCCGA CCGGCAGTAC TGCATGAGCT GGCGGTTGTG
AGCGTCCTTG CGCCGCTTCT CTGGCAGCAA CTCGCGCAGT
CGGCCCATCG CTTCATCGGT GCTGCTGGCC GCCCAGTGCT
CGTTCTCTGG CGTCCTGCTG TCGCAGGAAC GCGGCGAAGA
GACCGTCGTT GAGCGCGTCA GCCGGGTAGC GAAGTAGCCA
CGACGACCGG CGGGTCACGA GCAAGAGACC GCAGGACGAC

GCGTCAGCGT TGGGCGTCTC GCGCTCGCGG TAGGCGTGCT
TGAGACTGGC CGCCACGTTG CCCATTTTCG CCAGCTTCTT
GCATCGCATG ATCGCGTATG CGCAGTCGCA ACCCGCAGAG
CGCGAGCGCC ATCCGCACGA ACTCTGACCG GCGGTGCAAC
GGGTAAAAGC GGTCGAAGAA CGTAGCGTAC TAGCGCATAC
CCGCCATGCC TGCCCCTCCC TTTTGGTGTC CAACCGGCTC
GACGGGGGCA GCGCAAGGCG GTGCCTCCGG CGGGCCACTC
AATGCTTGAG TATACTCACT GGCGGTACGA ACGGGGAGGG
AAAACCACAG GTTGGCCGAG CTGCCCCCGT CGCGTTCCGC
CACGGAGGCC GCCCGGTGAG TTACGAACTC ATATGAGTGA
AGACTTTGCT TCGCAAAGTC GTGACCGCCT ACGGCGGCTG
CGGCGCCCTA CGGGCTTGCT CTCCGGGCTT CGCCCTGCGC
GGTCGCTGCG CTCCCTTGCC TCTGAAACGA AGCGTTTCAG
CACTGGCGGA TGCCGCCGAC GCCGCGGGAT GCCCGAACGA
GAGGCCCGAA GCGGGACGCG CCAGCGACGC GAGGGAACGG

SEQ ID: 04
GGGGAGCCGC GCCGAAGGCG TGGGGGAACC CCGCAGGGGT
GCCCTTCTTT GGGCACCAAA GAACTAGATA TAGGGCGAAA
TGCGAAAGAC TTAAAAATCA CCCCTCGGCC CGGCTTCCGC
ACCCCCTTGG GGCGTCCCCA CGGGAAGAAA CCCGTGGTTT
CTTGATCTAT ATCCCGCTTT ACGCTTTCTG AATTTTTAGT
ACAACTTAAA AAGGGGGGT ACGCAACAGC TCATTGCGGC
ACCCCCCGCA ATAGCTCATT GCGTAGGTTA AAGAAAATCT
GTAATTGACT GCCACTTTTA TGTTGAATTT TTTCCCCCCA
TGCGTTGTCG AGTAACGCCG TGGGGGGCGT TATCGAGTAA
CGCATCCAAT TTCTTTTAGA CATTAACTGA CGGTGAAAAT
CGCAACGCAT AATTGTTGTC GCGCTGCCGA AAAGTTGCAG
CTGATTGCGC ATGGTGCCGC AACCGTGCGG CACCCTACCG
CATGGAGATA AGCATGGCCA GCGTTGCGTA TTAACAACAG
CGCGACGGCT TTTCAACGTC GACTAACGCG TACCACGGCG
TTGGCACGCC GTGGGATGGC GTACCTCTAT TCGTACCGGT
CGCAGTCCAG AGAAATCGGC ATTCAAGCCA AGAACAAGCC
CGGTCACTGG GTGCAAACGG AACGCAAAGC GCATGAGGCG
TGGGCCGGGC TTATTGCGAG GCGTCAGGTC TCTTTAGCCG
TAAGTTCGGT TCTTGTTCGG GCCAGTGACC CACGTTTGCC
TTGCGTTTCG CGTACTCCGC ACCCGGCCCG AATAACGCTC
GAAACCCACG GCGGCAATGC TGCTGCATCA CCTCGTGGCG
CAGATGGGCC ACCAGAACGC CGTGGTGGTC AGCCAGAAGA
CACTTTCCAA GCTCATCGGA CTTTGGGTGC CGCCGTTACG
ACGACGTAGT GGAGCACCGC GTCTACCCGG TGGTCTTGCG
GCACCACCAG TCGGTCTTCT GTGAAAGGTT CGAGTAGCCT
```

-continued

```
CGTTCTTTGC GGACGGTCCA ATACGCAGTC AAGGACTTGG
TGGCCGAGCG CTGGATCTCC GTCGTGAAGC TCAACGGCCC
CGGCACCGTG TCGGCCTACG GCAAGAAACG CCTGCCAGGT
TATGCGTCAG TTCCTGAACC ACCGGCTCGC GACCTAGAGG
CAGCACTTCG AGTTGCCGGG GCCGTGGCAC AGCCGGATGC
TGGTCAATGA CCGCGTGGCG TGGGGCCAGC CCCGCGACCA
GTTGCGCCTG TCGGTGTTCA GTGCCGCCGT GGTGGTTGAT
CACGACGACC AGGACGAATC ACCAGTTACT GGCGCACCGC
ACCCCGGTCG GGGCGCTGGT CAACGCGGAC AGCCACAAGT
CACGGCGGCA CCACCAACTA GTGCTGCTGG TCCTGCTTAG
GCTGTTGGGG CATGGCGACC TGCGCCGCAT CCCGACCCTG
TATCCGGGCG AGCAGCAACT ACCGACCGGC CCCGGCGAGG
AGCCGCCCAG CCAGCCCGGC CGACAACCCC GTACCGCTGG
ACGCGGCGTA GGGCTGGGAC ATAGGCCCGC TCGTCGTTGA
TGGCTGGCCG GGGCCGCTCC TCGGCGGGTC GGTCGGGCCG
ATTCCGGGCA TGGAACCAGA CCTGCCAGCC TTGACCGAAA
CGGAGGAATG GGAACGGCGC GGGCAGCAGC GCCTGCCGAT
GCCCGATGAG CCGTGTTTTC TAAGGCCCGT ACCTTGGTCT
GGACGGTCGG AACTGGCTTT GCCTCCTTAC CCTTGCCGCG
CCCGTCGTCG CGGACGGCTA CGGGCTACTC GGCACAAAAG
TGGACGATGG CGAGCCGTTG GAGCCGCCGA CACGGGTCAC
GCTGCCGCGC CGGTAGCACT TGGGTTGCGC AGCAACCCGT
AAGTGCGCTG TTCCAGACTA ACCTGCTACC GCTCGGCAAC
CTCGGCGGCT GTGCCCAGTG CGACGGCGCG GCCATCGTGA
ACCCAACGCG TCGTTGGGCA TTCACGCGAC AAGGTCTGAT
TCGGCTGTAG CCGCCTCGCC GCCCTATACC TTGTCTGCCT
CCCCGCGTTG CGTCGCGGTG CATGGAGCCG GGCCACCTCG
ACCTGAATGG AAGCCGGCGG AGCCGACATC GGCGGAGCGG
CGGGATATGG AACAGACGGA GGGGCGCAAC GCAGCGCCAC
GTACCTCGGC CCGGTGGAGC TGGACTTACC TTCGGCCGCC
CACCTCGCTA ACGGATTCAC CGTTTTTATC AGGCTCTGGG
AGGCAGAATA AATGATCATA TCGTCAATTA TTACCTCCAC
GGGGAGAGCC TGAGCAAACT GTGGAGCGAT TGCCTAAGTG
GCAAAAATAG TCCGAGACCC TCCGTCTTAT TTACTAGTAT
AGCAGTTAAT AATGGAGGTG CCCCTCTCGG ACTCGTTTGA
GGCCTCAGGC ATTTGAGAAG CACACGGTCA CACTGCTTCC
GGTAGTCAAT AAACCGGTAA ACCAGCAATA GACATAAGCG
GCTATTTAAC GACCCTGCCC CCGGAGTCCG TAAACTCTTC
GTGTGCCAGT GTGACGAAGG CCATCAGTTA TTTGGCCATT
TGGTCGTTAT CTGTATTCGC CGATAAATTG CTGGGACGGG
TGAACCGACG ACCGGGTCGA ATTTGCTTTC GAATTTCTGC
CATTCATCCG CTTATTATCA CTTATTCAGG CGTAGCACCA
GGCGTTTAAG GGCACCAATA ACTTGGCTGC TGGCCCAGCT
TAAACGAAAG CTTAAAGACG GTAAGTAGGC GAATAATAGT
GAATAAGTCC GCATCGTGGT CCGCAAATTC CCGTGGTTAT
ACTGCCTTAA AAAAATTACG CCCCGCCCTG CCACTCATCG
CAGTCGGCCT ATTGGTTAAA AAATGAGCTG ATTTAACAAA
AATTTAACGC GAATTTTAAC TGACGGAATT TTTTTAATGC
GGGGCGGGAC GGTGAGTAGC GTCAGCCGGA TAACCAATTT
TTTACTCGAC TAAATTGTTT TTAAATTGCG CTTAAAATTG
AAAATATTAA CGCTTACAAT TTCCATTCGC CATTCAGGCT
GCGCAACTGT TGGGAAGGGC GATCGGTGCG GGCCTCTTCG
CTATTACGCC AGCTGGCGAA TTTTATAATT GCGAATGTTA
AAGGTAAGCG GTAAGTCCGA CGCGTTGACA CCCCTTCCCG
CTAGCCACGC CCGGAGAAGC GATAATGCGG TCGACCGCTT
AGGGGGATGT GCTGCAAGGC GATTAAGTTG GGTAACGCCA
GGGTTTTCCC AGTCACGACG TTGTAAAACG ACGGCCAGTG
AGCGCGCGTA ATACGACTCA TCCCCCTACA CGACGTTCCG
CTAATTCAAC CCATTGCGGT CCCAAAAGGG TCAGTGCTGC
AACATTTTGC TGCCGGTCAC TCGCGCGCAT TATGCTGAGT
CTATAGGGCG AATTGGAGCT CCACCGCGGT GGCGGCCGCT
CTAGAACTAG TGGATCCCCC GGGCTGCAGG AATTCGATAT
CAAGCTTTTA CGCCCCGCCC GATATCCCGC TTAACCTCGA
GGTGGCGCCA CCGCCGGCGA GATCTTGATC ACCTAGGGGG
CCCGACGTCC TTAAGCTATA GTTCGAAAAT GCGGGGCGGG
TGCCACTCAT CGCAGTACTG TTGTAATTCA TTAAGCATTC
TGCCGACATG GAAGCCATCA CAAACGGCAT GATGAACCTG
AATCGCCAGC GGCATCAGCA ACGGTGAGTA GCGTCATGAC
AACATTAAGT AATTCGTAAG ACGGCTGTAC CTTCGGTAGT
GTTTGCCGTA CTACTTGGAC TTAGCGGTCG CCGTAGTCGT
CCTTGTCGCC TTGCGTATAA TATTTGCCCA TGGTGAAAAC
GGGGGCGAAG AAGTTGTCCA TATTGGCCAC GTTTAAATCA
AAACTGGTGA AACTCACCCA GGAACAGCGG AACGCATATT
ATAAACGGGT ACCACTTTTG CCCCCGCTTC TTCAACAGGT
ATAACCGGTG CAAATTTAGT TTTGACCACT TGAGTGGGT
GGGATTGGCT GAGACGAAAA ACATATTCTC AATAAACCCT
TTAGGGAAAT AGGCCAGGTT TTCACCGTAA CACGCCACAT
CTTGCGAATA TATGTGTAGA CCCTAACCGA CTCTGCTTTT
TGTATAAGAG TTATTTGGGA AATCCCTTTA TCCGGTCCAA
AAGTGGCATT GTGCGGTGTA GAACGCTTAT ATACACATCT
```

```
AACTGCCGGA AATCGTCGTG GTATTCACTC CAGAGCGATG
AAAACGTTTC AGTTTGCTCA TGGAAAACGG TGTAACAAGG
GTGAACACTA TCCCATATCA TTGACGGCCT TTAGCAGCAC
CATAAGTGAG GTCTCGCTAC TTTTGCAAAG TCAAACGAGT
ACCTTTTGCC ACATTGTTCC CACTTGTGAT AGGGTATAGT
CCAGCTCACC GTCTTTCATT GCCATACGAA ATTCCGGATG
AGCATTCATC AGGCGGGCAA GAATGTGAAT AAAGGCCGGA
TAAAACTTGT GCTTATTTTT GGTCGAGTGG CAGAAAGTAA
CGGTATGCTT TAAGGCCTAC TCGTAAGTAG TCCGCCCGTT
CTTACACTTA TTTCCGGCCT ATTTTGAACA CGAATAAAAA
CTTTACGGTC TTTAAAAAGG CCGTAATATC CAGCTGAACG
GTCTGGTTAT AGGTACATTG AGCAACTGAC TGAAATGCCT
CAAAATGTTC TTTACGATGC GAAATGCCAG AAATTTTTCC
GGCATTATAG GTCGACTTGC CAGACCAATA TCCATGTAAC
TCGTTGACTG ACTTTACGGA GTTTTACAAG AAATGCTACG
CATTGGGATA TATCAACGGT GGTATATCCA GTGATTTTTT
TCTCCATATG GTTAACCTTA ATTAAGGGGT CGACGGGCCC
GGGATCCGAT GCTCTTCCGC GTAACCCTAT ATAGTTGCCA
CCATATAGGT CACTAAAAAA AGAGGTATAC CAATTGGAAT
TAATTCCCCA GCTGCCCGGG CCCTAGGCTA CGAGAAGGCG
TAAGATCTTT TACTAGTTCA GTCCATCTCG CCGTGTATGC
GGGCCTGACG GATCAACGTT CCCACCGAGC CAGTCGAGAT
GTTCATCTGG TCGGCGATCT ATTCTAGAAA ATGATCAAGT
CAGGTAGAGC GGCACATACG CCCGGACTGC CTAGTTGCAA
GGGTGGCTCG GTCAGCTCTA CAAGTAGACC AGCCGCTAGA
GCCGGTACTT CAAACCTTGT TTGCGCAGTT CCACAGCCTT
CTTGCGGCGT TCCTGCGCAC GAGCGATGTA GTCGCCTCGG
TCTTCGGCGA CGAGCCGTTT CGGCCATGAA GTTTGGAACA
AACGCGTCAA GGTGTCGGAA GAACGCCGCA AGGACGCGTG
CTCGCTACAT CAGCGGAGCC AGAAGCCGCT GCTCGGCAAA
GATGGTGCTT TTCGAGACGC CGAACTTGTC AGCCAACTCC
TGCGCGGTCT GCGTGCGACG CATCACGCGT TCTGCAGCAC
CCATCAGTCC GTCCCCTCTG CTACCACGAA AAGCTCTGCG
GCTTGAACAG TCGGTTGAGG ACGCGCCAGA CGCACGCTGC
GTAGTGCGCA AGACGTCGTG GGTAGTCAGG CAGGGGAGAC
CTGCTGCGAA CAGTGCCGAT CGATCGACCT TCTTGAGCTT
CGGCCGCGGC GCGGTGGCGT TCTTCCGTAC CGCTTCCGTT
TTTGCGCTGC TGCTCACTTT GACGACGCTT GTCACGGCTA
GCTAGCTGGA AGAACTCGAA GCCGGCGCCG CGCCACCGCA
AGAAGGCATG GCGAAGGCAA AAACGCGACG ACGAGTGAAA
GCCGCGGCGT GCCTGGATTT CGAGAACTC GGCGGCGGTG
AAGGTGCGGT GGGTCCAGTG GGCGACTGAT TTGCCGATCT
GCTCGGCCTC GGCCCGACTC CGGCGCCGCA CGGACCTAAA
AGCTCTTGAG CCGCCGCCAC TTCCACGCCA CCCAGGTCAC
CCGCTGACTA AACGGCTAGA CGAGCCGGAG CCGGGCTGAG
ATGGGGCCGA TCCCGTCGTT GGCGTCGAGG GTGAAGTTGG
TCAGGGCGGT GAAGTCGGTG ACCATCTGCC GCCACACAGT
GATCGACGGG TAGTTCTGTT TACCCCGGCT AGGGCAGCAA
CCGCAGCTCC CACTTCAACC AGTCCCGCCA CTTCAGCCAC
TGGTAGACGG CGGTGTGTCA CTAGCTGCCC ATCAAGACAA
TCCGGATCTC GCGGTAGGCC CATTCCCGGG TGCGGTCGAA
CAGTTCGACG TTCCGGCCCG TTTCGGTCCT GACCTGTGTC
TTGCGGCCGT AGTCCGGTGG AGGCCTAGAG CGCCATCCGG
GTAAGGGCCC ACGCCAGCTT GTCAAGCTGC AAGGCCGGGC
AAAGCCAGGA CTGGACACAG AACGCCGGCA TCAGGCCACC
GGCGGGAAA CGGTCACCGA GCGCTTTTGC GAGGCCTTTG
AGCGAGTACG GATCCGAGGG ACCCCAGACC GTCGTCCAGT
GCGGGTGGAT CGGGTTCTGG CCGCCCCTTT GCCAGTGGCT
CGCGAAAACG CTCCGGAAAC TCGCTCATGC CTAGGCTCCC
TGGGGTCTGG CAGCAGGTCA CGCCCACCTA GCCCAAGACC
GTGAGCTGCT GCGCGTAGCC CTGATCGGCG CCGACCACCG
AGGCGATCAG CCCCTGGTTC ACCCGGTCGT AGAGCCGCAG
CGGGCCCTGT CGGGCTGCCT CACTCGACGA CGCGCATCGG
GACTAGCCGC GGCTGGTGGC TCCGCTAGTC GGGGACCAAG
TGGGCCAGCA TCTCGGCGTC GCCCGGGACA GCCCGACGGA
GGAGGGTGTA GACCGGGCTT TCGAGCAGCC ACCACAGGTG
CGCGTGCTCG GTCGCGGGAT TGATCGTCAT CACGGTCGGA
TCGGGCAGAT CCGCGTTACG CCTCCCACAT CTGGCCCGAA
AGCTCGTCGG TGGTGTCCAC GCGCACGAGC CAGCGCCCTA
ACTAGCAGTA GTGCCAGCCT AGCCCGTCTA GGCGCAATGC
TGCGGCCCAC TGCGCCTGGT CGTCGTCCAC GTCGAGCACC
AAGCCCAACC TGATCGACGG GGTGCGGGCC GCAATGTAGC
GGCGGGTGAG CGCCTCCGCG ACGCCGGGTG ACGCGGACCA
GCAGCAGGTG CAGCTCGTGG TTCGGGTTGG ACTAGCTGCC
CCACGCCCGG CGTTACATCG CCGCCCACTC GCGGAGGCGC
CGCGGCTGCG GCCACTGCCC GTCCCGGACG TAGTCATCCG
TCGCGTGCGG GTATTTGAAC CGCCAGCGGT CCAACCAGGC
GTCAACAGCA GCGGTCATGA CGCGCCGACGC CGGTGACGGG
CAGGGCCTGC ATCAGTAGGC AGCGCACGCC CATAAACTTG
GCGGTCGCCA GGTTGGTCCG CAGTTGTCGT CGCCAGTACT
```

-continued

```
CCGCCAAGCT AGGGCCGGAT CTGTACCGAT CGGGGGAGGC
GCGCCGCAAA TTATTTAAGA GTCTCGCTAG CAAACCATGT
CAGGTGTTGC GGTGGGTTCC GGCGGTTCGA TCCCGGCCTA
GACATGGCTA GCCCCCTCCG CGCGGCGTTT AATAAATTCT
CAGAGCGATC GTTTGGTACA GTCCACAACG CCACCCAAGG
GGGTAAACCT CCACCCGAAT TATTTAAGAG TCTCGCTAGC
TAAGCCCTAT CTGATGCTGC GCGGGGGGTC CTTCGCACTG
AATCTCAAAG GTGGCCGGCT CCCATTTGGA GGTGGGCTTA
ATAAATTCTC AGAGCGATCG ATTCGGGATA GACTACGACG
CGCCCCCCAG GAAGCGTGAC TTAGAGTTTC ACCGGCCGA
GAATTTCGTC GCGCGAAAAC CTCCCTGGAC AGTTCTGGAA
TTCAGCAAGA GGTGTGTCTG AACTTCGGTG TTTTTTTGGG
GGGTGACTCC AGCGGGGTGG CTTAAAGCAG CGCGCTTTTG
GAGGGACCTG TCAAGACCTT AAGTCGTTCT CCACACAGAC
TTGAAGCCAC AAAAAAACCC CCCACTGAGG TCGCCCCACC
GCACAACGCG AACAGAGACC TTGTGTGTAC GACGGCGGGA
GGTAAGTCGG GTACGGCTCG GACTGCGGTA GAGCAACCGT
CGAATCGATT TCGAGCAGAG CGTGTTGCGC TTGTCTCTGG
AACACACATG CTGCCGCCCT CCATTCAGCC CATGCCGAGC
CTGACGCCAT CTCGTTGGCA GCTTAGCTAA AGCTCGTCTC
CGAGCAGAGC AAGATATTCC AAAACTCCGG GGTTCCTCGG
CGGCCTCCCC CGTCTGTTTG CTCAACCGAG GGAGACCTGG
CGGTCCCGCG TTTCCGGACG GCTCGTCTCG TTCTATAAGG
TTTTGAGGCC CCAAGGAGCC GCCGGAGGGG CAGACAAAC
GAGTTGGCTC CCTCTGGACC GCCAGGGCGC AAAGGCCTGC
CGCGGGACCG CCTACCGCTC GAGAGCGGAA GAGCATCTAG
ATGCATTCGC GAGGTACCCA GCTTTTGTTC CCTTTAGTGA
GGGTTAATTG CGCGCTTGGC GCGCCCTGGC GGATGGCGAG
CTCTCGCCTT CTCGTAGATC TACGTAAGCG CTCCATGGGT
CGAAAACAAG GGAAATCACT CCCAATTAAC GCGCGAACCG
GTAATCATGG TCATAGCTGT TTCCTGTGTG AAATTGTTAT
CCGCTCACAA TTCCACACAA CATACGAGCC GGAAGCATAA
AGTGTAAAGC CTGGGGTGCC CATTAGTACC AGTATCGACA
AAGGACACAC TTTAACAATA GGCGAGTGTT AAGGTGTGTT
GTATGCTCGG CCTTCGTATT TCACATTTCG ACCCCACGG
TAATGAGTGA GCTAACTCAC ATTAATTGCG TTGCGCTCAC
TGCCCGCTTT CCAGTCGGGA AACCTGTCGT GCCAGCTGCA
TTAATGAATC GGCCAACGCG ATTACTCACT CGATTGAGTG
TAATTAACGC AACGCGAGTG ACGGGCGAAA GGTCAGCCCT
TTGGACAGCA CGGTCGACGT AATTACTTAG CCGGTTGCGC
```

-continued

```
CGGGGAGAGG CGGTTTGCGT ATTGGGCGCA TGCATAAAAA
CTGTTGTAAT TCATTAAGCA TTCTGCCGAC ATGGAAGCCA
TCACAAACGG CATGATGAAC GCCCCTCTCC GCCAAACGCA
TAACCCGCGT ACGTATTTTT GACAACATTA AGTAATTCGT
AAGACGGCTG TACCTTCGGT AGTGTTTGCC GTACTACTTG
CTGAATCGCC AGCGGCATCA GCACCTTGTC GCCTTGCGTA
TAATATTTGC CCATGGGGGT GGGCGAAGAA CTCCAGCATG
AGATCCCCGC GCTGGAGGAT GACTTAGCGG TCGCCGTAGT
CGTGGAACAG CGGAACGCAT ATTATAAACG GGTACCCCCA
CCCGCTTCTT GAGGTCGTAC TCTAGGGGCG CGACCTCCTA
CATCCAGCCG GCGTCCCGGA AAACGATTCC GAAGCCCAAC
CTTTCATAGA AGGCGGCGGT GGAATCGAAA TCTCGTGATG
GCAGGTTGGG CGTCGCTTGG GTAGGTCGGC CGCAGGGCCT
TTTGCTAAGG CTTCGGGTTG GAAAGTATCT TCCGCCGCCA
CCTTAGCTTT AGAGCACTAC CGTCCAACCC GCAGCGAACC
TCGGTCATTT CGAACCCCAG AGTCCCGCTC AGAAGAACTC
GTCAAGAAGG CGATAGAAGG CGATGCGCTG CGAATCGGGA
GCGGCGATAC CGTAAAGCAC AGCCAGTAAA GCTTGGGGTC
TCAGGGCGAG TCTTCTTGAG CAGTTCTTCC GCTATCTTCC
GCTACGCGAC GCTTAGCCCT CGCCGCTATG GCATTTCGTG
GAGGAAGCGG TCAGCCCATT CGCCGCCAAG CTCTTCAGCA
ATATCACGGG TAGCCAACGC TATGTCCTGA TAGCGGTCCG
CCACACCCAG CCCGGCCACAG CTCCTTCGCC AGTCGGGTAA
GCGGCGGTTC GAGAAGTCGT TATAGTGCCC ATCGGTTGCG
ATACAGGACT ATCGCCAGGC GGTGTGGGTC GGCCGGTGTC
TCGATGAATC CAGAAAAGCG GCCATTTTCC ACCATGATAT
TCGGCAAGCA GGCATCGCCA TGGGTCACGA CGAGATCCTC
GCCGTCGGGC ATGCGCGCCT AGCTACTTAG GTCTTTTCGC
CGGTAAAAGG TGGTACTATA AGCCGTTCGT CCGTAGCGGT
ACCCAGTGCT GCTCTAGGAG CGGCAGCCCG TACGCGCGGA
TGAGCCTGGC GAACAGTTCG GCTGGCGCGA GCCCCTGATG
CTCTTCGTCC AGATCATCCT GATCGACAAG ACCGGCTTCC
ATCCGAGTAC GTGCTCGCTC ACTCGGACCG CTTGTCAAGC
CGACCGCGCT CGGGGACTAC GAGAAGCAGG TCTAGTAGGA
CTAGCTGTTC TGGCCGAAGG TAGGCTCATG CACGAGCGAG
GATGCGATGT TTCGCTTGGT GGTCGAATGG GCAGGTAGCC
GGATCAAGCG TATGCAGCCG CCGCATTGCA TCAGCCATGA
TGGATACTTT CTCGGCAGGA CTACGCTACA AAGCGAACCA
CCAGCTTACC CGTCCATCGG CCTAGTTCGC ATACGTCGGC
GGCGTAACGT AGTCGGTACT ACCTATGAAA GAGCCGTCCT
```

```
GCAAGGTGAG ATGACAGGAG ATCCTGCCCC GGCACTTCGC
CCAATAGCAG CCAGTCCCTT CCCGCTTCAG TGACAACGTC
GAGCACAGCT GCGCAAGGAA CGTTCCACTC TACTGTCCTC
TAGGACGGGG CCGTGAAGCG GGTTATCGTC GGTCAGGGAA
GGGCGAAGTC ACTGTTGCAG CTCGTGTCGA CGCGTTCCTT
CGCCCGTCGT GGCCAGCCAC GATAGCCGCG CTGCCTCGTC
CTGCAGTTCA TTCAGGGCAC CGGACAGGTC GGTCTTGACA
AAAAGAACCG GGCGCCCCTG GCGGGCAGCA CCGGTCGGTG
CTATCGGCGC GACGGAGCAG GACGTCAAGT AAGTCCCGTG
GCCTGTCCAG CCAGAACTGT TTTTCTTGGC CCGCGGGGAC
CGCTGACAGC CGGAACACGG CGGCATCAGA GCAGCCGATT
GTCTGTTGTG CCCAGTCATA GCCGAATAGC CTCTCCACCC
AAGCGGCCGG AGAACCTGCG GCGACTGTCG GCCTTGTGCC
GCCGTAGTCT CGTCGGCTAA CAGACAACAC GGGTCAGTAT
CGGCTTATCG GAGAGGTGGG TTCGCCGGCC TCTTGGACGC
TGCAATCCAT CTTGTTCAAT CATGCGAAAC GATCCTCATC
CTGTCTCTTG ATCAGATCTT GATCCCCTGC GCCATCAGAT
CCTTGGCGGC AAGAAAGCCA ACGTTAGGTA GAACAAGTTA
GTACGCTTTG CTAGGAGTAG GACAGAGAAC TAGTCTAGAA
CTAGGGACG CGGTAGTCTA GGAACCGCCG TTCTTTCGGT
TCCAGTTTAC TTTGCAGGGC TTCCCAACCT TACCAGAGGG
CGCCCCAGCT GGCAATTCCG GTTCGCTTGC TGTCCATAAA
ACCGCCCAGT CTAGCTATCG AGGTCAAATG AAACGTCCCG
AAGGGTTGGA ATGGTCTCCC GCGGGGTCGA CCGTTAAGGC
CAAGCGAACG ACAGGTATTT TGGCGGGTCA GATCGATAGC
CCATGTAAGC CCACTGCAAG CTACCTGCTT TCTCTTTGCG
CTTGCGTTTT CCCTTGTCCA GATAGCCCAG TAGCTGACAT
TCATCCCAGG TGGCACTTTT GGTACATTCG GGTGACGTTC
GATGGACGAA AGAGAAACGC GAACGCAAAA GGGAACAGGT
CTATCGGGTC ATCGACTGTA AGTAGGGTCC ACCGTGAAAA
CGGGGAAATG TGCGCGCCCG CGTTCCTGCT GGCGCTGGGC
CTGTTTCTGG CGCTGGACTT CCCGCTGTTC CGTCAGCAGC
TTTTCGCCCA CGGCCTTGAT GCCCCTTTAC ACGCGCGGGC
GCAAGGACGA CCGCGACCCG GACAAAGACC GCGACCTGAA
GGGCGACAAG GCAGTCGTCG AAAAGCGGGT GCCGGAACTA
GATCGCGGCG GCCTTGGCCT GCATATCCCG ATTCAACGGC
CCCAGGGCGT CCAGAACGGG CTTCAGGCGC TCCCGAAGGT
CTCGGGCCGT CTCTTGGGCT CTAGCGCCGC CGGAACCGGA
CGTATAGGGC TAAGTTGCCG GGGTCCCGCA GGTCTTGCCC
GAAGTCCGCG AGGGCTTCCA GAGCCCGGCA GAGAACCCGA
TGATCGGCCT TCTTGCGCAT CTCACGCGCT CCTGCGGCGG
CCTGTAGGGC AGGCTCATAC CCCTGCCGAA CCGCTTTTGT
CAGCCGGTCG GCCACGGCTT ACTAGCCGGA AGAACGCGTA
GAGTGCGCGA GGACGCCGCC GGACATCCCG TCCGAGTATG
GGGACGGCTT GGCGAAAACA GTCGGCCAGC CGGTGCCGAA
CCGGCGTCTC AACGCGCTTT GAGATTCCCA GCTTTTCGGC
CAATCCCTGC GGTGCATAGG CGCGTGGCTC GACCGCTTGC
GGGCTGATGG TGACGTGGCC GGCCGCAGAG TTGCGCGAAA
CTCTAAGGGT CGAAAAGCCG GTTAGGGACG CCACGTATCC
GCGCACCGAG CTGGCGAACG CCCGACTACC ACTGCACCGG
CACTGGTGGC CGCTCCAGGG CCTCGTAGAA CGCCTGAATG
CGCGTGTGAC GTGCCTTGCT GCCCTCGATG CCCCGTTGCA
GCCCTAGATC GGCCACAGCG GTGACCACCG GCGAGGTCCC
GGAGCATCTT GCGGACTTAC GCGCACACTG CACGGAACGA
CGGGAGCTAC GGGGCAACGT CGGGATCTAG CCGGTGTCGC
GCCGCAAACG TGGTCTGGTC GCGGGTCATC TGCGCTTTGT
TGCCGATGAA CTCCTTGGCC GACAGCCTGC CGTCCTGCGT
CAGCGGCACC ACGAACGCGG CGGCGTTTGC ACCAGACCAG
CGCCCAGTAG ACGCGAAACA ACGGCTACTT GAGGAACCGG
CTGTCGGACG GCAGGACGCA GTCGCCGTGG TGCTTGCGCC
TCATGTGCGG GCTGGTTTCG TCACGGTGGA TGCTGGCCGT
CACGATGCGA TCCGCCCCGT ACTTGTCCGC CAGCCACTTG
TGCGCCTTCT CGAAGAACGC AGTACACGCC CGACCAAAGC
AGTGCCACCT ACGACCGGCA GTGCTACGCT AGGCGGGGCA
TGAACAGGCG GTCGGTGAAC ACGCGGAAGA GCTTCTTGCG
CGCCTGCTGT TCTTGGCTGG CCGACTTCCA CCATTCCGGG
CTGGCCGTCA TGACGTACTC GACCGCCAAC ACAGCGTCCT
TGCGCCGCTT CTCTGGCAGC GCGGACGACA AGAACCGACC
GGCTGAAGGT GGTAAGGCCC GACCGGCAGT ACTGCATGAG
CTGGCGGTTG TGTCGCAGGA ACGCGGCGAA GAGACCGTCG
AACTCGCGCA GTCGGCCCAT CGCTTCATCG GTGCTGCTGG
CCGCCCAGTG CTCGTTCTCT GGCGTCCTGC TGGCGTCAGC
GTTGGGCGTC TCGCGCTCGC TTGAGCGCGT CAGCCGGGTA
GCGAAGTAGC CACGACGACC GGCGGGTCAC GAGCAAGAGA
CCGCAGGACG ACCGCAGTCG CAACCCGCAG AGCGCGAGCG
GGTAGGCGTG CTTGAGACTG GCCGCCACGT TGCCCATTTT
CGCCAGCTTC TTGCATCGCA TGATCGCGTA TGCCGCCATG
CCTGCCCCTC CCTTTTGGTG CCATCCGCAC GAACTCTGAC
CGGCGGTGCA ACGGGTAAAA GCGGTCGAAG AACGTAGCGT
ACTAGCGCAT ACGGCGGTAC GGACGGGGAG GGAAAACCAC
```

TCCAACCGGC TCGACGGGGG CAGCGCAAGG CGGTGCCTCC
GGCGGGCCAC TCAATGCTTG AGTATACTCA CTAGACTTTG
CTTCGCAAAG TCGTGACCGC AGGTTGGCCG AGCTGCCCCC
GTCGCGTTCC GCCACGGAGG CCGCCCGGTG AGTTACGAAC
TCATATGAGT GATCTGAAAC GAAGCGTTTC AGCACTGGCG
CTACGGCGGC TGCGGCGCCC TACGGGCTTG CTCTCCGGGC
TTCGCCCTGC GCGGTCGCTG CGCTCCCTTG CCAGCCCGTG
GATATGTGGA CGATGGCCGC GATGCCGCCG ACGCCGCGGG
ATGCCCGAAC GAGAGGCCCG AAGCGGGACG CGCCAGCGAC
GCGAGGGAAC GGTCGGGCAC CTATACACCT GCTACCGGCG
GAGCGGCCAC CGGCTGGCTC GCTTCGCTCG GCCCGTGGAC
AACCCTGCTG GACAAGCTGA TGGACAGGCT GCGCCTGCCC
ACGAGCTTGA CCACAGGGAT CTCGCCGGTG GCCGACCGAG
CGAAGCGAGC CGGGCACCTG TTGGGACGAC CTGTTCGACT
ACCTGTCCGA CGCGGACGGG TGCTCGAACT GGTGTCCCTA
TGCCCACCGG CTACCCAGCC TTCGACCACA TACCCACCGG
CTCCAACTGC GCGGCCTGCG GCCTTGCCCC ATCAATTTTT
TTAATTTTCT CTGGGGAAAA ACGGGTGGCC GATGGGTCGG
AAGCTGGTGT ATGGGTGGCC GAGGTTGACG CGCCGGACGC
CGGAACGGGG TAGTTAAAAA AATTAAAAGA CCCCCTTTT
GCCTCCGGCC TGCGGCCTGC GCGCTTCGCT TGCCGGTTGG
ACACCAAGTG GAAGGCGGGT CAAGGCTCGC GCAGCGACCG
CGCAGCGGCT TGGCCTTGAC CGGAGGCCGG ACGCCGGACG
CGCGAAGCGA ACGCCAACCT GTGGTTCAC CTTCCGCCCA
GTTCCGAGCG CGTCGCTGGC GCGTCGCCGA ACCGGAACTG
GCGCCTGGAA CGACCCAAGC CTATGCGAGT GGGGGCAGTC
GAAGGCGAAG CCCGCCCGCC TGCCCCCCGA GCCTCACGGC
GGCGAGTGCG GGGGTTCCAA CGCGGACCTT GCTGGGTTCG
GATACGCTCA CCCCCGTCAG CTTCCGCTTC GGGCGGGCGG
ACGGGGGGCT CGGAGTGCCG CCGCTCACGC CCCCAAGGTT
GGGGGCAGCG CCACCTTGGG CAAGGCCGAA GGCCGCGCAG
TCGATCAACA AGCCCCGGAG GGGCCACTTT TTGCCGGAG
CCCCCGTCGC GGTGGAACCC GTTCCGGCTT CCGGCGCGTC
AGCTAGTTGT TCGGGCCTC CCCGGTGAAA AACGGCCTC
SEQ ID: 05
MPELAVRTEF DYSSEIYKDA YSRINAIVIE GEQEAYSNYL
QMAELLPEDK EELTRLAKME NRHKKGFQAC GNNLQVNPDM
PYAQEFFAGL HGNFQHAFSE GKVVTCLLIQ ALIIEAFAIA
AYNIYIPVAD DFARKITEGV VKDEYTHLNY GEEWLKANFA
TAKEELEQAN KENLPLVWKM LNQVQGDAKV LGMEKEALVE
DFMISYGEAL SNIGFSTREI MRMSSYGLAG V

SEQ ID: 06
MFGLIGHLTS LEHAQAVAED LGYPEYANQG LDFWCSAPPQ
VVDNFQVKSV TGQVIEGKYV ESCFLPEMLT QRRIKAAIRK
ILNAMALAQK VGLDITALGG FSSIVFEEFN LKQNNQVRNV
ELDFQRFTTG NTHTAYVICR QVESGAKQLG IDLSQATVAV
CGATGDIGSA VCRWLDSKHQ VKELLLIARN RQRLENLQEE
LGRGKIMDLE TALPQADIIV WVASMPKGVE IAGEMLKKPC
LIVDGGYPKN LDTRVKADGV HILKGGIVEH SLDITWEIMK
IVEMDIPSRQ MFACFAEAIL LEFEGWRTNF SWGRNQISVN
KMEAIGEASV KHGFCPLVAL

SEQ ID: 07
CAGTCAATGG AGAGCATTGC CATAAGTAAA GGCATCCCCT
GCGTGATAAG ATTACCTTCA GAAAACAGAT AGTTGCTGGG
TTATCGCAGA TTTTTCTCGC GTCAGTTACC TCTCGTAACG
GTATTCATTT CCGTAGGGGA CGCACTATTC TAATGGAAGT
CTTTTGTCTA TCAACGACCC AATAGCGTCT AAAAAGAGCG
AACCAAATAA CTGTAAATAA TAACTGTCTC TGGGGCGACG
GTAGGCTTTA TATTGCCAAA TTTCGCCCGT GGGAGAAAGC
TAGGCTATTC AATGTTTATG TTGGTTTATT GACATTTATT
ATTGACAGAG ACCCCGCTGC CATCCGAAAT ATAACGGTTT
AAAGCGGGCA CCCTCTTTCG ATCCGATAAG TTACAAATAC
GAGGACTCCT

SEQ ID: 08
CCTGGCTCAG GACGAACGCT GGCGGCGTGC TTAACACATG
CAAGTCGAGC GGTAAGGCCC TTCGGGGTAC ACGAGCGGCG
AACGGGTGAG TAAACACGTGG GGACCGAGTC CTGCTTGCGA
CCGCCGCACG AATTGTGTAC GTTCAGCTCG CCATTCCGGG
AAGCCCCATG TGCTCGCCGC TTGCCCACTC ATTGTGCACC
GTGATCTGCC CTGCACTTCG GGATAAGCCT GGGAAACTGG
GTCTAATACC GGATATGACC TTCGGCTGCA TGGCTGAGGG
TGGAAAGGTT TACTGGTGCA CACTAGACGG ACGTGAAGC
CCTATTCGGA CCCTTTGACC CAGATTATGG CCTATACTGG
AAGCCGACGT ACCGACTCCC ACCTTTCCAA ATGACCACGT
GGATGGGCCC GCGGCCTATC AGCTTGTTGG TGGGGTAATG
GCCTACCAAG GCGACGACGG GTAGCCGACC TGAGAGGGTG
ACCGGCCACA CTGGGACTGA CCTACCCGGG CGCCGGATAG
TCGAACAACC ACCCCATTAC CGGATGGTTC CGCTGCTGCC
CATCGGCTGG ACTCTCCCAC TGGCCGGTGT GACCCTGACT
GACACGGCCC AGACTCCTAC GGGAGGCAGC AGTGGGGAAT
ATTGCACAAT GGGCGAAAGC CTGATGCAGC GACGCCGCGT
GAGGGATGAC GGCCTTCGGG CTGTGCCGGG TCTGAGGATG
CCCTCCGTCG TCACCCCTTA TAACGTGTTA CCCGCTTTCG

```
GACTACGTCG CTGCGGCGCA CTCCCTACTG CCGGAAGCCC
TTGTAAACCT CTTTCAGCAG GGACGAAGCG AAAGTGACGG
TACCTGCAGA AGAAGCACCG GCCAACTACG TGCCAGCAGC
CGCGGTAATA CGTAGGGTGC AACATTTGGA GAAAGTCGTC
CCTGCTTCGC TTTCACTGCC ATGGACGTCT TCTTCGTGGC
CGGTTGATGC ACGGTCGTCG GCGCCATTAT GCATCCCACG
AAGCGTTGTC CGGAATTACT GGGCGTAAAG AGCTCGTAGG
CGGTTTGTCG CGTCGTCTGT GAAAACTCAN AGCTCAACCT
CGAGCTTGCA GGCGATACGG TTCGCAACAG GCCTTAATGA
CCCGCATTTC TCGAGCATCC GCCAAACAGC GCAGCAGACA
CTTTTGAGTN TCGAGTTGGA GCTCGAACGT CCGCTATGCC
GCAGACTTGA GTACTGCAGG GGAGACTGGA ATTCCTGGTG
TAGCGGTGAA ATGCGCAGAT ATCAGGAGGA ACACCGGTGG
CGAAGGCGGG TCTCTGGGCA CGTCTGAACT CATGACGTCC
CCTCTGACCT TAAGGACCAC ATCGCCACTT TACGCGTCTA
TAGTCCTCCT TGTGGCCACC GCTTCCGCCC AGAGACCCGT
GTAACTGACG CTGAGGAGCG AAAGCGTGGG TAGCAAACAG
GATTAGATAC CCTGGTAGTC CACGCCGTAA ACGGTGGGCG
CTAGGTGTGG GTTTCCTTCC CATTGACTGC GACTCCTCGC
TTTCGCACCC ATCGTTTGTC CTAATCTATG GGACCATCAG
GTGCGGCATT TGCCACCCGC GATCCACACC CAAAGGAAGG
ACGGGATCCG TGCCGTAGTT AACGCATTAA GCGCCCCGCC
TGGGGAGTAC GGCCGCAAGG TTAAAACTCA AAGGAATTGA
CGGGGGCCCG CACAAGCGGC TGCCCTAGGC ACGGCATCAA
TTGCGTAATT CGCGGGCGG ACCCCTCATG CCGGCGTTCC
AATTTTGAGT TTCCTTAACT GCCCCCGGGC GTGTTCGCCG
GGAGCATGTG GATTAATTCG ATGCAACGCG AAGAACCTTA
CCTGGGTTTG ACATATACCG GAAAGCCGTA GAGATACCGC
CCCCCTTGTG GTCGGTATAC CCTCGTACAC CTAATTAAGC
TACGTTGCGC TTCTTGGAAT GGACCCAAAC TGTATATGGC
CTTTCGGCAT CTCTATGGCG GGGGGAACAC CAGCCATATG
AGGTGGTGCA TGGCTGTCGT CAGCTCGTGT CGTGAGATGT
TGGGTTAAGT CCCGCAACGA GCGCAACCCT TGTCTTATGT
TGCCAGCACG TAATGGTGGG TCCACCACGT ACCGACAGCA
GTCGAGCACA GCACTCTACA ACCCAATTCA GGGCGTTGCT
CGCGTTGGGA ACAGAATACA ACGGTCGTGC ATTACCACCC
GACTCGTAAG AGACTGCCGG GGTCAACTCG GAGGAAGGTG
GGGACGACGT CAAGTCATCA TGCCCCTTAT GTCCAGGGCT
TCACACATGC TACAATGGCC CTGAGCATTC TCTGACGGCC
CCAGTTGAGC CTCCTTCCAC CCCTGCTGCA GTTCAGTAGT
```

```
ACGGGGAATA CAGGTCCCGA AGTGTGTACG ATGTTACCGG
GGTACAGAGG GCTGCGATAC CGTGAGGTGG AGCGAATCCC
TTAAAGCCGG TCTCAGTTCG GATCGGGGTC TGCAACTCGA
CCCCGTGAAG TCGGAGTCGC CCATGTCTCC CGACGCTATG
GCACTCCACC TCGCTTAGGG AATTTCGGCC AGAGTCAAGC
CTAGCCCCAG ACGTTGAGCT GGGGCACTTC AGCCTCAGCG
TAGTAATCGC AGATCAGCAA CGCTGCGGTG AATACGTTCC
CGGGCCTTGT ACACACCGCC CGTCACGTCA TGAAAGTCGG
TAACACCCGA AGCCGGTGGC ATCATTAGCG TCTAGTCGTT
GCGACGCCAC TTATGCAAGG GCCCGGAACA TGTGTGGCGG
GCAGTGCAGT ACTTTCAGCC ATTGTGGGCT TCGGCCACCG
CTAACCCCTT GTGGGAGGGA GCCGTCGAAG GTGGGATCGG
CGATTGGGAC GAAGTCGTAA CAAGGTAGCC GTACCGGAAG
GGATTGGGGA ACACCCTCCC TCGGCAGCTT CCACCCTAGC
CGCTAACCCT GCTTCAGCAT TGTTCCATCG GCATGGCCTT
CC
```

SEQ ID: 09

```
TCAACGGAGA GTTTGATCCT GGCTCAGGAC GAACGCTGGC
GGCGTGCTTA ACACATGCAA GTCGAGCGGT AAGGCCCTTC
GGGGTACACG AGCGGCGAAC AGTTGCCTCT CAAACTAGGA
CCGAGTCCTG CTTGCGACCG CCGCACGAAT TGTGTACGTT
CAGCTCGCCA TTCCGGGAAG CCCCATGTGC TCGCCGCTTG
GGGTGAGTAA CACGTGGGTG ATCTGCCCTG CACTTCGGGA
TAAGCCTGGG AAACTGGGTC TAATACCGGA TATGACCTTC
GGCTGCATGG CCGTTGGTGG CCCACTCATT GTGCACCCAC
TAGACGGGAC GTGAAGCCCT ATTCGGACCC TTTGACCCAG
ATTATGGCCT ATACTGGAAG CCGACGTACC GGCAACCACC
AAAGGTTTAC TGGTGCAGGA TGGGCCCGCG GCCTATCAGC
TTGTTGGTGG GGTAATGGCC TACCAAGGCG ACGACGGGTA
GCCGACCTGA GAGGGTGACC TTTCCAAATG ACCACGTCCT
ACCCGGGCGC CGGATAGTCG AACAACCACC CCATTACCGG
ATGGTTCCGC TGCTGCCCAT CGGCTGGACT CTCCCACTGG
GGCCACACTG GGACTGAGAC ACGGCCCAGA CTCCTACGGG
AGGCAGCAGT GGGGAATATT GCACAATGGG CGAAAGCCTG
ATGCAGCGAC GCCGCGTGAG CCGGTGTGAC CCTGACTCTG
TGCCGGGTCT GAGGATGCCC TCCGTCGTCA CCCCTTATAA
CGTGTTACCC GCTTTCGGAC TACGTCGCTG CGGCGCACTC
GGATGACGGC CTTCGGGTTG TAAACCTCTT TCAGCAGGGA
CGAAGCGAAA GTGACGGTAC CTGCAGAAGA AGCACCGGCC
AACTACGTGC CAGCAGCCGC CTACTGCCGA GAAGCCCAAC
ATTTGGAGAA AGTCGTCCCT GCTTCGCTTT CACTGCCATG
```

-continued

```
GACGTCTTCT TCGTGGCCGG TTGATGCACG GTCGTCGGCG
GGTAATACGT AGGGTGCAAG CGTTGTCCGG AATTACTGGG
CGTAAAGAGC TCGTAGGCGG TTTGTCGCGT CGTCTGTGAA
AACTCGAGGC TCAACCTCGA CCATTATGCA TCCCACGTTC
GCAACAGGCC TTAATGACCC GCATTTCTCG AGCATCCGCC
AAACAGCGCA GCAGACACTT TGAGCTCCG AGTTGGAGCT
GCTTGCAGGC GATACGGGCA GACTTGAGTA CTGCAGGGGA
GACTGGAATT CCTGGTGTAG CGGTGAAATG CGCAGATATC
AGGAGGAACA CCGGTGGCGA CGAACGTCCG CTATGCCCGT
CTGAACTCAT GACGTCCCCT CTGACCTTAA GGACCACATC
GCCACTTTAC GCGTCTATAG TCCTCCTTGT GGCCACCGCT
AGGCGGGTCT CTGGGCAGTA ACTGACGCTG AGGAGCGAAA
GCGTGGGTAG CGAACAGGAT TAGATACCCT GGTAGTCCAC
GCCGTAAACG GTGGGCGCTA TCCGCCCAGA GACCCGTCAT
TGACTGCGAC TCCTCGCTTT CGCACCCATC GCTTGTCCTA
ATCTATGGGA CCATCAGGTG CGGCATTTGC CACCCGCGAT
GGTGTGGGTT CCTTCCACG GGATCCGTGC CGTAGCTAAC
GCATTAAGCG CCCCGCCTGG GGAGTACGGC CGCAAGGCTA
AAACTCAAAG GAATTGACGG CCACACCCAA AGGAAGGTGC
CCTAGGCACG GCATCGATTG CGTAATTCGC GGGGCGGACC
CCTCATGCCG GCGTTCCGAT TTTGAGTTTC CTTAACTGCC
GGGCCCGCAC AAGCGGCGGA GCATGTGGAT TAATTCGATG
CAACGCGAAG AACCTTACCT GGGTTTGACA TATACCGGAA
AGCTGCAGAG ATGTGCCCCC CCGGGCGTG TTCGCCGCCT
CGTACACCTA ATTAAGCTAC GTTGCGCTTC TTGGAATGGA
CCCAAACTGT ATATGGCCTT TCGACGTCTC TACACCGGGG
CCTTGTGGTC GGTATACAGG TGGTGCATGG CTGTCGTCAG
CTCGTGTCGT GAGATGTTGG GTTAAGTCCC GCAACGAGCG
CAACCCTTGT CTTATGTTGC GGAACACCAG CCATATGTCC
ACCACGTACC GACAGCAGTC GAGCACAGCA CTCTACAACC
CAATTCAGGG CGTTGCTCGC GTTGGGAACA GAATACAACG
CAGCACGTAA TGGTGGGGAC TCGTAAGAGA CTGCCGGGGT
CAACTCGGAG GAAGGTGGGG ACGACGTCAA GTCATCATGC
CCCTTATGTC CAGGGCTTCA GTCGTGCATT ACCACCCCTG
AGCATTCTCT GACGGCCCCA GTTGAGCCTC CTTCCACCCC
TGCTGCAGTT CAGTAGTACG GGGAATACAG GTCCCGAAGT
CACATGCTAC AATGGCCGGT ACAGAGGGCT GCGATACCGT
GAGGTGGAGC GAATCCCTTA AAGCCGGTCT CAGTTCGGAT
CGGGGTCTGC AACTCGACCC GTGTACGATG TTACCGGCCA
TGTCTCCCGA CGCTATGGCA CTCCACCTCG CTTAGGGAAT
```

```
TTCGGCCAGA GTCAAGCCTA GCCCCAGACG TTGAGCTGGG
CGTGAAGTCG GAGTCGCTAG TAATCGCAGA TCAGCAACGC
TGCGGTGAAT ACGTTCCCGG GCCTTGTACA CACCGCCCGT
CACGTCATGA AAGTCGGTAA GCACTTCAGC CTCAGCGATC
ATTAGCGTCT AGTCGTTGCG ACGCCACTTA TGCAAGGGCC
CGGAACATGT GTGGCGGGCA GTGCAGTACT TTCAGCCATT
CACCCGAAGC CGGTGGCCTA ACCCCTCGTG GGAGGGAGCC
GTCGAAGGTG GGATCGGCGA TTGGGACGAA GTCGTAACAA
GGTAGCCGTA CCGGAAGGTG GTGGGCTTCG GCCACCGGAT
TGGGGAGCAC CCTCCCTCGG CAGCTTCCAC CCTAGCCGCT
AACCCTGCTT CAGCATTGTT CCATCGGCAT GGCCTTCCAC
CGGCTGGATC ACCTCCTTTC TGCCGACCTA GTGGAGGAAA GA
```

SEQ ID: 10

```
ACGTGGCGGC ATGCCTTACA CATGCAAGTC GAACGGCAGC
GCGGACTTCG GTCTGGCGGC GAGTGGCGAA CGGGTGAGTA
ATACATCGGA ACGTACCCTG TGCACCGCCG TACGGAATGT
GTACGTTCAG CTTGCCGTCG CGCCTGAAGC CAGACCGCCG
CTCACCGCTT GCCCACTCAT TATGTAGCCT TGCATGGGAC
TTGTGGGGGA TAACTAGTCG AAAGATTAGC TAATACCGCA
TACGACCTGA GGGTGAAAGT GGGGGACCGC AAGGCCTCAC
GCAGCAGGAG CGGCCGATGT AACACCCCCT ATTGATCAGC
TTTCTAATCG ATTATGGCGT ATGCTGGACT CCCACTTTCA
CCCCCTGGCG TTCCGGAGTG CGTCGTCCTC GCCGGCTACA
CTGATTAGCT AGTTGGTGGG GTAAAGGCCC ACCAAGGCGA
CGATCAGTAG CTGGTCTGAG AGGACGATCA GCCACACTGG
GACTGAGACA CGGCCCAGAC GACTAATCGA TCAACCACCC
CATTTCCGGG TGGTTCCGCT GCTAGTCATC GACCAGACTC
TCCTGCTAGT CGGTGTGACC CTGACTCTGT GCCGGGTCTG
TCCTACGGGA GGCAGCAGTG GGGAATTTTG GACAATGGGG
GCAACCCTGA TCCAGCAATG CCGCGTGTGT GAAGAAGGCC
TTCGGGTTGT AAAGCACTTT AGGATGCCCC CGTCGTCAC
CCCTTAAAAC CTGTTACCCC CGTTGGGACT AGGTCGTTAC
GGCGCACACA CTTCTTCCGG AAGCCCAACA TTTCGTGAAA
TGTCCGGAAA GAAATCGCGC TGGTTAATAC CTGCGTGATG
ACGGTACCGG AAGAATAAGC ACCGGCTAAC TACGTGCCAG
CAGCCGCGGT AATACGTAGG ACAGGCCTTT CTTTAGCGCG
ACCAATTATG GACGCACTAC TGCCATGGCC TTCTTATTCG
TGGCCGATTG ATGCACGGTC GTCGGCGCCA TTATGCATCC
GTGCGAGCGT TAATCGGAAT TACTGGGCGT AAAGCGTGCG
CAGGCGGTTT TGTAAGACAG GCGTGAAATC CCCGGGCTTA
ACCTGGGAAT TGCGCTTGTG CACGCTCGCA ATTAGCCTTA
```

```
ATGACCCGCA TTTCGCACGC GTCCGCCAAA ACATTCTGTC

CGCACTTTAG GGGCCCGAAT TGGACCCTTA ACGCGAACAC

ACTGCAAGGC TAGAGTGCGT CAGAGGGGGG TAGAATTCCA

CGTGTAGCAG TGAAATGCGT AGAGATGTGG AGGAATACCG

ATGGCGAAGG CGAGCCCCCT TGACGTTCCG ATCTCACGCA

GTCTCCCCCC ATCTTAAGGT GCACATCGTC ACTTTACGCA

TCTCTACACC TCCTTATGGC TACCGCTTCC GCTCGGGGA

GGACCTTGAC TGACGCTCAT GCACGAAAGC GTGGGGAGCA

AACAGGATTA GATACCCTGG TAGTCCACGC CCTAAACGAT

GTCAACTAGT TGTTGGGATT CCTGGAACTG ACTGCGAGTA

CGTGCTTTCG CACCCCTCGT TTGTCCTAAT CTATGGGACC

ATCAGGTGCG GGATTTGCTA CAGTTGATCA ACAACCCTAA

CATTTTCTCA GTAACGTAGC TAACGCGTGA AGTTGACCGC

CTGGGGAGTA CGGCTGCAAG ATTAAAACTC AAAGGAATTG

ACGGGGACCC GCACAAGCGG GTAAAGAGT CATTGCATCG

ATTGCGCACT TCAACTGGCG GACCCCTCAT GCCGACGTTC

TAATTTTGAG TTTCCTTAAC TGCCCCTGGG CGTGTTCGCC

TGGATGATGT GGATTAATTC GATGCAACGC GAAAAACCTT

ACCTACCCTT GACATGCCCT AACGAAGCAG AGATGCATTA

GTGCCCGCAA AGGGAAAGTG ACCTACTACA CCTAATTAAG

CTACGTTGCG CTTTTTGGAA TGGATGGGAA CTGTACGGGA

TTGCTTCGTC TCTACGTAAT CACGGGCGTT TCCCTTTCAC

GGACACAGGT GCTGCATGGC TGTCGTCAGC TCGTGTCGTG

AGATGTTGGG TTAAGTCCCG CAACGAGCGC AACCCTTGTC

TCTAGTTGCC TACGCAAGAG CCTGTGTCCA CGACGTACCG

ACAGCAGTCG AGCACAGCAC TCTACAACCC AATTCAGGGC

GTTGCTCGCG TTGGGAACAG AGATCAACGG ATGCGTTCTC

CACTCTAGAG AGACTGCCGG TGACAAACCG GAGGAAGGTG

GGGATGACGT CAAGTCCTCA TGGCCCTTAT GGGTAGGGCT

TCACACGTCA TACAATGGTG GTGAGATCTC TCTGACGGCC

ACTGTTTGGC CTCCTTCCAC CCCTACTGCA GTTCAGGAGT

ACCGGGAATA CCCATCCCGA AGTGTGCAGT ATGTTACCAC

CGTACGAGG GTTGCCAACC CGCGAGGGGG AGCTAATCCC

AGAAAACGCA TCGTAGTCCG GATCGTAGTC TGCAACTCGA

CTACGTGAAG CTGGAATCGC GCATGTCTCC CAACGGTTGG

GCGCTCCCCC TCGATTAGGG TCTTTTGCGT AGCATCAGGC

CTAGCATCAG ACGTTGAGCT GATGCACTTC GACCTTAGCG

TAGTAATCGC GGATCAGCAT GCCGCGGTGA ATACGTTCCC

GGGTCTTGTA CACACCGCCC GTCACACCAT GGGAGTGGGT

TTTGCCAGAA GTAGTTAGCC ATCATTAGCG CCTAGTCGTA

CGGCGCCACT TATGCAAGGG CCCAGAACAT GTGTGGCGGG

CAGTGTGGTA CCCTCACCCA AAACGGTCTT CATCAATCGG

TAACCGCAAG GAGGGCGATT ACCACGGCAG GGTTCATGAC

TGGGGTGAAG TCGTAACAAG GTATTGGCGT TCCTCCCGCT

AATGGTGCCG TCCCAAGTAC TGACCCCACT TCAGCATTGT TCCA
```

SEQ ID: 11

MASIEDILEL EALEKDIFRG AVHPSVLKRT FGGQVAGQSL

VSAVRTVDER FEVHSLHGYF LRPGNPTEPT VYLVDRIRDG

RSFCTRRVTG IQDGKAIFTM SASFHSQDEG IEHQDTMPSV

PEPEELVDAQ TVEEMAATDL YREWKEWDVR IVPAGCTGKT

PGIAAKQRVW MRYRNKLPDD QVFHICTLAY LSDMTLLGAS

KVPHPGVVTQ TASLDHAMWF LRPFRADEWL LYDQTSPSAG

FGRALTQGRM FDRKGTMVAA VVQEGLTRIQ RDQDQRDIET GNMA

In some embodiments, the cell comprises a plasmid that contains one or more exogenous nucleic acid sequences encoding enzymes or proteins that include but are not limited to one or more of the following: an acyl carrier protein, a TE, a FAR, a FadR, a FAD, a fatty aldehyde reductase, a cytochrome P450 enzyme, a NADH or NADPH cytochrome P450 reductase, a desaturase, a hydroxylase, and an antibiotic resistance enabling protein; wherein the plasmid is at least 20, 30, 40, 50, 60, 70, 80, 90, 95, 96, 97, 98, or 99% homologous to SEQ ID NO:1, SEQ ID NO:2, SEQ ID NO:3, or SEQ ID NO:4.

In one embodiment, the exogenous gene encodes a FadR. In some cases, the reductase encoded by the exogenous gene catalyzes the reduction of an 8 to 18-carbon fatty acyl-CoA to a corresponding aldehyde. In one embodiment, the reductase encoded by the exogenous gene catalyzes the reduction of a 12-carbon fatty acyl-CoA to dodecanal.

In some embodiments, the invention relates to a bacterial cell or a compositions comprising at least one bacterial cell that comprises at least a first and a second exogenous nucleic acid sequence, wherein the first nucleic acid sequence encodes a FadR or a functional fragment of a FadR and the second exogenous nucleic acid sequence encodes a fatty acyl-CoA ligase or a functional fragment thereof. In some embodiments, the functional fragments of the enzymes encoded by the one or more exogenous nucleic acid sequences are at least 40, 45, 50, 55, 60, 65, 70, 75, 80, 85, 90, 91, 92, 93, 94, 95, 96, 97, 98, or 99% homologous to the nucleic acid sequences that encode the full-length amino acid sequence upon which the functional fragment is based. Any enzyme disclosed in this application and part of the invention may be replaced with a functional fragment. Any composition or cell disclosed in the application may be used in any disclosed method of this application.

In some embodiments, the genetic constructs contain sequences directing transcription and translation of the relevant exogenous (either heterologous or homologous) gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. In some cells the exogenous gene is coding sequence and is in operable linkage with a promoter, and in some embodiments the promoter is derived from a gene endogenous to a species of the genus *Rhodococcus* or *Ralstonia*. Initiation control regions or promoters, which are useful to drive expression of the instant ORFs in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO; and lac, ara, tet, trp, IPL, IPR, T7, tac, and trc as well as the amy, apr, npr promoters and various phage promoters useful for expression in the lipid-producing bacteria of the present invention. In other embodiments the promoter is upregulated in response to reduction or elimination of a cofactor in the culture media of the cell, such as at least a 3-fold upregulation as determined by transcript abundance in a cell when the cell is exposed to extracellular environment changes from containing at least 10 mM or 5 mM cofactor to containing no cofactor.

Termination control regions may also be derived from various genes native to the preferred hosts. Optionally, the genetic constructs of the present invention do not comprise a termination control region.

In some embodiments, the bacterial cell or the composition comprising the bacterial cell comprises at least one genetic construct, which comprises one or more coding sequences. In some embodiments, the invention relates to the bacterial cell or the composition comprising at least one bacterial cell wherein the at least one cell comprises two or more genetic constructs, three or more genetic constructs, or four or more genetic constructs, each comprising one or more coding sequences. In some embodiments, the coding sequences of the claimed invention encode at least one protein that modifies or accelerates lipid production in the host cell. In some embodiments the coding sequence encodes at least one protein that alters the levels of individual lipids or hydrocarbons produced by the cell as compared to the same cell not modified by an exogenous nucleic acid sequence. In some embodiments, the coding sequence may encode at least one protein that alters the amount of one specific lipid or hydrocarbon molecule of the cell as compared to the same cell not modified by the nucleic acid. For example, in one embodiment, the one or more exogenous nucleic acid sequence encodes at least one lipid pathway enzyme that causes an increase in the ratio of C14:C16:C18 unsaturated lipids or desaturated hydrocarbons produced or secreted by the cell as compared to the C14:C16:C18 unsaturated lipids or desaturated hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of C14:C16:C18 unsaturated lipids or desaturated hydrocarbons produced or secreted by the cell as compared to the C14:C16:C18 unsaturated lipids or desaturated hydrocarbons produced or secreted by the same cell not transformed with the nucleic acid sequence that encodes the lipid pathway enzyme. In some embodiments, the one or more cells comprising one or more exogenous nucleic acid sequences produces more hydrocarbon than the same one or more cells not transformed or modified with the one or more exogenous nucleic acid sequences.

In some embodiments, the bacterial cell produces and/or secretes one or more unsaturated lipids or hydrocarbons in a ratio greater than the ratio of unsaturated lipids or hydrocarbons produced and/or secreted by the same cell not comprising the one or more exogenous nucleic acid sequences. In some embodiments, the bacterial cell produces and/or secretes one or more unsaturated lipids or hydrocarbons, wherein at least 50% of the one or more lipids or hydrocarbons have 8 to 18 carbon atoms. In some embodiments, the bacterial cell produces and/or secretes one or more lipids or hydrocarbons, wherein at least 60% of the one or more lipids or hydrocarbons have 8 to 18 carbon atoms. In some embodiments, the bacterial cell produces and/or secretes one or more lipids or hydrocarbons, wherein at least 70% of the one or more lipids or hydrocarbons have 8 to 18 carbon atoms. In some embodiments, the bacterial cell produces and/or secretes one or more lipids or hydrocarbons, wherein at least 75% of the one or more lipids or hydrocarbons have 8 to 18 carbon atoms. In some embodiments, the bacterial cell produces and/or secretes one or more lipids or hydrocarbons, wherein at least 80% of the one or more lipids or hydrocarbons have 8 to 18 carbon atoms.

In some embodiments, the invention relates to a composition comprising a microorganism that converts syngas and/or gaseous $CO_2$ and/or a mixture of $CO_2$ gas and $H_2$ gas into one or more unsaturated hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase, wherein the one or more hydrocarbons have a carbon chain length of at least 8 carbon atoms. In some embodiments, The invention relates to a composition comprising a microorganism that converts syngas and/or gaseous $CO_2$ and/or a mixture of $CO_2$ gas and $H_2$ gas into one or more unsaturated hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the one or more hydrocarbons comprise a mixture of hydrocarbon molecules having a carbon chain length from 8 carbon atoms to 18 carbon atoms. In some embodiments, the invention relates to a composition comprising a microorganism that converts syngas and/or gaseous $CO_2$ and/or a mixture of $CO_2$ gas and $H_2$ gas into one or more unsaturated lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the one or more lipids comprise a quantity of at least one alkene, or alkyne at a level higher than the quantity of the alkene, alkyne in the same microorganism not comprising the heterologous nucleic acid sequences. In some embodiments, the invention relates to a composition comprising a microorganism that converts syngas and/or gaseous $CO_2$ and/or a mixture of $CO_2$ gas and $H_2$ gas into one or more unsaturated lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 60% of one or more lipids by weight.

In some embodiments, the invention relates to a composition comprising a microorganism that converts syngas and/or gaseous CO2 and/or a mixture of CO2 gas and H2 gas into one or more unsaturated lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 65% of one or more lipids by weight. In some embodiments, the invention relates to a composition comprising a microorganism that converts syngas and/or gaseous CO2 and/or a mixture of CO2 gas and H2 gas into one or more unsaturated lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 70% of one or more hydrocarbons by weight.

In some embodiments, the invention relates to a composition comprising a microorganism that converts syngas and/or gaseous CO2 and/or a mixture of CO2 gas and H2 gas into one or more unsaturated lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 75% of one or more lipids by weight. In some embodiments, the invention relates to a composition comprising a microorganism that converts syngas and/or gaseous CO2 and/or a mixture of CO2 gas and H2 gas into one or more unsaturated lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 80% of one or more lipids by weight.

In some embodiments, the invention relates to a composition comprising a microorganism that converts syngas and/or gaseous CO2 and/or a mixture of CO2 gas and H2 gas into one or more unsaturated lipids, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the microorganism produces and/or secretes at least 85% of one or more lipids by weight. In some embodiments, the invention relates to a composition comprising a microorganism that converts syngas and/or gaseous CO2 and/or a mixture of CO2 gas and H2 gas into one or more unsaturated hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein less than 10% by weight of the hydrocarbons produced is methane. In some embodiments, the invention relates to a composition comprising a microorganism that converts syngas and/or gaseous CO2 and/or a mixture of CO2 gas and H2 gas into one or more organic compounds, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein less than 10% by weight of the organic compounds produced are organic acids with carbon chain length of four carbons or less.

In some embodiments, the invention relates to a composition comprising a microorganism that converts syngas and/or gaseous CO2 and/or a mixture of CO2 gas and H2 gas into one or more unsaturated hydrocarbons, wherein the microorganism comprises at least a first and a second exogenous nucleic acid sequence, wherein the first exogenous nucleic acid sequence encodes fatty acid acyl-ACP reductase and the second exogenous nucleic acid sequence encodes a fatty acid aldehyde decarbonylase; wherein the hydrocarbons produced comprise a mixture of at least two hydrocarbons having a carbon backbone from 8 to 18 carbon atoms.

The present invention also relates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous CO2 and/or gaseous H2 and/or syngas into lipids. In some embodiments, the invention relates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous CO2 and/or gaseous H2 and/or syngas into lipid; wherein the cell produces and/or secretes at least 75% of one or more hydrocarbons by weight. In some embodiments, the invention elates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous CO2 and/or gaseous H2 and/or syngas into lipid; wherein the cell produces and/or secretes at least 75% of one or more hydrocarbons by weight when cultured at least 42 degrees Celsius for at least 1 hour. In some embodiments, the bacterial cell is cultured without exposure to light.

In some embodiments, the invention relates to a bacterial cell comprising at least two exogenous nucleic acid sequences, wherein the at least two exogenous nucleic acid sequences encode fatty acid acyl-ACP reductase and fatty acid aldehyde decarbonylase, and wherein the cell converts gaseous CO2 and/or gaseous H2 and/or syngas into a hydrocarbon or mixture of hydrocarbons, and/or other lipids; wherein the cell is a strain of *Rhodococcus opacus*.

In some embodiments, the invention relates to a bacterial cell comprising at least two exogenous nucleic acid sequences, wherein the at least two exogenous nucleic acid sequences encode fatty acid aldehyde acyl-ACP and fatty acid aldehyde decarbonylase, and wherein the cell converts gaseous CO2 and/or gaseous H2 and/or syngas into a hydrocarbon or mixture of hydrocarbons, and/or other lipids; wherein the cell is a strain of *Cupriavidus necator*.

In some embodiments, the invention relates to a bacterial cell comprising a first, a second, and a third exogenous nucleic acid sequence, wherein the first exogenous nucleic acid sequence encodes fatty acid acyl-ACP reductase, the second exogenous nucleic acid sequence encodes a fatty acid aldehyde decarbonylase, and the third exogenous nucleic acid sequence encodes a thioesterase; and wherein the cell converts gaseous CO2 and/or gaseous H2 and/or syngas into a lipid or mixture of lipids. In some embodiments, the bacterial cell comprises no more than eight exogenous nucleic acids that encode a lipid pathway enzyme. In some embodiments, the bacterial cell comprises no more than seven exogenous nucleic acids that encode a lipid pathway enzyme. In some embodiments, the bacterial cell comprises no more than six exogenous nucleic acids that encode a lipid pathway enzyme. In some embodiments, the bacterial cell comprises no more than five exogenous nucleic acids that encode a lipid pathway enzyme. In some embodiments, the bacterial cell comprises no more than four exogenous nucleic acids that encode a lipid pathway enzyme. In some embodiments, the bacterial cell comprises no more than three exogenous nucleic acids that encode a lipid pathway enzyme. In some embodiments, the bacterial cell comprises no more than two exogenous nucleic acids that encode a lipid pathway enzyme. In some embodiments, the bacterial cell comprises no more than one exogenous nucleic acid that encodes a lipid pathway enzyme. In some embodiments, the bacterial cell comprises no more than eight exogenous nucleic acids that encode a protein. In some embodiments, the bacterial cell comprises no more than seven exogenous nucleic acids that encode a protein. In some embodiments, the bacterial cell comprises no more than six exogenous nucleic acids that encode a protein. In some embodiments, the bacterial cell comprises no more than five exogenous nucleic acids that encode a protein. In some embodiments, the bacterial cell comprises no more than four exogenous nucleic acids that encode a protein. In some embodiments, the bacterial cell comprises no more than three exogenous nucleic acids that encode a protein. In some embodiments, the bacterial cell comprises no more than two exogenous nucleic acids that encode a protein. In some embodiments, the bacterial cell comprises no more than one exogenous nucleic acid that encodes a protein.

In some embodiments, the molecule is chosen from one or more alkene, alkyne, unsaturated fatty acid, hydroxyacid and/or dicarboxylic acid (diacid). In some embodiments, the method produces a lipid or mixture of lipids at a quantity higher than the quantity of lipid or mixture of lipids in the same bacterial cell population not comprising the exogenous nucleic acids described herein. In some embodiments the one or more lipids comprise a quantity of at least one alkene, alkyne, unsaturated fatty acid, hydroxyacid and/or diacid at a level higher than the quantity of the alkene, alkyne, unsaturated fatty acid, hydroxyacid and/or diacid in the same microorganism not comprising the exogenous nucleic acid sequences. In some embodiments, the method comprises a population of microorganisms or bacterial cell described herein that produces and/or secretes lipids of a weight equal to or greater than 10% of the total percentage of cellular dry matter. In some embodiment, the method comprises a population of microorganisms or bacterial cell described herein that produces and/or secretes lipids of a weight equal to or greater than 20% of the total percentage of cellular dry matter. In some embodiment, the method comprises a population of microorganisms or bacterial cell described herein that produces and/or secretes lipids of a weight equal to or greater than 30% of the total percentage of cellular dry matter. In some embodiments, the method comprises a population of microorganisms or bacterial cell described herein that produces and/or secretes lipids of a weight equal to or greater than 40% of the total percentage of cellular dry matter. In some embodiment, the method comprises a population of microorganisms or bacterial cell described herein that produces and/or secretes lipids of a weight equal to or greater than 50% of the total percentage of cellular dry matter. In some embodiment, the method comprises a population of microorganisms or bacterial cells described herein that produces and/or secretes lipids of a weight equal to or greater than 60% of the total percentage of cellular dry matter. In some embodiments, the method comprises a population of microorganisms or bacterial cells described herein that produces and/or secretes lipids of a weight equal to or greater than 70% of the total percentage of cellular dry matter. In some embodiments, the method comprises a population of microorganisms or bacterial cell described herein that produces of secretes lipids of a weight equal to or greater than 75% of the total percentage of cellular dry matter. In some embodiment, the method comprises a population of microorganisms or bacterial cell described herein that produces of secretes lipids of a weight equal to or greater than 80% of the total percentage of cellular dry matter. In some embodiments, the method comprises a population of microorganisms or bacterial cell described herein that produces of secretes lipids of a weight equal to or greater than 85% of the total percentage of cellular dry matter. In some embodiments, the bacterial cell or composition comprising the bacterial cell produces and/or secretes at least 10% of the total percentage of the cellular dry matter or 10% by weight. In some embodiment, the method comprises a population of microorganisms comprising a bacterial cell described herein that produces or secretes lipids, wherein at least 5% of the lipids have carbon backbones from 8 to 18 carbon atoms in length. In some embodiment, the method comprises a population of microorganisms comprising a bacterial cell described herein that produces or secretes lipids, wherein at least 10% of the lipids have carbon backbones from 8 to 18 carbon atoms in length. In some embodiments, the method comprises a population of microorganisms comprising a bacterial cell described herein that produces or secretes lipids, wherein at least 15% of the lipids have carbon backbones from 8 to 18 carbon atoms in length. In some embodiments, the method comprises a population of microorganisms comprising a bacterial cell described herein that produces or secretes lipids, wherein at least 20% of the lipids have carbon backbones from 8 to 18 carbon atoms in length.

In some embodiments of the invention, the invention relates to a method of fixing carbon from a gaseous feedstock containing carbonaceous molecules, wherein the method comprises the step of exposing a composition comprising a bacterial cell to syngas and/or gaseous CO2 and/or gaseous H2; wherein the bacterial cell comprises at least one exogenous nucleic acid sequence. In some embodiments the exogenous nucleic acid sequences are fatty acid acyl-ACP reductase or a fatty acid aldehyde decarbonylase. In some embodiments of the method, the bacterial cell comprises at least a first and a second exogenous nucleic acid sequence, wherein the first exogenous nucleic acid sequence encodes a fatty acid acyl-ACP reductase and the second exogenous nucleic acid sequence encodes a fatty acid aldehyde decarbonylase. In some embodiments, the bacterial cell is *Rhodococcus opacus* or the population of microorganisms comprises a *Rhodococcus* cell. In some embodiments, the bacterial cell is *Cupriavidus necator* or the population of microorganisms comprises a *Cupriavidus* cell. In some embodiments, the bacterial cell comprises at least a first, a second, and a third exogenous nucleic acid sequence, wherein the first exogenous nucleic acid sequence encodes a fatty acid acyl-ACP reductase, the second exogenous nucleic acid sequence encodes a fatty acid aldehyde decarbonylase, and the third exogenous nucleic acid sequence encodes a thioesterase. In some embodiments, the bacterial cell comprises no more than five exogenous nucleic acid sequences that encode a lipid pathway enzyme. In some embodiments the bacterial cell comprises at least a first and a second exogenous nucleic acid sequence but no more than five exogenous nucleic acid sequences, wherein the first exogenous nucleic acid sequence encodes fatty acid acyl-ACP reductase and the second exogenous nucleic acid sequence encodes a fatty acid aldehyde decarbonylase.

In some embodiments, the invention relates to a method of producing one or more alkene, alkyne, unsaturated fatty acid, hydroxyacid and/or diacid or any combination thereof comprising exposing a bacterial cell to syngas and/or gaseous CO2 or a mixture of gaseous CO2 and gaseous H2; wherein the bacterial cell is capable of fixing gaseous CO2 into one or more alkene, alkyne, unsaturated fatty acid, hydroxy acid and/or diacid and wherein the microorganism comprises at least a first exogenous nucleic acid and a second exogenous nucleic acid, wherein the first exogenous nucleic acid encodes fatty acid acyl-ACP reductase and the second exogenous nucleic acid encodes fatty acid aldehyde decarbonylase. In some embodiments, the first and second exogenous nucleic acids are heterologous nucleic acid sequences. In some embodiments, the bacterial cell comprises at least a first, a second, and a third exogenous nucleic acid sequence, wherein the first exogenous nucleic acid sequence encodes a fatty acid acyl-ACP reductase, the second exogenous nucleic acid sequence encodes a fatty acid aldehyde decarbonylase, and the third exogenous nucleic acid sequence encodes a thioesterase. In some embodiments, the bacterial cell comprises at least a first exogenous nucleic acid sequence, wherein the first exogenous nucleic acid sequence encodes a thioesterase. In some embodiments, the bacterial cell comprises no more than five exogenous nucleic acid sequences that encode a lipid pathway enzyme.

In some embodiments, the one or more exogenous nucleic acid sequence encodes at least one lipid pathway enzyme that causes an increase in the ratio of C12:C14:C16 lipids or hydrocarbons produced or secreted by the cell as compared to the C12:C14:C16 lipids or hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of C12:C14:C16 lipids or hydrocarbons produced or secreted by the cell as compared to the C12:C14:C16 lipids or hydrocarbons produced or secreted by the same cell not transformed with the nucleic acid sequence that encodes the lipid pathway enzyme. In some embodiments, the one or more exogenous nucleic acid sequence encodes at least one lipid pathway enzyme that causes an increase in the ratio of C13:C15:C17 lipids or hydrocarbons produced or secreted by the cell as compared to the C13:C15:C17 lipids or hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of C13:C15:C17 lipids or hydrocarbons produced or secreted by the cell as compared to the C13:C15:C17 lipids or hydrocarbons produced or secreted by the same cell not transformed with the nucleic acid sequence that encodes the lipid pathway enzyme. In some embodiments, the one or more exogenous nucleic acid sequence encodes at least one lipid pathway enzyme that causes an increase in the ratio of odd-carbon numbered lipids or hydrocarbons produced or secreted by the cell as compared to the odd-carbon numbered lipids or hydrocarbons produced or secreted by the same cell not transformed with the nucleic acid sequence that encodes the lipid pathway enzyme. In some embodiments, the one or more exogenous nucleic acid sequence encodes at least one lipid pathway enzyme that causes a decrease in the ratio of odd-carbon numbered lipids or hydrocarbons produced or secreted by the cell as compared to the odd-carbon numbered lipids or hydrocarbons produced or secreted by the same cell not transformed with the nucleic acid sequence that encodes the lipid pathway enzyme. In one embodiment, the one or more exogenous nucleic acid sequence encodes at least one lipid pathway enzyme that causes a decrease in the ratio of even:odd carbon numbered lipids or hydrocarbons produced or secreted by the cell as compared to the ratio of even:odd carbon numbered lipids or hydrocarbons produced or secreted by the same cell not transformed with the nucleic acid sequence that encodes the one or more lipid pathway enzymes. In one embodiment, the one or more exogenous nucleic acid sequence encodes at least one lipid pathway enzyme that causes a increase in the ratio of even:odd carbon numbered lipids or hydrocarbons produced or secreted by the cell as compared to the ratio of even:odd carbon numbered lipids or hydrocarbons produced or secreted by the same cell not transformed with the nucleic acid sequence that encodes the one or more lipid pathway enzymes.

In some embodiments the exogenous gene or genes codes for enzymes or proteins including but not limited to one or more of the following: an acyl carrier protein, a TE, a FAR, a FadR, a FAD, a fatty aldehyde reductase, a cytochrome P450 enzyme, a NADH or NADPH cytochrome P450 reductase, a desaturase, a hydroxylase, and an antibiotic resistance enabling protein. In some embodiments, the coding sequence comprises an exogenous nucleic acid sequence that encodes a TE that catalyzes hydrolysis of one or more fatty acyl-ACP substrates with chain lengths ranging over C8, C9, C10, C11, C12, C13, C14, C15, C16, C17, or C18. In some embodiments, the cell comprises a plasmid that contains one or more exogenous nucleic acid sequences that encode an amino acid sequence for an enzyme or protein such as but not limited to one or more of the following: an acyl carrier protein, a TE, a FAR, a FadR, a FAD, a fatty aldehyde reductase, a cytochrome P450 enzyme, a NADH or NADPH cytochrome P450 reductase, a desaturase, a hydroxylase, and an antibiotic resistance enabling protein. In some embodiments, the one or more exogenous nucleic acid sequences comprise SEQ ID NO:5 or a functional fragment thereof that is at least 70%, 75%, 80%, 85%, 90%, 91%, 92%, 93%, 94%, 95%, 96%, 97%, 98%, or 99% homologous to SEQ ID NO:5. In some embodiments, the one or more exogenous nucleic acid sequences comprise SEQ ID NO:6 or a functional fragment thereof that is at least 70%, 75%, 80%, 85%, 90%, 91%, 92%, 93%, 94%, 95%, 96%, 97%, 98%, or 99% homologous to SEQ ID NO:6.

In further embodiments, at least one coding sequence of the at least one exogenous nucleic acid sequence encodes a lipid pathway enzyme. In some embodiments, the at least one coding sequence of the at least one exogenous nucleic acid sequence encodes a lipid modification enzyme. In some embodiments, the composition or cell comprises a nucleic acid that encodes at least one fatty acid decarbonylase, at least one fatty acid reductase, a thioesterase, or any combination of any one more full-length lipid pathway enzymes or functional fragments thereof. In some embodiments the one or more exogenous nucleic acid sequences are integrated into the genome of the cell. In some embodiments, the one or more exogenous nucleic acid sequences are on an episomal plasmid within the transformed host cell.

Methods of Isolation and Purification

Following the methods of the present invention microorganisms are grown and maintained for the production of lipids in a medium containing a gaseous carbon source, such as but not limited to syngas or producer gas, in the absence of light; such growth is known as chemotrophic growth. In some embodiments, the invention relates to methods of cultivating oleaginous cells for the large-scale production of oil and/or fuel. In some embodiments, the invention relates to methods of cultivating oleaginous cells in bioreactors 50,000 liters or greater in volume, which are conventionally constructed out of low cost, sturdy, and opaque materials such as steel or reinforced concrete or earthworks. The size, depth, and construction of such bioreactors dictate that the cells will be grown in near or total darkness. In some embodiments, the oleaginous microorganisms are cultured for the synthesis of lipids in accordance with the methods of the present invention in a medium containing gaseous inorganic carbon, such as but not limited to syngas or producer gas, as the primary or sole carbon source, and without any exposure to light. This type of growth is known as chemoautotrophic growth.

To give an illustration, a bioreactor containing nutrient medium is inoculated with of oleaginous bacterial cells; generally there will follow a lag phase prior to the cells beginning to double. After the lag phase, the cell doubling time decreases and the culture goes into the logarithmic phase. The logarithmic phase is eventually followed by an increase of the doubling time that, while not intending to be limited by theory, is thought to result from either a depletion of nutrients including nitrogen sources, or a rise in the concentration of inhibitory chemicals, or quorum sensing by the microbes. The growth slows down and then ceases when the culture goes into the stationary phase. In order to harvest cell mass with high lipid content, the culture is generally harvested late in the logarithmic phase or in the stationary phase. In some embodiments, the cells are harvested in logarithmic phase. In some embodiments, the cells are harvested in stationary phase. The accumulation of lipid can generally be triggered by the depletion of the nitrogen source or another key nutrient excepting the carbon or the energy source (e.g. hydrogen). This signals the cells to store lipids produced from the excess carbon and energy sources. Optimization of lipid production and the targeting of specific lipid distributions can be achieved by control of bioreactor conditions and/or nutrient levels and/or through genetic modifications of the cells. In some embodiments the lipid production and distribution of lipid molecules produced is optimized through one or more of the following: control of bioreactor conditions, control of nutrient levels, genetic modifications of the cells.

The synthesis of lipids by the microbes disclosed in the present invention can happen during the logarithmic phase and afterwards during the stationary phase when cell doubling has stopped provided there is an ample supply of carbon and energy sources, In some embodiments, microorganisms grown using conditions described herein and known in the art comprise at least 20% lipid content by weight, but under chemotrophic conditions, comprise at least 10% lipid content by weight. In some embodiments, under chemotrophic conditions, the microorganisms of the present invention comprise at least about 10, 15, 20, 25, 30, 35, or 40% by weight of lipids, at least about 50% by weight, or at least about 60% by weight of lipids. Improved lipid yield and/or lower production costs can be achieved by controlling process parameters. In certain embodiments, a bacterium is grown in a nutrient media and/or gas mix having a nitrogen, oxygen, phosphorous, or sulfur limitation, while a gaseous carbon and energy source such as syngas is provided in excess. Lipid yield is generally higher in microbial cultures grown with a nitrogen limitation versus microbial cultures grown without nitrogen limitation. In certain embodiments, lipid yield rises by at least: 10%, 50%, 100%, 200%, 500%, or 1000%. The microbial growth can occur with nutrient limitation for a part or for all of the fermentation run. Feeding an excess of energy and carbon source to a population of oleaginous microbes, but little or no nitrogen, can produce a rise in cellular lipid content. In some embodiments, microbial growth occurs on limited amounts of nitrogen or in the complete absence of nitrogen.

Genes are well known in the art that code for cofactors useful in the present invention, or that are involved in synthesizing such cofactors.

In another embodiment, genes that code for cofactors useful in the present invention, or that are involved in synthesizing such cofactors, are put in oleaginous bacteria, using the constructs and methods such as described above. Lipid yield is improved in another embodiment by growing an oleaginous bacteria with one or more lipid pathway enzyme cofactor(s) added to the culture environment. The lipid yield is generally improved in the presence of a certain concentration of the cofactor(s) compared to lipid yield without supplemental cofactor(s). In some embodiments, the cofactor(s) are delivered to the culture by having a microbe (e.g., bacteria) present in the culture that contains an exogenous gene coding for the cofactor(s) at a concentration sufficient to increase lipid yield as compared to the lipid yield of the microbe in the absence of the cofactor. Cofactor(s) may also be delivered to a culture by having a microbe (e.g., bacteria) present in the culture that contains an exogenous gene that coding for a protein involved in the cofactor synthesis. In some embodiments, any vitamin needed for the proper function of a lipid pathway enzyme including biotin and/or pantothenate is included in the culture environment.

The specific examples of bioreactors, culture conditions, heterotrophic and chemotrophic growth, maintenance, and lipid production methods described herein can be combined in any suitable manner to improve efficiencies of microbial growth and lipid and/or protein production.

In another aspect of the invention, the invention relates to a method of producing a molecule or mixture of molecules in a microorganism population comprising the cell or the composition described herein, wherein the method comprises: culturing a population of microorganisms comprising the cell or the composition described herein in a feedstock comprising syngas and/or gaseous CO2 and/or a mixture of CO2 gas and H2 gas.

In another aspect of the invention, the invention relates to a method of producing a hydrocarbon or mixture of hydrocarbons in a microorganism population comprising the cell or the composition described herein, wherein the method comprises: culturing a population of microorganisms comprising the cell or the composition described herein in a feedstock comprising syngas and/or gaseous CO2 and/or a mixture of CO2 gas and H2 gas.

In another aspect of the invention, the invention relates to a method of producing a lipid or mixture of lipids in a microorganism population comprising the cell or the composition described herein, wherein the method comprises: culturing a population of microorganisms comprising the cell or the composition described herein in a feedstock comprising syngas and/or gaseous CO2 and/or a mixture of CO2 gas and H2 gas.

In another aspect of the invention, the invention relates to a method of producing an alkene or mixture of alkenes in a microorganism population comprising the cell or the composition described herein, wherein the method comprises: culturing a population of microorganisms comprising the cell or the composition described herein in a feedstock comprising syngas and/or gaseous CO2 and/or a mixture of CO2 gas and H2 gas.

In another aspect of the invention, the invention relates to a method of producing an alkyne or mixture of alkynes in a microorganism population comprising the cell or the composition described herein, wherein the method comprises: culturing a population of microorganisms comprising the cell or the composition described herein in a feedstock comprising syngas and/or gaseous CO2 and/or a mixture of CO2 gas and H2 gas.

In some embodiments, the methods of the claimed invention do not rely on desulfonation to produce and/or secrete one or more hydrocarbons. In some embodiments, an exogenous nucleic acid is introduced into the cells of the claimed invention to silence or disrupt transcription of endogenous genes of the cell that encode enzymes capable of desulfonation of commercial surfactants under conditions and for a time period sufficient for growth of the cell with a gaseous feedstock comprising a gas comprising carbon.

In some embodiments, the feedstock does not include linoleic acid.

The following documents are incorporated herein by reference in their entirety for all purposes: U.S. Provisional Patent Application No. 61/328,184, filed Apr. 27, 2010 and entitled "USE OF OXYHYDROGEN MICROORGANISMS FOR NON-PHOTOSYNTHETIC CARBON CAPTURE AND CONVERSION OF INORGANIC CARBON SOURCES INTO USEFUL ORGANIC COMPOUNDS"; International Patent Application Serial No. PCT/US2010/001402, filed May 12, 2010, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS"; and U.S. Patent Application Publication No. 2010/0120104, filed Nov. 6, 2009, entitled "BIOLOGICAL AND CHEMICAL PROCESS UTILIZING CHEMOAUTOTROPHIC MICROORGNISMS FOR THE CHEMOSYTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS.

Doan T T P, Carlsson A S, Hamberg M, Bulow L, Stymne S, Olsson P, Functional expression of five *Arabidopsis* fatty acyl-CoA reductase genes in *Escherichia coli*, J Plant Phys 166 (2008):787-96.

Kavanagh K L, Jornvall H, Persson B, Oppermann U, The SDR superfamily: functional and structural diversity within a family of metabolic and regulatory enzymes, Cell Mol Life Sci 65 (2008) 3895-3906.

Labesse G, Vidal-Cros A, Chomilier J, Gaudry M, Mornon J-P, Structural comparisons lead to the definition of a new superfamily of NAD(P)(H)-accepting oxidoreductases: the single-domain reductases/epimerases/dehydrogenases (the 'RED' family), Biochem J (1994) 304:95-99.

The following examples are intended to illustrate certain embodiments of the present invention, but do not exemplify the full scope of the invention. Various publications, including patents, published applications, technical articles and scholarly articles are cited throughout the specification. Each of these cited publications is incorporated by reference herein, in its entirety.

EXAMPLE 1

Characterization of Organisms Sharing High 16SrRNA Sequence Similarity

Figure 2:
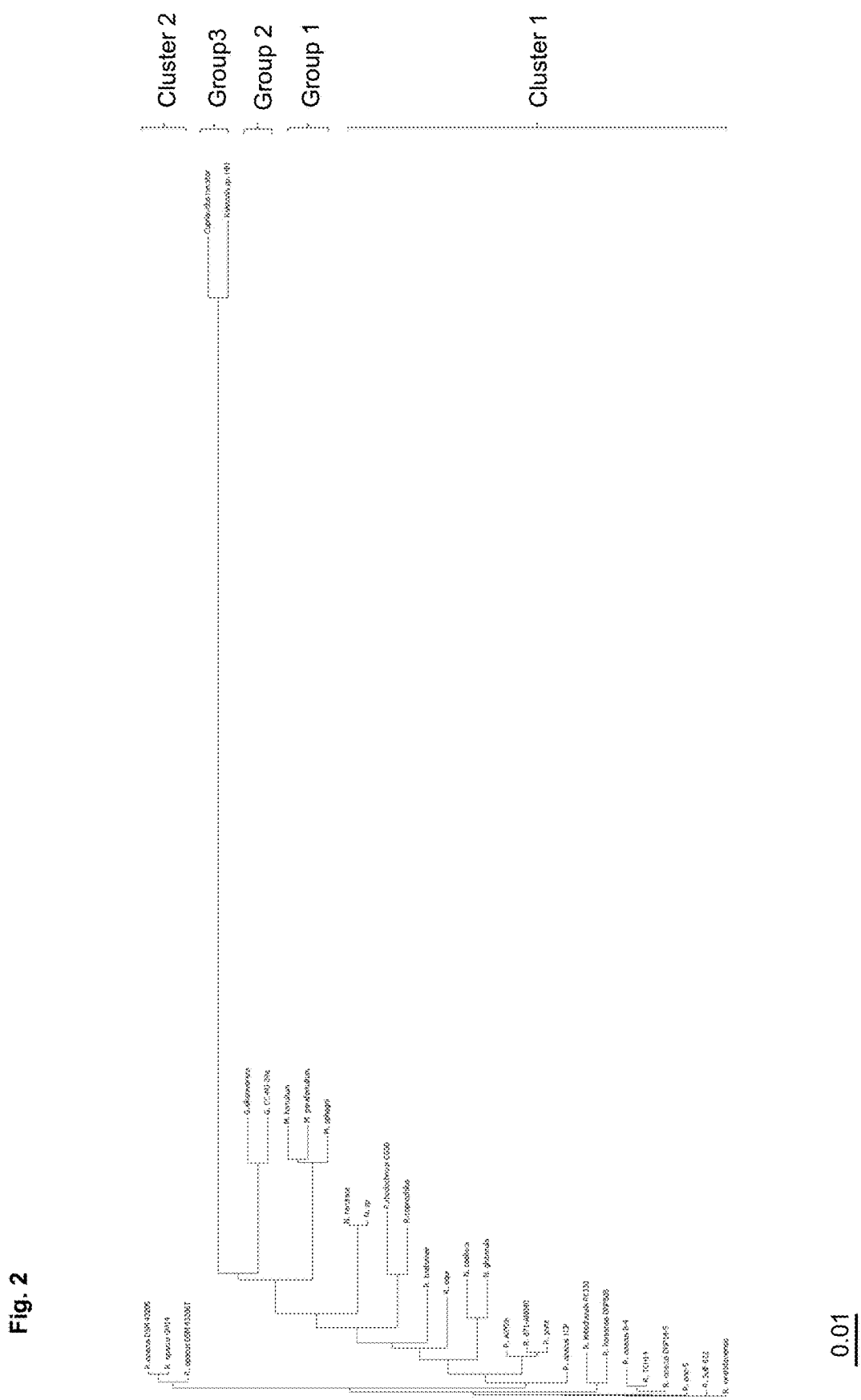
FIG. 2 shows the 16S rRNA gene based-rooted phylogenetic tree of gordoniaceae, mycobacteriaceae, nocardiaceae and burkholderiaceae.
Figure 4A:
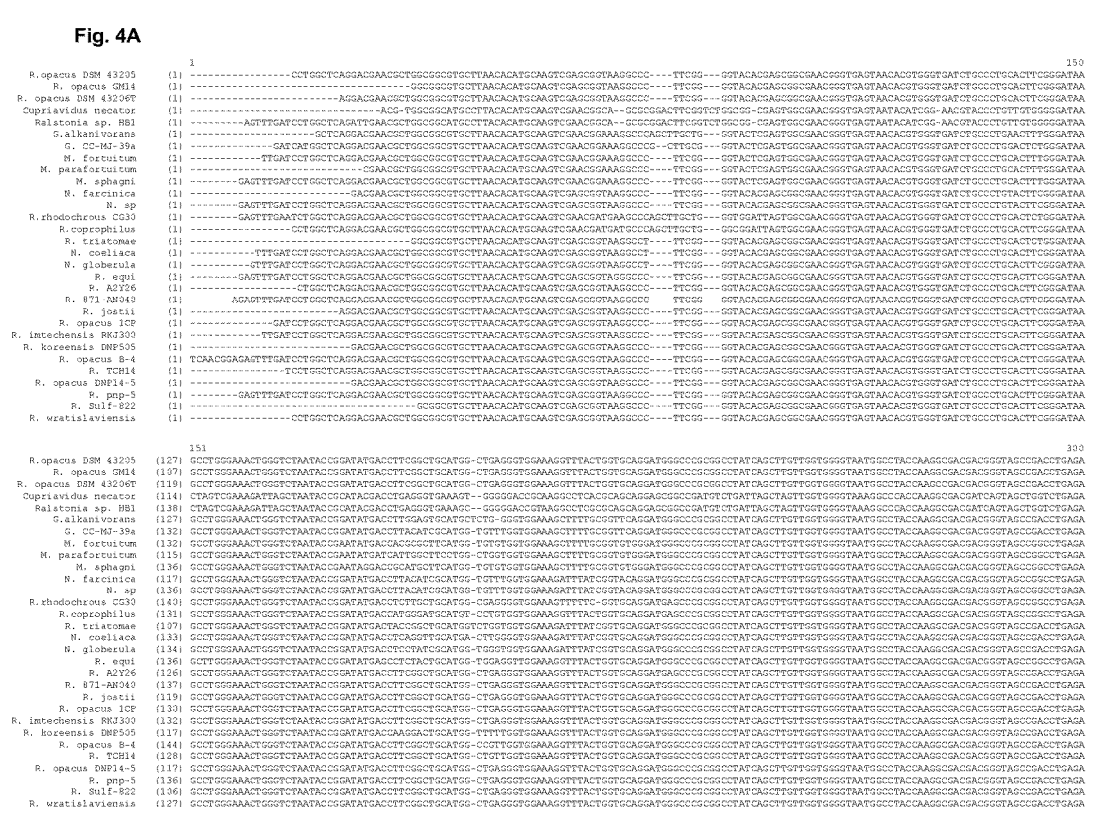
Figure 4B:
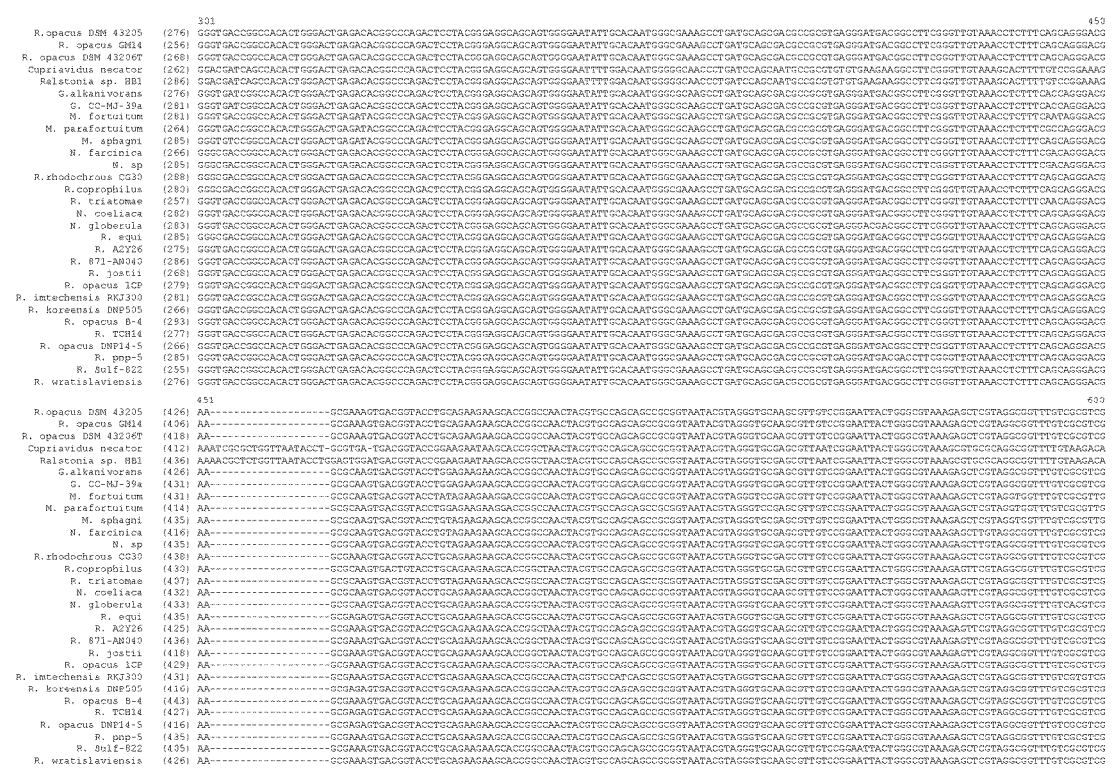
Figure 4C:
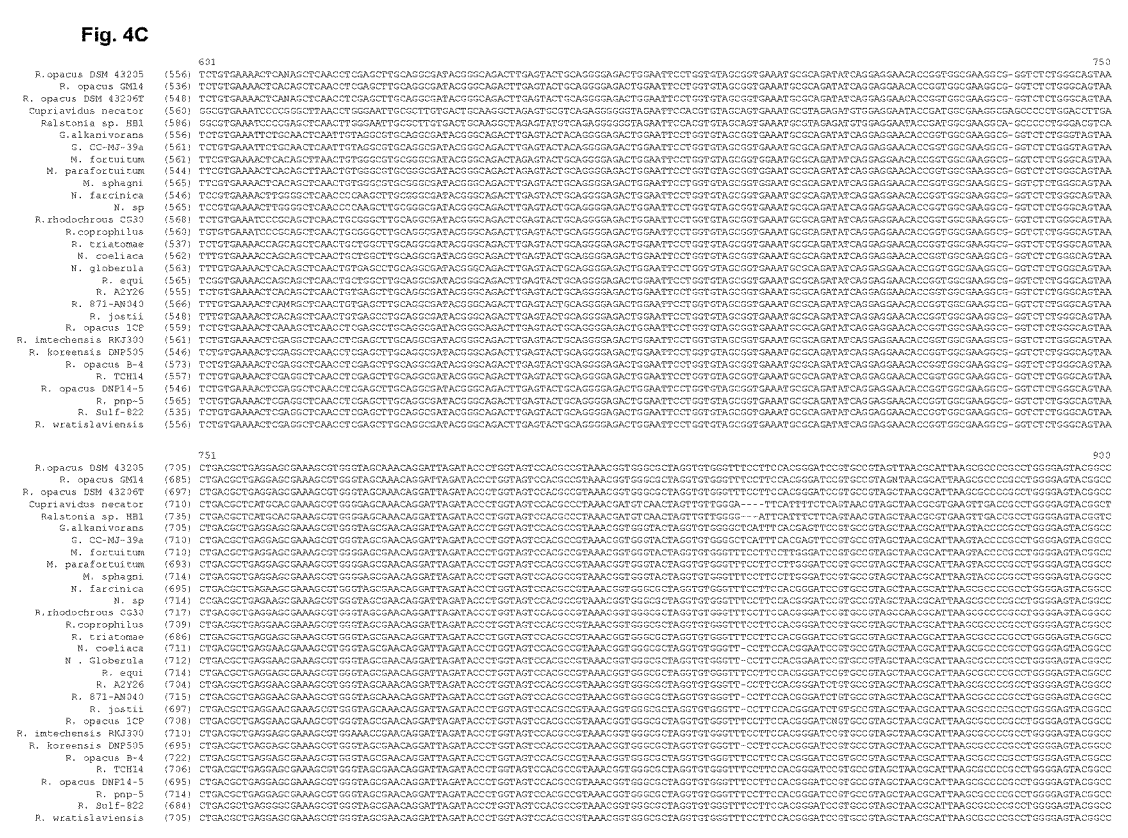
Figure 4D:
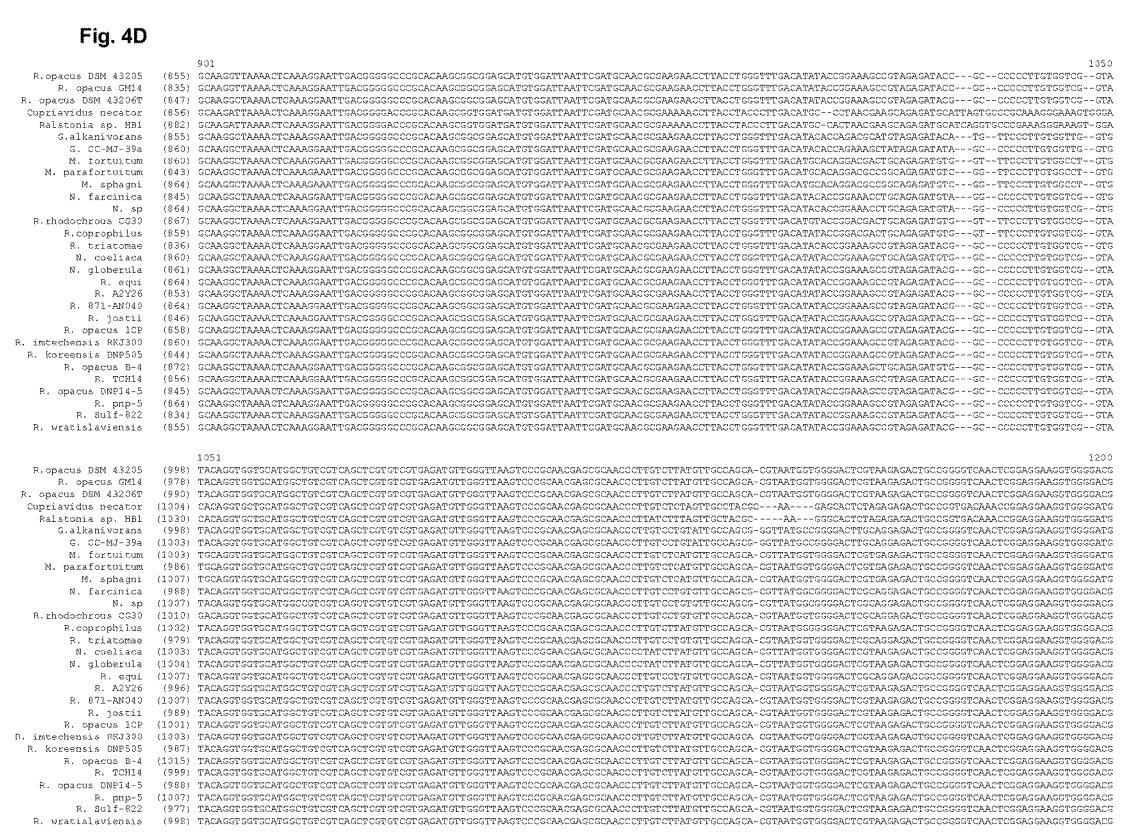
Figure 4E:
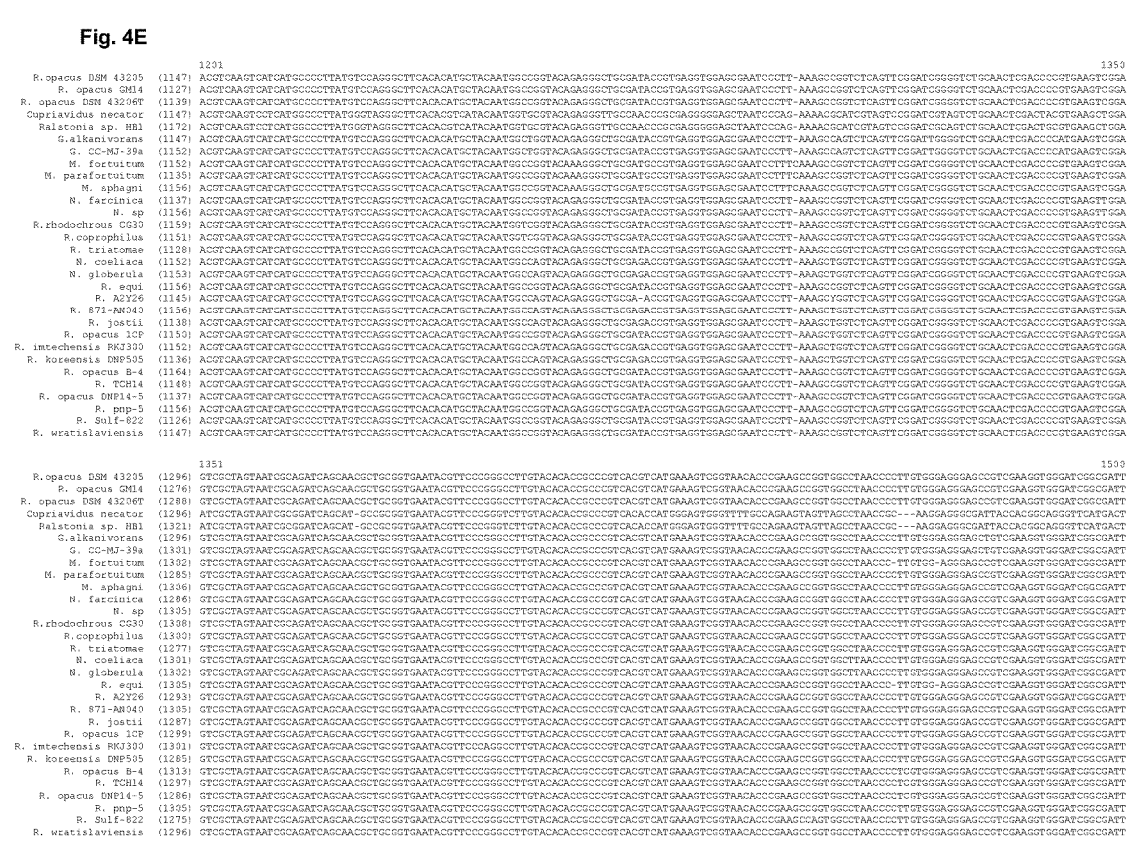

To identify organisms closely related to *R. opacus* strain (DSM43205), a basic local alignment search (BLASTR) with the BLASTN programs search of nucleotide databases using the 16S rRNA (NR_026186.1) was carried out. The phylogenetic relationships, based on the 16S rRNA gene sequence homology, between the tested strain and the reference strains of the suborder corynebacterineae (corynebacterium, gordoniaceae, mycobacteriaceae and nocardiaceae) and the family burkholderiaceae (genus *cupriavidus* and *ralstonia*) are shown in FIG. 2. The nocardiaceae are related and form two clusters of organisms: clusturel that contains 20 organisms from the genus *nocardia* and *rhodococcus* and cluster 2 that contains 3 *R. opacus* strains (DSM43205, GM14 and DSM43206). The gordoniaceae, mycobacteriaceae and burkholderiaceae form 3 separated groups (1, 2 and 3). The gram positive chemoautotroph lipid accumulating strain *R. opacus* (DSM43205; NR_026186.1) exhibits high sequence similarity to cluster 1 (94.3-99.1%) and to the gram positive groups 1 and 2 (92.7-93.5% and 93.3-93.6% respectively) (FIGS. 3 and 4). The sequence similarity to the gram-negative chemoautotroph poly(3-hydroxybutyrate) (PHB) accumulating strains in group 3 is 73.7%.

EXAMPLE 2

Plasmid Design and Construction

To generate an *E. coli* Rhodococci shuttle vector suitable for electroporation, the plasmid pSeqCO1 (SEQ ID: 01) was constructed with the genetic elements described in FIG. 10A. pSeqCO1 consists of the replication gene operon, ampicillin and kanamycin resistance genes, LacZ operon and the multiple cloning site as described in FIG. 10B and FIG. 11A. For replication in Rhodococci, the DNA fragment of the repAB operon (1744 bp downsteam from the XhoI restriction site in the native pKNR01 plasmid of the bacteria *Rhodococcus opacus* B4; Na et al. 2005, J Biosci Bioeng. 99: 408-414) was synthesized with the restriction sites KpnI and SalI and cloned into PUC 18 digested with KpnI and SalI. The resultant vector was digested with SpeI and BglII and ligated with the PCR product of the Kanamycin resistance gene from pBBR1MCS-2 (Kovach et al. 1995 Gene 166: 175-176) digested with the engineered restriction sites SpeI and BglII to give pSeqCO1.

To generate an *E. coli-cupriavidus* shuttle vector suitable for electroporation and bacterial conjugation, the plasmid pSeqCO2 (SEQ ID: 02) was used with the genetic elements described in FIG. 10A. pSeqCO2 (SEQ ID: 02; FIGS. 10 and 11B) is the plasmid pBBR1MCS-2 described in Kovach et al. (1995 Gene 166: 175-176) that contains the IncQ like replication gene, Mob gene that mobilized when the RK2 transfer functions are provided in trans, kanamycin resistance gene, LacZ operon and the multiple cloning site as described in FIG. 10B and FIG. 11B.

Pver1 (SEQ ID: 03; FIGS. 10 and 11C) is an *E. coli-cupriavidus*-Rhodococci shuttle vector suitable for electroporation and bacterial conjugation. The plasmid was generated by cloning the repAB operon (described in pSeqCO1) into pSeqCO2 using the KpnI and SalI restriction sites.

Pver2 (SEQ ID: 04; FIGS. 10 and 11D) is an *E. coli-cupriavidus*-Rhodococci shuttle vector suitable for electroporation and bacterial conjugation. The plasmid was generated by cloning the synthesized chloramphenicol gene (Alton and Vapnek Nature 1979 282: 864-869) with the engineered restriction sites SalI and HindIII into Pver1.

The genes FadDR (SEQ ID: 05) and Fad (SEQ ID: 06) and the rbcLXS promoter (SEQ ID: 7) were PCR amplified from the cyanobacterium *Synechocystis* sp. PCC 6803 genome and cloned into gateway plasmid to give pFUEL. A 4 kBp XhoI BamHI fragment that contains FadDR, Fad and rbcLXS was rescued from pFUEL and cloned into pSeqCO2 digested XhoI BamHI with to give pSeqCO2::FUEL (FIG. 14).

EXAMPLE 3

Microorganism Transformation

Transformation of Rhodococci was carried out using the plasmids pSeqCO1 and pVer1 (FIG. 12) as described below.

Rhodococci competent cells were prepared by incubating a single colony 2 ml NB medium (5 g/L peptone, 1 g/L meat extract, 2 g/L yeast extract, 5 g/L NaCl; pH=7.0±0.2) at 30° C. overnight. One ml was inoculated to 50 ml NB medium supplemented with 0.85% (w/v) glycine and 1% (w/v) sucrose in a 250 ml baffled Erlenmeyer Flask and incubated to a cell density of O.D600=0.5. Cells were collected by centrifugation at 3,000×g for 10 min at 4° C. and washed 3 times with 50 ml (each) of sterile ice-cold double distilled water (ddH2O). Cells were concentrated 20-fold by re-suspending the collected cells in 2.5 ml of ddH2O and 400 μl aliquots stored in1.5 ml tube at −70° C. Electroporation was carried out by thawing the competent cells on ice and mixing with the plasmid DNA (final concentration 0.1-0.25 μg/ml). The competent cells and plasmid DNA mixture was incubated at 40° C. for 5 min, transferred into 0.2 cm width and electroporated using a single-pulse electroporation (10 kV/cm, 600Ω, 25 μF and 3-5 ms pulse time). The pulsed cells were regenerated at 30° C. for 4 h (DSM 44193) and 6 h (DSM 43205) in the presence of 600 μl NB. Transformants were selected after cultivation for 3-4 days at 30° C. on NB-agar plate containing kanamycin (75 μg/ml). As shown in FIG. 12, the plasmids pSeqCO1 and pVer1 confer resistance to kanamycin (75 μg/ml) in transformed *R. opacus* strains (44193 and 43205). Untransformed *R. opacus* strains (44193 and 43205) (NC) were sensitive to the concentration described above.

Transformation of genus *cupriavidus* was carried out using the plasmids pSeqCO2 (FIG. 12) as described below.

*Cupriavidus necator* (DSM531) competent cells were prepared by incubating a single colony in 5 ml NR medium (10 g/l polypeptone, 10 g/l yeast extract, 5 g/l beef extract and 5 g/l ammonium sulfate; pH 7.0) at 30° C. overnight. The pre-culture was inoculated into 100 ml of fresh NR medium and incubated to a cell density of O.D600=0.8. Cells were collected by centrifugation at 3,000×g for 10 min at 4° C. and washed 3 times with 50 ml (each) of sterile ice-cold ddH2O. The collected cells were re-suspended in 400 μl of 10% (v/v) sterile glycerol in sterile ice-cold ddH2O and stored in 50 μl aliquots at −70° C.

For electroporation, the competent cells were thawed on ice, transferred into 0.2 cm width of ice cold cuvette and gently mixed with 1 μg of plasmid DNA. Cells were electroporated using a single-pulse electroporation (11.5 kV/cm, 25 μF and 5 ms pulse time). The pulsed cells were transferred into 1 ml of fresh NR medium and culture for 2 h at 30° C. Transformants were selected after cultivation for 48 h at 30° C. on NR-agar plate containing kanamycin (200 μg/ml). As shown in FIG. 12, the plasmid pSeqCO2 confers resistance to kanamycin (200 μg/ml) in transformed *Cupriavidus necator* (DSM531). Untransformed *Cupriavidus necator* (DSM531) cells (NC) were sensitive to the concentration described above.

EXAMPLE 4

Inoculation and Growth Conditions

Organisms from the genus *rhodococcus* and from the genus *cupriavidus* were tested for their ability to grow on different carbon sources (FIG. 5). Colonies from strains grown on LB agar plates at 30° C. were transferred into flasks containing 10% (v/v) of the indicated media for 3-20 days at 30° C. and 250 rpm. *R. opacus* strain DSM 44193 exhibited growth only under heterotrophic growth conditions as measured by optical density (OD) at 650 nm on MSM medium (1 L Medium A: 9 g Na2HPO412H2O, 1.5 g H2PO4, 1.0 g NH4Cl and 0.2 g MgSO4.7H2O per 1 L; 10 ml Medium B: 50 mg Ferric ammonium citrate and 100 mg CaCl2 per 100 ml; 10 ml Medium C: 5 g NaHCO3 per 100 ml; and 1 ml Trace Mineral Solution: 100 mg ZnSO4.7H2O, 30 mg MnCl2. 4H20, 300 mg H3BO3, 200 mg COCL2.6H20, 10 mg CuCl2.2H2O, 20 mg NiCl2.6H2O and 30 mg Na2MoO4.2H2O per 1 L) supplemented with 40 g/L glucose. *R. opacus* strain DSM 43205 showed identical growth rates under heterotrophic conditions reaching O.D=9.0. Strain DSM 43205 was also able to grow on chemoautotrophic conditions (MSM medium supplemented with 66.7% H2, 9.5% CO2, 5% O2 and 18.8% N2) and heterotrophically on a single carbon compound as the solely carbon source (MSM medium supplemented with 25 g/l methanol). *Rhodococcus* sp. (DSM 3346) exhibited growth under heterotrophic conditions and chemoautotrophic conditions (DSMZ Medium 81: 1 L of Mineral Medium for chemolithotrophic growth: 2.9 g Na2HPO4.2H2O, 2.3 g KH2PO4, 1.0 g NH4Cl, 0.5 g MgSO4.7H2O, 0.5 g NaHCO3, 0.01 g CaCl.2H2O and 0.05 g Fe(NH4) citrate per 1 L; and 5 ml Trace Mineral Solution, supplemented with 80% H2, 10% CO2 and 10% O2). *Cupriavidus necator* (DSM 531) was able to grow under heterotrophic and chemoautotrophic conditions (media described for Strain DSM 43205) (FIG. 5 and FIG. 22). *Cupriavidus necator* (DSM 531) transformed with pSeqCO2 was able to grow on LB media supplemented with 300 400 and 500 μg/mlkanamycin exhibiting O.D600 of 1.47, 1.52 and 1.51 respectively (FIG. 13). Untransformed cells exhibited growth on control (LB only) and some growth on 300 μg/mlkanamycin while no growth was detected on 400 and 500 μg/mlkanamycin.

EXAMPLE 5

Lipid Profiles
Production of Fatty Acid

Under heterotrophic growth conditions strains DSM 44193, DSM 43205, DSM 3346 and DSM 531 produce lipid (FIG. 6). Lipid content determined by gas chromatography analysis of cells harvested after 72 hr (unless otherwise indicated) showed over 19% of cellular dry matter (CDM) determined gravimetrically for strains DSM 44193, DSM 43205 and DSM 3346. The lipid content of DSM 43205 was higher than 10% of under chemoautotrophic conditions.

Under heterotrophic growth conditions DSM 44193 produces 32%, 26% and 21% of 16, 17 and 18-carbon fatty acid respectively (FIG. 7). DSM43205 produces similar amounts of 16, 17 and 18-carbon fatty acid (30%, 24% and 32% respectively) (FIG. 8A). Chemoautotrophic growth condition significantly reduces the 17-carbon fatty acid abundance (6%) and maintains similar levels of 16 and 18-carbon fatty acid (36% and 27% respectively) (FIG. 8B). DSM3346 exhibits similar fatty acid distribution of 16, 17 and 18-carbon fatty acid (39%, 24% and 25% respectively) (FIG. 9A) under heterotrophic growth. Chemoautotrophic growth condition significantly increases the 16-carbon fatty acid levels (66%) and reduces the 17 and 18-carbon fatty acid levels (4%, 14%)(FIG. 9B).

EXAMPLE 6

Production of Hydrocarbons

To redirect carbon flux from fatty acid toward hydrocarbon biosynthesis, the genes Fatty acyl-CoA/Fatty acyl-ACP reductase (FadR) and Fatty aldehyde decarbonylase (FAD) from the decarbonylation pathway of cyanobacteria (indicated in red) were expressed in *Cupriavidus necator* (DSM 531).

The plasmid pSeqCO2::FUEL (FIG. 14) described in the text was introduced into *Cupriavidus necator* (DSM 531) as described above and 2 independent transformants (Cn-FUEL2.1 and Cn-FUEL2.2) were selected. One hundred ml of Cn-FUEL2.1, Cn-FUEL2.2 and control cells (empty plasmid: Cn-P) were incubated on LB medium with 400 µg/mlkanamycin for 30 hr. Cells were harvested at 3,000×g for 10 min at 4° C. and pellet was analyzed by GC/MS. Cn-FUEL2.1 (FIG. 15A) and Cn-FUEL2.2 showed a specific peak at 45.00 min compared to control Cn-P (FIG. 15B) indicating the presence of hydrocarbons in the engineered strains. Cn-FUEL2.1, Cn-FUEL2.2 produced high levels (over 2%) of unique molecules such as: Spiro[4.5]decane, Bicyclo[10.8.0]eicosane, cis,cis-1,6-Dimethylspiro[4.5]decane, 1,19-Eicosadiene, Cyclooctacosane, Bicyclo[10.8.0] eicosane, 1-Pentadecyne, 1-Pentadecyne, Heptacosyl acetate, 5-Cyclohexyl-1-pentene, 1-Hexadecyne and Cyclodecacyclotetradecene, -eicosahydro (FIGS. 16 and 17).

The effect of the production of hydrocarbons on fatty acid distribution is shown in FIG. 18. The fatty acids profile of 2 independent control experiments (Cn-P) shows predominantly 16-carbon (63% and 61%) and 18-carbon (33% and 32%) fatty acids. In contrast, Cn-FUEL2.1 and Cn-FUEL2.2 exhibit significantly lower levels of 16-carbon (29%, 33% respectively) and 18-carbon (3% and 2% respectively) fatty acids. Cn-FUEL2.1 and Cn-FUEL2.2 show a significant increase in the 15-carbon fatty acid (50% and 45% respectively) compared to 0.08% and 0.09% in the control strains Cn-P.

EXAMPLE 7

Purification
Purification Hydrocarbons

To produce hydrocarbons in bacteria, genes from the decarbonylation pathway of cyanobacteria, including but not limited to, the FadR (SEQ ID: 05) and FAD (SEQ ID: 06) genes will be cloned into pVer2 (SEQ ID: 04) to give pVer2::FUEL. Bacteria, including but not limited to, *R. opacus* strain (DSM43205) will be transformed with the plasmid pVer2::FUEL by electroporation and grown in 100 ml LB medium supplemented with 75 µg/mlkanamycin for 30 hr. The cells (2×50 ml) will be harvested at 3,000×g for 10 min at 4° C. and the pellet and the supernatant further analyzed. Analysis of hydrocarbons from the cell pellet will be carried out in 25 mm×150 mm glass tube in the presence of 50 µL of Eicosane standard (approx 200 µg/ml) and 50 µl lipid standard (~200 ug/ml). Pellet will be extracted with 5 mL chloroform, 10 ml methanol, 4 ml phosphate buffer (phosphate buffer reagent: 50 mM, pH 7.4, 8.7 g K2HPO4 in 1 L water, and about 2.5 ml 6N HCl to adjust pH=7.4, and 50 ml chloroform per 1 L buffer). The mixture will be vortexed for 30 sec, sonicated for 2 min and incubated in dark for at least 3 hr. Phases will be separated in the presence of 5 mL chloroform and 5 ml ddH2O, vortexed and spun down 2000 rpm for 1 min. The bottom layer will be transferred with a glass Pasteur pipette to clean 16 mm×125 mm glass tube with Teflon-lined screw top and dried under N2. The dried extract will be re-suspended in hexane and analyzed by Gas Chromatography for the presence of hydrocarbons, including but not limited to 1-Hexadecyne.

Purification of Fatty Acids

To modify the fatty acid distribution in bacteria, thioesterases that regulate the fatty acid chain length, including but not limited to the YP_002784058.1 gene will be cloned into pVer2 (SEQ ID: 04) to give pVer2::TE. Bacteria, including but not limited to, *R. opacus* strain (DSM43205) will be transformed with the plasmid pVer2::TE by electroporation and grown in 100 ml LB medium supplemented with 75 µg/mlkanamycin for 30 hr. The cells (2×50 ml) will be harvested at 3,000×g for 10 min at 4° C. and the pellet and the supernatant further analyzed. Analysis of fatty acids from the cell pellet will be carried out in 25 mm×150 mm glass tube in the presence of 504 of Eicosane standard (approx 200 µg/mL) and 50 µL lipid standard (~200 ug/ml). Pellet will be extracted with 5 ml chloroform, 10 ml methanol, 4 ml phosphate buffer (phosphate buffer reagent: 50 mM, pH 7.4, 8.7 g K2HPO4 in 1 L water, and about 2.5 mL 6N HCl to adjust pH=7.4, and 50 ml chloroform per 1 L buffer). The mixture will be vortexed for 30 sec, sonicated for 2 min and incubated in dark for at least 3 hr. Phases will be separated in the presence of 5 ml chloroform and 5 ml ddH2O, vortexed and spun down 2000 rpm for 1 min. The bottom layer will be transferred with a glass Pasteur pipette to clean 16 mm×125 mm glass tube with Teflon-lined screw top and dried under N2. The dried extract will be re-suspended 1.5 ml of a 10:1:1 mixture of Methanol:CHCl3: concentrated HCl, vortexed and incubated in 60° C. for 14-16 hr (overnight). The extracts will be cooled and 2 ml of ddH2O and 2 ml of hexane will be added, vortexed and centrifuged for 5 min at 2000 rpm for phase separation. The top hexane layer will be transferred to clean 16 mm tube. An additional two hexane extractions (vortex, centrifugation and phase separation) will be carried out in the extract tube. The hexane extracts will be dried in a GC vial and analyzed by Gas Chromatography for the presence of fatty acids, including but not limited to dodecanoic acid.

EXAMPLE 8

Dicarboxylic acids with targeted chain length. Genetically engineer bacteria from the suborder corynebacterineae or the family burkholderiaceae to express thioesterases which yield different length fatty acids. For example the YP_002784058.1 gene mentioned previously or:

| UniProt Entry | Protein name | Organism | C length |
| --- | --- | --- | --- |
| FATB_GOSHI | Myristoyl-acyl carrier protein thioesterase | Gossypium hirsutum | 16:0 |
| FATB_UMBCA | Lauroyl-acyl carrier protein thioesterase | Umbelliularia californica | 12:0 |
| FATB_CINCA | Myristoyl-acyl carrier protein thioesterase | Cinnamomum camphora | 14:0 |
| FATA_CORSA | Oleoyl- acyl carrier protein thioesterase | Coriandrum sativum | 18:0 |
| FATB_CUPHO | Myristyl- acyl carrier protein thioesterase | Cyphea hookeriana | 16:0 |

Thioesterases generating shorter chain fatty acids (e.g., C10:0 or C12:0) will be identified and incorporated into the bacteria from the suborder corynebacterineae and the family burkholderiaceae.

Extract the resulting lipids and provide as the sole source of carbon to a culture of Candida tropicalis ATCC 20336, which contains the relevant enzymatic pathways to produce the alpha, omega-dicarboxylic acids. Identify and purify dicarboxylic acid end products from second culture.

EXAMPLE 8

Dicarboxylic Acids with Targeted Chain Length

As in previous example, engineer host strain bacteria from the suborder corynebacterineae or the family burkholderiaceae to express thioesterases which yield targeted chain length fatty acids.

Also, engineer into host strain cytochrome P450 pathway from Candida tropicalis, including the CYP52A genes with NADPH cytochrome P450 reductase to generate dicarboxylic acid from the fatty acids. Craft et al. have identified the key genes for generation of alpha, omega-dicarboxylic acids in Candida tropicalis: CYP52A13, CYP52A14, CYP52A17, CYP52A18, and CYP52A12 along with the corresponding reductase (Craft 2003).

Perform a single culture, which generates appropriate length fatty acids, then modifies to attach a second carboxylic acid.

EXAMPLE 9

Dicarboxylic Acids

Culture the hyperthermophilic archaeon Pyrococcus furiosus in order to generate the dicarboxylic acids described in Carballeira et al. (Carballeira 1997). Determine genetic machinery for generating these dicarboxylic acids, and compare P furiosus genome with the bacteria from the suborder corynebacterineae and the family burkholderiaceae genomes. Move the relevant genetic modules from the P furiosus into the bacteria from the suborder corynebacterineae and the family burkholderiaceae in order to post-process lipids into dicarboxylic acids. This can be combined with genes which produce shorter fatty acids through the appropriate thioesterases.

EXAMPLE 10

Hydroxy-acids. For generating omega-hydroxylated fatty acids, incorporate vicia sativa P450-dependent fatty acid omega hydroxylase into the bacteria from the suborder corynebacterineae and the family burkholderiaceae cell line. This enzyme hydroxylates myristic acid (C14), lauric acid (C12), pamitic acid (C16), but not oleic acid (C18).

EXAMPLE 11

Hydroxy-acids. For generating in-chain hydroxylated fatty acids, incorporate CYP81B1 (H tuberosus) or CYP709C1 (unknown) fatty acid hydroxylases into the bacteria from the suborder corynebacterineae and the family burkholderiaceae cell line. The CYP81B1 enzyme omega-1 and omega-5 mono-hydroxylates capric (C10:0), lauric (C12:0), and myristic (C14:0) (Pompon 1996). The CYP709C1 gene hydroxylates the omega-1 and omega-2 positions independent of chain length (Kandel 2005).

Specific preferred embodiments of the present invention have been described here in sufficient detail to enable those skilled in the art to practice the full scope of invention. However it is to be understood that many possible variations of the present invention, which have not been specifically described, still fall within the scope of the present invention and the appended claims. Hence these descriptions given herein are added only by way of example and are not intended to limit, in any way, the scope of this invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of"

"Consisting essentially of," when used in the claims, shall have its ordinary meaning as used in the field of patent law.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

What is claimed is:

1. A composition comprising a microorganism in a culture medium that is in contact with a gaseous feedstock that comprises:

$CO_2$; $H_2$ and/or CO; and $O_2$, wherein said culture medium does not comprise an organic carbon source as a primary source of carbon for microbial growth or biosynthesis, wherein said primary or sole source of carbon for microbial growth or biosynthesis is inorganic carbon, wherein said microorganism is a member of the genus *Cupriavidus* and is capable of chemoautotrophic metabolism;

wherein said microorganism chemoautotrophically incorporates $CO_2$, from said gaseous feedstock into organic compounds comprising one or more lipids or hydrocarbons in said culture medium, wherein said $H_2$ and/or CO serves as an inorganic electron donor and is utilized by said microorganism as an energy source and as a reducing agent for said production of said organic compounds, wherein said $O_2$ serves as an electron acceptor for generation of intracellular energy carriers, wherein $H_2O$ is produced in the generation of intracellular energy carriers in said microorganism via an oxyhydrogen reaction, wherein less than 10% by weight of said organic compounds produced is acetic acid or butyric acid and wherein less than 10% by weight of said hydrocarbons produced is methane, wherein less than 10% by weight of said organic compounds produced are organic acids with carbon chain length of four carbons or less, and wherein said microorganism comprises at least a first exogenous nucleic acid sequence encoding a fatty acid aldehyde acyl-ACP reductase and a fatty acid aldehyde decarbonylase, or comprises at least a first exogenous nucleic acid encoding a thioesterase, or comprises at least a first exogenous nucleic acid encoding a fatty acyl-CoA/fatty acyl-ACP reductase, and wherein said one or more lipids or hydrocarbons comprises one or more of Spiro[4.5]decane; 11-Hexacosyne; 9-Tricosene, (Z)-; Triacontyl acetate; 1-Heptacosanol; 5-Nonadecen-1-ol; Nonadecyl trifluoroacetate; Bicyclo[10.8.0]eicosane; (E)-, cis,cis-1,6-Dimethylspiro[4.5]decane; 1,19-Eicosadiene; Cyclododecene, 1-methyl-; Cyclooctacosane; Bicyclo[10.8.0]eicosane, cis-; 1-Pentadecyne; Heptacosyl acetate; Cyclotetracosane; 5-Cyclohexyl-1-pentene; Cyclododecene, 1-methyl-; 1-Hexadecyne; 1,21-Docosadiene; Cyclodecacyclotetradecene, -eicosahydro-; 17-Pentatriacontene; and Squalene.

2. The composition of claim 1, wherein said microorganism comprises at least a first and a second exogenous nucleic acid sequence but no more than five exogenous nucleic acid sequences.

3. The composition of claim 1, wherein said exogenous nucleic acid sequence consists of a first, a second, and a third exogenous nucleic acid sequence, wherein said first exogenous nucleic acid sequence encodes fatty acid aldehyde acyl-ACP reductase, said second exogenous nucleic acid sequence encodes a fatty acid aldehyde decarbonylase, and said third exogenous nucleic acid sequence encodes a thioesterase.

4. The composition of claim 1, wherein said exogenous nucleic acid sequence consists of a first and a second exogenous nucleic acid sequence, wherein said first exogenous nucleic acid sequence encodes fatty acid aldehyde acyl-ACP reductase and said second exogenous nucleic acid sequence encodes a fatty acid aldehyde decarbonylase.

5. The composition of claim 1, wherein said microorganism produces and/or secretes at least 60% of one or more lipids or hydrocarbons by weight.

6. The composition of claim 1, wherein said gaseous feedstock comprises syngas.

7. The composition of claim 1, further comprising said one or more lipids or hydrocarbons produced by said microorganism.

8. The composition of claim 1, wherein said microorganism is *Cupriavidus necator*.

9. The composition of claim 8, wherein said microorganism is *Cupriavidus necator* DSM 531.

10. The composition of claim 1, wherein said intracellular energy carriers comprise Adenosine-5'-triphosphate (ATP).

11. The composition of claim 1, wherein said inorganic electron donor consists of $H_2$, and wherein said gaseous feedstock does not comprise syngas.

12. The composition of claim 1, wherein said exogenous nucleic acid sequence consists of an exogenous nucleic acid sequence that encodes a thioesterase.

* * * * *

SEQUENCE LISTING

```
<160> NUMBER OF SEQ ID NOS: 41

<210> SEQ ID NO 1
<211> LENGTH: 10560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tcgcgcgttt cggtgatgac ggtgaaaacc tctgacacat gcagctcccg gagacggtca      60
cagcttgtct gtaagcggat gccgggagca gacaagcccg agcgcgcaaa gccactactg     120
ccacttttgg agactgtgta cgtcgagggc ctctgccagt gtcgaacaga cattcgccta     180
cggccctcgt ctgttcgggc tcagggcgcg tcagcgggtg ttggcgggtg tcggggctgg     240
cttaactatg cggcatcaga gcagattgta ctgagagtgc accatatgcg gtgtgaaata     300
agtcccgcgc agtcgcccac aaccgcccac agccccgacc gaattgatac gccgtagtct     360
cgtctaacat gactctcacg tggtatacgc cacactttat ccgcacagat gcgtaaggag     420
aaaataccgc atcaggcgcc attcgccatt caggctgcgc aactgttggg aagggcgatc     480
ggtgcgggcc tcttcgctat ggcgtgtcta cgcattcctc ttttatggcg tagtccgcgg     540
taagcggtaa gtccgacgcg ttgacaaccc ttcccgctag ccacgcccgg agaagcgata     600
tacgccagct ggcgaaaggg ggatgtgctg caaggcgatt aagttgggta acgccagggt     660
tttcccagtc acgacgttgt aaaacgacgg ccagtgccaa atgcggtcga ccgctttccc     720
cctacacgac gttccgctaa ttcaacccat tgcggtccca aaagggtcag tgctgcaaca     780
ttttgctgcc ggtcacggtt gcttgcatgc ctgcaggtcg acgggcccgg gatccgatgc     840
tcttccgcta agatctgccg cggccgcgtc ctcagaagaa ctcgtcaaga aggcgataga     900
cgaacgtacg gacgtccagc tgcccgggcc ctaggctacg agaaggcgat tctagacggc     960
gccggcgcag gagtcttctt gagcagttct tccgctatct aggcgatgcg ctgcgaatcg    1020
ggagcggcga taccgtaaag cacgaggaag cggtcagccc attcgccgcc aagctcttca    1080
gcaatatcac gggtagccaa tccgctacgc gacgcttagc cctcgccgct atggcatttc    1140
gtgctccttc gccagtcggg taagcggcgg ttcgagaagt cgttatagtg cccatcggtt    1200
cgctatgtcc tgatagcggt ccgccacacc cagccggcca cagtcgatga atccagaaaa    1260
gcggccattt tccaccatga tattcggcaa gcaggcatcg gcgatacagg actatcgcca    1320
ggcggtgtgg gtcggccggt gtcagctact taggtctttt cgccggtaaa aggtggtact    1380
ataagccgtt cgtccgtagc ccatgggtca cgacgagatc ctcgccgtcg ggcatgcgcg    1440
ccttgagcct ggcgaacagt tcggctggcg cgagccctg atgctcttcg tccagatcat    1500
ggtacccagt gctgctctag gagcggcagc ccgtacgcgc ggaactcgga ccgcttgtca    1560
agccgaccgc gctcggggac tacgagaagc aggtctagta cctgatcgac aagaccggct    1620
```

```
tccatccgag tacgtgctcg ctcgatgcga tgtttcgctt ggtggtcgaa tgggcaggta    1680
gccggatcaa gcgtatgcag ggactagctg ttctggccga aggtaggctc atgcacgagc    1740
gagctacgct acaaagcgaa ccaccagctt acccgtccat cggcctagtt cgcatacgtc    1800
ccgccgcatt gcatcagcca tgatggatac tttctcggca ggagcaaggt gggatgacag    1860
gagatcctgc cccggcactt cgcccaatag cagccagtcc ggcggcgtaa cgtagtcggt    1920
actacctatg aaagagccgt cctcgttcca ccctactgtc ctctaggacg gggccgtgaa    1980
gcgggttatc gtcggtcagg cttcccgctt cagtgacaac gtcgagcaca gctgcgcaag    2040
gaacgcccgt cgtggccagc cacgatagcc gcgctgcctc gtcctgcagt tcattcaggg    2100
gaagggcgaa gtcactgttg cagctcgtgt cgacgcgttc cttgcgggca gcaccggtcg    2160
gtgctatcgg cgcgacggag caggacgtca agtaagtccc caccggacag gtcggtcttg    2220
acaaaaagaa ccgggcgccc ctgcgctgac agccggaaca cggcggcatc agagcagccg    2280
attgtctgtt gtgcccagtc gtggcctgtc cagccagaac tgttttcttt ggcccgcggg    2340
gacgcgactg tcggccttgt gccgccgtag tctcgtcggc taacagacaa cacgggtcag    2400
atagccgaat agcctctcca cccaagcggc cggagaacct gcgtgcaatc catcttgttc    2460
aatcatgata tcccttaatt aaccgttaac actagttcag tatcggctta tcggagaggt    2520
gggttcgccg gcctcttgga cgcacgttag gtagaacaag ttagtactat agggaattaa    2580
ttggcaattg tgatcaagtc tccatctcgc cgtgtatgcg ggcctgacgg atcaacgttc    2640
ccaccgagcc agtcgagatg ttcatctggt cggcgatctg ccggtacttc aaaccttgtt    2700
aggtagagcg gcacatacgc ccggactgcc tagttgcaag ggtggctcgg tcagctctac    2760
aagtagacca gccgctagac ggccatgaag tttggaacaa tgcgcagttc cacagccttc    2820
ttgcggcgtt cctgcgcacg agcgatgtag tcgcctcggt cttcggcgac gagccgtttg    2880
atggtgcttt tcgagacgcc acgcgtcaag gtgtcggaag aacgccgcaa ggacgcgtgc    2940
tcgctacatc agcggagcca gaagccgctg ctcggcaaac taccacgaaa agctctgcgg    3000
gaacttgtca gccaactcct gcgcggtctg cgtgcgacgc atcacgcgtt ctgcagcacc    3060
catcagtccg tcccctctgc tgctgcgaac agtgccgatc cttgaacagt cggttgagga    3120
cgcgccagac gcacgctgcg tagtgcgcaa gacgtcgtgg gtagtcaggc aggggagacg    3180
acgacgcttg tcacggctag gatcgaccct cttgagcttc ggccgcggcg cggtggcgtt    3240
cttccgtacc gcttccgttt tgcgctgct gctcactttg ccgcggcgtg cctggatttt    3300
ctagctggaa gaactcgaag ccggcgccgc gccaccgcaa gaaggcatgg cgaaggcaaa    3360
aacgcgacga cgagtgaaac ggcgccgcac ggacctaaaa cgagaactcg gcggcggtga    3420
aggtgcggtg ggtccagtgg gcgactgatt tgccgatctg ctcggcctcg gcccgactca    3480
tggggccgat cccgtcgttg gctcttgagc cgccgccact tccacgccac ccaggtcacc    3540
cgctgactaa acggctagac gagccggagc cgggctgagt accccggcta gggcagcaac    3600
gcgtcgaggg tgaagttggt cagggcggtg aagtcggtga ccatctgccg ccacacagtg    3660
atcgacgggt agttctgttt ccggatctcg cggtaggccc cgcagctccc acttcaacca    3720
gtcccgccac ttcagccact ggtagacggc ggtgtgtcac tagctgccca tcaagacaaa    3780
ggcctagagc gccatccggg attcccgggt gcggtcgaac agttcgacgt tccggcccgt    3840
ttcggtcctg acctgtgtct tgcggccgta gtccggtggg gcggggaaac ggtcaccgag    3900
taagggccca cgccagcttg tcaagctgca aggccgggca aagccaggac tggacacaga    3960
acgccggcat caggccaccc cgccccttg ccagtggctc cgcttttgcg aggcctttga    4020
```

```
gcgagtacgg atccgaggga ccccagaccg tcgtccagtg cgggtggatc gggttctggg    4080
tgagctgctg cgcgtagccc gcgaaaacgc tccggaaact cgctcatgcc taggctcccc    4140
ggggtctggc agcaggtcac gcccacctag cccaagaccc actcgacgac gcgcatcggg    4200
tgatcggcgc cgaccaccga ggcgatcagc ccctggttca cccggtcgta gagccgcagc    4260
gggccctgtc gggctgcctg gagggtgtag accgggcttt actagccgcg gctggtggct    4320
ccgctagtcg gggaccaagt gggccagcat ctcggcgtcg cccgggacag cccgacggac    4380
ctcccacatc tggcccgaaa cgagcagcca ccacaggtgc gcgtgctcgg tcgcgggatt    4440
gatcgtcatc acggtcggat cgggcagatc cgcgttacgt gcggcccact gcgcctggtc    4500
gctcgtcggt ggtgtccacg cgcacgagcc agcgccctaa ctagcagtag tgccagccta    4560
gcccgtctag gcgcaatgca cgccgggtga cgcggaccag gtcgtccacg tcgagcacca    4620
agcccaacct gatcgacggg gtgcgggccg caatgtagcg gcgggtgagc gcctccgcgc    4680
gcggctgcgg ccactgcccg cagcaggtgc agctcgtggt tcggggttgga ctagctgccc    4740 cacgcccggc gttacatcgc cgcccactcg cggaggcgcg cgccgacgcc ggtgacgggc    4800
tcccggacgt agtcatccgt cgcgtgcggg tatttgaacc gccagcggtc caaccaggcg    4860
tcaacagcag cggtcatgac cgccaagcta gggccggatc agggcctgca tcagtaggca    4920
gcgcacgccc ataaacttgg cggtcgccag gttggtccgc agttgtcgtc gccagtactg    4980
gcggttcgat cccggcctag tgtaccgatc ggggggaggcg cgccgcaaat tatttaagag    5040
tctcgctagc aaaccatgtc aggtgttgcg gtgggttccg ggtaaacctc cacccgaatt    5100
acatggctag cccccctccgc gcggcgttta ataaattctc agagcgatcg tttggtacag    5160
tccacaacgc cacccaaggc ccatttggag gtgggcttaa atttaagagt ctcgctagct    5220
aagccctatc tgatgctgcg cggggggtcc ttcgcactga atctcaaagg tggccggctg    5280
aatttcgtcg cgcgaaaacc taaattctca gagcgatcga ttcgggatag actacgacgc    5340 gcccccccagg aagcgtgact tagagttttcc accggccgac ttaaagcagc gcgcttttgg    5400
tccctggaca gttctggaat tcagcaagag gtgtgtctga acttcggtgt ttttttgggg    5460
ggtgactcca gcggggtggg cacaacgcga acagagacct agggacctgt caagaccttta    5520 agtcgttctc cacacagact tgaagccaca aaaaaacccc ccactgaggt cgccccaccc    5580
gtgttgcgct tgtctctgga tgtgtgtacg acggcgggag gtaagtcggg tacggctcgg    5640
actgcggtag agcaaccgtc gaatcgattt cgagcagagc gagcagagca agatattcca    5700
acacacatgc tgccgccctc cattcagccc atgccgagcc tgacgccatc tcgttggcag    5760
cttagctaaa gctcgtctcg ctcgtctcgt tctataaggt aaactccggg gttcctcggc    5820
ggcctccccc gtctgtttgc tcaaccgagg gagacctggc ggtcccgcgt ttccggacgc    5880
gcgggaccgc ctaccgctcg tttgaggccc caaggagccg ccggaggggg cagacaaacg    5940
agttggctcc ctctggaccg ccagggcgca aaggcctgcg cgccctggcg gatgcgagc    6000 agagcggaag agcatctaga tgcattcgcg aggtaccgag ctcgaattcg taatcatggt    6060
catagctgtt tcctgtgtga aattgttatc cgctcacaat tctcgccttc tcgtagatct    6120
acgtaagcgc tccatggctc gagcttaagc attagtacca gtatcgacaa aggacacact    6180
ttaacaatag gcgagtgtta tccacacaac atacgagccg gaagcataaa gtgtaaagcc    6240
tggggtgcct aatgagtgag ctaactcaca ttaattgcgt tgcgctcact gcccgctttc    6300
aggtgtgttg tatgctcggc cttcgtattt cacatttcgg accccacgga ttactcactc    6360
```

```
gattgagtgt aattaacgca acgcgagtga cgggcgaaag cagtcgggaa acctgtcgtg    6420
ccagctgcat taatgaatcg gccaacgcgc ggggagaggc ggtttgcgta ttgggcgctc    6480
ttccgcttcc tcgctcactg gtcagccctt tggacagcac ggtcgacgta attacttagc    6540
cggttgcgcg cccctctccg ccaaacgcat aacccgcgag aaggcgaagg agcgagtgac    6600
actcgctgcg ctcggtcgtt cggctgcggc gagcggtatc agctcactca aaggcggtaa    6660
tacggttatc cacagaatca ggggataacg caggaaagaa tgagcgacgc gagccagcaa    6720
gccgacgccg ctcgccatag tcgagtgagt ttccgccatt atgccaatag gtgtcttagt    6780
cccctattgc gtcctttctt catgtgagca aaaggccagc aaaaggccag gaaccgtaaa    6840
aaggccgcgt tgctggcgtt tttccatagg ctccgccccc ctgacgagca tcacaaaaat    6900
gtacactcgt tttccggtcg ttttccggtc cttggcattt ttccggcgca acgaccgcaa    6960
aaaggtatcc gaggcggggg gactgctcgt agtgttttta cgacgctcaa gtcagaggtg    7020
gcgaaacccg acaggactat aaagatacca ggcgtttccc cctggaagct ccctcgtgcg    7080
ctctcctgtt ccgaccctgc gctgcgagtt cagtctccac cgctttgggc tgtcctgata    7140
tttctatggt ccgcaaaggg ggaccttcga gggagcacgc gagaggacaa ggctgggacg    7200
cgcttaccgg atacctgtcc gccttctcc cttcgggaag cgtggcgctt tctcatagct    7260
cacgctgtag gtatctcagt tcggtgtagg tcgttcgctc gcgaatggcc tatggacagg    7320
cggaaagagg gaagcccttc gcaccgcgaa agagtatcga gtgcgacatc catagagtca    7380
agccacatcc agcaagcgag caagctgggc tgtgtgcacg aacccccgt tcagcccgac    7440 cgctgcgcct tatccggtaa ctatcgtctt gagtccaacc cggtaagaca cgacttatcg    7500
gttcgacccg acacacgtgc ttgggggca agtcgggctg gcgacgcgga ataggccatt    7560
gatagcagaa ctcaggttgg gccattctgt gctgaatagc ccactggcag cagccactgg    7620
taacaggatt agcagagcga ggtatgtagg cggtgctaca gagttcttga agtggtggcc    7680
taactacggc tacactagaa ggtgaccgtc gtcggtgacc attgtcctaa tcgtctcgct    7740
ccatacatcc gccacgatgt ctcaagaact tcaccaccgg attgatgccg atgtgatctt    7800
ggacagtatt tggtatctgc gctctgctga agccagttac cttcggaaaa agagttggta    7860
gctcttgatc cggcaaacaa accaccgctg gtagcggtgg cctgtcataa accatagacg    7920
cgagacgact tcggtcaatg gaagcctttt tctcaaccat cgagaactag gccgtttgtt    7980
tggtggcgac catcgccacc ttttttttgtt tgcaagcagc agattacgcg cagaaaaaaa    8040
ggatctcaag aagatccttt gatcttttct acggggtctg acgctcagtg gaacgaaaac    8100
aaaaaaacaa acgttcgtcg tctaatgcgc gtcttttttt cctagagttc ttctaggaaa    8160
ctagaaaaga tgccccagac tgcgagtcac cttgcttttg tcacgttaag ggattttggt    8220
catgagatta tcaaaaagga tcttcaccta gatcctttta aattaaaaat gaagttttaa    8280
atcaatctaa agtatatatg agtgcaattc cctaaaacca gtactctaat agtttttcct    8340
agaagtggat ctaggaaaat ttaatttta cttcaaaatt tagttagatt tcatatatac    8400
agtaaacttg gtctgacagt taccaatgct taatcagtga ggcacctatc tcagcgatct    8460
gtctatttcg ttcatccata gttgcctgac tccccgtcgt tcatttgaac cagactgtca    8520
atggttacga attagtcact ccgtggatag agtcgctaga cagataaagc aagtaggtat    8580
caacggactg aggggcagca gtagataact acgatacggg agggcttacc atctggcccc    8640
agtgctgcaa tgataccgcg agaccacgc tcaccggctc cagatttatc agcaataaac    8700
catctattga tgctatgccc tcccgaatgg tagaccgggg tcacgacgtt actatggcgc    8760
```

```
tctgggtgcg agtggccgag gtctaaatag tcgttatttg cagccagccg aagggccga    8820 gcgcagaagt ggtcctgcaa ctttatccgc ctccatccag tctattaatt gttgccggga    8880
agctagagta agtagttcgc gtcggtcggc cttcccggct cgcgtcttca ccaggacgtt    8940
gaaataggcg gaggtaggtc agataattaa caacggccct tcgatctcat tcatcaagcg    9000
cagttaatag tttgcgcaac gttgttgcca ttgctacagg catcgtggtg tcacgctcgt    9060
cgtttggtat ggcttcattc agctccggtt cccaacgatc gtcaattatc aaacgcgttg    9120
caacaacggt aacgatgtcc gtagcaccac agtgcgagca gcaaaccata ccgaagtaag    9180
tcgaggccaa gggttgctag aaggcgagtt acatgatccc ccatgttgtg caaaaagcg    9240 gttagctcct tcggtcctcc gatcgttgtc agaagtaagt tggccgcagt gttatcactc    9300
ttccgctcaa tgtactaggg ggtacaacac gttttttcgc caatcgagga agccaggagg    9360
ctagcaacag tcttcattca accggcgtca caatagtgag atggttatgg cagcactgca    9420
taattctctt actgtcatgc catccgtaag atgcttttct gtgactggtg agtactcaac    9480
caagtcattc tgagaatagt taccaatacc gtcgtgacgt attaagagaa tgacagtacg    9540
gtaggcattc tacgaaaaga cactgaccac tcatgagttg gttcagtaag actcttatca    9600
gtatgcggcg accgagttgc tcttgcccgg cgtcaatacg ggataatacc gcgccacata    9660
gcagaacttt aaaagtgctc atcattggaa aacgttcttc catacgccgc tggctcaacg    9720
agaacgggcc gcagttatgc cctattatgg cgcggtgtat cgtcttgaaa ttttcacgag    9780
tagtaacctt ttgcaagaag ggggcgaaaa ctctcaagga tcttaccgct gttgagatcc    9840
agttcgatgt aacccactcg tgcacccaac tgatcttcag catcttttac tttcaccagc    9900
ccccgctttt gagagttcct agaatggcga caactctagg tcaagctaca ttgggtgagc    9960
acgtgggttg actagaagtc gtagaaaatg aaagtggtcg gtttctgggt gagcaaaaac    10020
aggaaggcaa aatgccgcaa aaagggaat aagggcgaca cggaaatgtt gaatactcat    10080
actcttcctt tttcaatatt caaagaccca ctcgtttttg tccttccgtt ttacggcgtt    10140 ttttcccctta ttcccgctgt gcctttacaa cttatgagta tgagaaggaa aaagttataa    10200
attgaagcat ttatcagggt tattgtctca tgagcggata catatttgaa tgtatttaga    10260
aaaataaaca aatagggtt ccgcgcacat ttccccgaaa taacttcgta aatagtccca    10320
ataacagagt actcgcctat gtataaactt acataaatct ttttatttgt ttatcccaa    10380 ggcgcgtgta aaggggcttt agtgccacct gacgtctaag aaaccattat tatcatgaca    10440
ttaacctata aaaataggcg tatcacgagg cccttcgtc tcacggtgga ctgcagattc    10500
tttggtaata atagtactgt aattggatat ttttatccgc atagtgctcc gggaaagcag    10560
```

<210> SEQ ID NO 2
<211> LENGTH: 10288
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 2

```
ggggagccgc gccgaaggcg tgggggaacc ccgcagggt gcccttcttt gggcaccaaa       60
gaactagata tagggcgaaa tgcgaaagac ttaaaaatca cccctcggcg cggcttccgc      120 accccttgg ggcgtcccca cgggaagaaa cccgtggttt cttgatctat atccgctttt      180
acgctttctg aattttttagt acaacttaaa aaggggggt acgcaacagc tcattgcggc      240
```

```
accccccgca atagctcatt gcgtaggtta agaaaatct  gtaattgact gccactttta    300
tgttgaattt  ttcccccca  tgcgttgtcg agtaacgccg tggggggcgt tatcgagtaa    360
cgcatccaat  ttcttttaga cattaactga cggtgaaaat cgcaacgcat aattgttgtc    420
gcgctgccga  aaagttgcag ctgattgcgc atggtgccgc aaccgtgcgg caccctaccg    480
catggagata  agcatggcca gcgttgcgta ttaacaacag cgcgacggct tttcaacgtc    540
gactaacgcg  taccacggcg ttggcacgcc gtgggatggc gtacctctat cgtaccggt     600
cgcagtccag  agaaatcggc attcaagcca agaacaagcc cggtcactgg gtgcaaacgg    660
aacgcaaagc  gcatgaggcg tgggccgggc ttattgcgag cgtcaggtc  tctttagccg    720
taagttcggt  tcttgttcgg gccagtgacc cacgtttgcc ttgcgtttcg cgtactccgc    780
acccggcccg  aataacgctc gaaacccacg gcggcaatgc tgctgcatca cctcgtggcg    840
cagatgggcc  accagaacgc cgtggtggtc agccagaaga cactttccaa gctcatcgga    900
ctttgggtgc  cgccgttacg acgacgtagt ggagcaccgc gtctaccgg  tggtcttgcg    960
gcaccaccag  tcggtcttct gtgaaaggtt cgagtagcct cgttctttgc ggacggtcca   1020
atacgcagtc  aaggacttgg tggccgagcg ctggatctcc gtcgtgaagc tcaacggccc   1080
cggcaccgtg  tcggcctacg gcaagaaacg cctgccaggt tatgcgtcag ttcctgaacc   1140
accggctcgc  gacctagagg cagcacttcg agttgccggg gccgtggcac agccggatgc   1200
tggtcaatga  ccgcgtggcg tggggccagc cccgcgacca gttgcgcctg tcggtgttca   1260
gtgccgccgt  ggtggttgat cacgacgacc aggacgaatc accagttact ggcgcaccgc   1320
accccggtcg  gggcgctggt caacgcggac agccacaagt cacggcggca ccaccaacta   1380
gtgctgctgg  tcctgcttag gctgttgggg catggcgacc tgcgccgcat cccgaccctg   1440
tatccgggcg  agcagcaact accgaccggc cccggcgagg agccgcccag ccagcccggc   1500
cgacaacccc  gtaccgctgg acgcggcgta gggctgggac ataggccgc  tcgtcgttga   1560
tggctggccg  gggccgctcc tcggcgggtc ggtcgggccg attccgggca tggaaccaga   1620
cctgccagcc  ttgaccgaaa cggaggaatg ggaacggcgc gggcagcagc gcctgccgat   1680
gcccgatgag  ccgtgttttc taaggcccgt accttggtct ggacggtcgg aactggcttt   1740
gcctccttac  ccttgccgcg cccgtcgtcg cggacggcta cgggctactc ggcacaaaag   1800
tggacgatgg  cgagccgttg gagccgccga cacgggtcac gctgccgcgc cggtagcact   1860
tgggttgcgc  agcaacccgt aagtgcgctg ttccagacta acctgctacc gctcggcaac   1920
ctcggcggct  gtgcccagtg cgacggcgcg gccatcgtga acccaacgcg tcgttgggca   1980
ttcacgcgac  aaggtctgat tcggctgtag ccgcctcgcc gccctatacc ttgtctgcct   2040
ccccgcgttg  cgtcgcggtg catggagccg ggccacctcg acctgaatgg aagccggcgg   2100
agccgacatc  ggcggagcgg cgggatatgg aacagacgga ggggcgcaac gcagcgccac   2160
gtacctcggc  ccggtggagc tggacttacc ttcggccgcc cacctcgcta acggattcac   2220
cgtttttatc  aggctctggg aggcagaata atgatcata  tcgtcaatta ttacctccac   2280
ggggagagcc  tgagcaaact gtggagcgat tgcctaagtg gcaaaaatag tccgagaccc   2340
tccgtcttat  ttactagtat agcagttaat aatggaggtg ccctctcgg  actcgtttga   2400
ggcctcaggc  atttgagaag cacacggtca cactgcttcc ggtagtcaat aaaccggtaa   2460
accagcaata  gacataagcg gctatttaac gaccctgccc ccggagtccg taaactcttc   2520
gtgtgccagt  gtgacgaagg ccatcagtta tttggccatt tggtcgttat ctgtattcgc   2580
```

```
cgataaattg ctgggacggg tgaaccgacg accgggtcga atttgctttc gaatttctgc    2640
cattcatccg cttattatca cttattcagg cgtagcacca ggcgtttaag ggcaccaata    2700
acttggctgc tggcccagct taaacgaaag cttaaagacg gtaagtaggc gaataatagt    2760
gaataagtcc gcatcgtggt ccgcaaattc ccgtggttat actgccttaa aaaaattacg    2820
ccccgccctg ccactcatcg cagtcggcct attggttaaa aaatgagctg atttaacaaa    2880
aatttaacgc gaattttaac tgacggaatt ttttaatgc ggggcgggac ggtgagtagc     2940
gtcagccgga taaccaattt tttactcgac taaattgttt ttaaattgcg cttaaaattg    3000
aaaatattaa cgcttacaat ttccattcgc cattcaggct gcgcaactgt tgggaagggc    3060
gatcggtgcg ggcctcttcg ctattacgcc agctggcgaa ttttataatt gcgaatgtta    3120
aaggtaagcg gtaagtccga cgcgttgaca acccttcccg ctagccacgc ccggagaagc    3180
gataatgcgg tcgaccgctt aggggatgt gctgcaaggc gattaagttg ggtaacgcca     3240
gggttttccc agtcacgacg ttgtaaaacg acggccagtg agcgcgcgta atacgactca    3300
tccccctaca cgacgttccg ctaattcaac ccattgcggt cccaaagggg tcagtgctgc    3360
aacattttgc tgccggtcac tcgcgcgcat tatgctgagt ctatagggcg aattggagct    3420
ccaccgcggt ggcggccgct ctagaactag tggatccccc gggctgcagg aattcgatat    3480
caagcttatc gataccgtcg gatatcccgc ttaacctcga ggtggcgcca ccgccggcga    3540
gatcttgatc acctagggg cccgacgtcc ttaagctata gttcgaatag ctatggcagc     3600
acctcgaggg ggggcccggt acccagcttt tgttcccttt agtgagggtt aattgcgcgc    3660
ttggcgtaat catggtcata gctgtttcct gtgtgaaatt tggagctccc ccccgggcca    3720
tgggtcgaaa acaagggaaa tcactcccaa ttaacgcgcg aaccgcatta gtaccagtat    3780
cgacaaagga cacactttaa gttatccgct cacaattcca cacaacatac gagccggaag    3840
cataaagtgt aaagcctggg gtgcctaatg agtgagctaa ctcacattaa ttgcgttgcg    3900
caataggcga gtgttaaggt gtgttgtatg ctcggccttc gtatttcaca tttcggaccc    3960
cacggattac tcactcgatt gagtgtaatt aacgcaacgc ctcactgccc gctttccagt    4020
cgggaaacct gtcgtgccag ctgcattaat gaatcggcca acgcgcgggg agaggcggtt    4080
tgcgtattgg gcgcatgcat gagtgacggg cgaaaggtca gcccttttgga cagcacggtc    4140
gacgtaatta cttagccggt tgcgcgcccc tctccgccaa acgcataacc cgcgtacgta    4200
aaaaactgtt gtaattcatt aagcattctg ccgacatgga agccatcaca aacggcatga    4260
tgaacctgaa tcgccagcgg catcagcacc ttgtcgcctt ttttgacaa cattaagtaa     4320
ttcgtaagac ggctgtacct tcggtagtgt ttgccgtact acttggactt agcggtcgcc    4380
gtagtcgtgg aacagcggaa gcgtataata tttgcccatg ggggtgggcg aagaactcca    4440
gcatgagatc cccgcgctgg aggatcatcc agccggcgtc ccggaaaacg attccgaagc    4500
cgcatattat aaacgggtac ccccaccgc ttcttgaggt cgtactctag gggcgcgacc     4560
tcctagtagg tcgccgcag ggccttttgc taaggcttcg ccaaccttc atagaaggcg      4620
gcggtggaat cgaaatctcg tgatggcagg ttgggcgtcg cttggtcggt catttcgaac    4680
cccagagtcc cgctcagaag ggttggaaag tatcttccgc cgccacctta gctttagagc    4740
actaccgtcc aacccgcagc gaaccagcca gtaaagcttg gggtctcagg gcgagtcttc    4800
aactcgtcaa gaaggcgata gaaggcgatg cgctgcgaat cgggagcggc gataccgtaa    4860
agcacgagga agcggtcagc ccattcgccg ccaagctctt tgagcagtt cttccgctat     4920
cttccgctac gcgacgctta gccctcgccg ctatggcatt tcgtgctcct tcgccagtcg    4980
```

```
ggtaagcggc ggttcgagaa cagcaatatc acgggtagcc aacgctatgt cctgatagcg    5040
gtccgccaca cccagccggc cacagtcgat gaatccagaa aagcggccat tttccaccat    5100
gtcgttatag tgcccatcgg ttgcgataca ggactatcgc caggcggtgt gggtcggccg    5160
gtgtcagcta cttaggtctt ttcgccggta aaggtggta gatattcggc aagcaggcat     5220
cgccatgggt cacgacgaga tcctcgccgt cgggcatgcg cgccttgagc ctggcgaaca    5280
gttcggctgg cgcgagcccc ctataagccg ttcgtccgta gcggtaccca gtgctgctct    5340
aggagcggca gcccgtacgc gcggaactcg gaccgcttgt caagccgacc gcgctcgggg    5400
tgatgctctt cgtccagatc atcctgatcg acaagaccgg cttccatccg agtacgtgct    5460
cgctcgatgc gatgtttcgc ttggtggtcg aatgggcagg actacgagaa gcaggtctag    5520
taggactagc tgttctggcc gaaggtaggc tcatgcacga gcgagctacg ctacaaagcg    5580
aaccaccagc ttacccgtcc tagccggatc aagcgtatgc agccgccgca ttgcatcagc    5640
catgatggat actttctcgg caggagcaag gtgagatgac aggagatcct gccccggcac    5700
atcggcctag ttcgcatacg tcggcggcgt aacgtagtcg gtactaccta tgaaagagcc    5760
gtcctcgttc cactctactg tcctctagga cggggccgtg ttcgcccaat agcagccagt    5820
cccttcccgc ttcagtgaca acgtcgagca cagctgcgca aggaacgccc gtcgtggcca    5880
gccacgatag ccgcgctgcc aagcgggtta tcgtcggtca gggaagggcg aagtcactgt    5940
tgcagctcgt gtcgacgcgt tccttgcggg cagcaccggt cggtgctatc ggcgcgacgg    6000
tcgtcctgca gttcattcag ggcaccggac aggtcggtct tgacaaaaag aaccgggcgc    6060
ccctgcgctg acagccggaa cacggcggca tcagagcagc agcaggacgt caagtaagtc    6120
ccgtggcctg tccagccaga actgttttt ttggcccgcg gggacgcgac tgtcggcctt     6180
gtgccgccgt agtctcgtcg cgattgtctg ttgtgcccag tcatagccga atagcctctc    6240
cacccaagcg gccggagaac ctgcgtgcaa tccatcttgt tcaatcatgc gaaacgatcc    6300
gctaacagac aaacacgggtc agtatcggct tatcggagag gtgggttcgc cggcctcttg    6360
gacgcacgtt aggtagaaca agttagtacg ctttgctagg tcatcctgtc tcttgatcag    6420
atcttgatcc cctgcgccat cagatccttg gcggcaagaa agccatccag tttactttgc    6480
agggcttccc aaccttacca agtaggacag agaactagtc tagaactagg gacgcggta     6540 gtctaggaac cgccgttctt tcggtaggtc aaatgaaacg tcccgaaggg ttggaatggt    6600
gagggcgccc cagctggcaa ttccggttcg cttgctgtcc ataaaaccgc ccagtctagc    6660
tatcgccatg taagcccact gcaagctacc tgctttctct ctcccgcggg gtcgaccgtt    6720
aaggccaagc gaacgacagg tattttggcg ggtcagatcg atagcggtac attcgggtga    6780
cgttcgatgg acgaaagaga ttgcgcttgc gttttccctt gtccagatag cccagtagct    6840
gacattcatc ccaggtggca cttttcgggg aaatgtgcgc gcccgcgttc ctgctggcgc    6900
aacgcgaacg caaagggaa caggtctatc gggtcatcga ctgtaagtag gtccaccgt      6960 gaaaagcccc tttacacgcg cgggcgcaag gacgaccgcg tgggcctgtt tctggcgctg    7020
gacttcccgc tgttccgtca gcagcttttc gcccacggcc ttgatgatcg cggcggcctt    7080
ggcctgcata tcccgattca acccggacaa agaccgcgac ctgaagggcg acaaggcagt    7140
cgtcgaaaag cgggtgccgg aactactagc gccgccggaa ccggacgtat agggctaagt    7200
acggccccag ggcgtccaga acgggcttca ggcgctcccg aaggtctcgg gccgtctctt    7260
gggcttgatc ggccttcttg cgcatctcac gcgctcctgc tgccggggtc ccgcaggtct    7320
```

```
tgcccgaagt ccgcgagggc ttccagagcc cggcagagaa cccgaactag ccggaagaac    7380
gcgtagagtg cgcgaggacg ggcggcctgt agggcaggct catacccctg ccgaaccgct    7440
tttgtcagcc ggtcggccac ggcttccggc gtctcaacgc gctttgagat tcccagcttt    7500
ccgccggaca tcccgtccga gtatggggac ggcttggcga aaacagtcgg ccagccggtg    7560
ccgaaggccg cagagttgcg cgaaactcta agggtcgaaa tcggccaatc cctgcggtgc    7620
ataggcgcgt ggctcgaccg cttgcgggct gatggtgacg tgcccactg gtggccgctc     7680 cagggcctcg tagaacgcct agccggttag ggacgccacg tatccgcgca ccgagctggc    7740
gaacgcccga ctaccactgc accgggtgac caccggcgag gtcccggagc atcttgcgga    7800
gaatgcgcgt gtgacgtgcc ttgctgccct cgatgccccg ttgcagccct agatcggcca    7860
cagcggccgc aaacgtggtc tggtcgcggg tcatctgcgc cttacgcgca cactgcacgg    7920
aacgacggga gctacggggc aacgtcggga tctagccggt gtcgccggcg tttgcaccag    7980
accagcgccc agtagacgcg tttgttgccg atgaactcct tggccgacag cctgccgtcc    8040
tgcgtcagcg gcaccacgaa cgcggtcatg tgcgggctgg tttcgtcacg gtggatgctg    8100
aaacaacggc tacttgagga accggctgtc ggacggcagg acgcagtcgc cgtggtgctt    8160
gcgccagtac acgcccgacc aaagcagtgc cacctacgac gccgtcacga tgcgatccgc    8220
cccgtacttg tccgccagcc acttgtgcgc cttctcgaag aacgccgcct gctgttcttg    8280
gctggccgac ttccaccatt cggcagtgct acgctaggcg gggcatgaac aggcggtcgg    8340
tgaacacgcg gaagagcttc ttgcggcgga cgacaagaac cgaccggctg aaggtggtaa    8400
ccgggctggc cgtcatgacg tactcgaccg ccaacacagc gtccttgcgc cgcttctctg    8460
gcagcaactc gcgcagtcgg cccatcgctt catcggtgct ggcccgaccg gcagtactgc    8520
atgagctggc ggttgtgtcg caggaacgcg gcgaagagac cgtcgttgag cgcgtcagcc    8580
gggtagcgaa gtagccacga gctggccgcc cagtgctcgt tctctggcgt cctgctggcg    8640
tcagcgttgg gcgtctcgcg ctcgcggtag gcgtgcttga gactggccgc cacgttgccc    8700
cgaccggcgg gtcacgagca agagaccgca ggacgaccgc agtcgcaacc cgcagagcgc    8760
gagcgccatc cgcacgaact ctgaccggcg gtgcaacggg attttcgcca gcttcttgca    8820
tcgcatgatc gcgtatgccg ccatgcctgc ccctcccttt tggtgtccaa ccggctcgac    8880
gggggcagcg caaggcggtg taaaagcggt cgaagaacgt agcgtactag cgcatacggc    8940
ggtacggacg gggagggaaa accacaggtt ggccgagctg cccccgtcgc gttccgccac    9000
cctccggcgg gccactcaat gcttgagtat actcactaga ctttgcttcg caaagtcgtg    9060
accgcctacg gcggctgcgg cgccctacgg gcttgctctc ggaggccgcc cggtgagtta    9120
cgaactcata tgagtgatct gaacgaagc gtttcagcac tggcggatgc cgccgacgcc     9180
gcgggatgcc cgaacgagag cgggcttcgc cctgcgcggt cgctgcgctc ccttgccagc    9240
ccgtggatat gtggacgatg gccgcgagcg gccaccggct ggctcgcttc gctcggcccg    9300
gcccgaagcg ggacgcgcca gcgacgcgag ggaacggtcg ggcacctata cacctgctac    9360
cggcgctcgc cggtggccga ccgagcgaag cgagccgggc tggacaaccc tgctggacaa    9420
gctgatggac aggctgcgcc tgcccacgag cttgaccaca gggattgccc accggctacc    9480
cagccttcga ccacataccc acctgttggg acgacctgtt cgactacctg tccgacgcgg    9540
acgggtgctc gaactggtgt ccctaacggg tggccgatgg gtcggaagct ggtgtatggg    9600
accgctccca actgcgcggc ctgcggcctt gccccatcaa tttttttaat tttctctggg    9660
gaaaagcctc cggcctgcgg cctgcgcgct tcgcttgccg tggccgaggt tgacgcgccg    9720
```

```
gacgccggaa cggggtagtt aaaaaaatta aaagagaccc cttttcggag gccggacgcc    9780
ggacgcgcga agcgaacggc gttggacacc aagtggaagg cgggtcaagg ctcgcgcagc    9840
gaccgcgcag cggcttggcc ttgacgcgcc tggaacgacc caagcctatg cgagtggggg    9900
caacctgtgg ttcaccttcc gcccagttcc gagcgcgtcg ctggcgcgtc gccgaaccgg    9960
aactgcgcgg accttgctgg gttcggatac gctcaccccc cagtcgaagg cgaagcccgc   10020
ccgcctgccc cccgagcctc acggcggcga gtgcggggg tccaagggg cagcgccacc     10080 ttgggcaagg ccgaaggccg gtcagcttcc gcttcgggcg ggcggacggg gggctcggag   10140
tgccgccgct cacgccccca aggttccccc gtcgcggtgg aacccgttcc ggcttccggc   10200
cgcagtcgat caacaagccc cggaggggcc acttttgcc ggaggcgtca gctagttgtt    10260
cggggcctcc ccggtgaaaa acggcctc                                     10288
```

<210> SEQ ID NO 3
<211> LENGTH: 12758
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ggggagccgc gccgaaggcg tgggggaacc ccgcaggggt gcccttcttt gggcaccaaa      60
gaactagata tagggcgaaa tgcgaaagac ttaaaaatca cccctcggcg cggcttccgc     120
acccccttgg ggcgtcccca cgggaagaaa cccgtggttt cttgatctat atcccgcttt     180
acgctttctg aatttttagt acaacttaaa aaggggggt acgcaacagc tcattgcggc     240
accccccgca atagctcatt gcgtaggtta aagaaaatct gtaattgact gccacttta     300 tgttgaattt tttccccca tgcgttgtcg agtaacgccg tgggggcgt tatcgagtaa      360 cgcatccaat ttcttttaga cattaactga cggtgaaaat cgcaacgcat aattgttgtc    420
gcgctgccga aaagttgcag ctgattgcgc atggtgccgc aaccgtgcgg caccctaccg    480
catggagata agcatggcca gcgttgcgta ttaacaacag cgcgacggct tttcaacgtc    540
gactaacgcg taccacggcg ttggcacgcc gtgggatggc gtacctctat tcgtaccggt    600
cgcagtccag agaaatcggc attcaagcca agaacaagcc cggtcactgg gtgcaaacgg    660
aacgcaaagc gcatgaggcg tgggccgggc ttattgcgag gcgtcaggtc tctttagccg    720
taagttcggt tcttgttcgg gccagtgacc cacgtttgcc ttgcgtttcg cgtactccgc    780
acccggcccg aataacgctc gaaacccacg gcggcaatgc tgctgcatca cctcgtggcg    840
cagatgggcc accagaacgc cgtggtggtc agccagaaga cactttccaa gctcatcgga    900
ctttgggtgc cgccgttacg acgacgtagt ggagcaccgc gtctaccgg tggtcttgcg     960 gcaccaccag tcggtcttct gtgaaaggtt cgagtagcct cgttctttgc ggacggtcca    1020
atacgcagtc aaggacttgg tggccgagcg ctggatctcc gtcgtgaagc tcaacggccc    1080
cggcaccgtg tcggcctacg gcaagaaacg cctgccaggt tatgcgtcag ttcctgaacc    1140
accggctcgc gacctagagg cagcacttcg agttgccggg gccgtggcac agccggatgc    1200
tggtcaatga ccgcgtggcg tggggccagc ccgcgaccca gttgcgcctg tcggtgttca    1260
gtgccgccgt ggtggttgat cacgacgacc aggacgaatc accagttact ggcgcaccgc    1320
accccggtcg gggcgctggt caacgcggac agcacaagt cacggcggca ccaccaacta    1380
gtgctgctgg tcctgcttag gctgttgggg catggcgacc tgcgccgcat cccgaccctg    1440
```

```
tatccgggcg agcagcaact accgaccggc cccggcgagg agccgcccag ccagcccggc    1500
cgacaacccc gtaccgctgg acgcggcgta gggctgggac ataggcccgc tcgtcgttga    1560
tggctggccg gggccgctcc tcggcgggtc ggtcgggccg attccgggca tggaaccaga    1620
cctgccagcc ttgaccgaaa cggaggaatg ggaacggcgc gggcagcagc gcctgccgat    1680
gcccgatgag ccgtgttttc taaggcccgt accttggtct ggacggtcgg aactggcttt    1740
gcctccttac ccttgccgcg cccgtcgtcg cggacggcta cgggctactc ggcacaaaag    1800
tggacgatgg cgagccgttg gagccgccga cacgggtcac gctgccgcgc cggtagcact    1860
tgggttgcgc agcaacccgt aagtgcgctg ttccagacta acctgctacc gctcggcaac    1920
ctcggcggct gtgcccagtg cgacggcgcg gccatcgtga acccaacgcg tcgttgggca    1980
ttcacgcgac aaggtctgat tcggctgtag ccgcctcgcc gccctatacc ttgtctgcct    2040
ccccgcgttg cgtcgcggtg catggagccg ggccacctcg acctgaatgg aagccggcgg    2100
agccgacatc ggcggagcgg cgggatatgg aacagacgga ggggcgcaac gcagcgccac    2160
gtacctcggc ccggtggagc tggacttacc ttcgccgcc cacctcgcta acggattcac    2220
cgtttttatc aggctctggg aggcagaata aatgatcata tcgtcaatta ttacctccac    2280
ggggagagcc tgagcaaact gtggagcgat tgcctaagtg gcaaaaatag tccgagaccc    2340
tccgtcttat ttactagtat agcagttaat aatggaggtg cccctctcgg actcgtttga    2400
ggcctcaggc atttgagaag cacacggtca cactgcttcc ggtagtcaat aaaccggtaa    2460
accagcaata gacataagcg gctatttaac gaccctgccc ccggagtccg taaactcttc    2520
gtgtgccagt gtgacgaagg ccatcagtta tttggccatt tggtcgttat ctgtattcgc    2580
cgataaattg ctgggacggg tgaaccgacg accgggtcga atttgctttc gaatttctgc    2640
cattcatccg cttattatca cttattcagg cgtagcacca ggcgtttaag ggcaccaata    2700
acttggctgc tggcccagct taaacgaaag cttaaagacg gtaagtaggc gaataatagt    2760
gaataagtcc gcatcgtggt ccgcaaattc ccgtggttat actgccttaa aaaaattacg    2820
ccccgccctg ccactcatcg cagtcggcct attggttaaa aaatgagctg atttaacaaa    2880
aatttaacgc gaattttaac tgacggaatt tttttaatgc ggggcgggac ggtgagtagc    2940
gtcagccgga taaccaattt tttactcgac taaattgttt ttaaattgcg cttaaaattg    3000
aaaatattaa cgcttacaat ttccattcgc cattcaggct cgcaactgt tgggaagggc    3060 gatcggtgcg ggcctcttcg ctattacgcc agctggcgaa ttttataatt gcgaatgtta    3120
aaggtaagcg gtaagtccga cgcgttgaca acccttcccg ctagccacgc ccggagaagc    3180
gataatgcgg tcgaccgctt aggggatgt gctgcaaggc gattaagttg ggtaacgcca    3240
gggttttccc agtcacgacg ttgtaaaacg acggccagtg agcgcgcgta atacgactca    3300
tccccctaca cgacgttccg ctaattcaac ccattgcggt cccaaagggg tcagtgctgc    3360 aacatttgc tgccggtcac tcgcgcgcat tatgctgagt ctataggcg aattggagct    3420 ccaccgcggt ggcggccgct ctagaactag tggatccccc gggctgcagg aattcgatat    3480
caagcttatc gataccgtcg gatatcccgc ttaacctcga ggtggcgcca ccgccggcga    3540
gatcttgatc acctagggg cccgacgtcc ttaagctata gttcgaatag ctatggcagc    3600
acgggcccgg gatccgatgc tcttccgcta agatctttta ctagttcagt ccatctcgcc    3660
gtgtatgcgg gcctgacgga tcaacgttcc caccgagcca tgcccgggcc ctaggctacg    3720
agaaggcgat tctagaaaat gatcaagtca ggtagagcgg cacatacgcc cggactgcct    3780
```

```
agttgcaagg gtggctcggt gtcgagatgt tcatctggtc ggcgatctgc cggtacttca   3840
aaccttgttt gcgcagttcc acagccttct tgcggcgttc ctgcgcacga gcgatgtagt   3900
cagctctaca agtagaccag ccgctagacg gccatgaagt ttggaacaaa cgcgtcaagg   3960
tgtcggaaga acgccgcaag gacgcgtgct cgctacatca cgcctcggtc ttcggcgacg   4020
agccgtttga tggtgctttt cgagacgccg aacttgtcag ccaactcctg cgcggtctgc   4080
gtgcgacgca tcacgcgttc gcggagccag aagccgctgc tcggcaaact accacgaaaa   4140
gctctgcggc ttgaacagtc ggttgaggac gcgccagacg cacgctgcgt agtgcgcaag   4200
tgcagcaccc atcagtccgt ccctctgct gctgcgaaca gtgccgatcg atcgaccttc   4260
ttgagcttcg gccgcggcgc ggtggcgttc ttccgtaccg acgtcgtggg tagtcaggca   4320
ggggagacga cgacgcttgt cacggctagc tagctggaag aactcgaagc cggcgccgcg   4380
ccaccgcaag aaggcatggc cttccgtttt tgcgctgctg ctcactttgc cgcggcgtgc   4440
ctggattttc gagaactcgg cggcggtgaa ggtgcggtgg gtccagtggg cgactgattt   4500
gaaggcaaaa acgcgacgac gagtgaaacg cgccgcacg gacctaaaag ctcttgagcc   4560
gccgccactt ccacgccacc caggtcaccc gctgactaaa gccgatctgc tcggcctcgg   4620
cccgactcat ggggccgatc ccgtcgttgg cgtcgagggt gaagttggtc agggcggtga   4680
agtcggtgac catctgccgc cggctagacg agccggagcc gggctgagta ccccggctag   4740
ggcagcaacc gcagctccca cttcaaccag tcccgccact tcagccactg gtagacggcg   4800
cacacagtga tcgacgggta gttctgtttc cggatctcgc ggtaggccca ttcccgggtg   4860
cggtcgaaca gttcgacgtt ccggcccgtt tcggtcctga gtgtgtcact agctgcccat   4920
caagacaaag gcctagagcg ccatccgggt aagggcccac gccagcttgt caagctgcaa   4980
ggccgggcaa agccaggact cctgtgtctt gcggccgtag tccggtgggg cggggaaacg   5040
gtcaccgagc gcttttgcga ggcctttgag cgagtacgga tccgagggac cccagaccgt   5100
ggacacagaa cgccggcatc aggccacccc gccccttgc cagtggctcg cgaaaacgct   5160
ccggaaactc gctcatgcct aggctccctg gggtctggca cgtccagtgc gggtggatcg   5220
ggttctgggt gagctgctgc gcgtagccct gatcggcgcc gaccaccgag gcgatcagcc   5280
cctggttcac ccggtcgtag gcaggtcacg cccacctagc ccaagaccca ctcgacgacg   5340
cgcatcggga ctagccgcgg ctggtggctc cgctagtcgg ggaccaagtg ggccagcatc   5400
agccgcagcg ggccctgtcg ggctgcctgg agggtgtaga ccgggctttc gagcagccac   5460
cacaggtgcg cgtgctcggt cgcgggattg atcgtcatca tcggcgtcgc ccgggacagc   5520
ccgacggacc tcccacatct ggcccgaaag ctcgtcggtg gtgtccacgc gcacgagcca   5580
gcgccctaac tagcagtagt cggtcggatc gggcagatcc gcgttacgtg cggcccactg   5640
cgcctggtcg tcgtccacgt cgagcaccaa gcccaacctg atcgacgggg tgcgggccgc   5700
gccagcctag cccgtctagg cgcaatgcac gccgggtgac gcggaccagc agcaggtgca   5760
gctcgtggtt cgggttggac tagctgcccc acgcccggcg aatgtagcgg cgggtgagcg   5820
cctccgcgcg cggctgcggc cactgcccgt cccggacgta gtcatccgtc gcgtgcgggt   5880
atttgaaccg ccagcggtcc ttacatcgcc gcccactcgc ggaggcgcgc gccgacgccg   5940
gtgacgggca gggcctgcat cagtaggcag cgcacgccca taaacttggc ggtcgccagg   6000
aaccaggcgt caacagcagc ggtcatgacc gccaagctag gccggatct gtaccgatcg   6060 ggggaggcgc gccgcaaatt atttaagagt ctcgctagca ttggtccgca gttgtcgtcg   6120
ccagtactgg cggttcgatc ccggcctaga catggctagc cccctccgcg cggcgtttaa   6180
```

```
taaattctca gagcgatcgt aaccatgtca ggtgttgcgg tgggttccgg gtaaacctcc    6240
acccgaatta tttaagagtc tcgctagcta agccctatct gatgctgcgc gggggggtcct   6300
ttggtacagt ccacaacgcc acccaaggcc catttggagg tgggcttaat aaattctcag    6360
agcgatcgat tcgggataga ctacgacgcg cccccccagga tcgcactgaa tctcaaaggt   6420
ggccggctga atttcgtcgc gcgaaaacct ccctggacag ttctggaatt cagcaagagg    6480
tgtgtctgaa cttcggtgtt agcgtgactt agagtttcca ccggccgact taaagcagcg    6540
cgcttttgga gggacctgtc aagaccttaa gtcgttctcc acacagactt gaagccacaa    6600
ttttttggggg gtgactccag cggggtgggc acaacgcgaa cagagacctt gtgtgtacga   6660
cggcgggagg taagtcgggt acggctcgga ctgcggtaga aaaaaccccc cactgaggtc    6720
gccccacccg tgttgcgctt gtctctggaa cacacatgct gccgccctcc attcagccca    6780
tgccgagcct gacgccatct gcaaccgtcg aatcgatttc gagcagagcg agcagagcaa    6840
gatattccaa aactccgggg ttcctcggcg gcctcccccg tctgtttgct caaccgaggg    6900
cgttggcagc ttagctaaag ctcgtctcgc tcgtctcgtt ctataaggtt ttgaggcccc    6960
aaggagccgc cggaggggggc agacaaacga gttggctccc agacctggcg gtcccgcgtt   7020
tccggacgcg cgggaccgcc taccgctcga gagcggaaga gcatctagat gcattcgcga    7080
ggtacccagc ttttgttccc tctggaccgc cagggcgcaa aggcctgcgc gccctggcgg    7140
atggcgagct ctcgccttct cgtagatcta cgtaagcgct ccatgggtcg aaaacaaggg    7200
tttagtgagg gttaattgcg cgcttggcgt aatcatggtc atagctgttt cctgtgtgaa    7260
attgttatcc gctcacaatt ccacacaaca tacgagccgg aaatcactcc caattaacgc    7320
gcgaaccgca ttagtaccag tatcgacaaa ggacacactt taacaatagg cgagtgttaa    7380
ggtgtgttgt atgctcggcc aagcataaag tgtaaagcct ggggtgccta atgagtgagc    7440
taactcacat taattgcgtt gcgctcactg cccgctttcc agtcgggaaa cctgtcgtgc    7500
ttcgtatttc acatttcgga ccccacggat tactcactcg attgagtgta attaacgcaa    7560
cgcgagtgac gggcgaaagg tcagcccttt ggacagcacg cagctgcatt aatgaatcgg    7620
ccaacgcgcg gggagaggcg gtttgcgtat tgggcgcatg cataaaaact gttgtaattc    7680
attaagcatt ctgccgacat gtcgacgtaa ttacttagcc ggttgcgcgc ccctctccgc    7740
caaacgcata acccgcgtac ggaagccatc acaaacggca tgatgaacct gaatcgccag    7800
cggcatcagc accttgtcgc cttgcgtata atatttgccc atggggggtgg gcgaagaact   7860
ccttcggtag tgtttgccgt actacttgga cttagcggtc gccgtagtcg tggaacagcg    7920
gaacgcatat tataaacggg tacccccacc cgcttcttga ccagcatgag atccccgcgc    7980
tggaggatca tccagccggc gtcccggaaa acgattccga agcccaacct ttcatagaag    8040
gcggcggtgg aatcgaaatc ggtcgtactc taggggcgcg acctcctagt aggtcggccg    8100
cagggccttt tgctaaggct tcgggttgga aagtatcttc cgccgccacc ttagctttag    8160
tcgtgatggc aggttgggcg tcgcttggtc ggtcatttcg aaccccagag tcccgctcag    8220
aagaactcgt caagaaggcg atagaaggcg atgcgctgcg agcactaccg tccaacccgc    8280
agcgaaccag ccagtaaagc ttggggtctc agggcgagtc ttcttgagca gttcttccgc    8340
tatcttccgc tacgcgacgc aatcgggagc ggcgataccg taaagcacga ggaagcggtc    8400
agcccattcg ccgccaagct cttcagcaat atcacgggta gccaacgcta tgtcctgata    8460
ttagccctcg ccgctatggc atttcgtgct ccttcgccag tcgggtaagc ggcggttcga    8520
```

```
gaagtcgtta tagtgcccat cggttgcgat acaggactat gcggtccgcc acacccagcc  8580
ggccacagtc gatgaatcca gaaaagcggc cattttccac catgatattc ggcaagcagg  8640
catcgccatg ggtcacgacg cgccaggcgg tgtgggtcgg ccggtgtcag ctacttaggt  8700
cttttcgccg gtaaaaggtg gtactataag ccgttcgtcc gtagcggtac ccagtgctgc  8760
agatcctcgc cgtcgggcat gcgcgccttg agcctggcga acagttcggc tggcgcgagc  8820
ccctgatgct cttcgtccag atcatcctga tcgacaagac tctaggagcg gcagcccgta  8880
cgcgcggaac tcggaccgct tgtcaagccg accgcgctcg gggactacga gaagcaggtc  8940
tagtaggact agctgttctg cggcttccat ccgagtacgt gctcgctcga tgcgatgttt  9000
cgcttggtgg tcgaatgggc aggtagccgg atcaagcgta tgcagccgcc gcattgcatc  9060
gccgaaggta ggctcatgca cgagcgagct acgctacaaa gcgaaccacc agcttacccg  9120
tccatcggcc tagttcgcat acgtcggcgg cgtaacgtag agccatgatg gatactttct  9180
cggcaggagc aaggtgagat gacaggagat cctgccccgg cacttcgccc aatagcagcc  9240
agtcccttcc cgcttcagtt cggtactacc tatgaaagag ccgtcctcgt tccactctac  9300
tgtcctctag gacggggccg tgaagcgggt tatcgtcggt cagggaaggg cgaagtcaca  9360
caacgtcgag cacagctgcg caaggaacgc ccgtcgtggc cagccacgat agccgcgctg  9420
cctcgtcctg cagttcattc agggcaccgg acaggtcggt gttgcagctc gtgtcgacgc  9480
gttccttgcg ggcagcaccg gtcggtgcta tcggcgcgac ggagcaggac gtcaagtaag  9540
tcccgtggcc tgtccagcct cttgacaaaa agaaccgggc gccctgcgc tgacagccgg  9600
aacacggcgg catcagagca gccgattgtc tgttgtgccc agtcatagcc gaatagccta  9660
gaactgtttt tcttggcccg cggggacgcg actgtcggcc ttgtgccgcc gtagtctcgt  9720
cggctaacag acaacacggg tcagtatcgg cttatcggac tccacccaag cggccggaga  9780
acctgcgtgc aatccatctt gttcaatcat gcgaaacgat cctcatcctg tctcttgatc  9840
agatcttgat cccctgcgcg aggtgggttc gccggcctct tggacgcacg ttaggtagaa  9900
caagttagta cgctttgcta ggagtaggac agagaactag tctagaacta ggggacgcgc  9960
atcagatcct tggcggcaag aaagccatcc agtttacttt gcagggcttc ccaaccttac 10020
cagagggcgc cccagctggc aattccggtt cgcttgctgg tagtctagga accgccgttc 10080
tttcggtagg tcaaatgaaa cgtcccgaag ggttggaatg gtctcccgcg gggtcgaccg 10140
ttaaggccaa gcgaacgact ccataaaacc gcccagtcta gctatcgcca tgtaagccca 10200
ctgcaagcta cctgctttct cttttgcgctt gcgttttccc ttgtccagat agcccagtaa 10260
ggtattttgg cgggtcagat cgatagcggt acattcgggt gacgttcgat ggacgaaaga 10320
gaaacgcgaa cgcaaagggg aacaggtcta tcgggtcatg ctgacattca tcccaggtgg 10380
cacttttcgg ggaaatgtgc gcgcccgcgt tcctgctggc gctgggcctg tttctggcgc 10440
tggacttccc gctgttccgc gactgtaagt agggtccacc gtgaaaagcc cctttacacg 10500
cgcgggcgca aggacgaccg cgaccccggac aaagaccgcg acctgaaggg cgacaaggct 10560
cagcagcttt tcgcccacgg ccttgatgat cgcggcggcc ttggcctgca tatcccgatt 10620
caacggcccc agggcgtcca gaacgggctt caggcgctca gtcgtcgaaa agcgggtgcc 10680
ggaactacta gcgccgccgg aaccggacgt ataggctaa gttgccgggg tcccgcaggt 10740
cttgcccgaa gtccgcgacc gaaggtctcg ggccgtctct tgggcttgat cggccttctt 10800
gcgcatctca cgcgctcctg cggcggcctg tagggcagga tcatacccct gccgaaccgg 10860
cttccagagc ccggcagaga acccgaacta gccggaagaa cgcgtagagt gcgcgaggac 10920
```

```
gccgccggac atcccgtccg agtatgggga cggcttgggc ttttgtcagc cggtcggcca    10980
cggcttccgg cgtctcaacg cgctttgaga ttcccagctt ttcggccaat ccctgcggtg    11040
cataggcgcg tggctcgacg aaaacagtcg gccagccggt gccgaaggcc gcagagttgc    11100
gcgaaactct aagggtcgaa aagccggtta gggacgccac gtatccgcgc accgagctcc    11160
gcttgcgggc tgatggtgac gtggcccact ggtggccgct ccagggcctc gtagaacgcc    11220
tgaatgcgcg tgtgacgtgc cttgctgccc tcgatgccgg cgaacgcccg actaccactg    11280
caccgggtga ccaccggcga ggtcccggag catcttgcgg acttacgcgc acactgcacg    11340
gaacgacggg agctacggcc gttgcagccc tagatcggcc acagcggccg caaacgtggt    11400
ctggtcgcgg gtcatctgcg ctttgttgcc gatgaactcc ttggccgaca gcctgccggg    11460
caacgtcggg atctagccgg tgtcgccggc gtttgcacca gccagcgcc cagtagacgc    11520 gaaacaacgg ctacttgagg aaccggctgt cggacggctc ctgcgtcagc ggcaccacga    11580
acgcggtcat gtgcgggctg gtttcgtcac ggtggatgct ggccgtcacg atgcgatccg    11640
ccccgtactt gtccgccaag gacgcagtcg ccgtggtgct gcgccagta cacgcccgac    11700 caaagcagtg ccacctacga ccggcagtgc tacgctaggc ggggcatgaa caggcggtgc    11760
cacttgtgcg ccttctcgaa gaacgccgcc tgctgttctt ggctggccga cttccaccat    11820
tccgggctgg ccgtcatgac gtactcgacc gccaacaccg gtgaacacgc ggaagagctt    11880
cttgcggcgg acgacaagaa ccgaccggct gaaggtggta aggcccgacc ggcagtactg    11940
catgagctgg cggttgtgag cgtccttgcg ccgcttctct ggcagcaact cgcgcagtcg    12000
gcccatcgct tcatcggtgc tgctggccgc ccagtgctcg ttctctggcg tcctgctgtc    12060
gcaggaacgc ggcgaagaga ccgtcgttga gcgcgtcagc cgggtagcga agtagccacg    12120
acgaccggcg ggtcacgagc aagagaccgc aggacgacgc gtcagcgttg ggcgtctcgc    12180
gctcgcggta ggcgtgcttg agactggccg ccacgttgcc cattttcgcc agcttcttgc    12240
atcgcatgat cgcgtatgcg cagtcgcaac ccgcagagcg cgagcgccat ccgcacgaac    12300
tctgaccggc ggtgcaacgg gtaaaagcgg tcgaagaacg tagcgtacta gcgcataccc    12360
gccatgcctg cccctcccctt ttggtgtcca accggctcga cggggcagc gcaaggcggt    12420 gcctccggcg ggccactcaa tgcttgagta tactcactgg cggtacggac ggggagggaa    12480
aaccacaggt tggccgagct gccccgtcg cgttccgcca cggaggccgc ccggtgagtt    12540
acgaactcat atgagtgaag actttgcttc gcaaagtcgt gaccgcctac ggcggctgcg    12600
gcgccctacg ggcttgctct ccgggcttcg ccctgcgcgg tcgctgcgct cccttgcctc    12660
tgaaacgaag cgtttcagca ctggcggatg ccgccgacgc cgcgggatgc ccgaacgaga    12720
ggcccgaagc gggacgcgcc agcgacgcga gggaacgg                           12758
```

<210> SEQ ID NO 4
<211> LENGTH: 15158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
ggggagccgc gccgaaggcg tgggggaacc ccgcaggggt gcccttcttt gggcaccaaa      60
gaactagata tagggcgaaa tgcgaaagac ttaaaaatca cccctcggcg cggcttccgc     120 accccttgg ggcgtcccca cgggaagaaa cccgtggttt cttgatctat atcccgcttt     180
```

-continued

```
acgctttctg aattttagt acaacttaaa aaaggggggt acgcaacagc tcattgcggc    240
accccccgca atagctcatt gcgtaggtta aagaaaatct gtaattgact gccactttta    300
tgttgaattt ttccccccca tgcgttgtcg agtaacgccg tgggggcgt tatcgagtaa    360 cgcatccaat ttcttttaga cattaactga cggtgaaaat cgcaacgcat aattgttgtc    420
gcgctgccga aaagttgcag ctgattgcgc atggtgccgc aaccgtgcgg caccctaccg    480 catgagata agcatggcca gcgttgcgta ttaacaacag cgcgacggct tttcaacgtc    540
gactaacgcg taccacggcg ttggcacgcc gtgggatggc gtacctctat tcgtaccggt    600
cgcagtccag agaaatcggc attcaagcca agaacaagcc cggtcactgg gtgcaaacgg    660
aacgcaaagc gcatgaggcg tgggccgggc ttattgcgag gcgtcaggtc tctttagccg    720
taagttcggt tcttgttcgg gccagtgacc cacgtttgcc ttgcgtttcg cgtactccgc    780
acccggcccg aataacgctc gaaacccacg gcggcaatgc tgctgcatca cctcgtggcg    840
cagatgggcc accagaacgc cgtggtggtc agccagaaga cactttccaa gctcatcgga    900 cttttgggtgc cgccgttacg acgacgtagt ggagcaccgc gtctaccgg tggtcttgcg    960 gcaccaccag tcggtcttct gtgaaaggtt cgagtagcct cgttctttgc ggacggtcca   1020
atacgcagtc aaggacttgg tggccgagcg ctggatctcc gtcgtgaagc tcaacggccc   1080
cggcaccgtg tcggcctacg gcaagaaacg cctgccaggt tatgcgtcag ttcctgaacc   1140
accggctcgc gacctagagg cagcacttcg agttgccggg gccgtggcac agccggatgc   1200
tggtcaatga ccgcgtggcg tggggccagc ccgcgacca gttgcgcctg tcggtgttca   1260
gtgccgccgt ggtggttgat cacgacgacc aggacgaatc accagttact ggcgcaccgc   1320
accccggtcg gggcgctggt caacgcggac agccacaagt cacggcggca ccaccaacta   1380
gtgctgctgg tcctgcttag gctgttgggg catggcgacc tgcgccgcat cccgaccctg   1440
tatccgggcg agcagcaact accgaccggc cccggcgagg agccgcccag ccagcccggc   1500
cgacaacccc gtaccgctgg acgcggcgta gggctgggac ataggcccgc tcgtcgttga   1560
tggctggccg gggccgctcc tcggcgggtc ggtcgggccg attccgggca tggaaccaga   1620
cctgccagcc ttgaccgaaa cggaggaatg ggaacggcgc gggcagcagc gcctgccgat   1680
gcccgatgag ccgtgttttc taaggcccgt accttggtct ggacggtcgg aactggcttt   1740
gcctccttac ccttgccgcg cccgtcgtcg cggacggcta cgggctactc ggcacaaaag   1800
tggacgatgg cgagccgttg gagccgccga cacgggtcac gctgccgcgc cggtagcact   1860
tgggttgcgc agcaacccgt aagtgcgctg ttccagacta acctgctacc gctcggcaac   1920
ctcggcggct gtgcccagtg cgacggcgcg gccatcgtga acccaacgcg tcgttgggca   1980
ttcacgcgac aaggtctgat tcggctgtag ccgcctcgcc gccctatacc ttgtctgcct   2040
ccccgcgttg cgtcgcggtg catggagccg ggccacctcg acctgaatgg aagccggcgg   2100
agccgacatc ggcggagcgg cgggatatgg aacagacgga ggggcgcaac gcagcgccac   2160
gtacctcggc ccgtggagc tggacttacc ttcggccgcc cacctcgcta acggattcac   2220
cgtttttatc aggctctggg aggcagaata aatgatcata tcgtcaatta ttacctccac   2280
ggggagagcc tgagcaaact gtggagcgat tgcctaagtg gcaaaaatag tccgagaccc   2340
tccgtcttat ttactagtat agcagttaat aatggaggtg cccctctcgg actcgtttga   2400
ggcctcaggc atttgagaag cacacggtca cactgcttcc ggtagtcaat aaaccggtaa   2460
accagcaata gacataagcg gctatttaac gaccctgccc ccggagtccg taaactcttc   2520
```

```
gtgtgccagt gtgacgaagg ccatcagtta tttggccatt tggtcgttat ctgtattcgc   2580
cgataaattg ctgggacggg tgaaccgacg accgggtcga atttgctttc gaatttctgc   2640
cattcatccg cttattatca cttattcagg cgtagcacca ggcgtttaag ggcaccaata   2700
acttggctgc tggcccagct taaacgaaag cttaaagacg gtaagtaggc gaataatagt   2760
gaataagtcc gcatcgtggt ccgcaaattc ccgtggttat actgccttaa aaaaattacg   2820
ccccgccctg ccactcatcg cagtcggcct attggttaaa aaatgagctg atttaacaaa   2880
aatttaacgc gaattttaac tgacggaatt tttttaatgc ggggcgggac ggtgagtagc   2940
gtcagccgga taaccaattt tttactcgac taaattgttt ttaaattgcg cttaaaattg   3000
aaaatattaa cgcttacaat ttccattcgc cattcaggct gcgcaactgt tgggaagggc   3060
gatcggtgcg ggcctcttcg ctattacgcc agctggcgaa ttttataatt gcgaatgtta   3120
aaggtaagcg gtaagtccga cgcgttgaca acccttcccg ctagccacgc ccggagaagc   3180
gataatgcgg tcgaccgctt aggggatgt gctgcaaggc gattaagttg gtaacgcca    3240 gggttttccc agtcacgacg ttgtaaaacg acggccagtg agcgcgcgta atacgactca   3300 tcccccta ca cgacgttccg ctaattcaac ccattgcggt cccaaaaggg tcagtgctgc   3360
aacattttgc tgccggtcac tcgcgcgcat tatgctgagt ctatagggcg aattggagct   3420
ccaccgcggt ggcggccgct ctagaactag tggatccccc gggctgcagg aattcgatat   3480 caagcttta cgccccgccc gatatcccgc ttaacctcga ggtggcgcca ccgccggcga   3540
gatcttgatc acctagggggcccgacgtcc ttaagctata gttcgaaaat gcggggcggg   3600
tgccactcat cgcagtactg ttgtaattca ttaagcattc tgccgacatg gaagccatca   3660
caaacggcat gatgaacctg aatcgccagc ggcatcagca acggtgagta gcgtcatgac   3720
aacattaagt aattcgtaag acggctgtac cttcggtagt gtttgccgta ctacttggac   3780
ttagcggtcg ccgtagtcgt ccttgtcgcc ttgcgtataa tatttgccca tggtgaaaac   3840
gggggcgaag aagttgtcca tattggccac gtttaaatca aaactggtga aactcaccca   3900
ggaacagcgg aacgcatatt ataaacgggt accacttttg cccccgcttc ttcaacaggt   3960
ataaccggtg caaatttagt tttgaccact ttgagtgggt gggattggct gagacgaaaa   4020
acatattctc aataaaccct ttagggaaat aggccaggtt ttcaccgtaa cacgccacat   4080
cttgcgaata tatgtgtaga ccctaaccga ctctgctttt tgtataagag ttatttggga   4140 aatccctta tccggtccaa aagtggcatt gtgcggtgta aacgcttat atacacatct    4200 aactgccgga aatcgtcgtg gtattcactc cagagcgatg aaaacgtttc agtttgctca   4260
tggaaaacgg tgtaacaagg gtgaacacta tcccatatca ttgacggcct ttagcagcac   4320
cataagtgag gtctcgctac ttttgcaaag tcaaacgagt accttttgcc acattgttcc   4380
cacttgtgat agggtatagt ccagctcacc gtctttcatt gccatacgaa attccggatg   4440
agcattcatc aggcgggcaa gaatgtgaat aaaggccgga taaaacttgt gcttattttt   4500
ggtcgagtgg cagaaagtaa cggtatgctt taaggcctac tcgtaagtag tccgcccgtt   4560
cttacactta tttccggcct attttgaaca cgaataaaaa ctttacggtc tttaaaaagg   4620
ccgtaatatc cagctgaacg gtctggttat aggtacattg agcaactgac tgaaatgcct   4680
caaaatgttc tttacgatgc gaaatgccag aaatttttcc ggcattatag gtcgacttgc   4740
cagaccaata tccatgtaac tcgttgactg actttacgga gttttacaag aaatgctacg   4800
cattgggata tatcaacggt ggtatatcca gtgattttttt tctccatatg gttaacctta   4860 attaagggggt cgacgggccc gggatccgat gctcttccgc gtaaccctat atagttgcca   4920
```

```
ccatataggt cactaaaaaa agaggtatac caattggaat taattcccca gctgcccggg    4980
ccctaggcta cgagaaggcg taagatcttt tactagttca gtccatctcg ccgtgtatgc    5040
gggcctgacg gatcaacgtt cccaccgagc cagtcgagat gttcatctgg tcggcgatct    5100
attctagaaa atgatcaagt caggtagagc ggcacatacg cccggactgc ctagttgcaa    5160
gggtggctcg gtcagctcta caagtagacc agccgctaga gccggtactt caaaccttgt    5220
ttgcgcagtt ccacagcctt cttgcggcgt tcctgcgcac gagcgatgta gtcgcctcgg    5280
tcttcggcga cgagccgttt cggccatgaa gtttggaaca aacgcgtcaa ggtgtcggaa    5340
gaacgccgca aggacgcgtg ctcgctacat cagcggagcc agaagccgct gctcggcaaa    5400
gatggtgctt ttcgagacgc cgaacttgtc agccaactcc tgcgcggtct gcgtgcgacg    5460
catcacgcgt tctgcagcac ccatcagtcc gtcccctctg ctaccacgaa aagctctgcg    5520
gcttgaacag tcggttgagg acgcgccaga cgcacgctgc gtagtgcgca agacgtcgtg    5580
ggtagtcagg caggggagac ctgctgcgaa cagtgccgat cgatcgacct tcttgagctt    5640
cggccgcggc gcggtggcgt tcttccgtac cgcttccgtt tttgcgctgc tgctcacttt    5700
gacgacgctt gtcacggcta gctagctgga agaactcgaa gccggcgccg cgccaccgca    5760
agaaggcatg gcgaaggcaa aaacgcgacg acgagtgaaa gccgcggcgt gcctggattt    5820
tcgagaactc ggcggcggtg aaggtgcggt gggtccagtg ggcgactgat ttgccgatct    5880
gctcggcctc ggcccgactc cggcgccgca cggacctaaa agctcttgag ccgccgccac    5940
ttccacgcca cccaggtcac ccgctgacta aacggctaga cgagccggag ccgggctgag    6000
atggggccga tcccgtcgtt ggcgtcgagg gtgaagttgg tcagggcggt gaagtcggtg    6060
accatctgcc gccacacagt gatcgacggg tagttctgtt taccccggct agggcagcaa    6120
ccgcagctcc cacttcaacc agtcccgcca cttcagccac tggtagacgg cggtgtgtca    6180
ctagctgccc atcaagacaa tccggatctc gcggtaggcc cattcccggg tgcggtcgaa    6240
cagttcgacg ttccggcccg tttcggtcct gacctgtgtc ttgcggccgt agtccggtgg    6300
aggcctagag cgccatccgg gtaagggccc acgccagctt gtcaagctgc aaggccgggc    6360
aaagccagga ctggacacag aacgccggca tcaggccacc ggcggggaaa cggtcaccga    6420
gcgcttttgc gaggcctttg agcgagtacg gatccgaggg accccagacc gtcgtccagt    6480
gcgggtggat cgggttctgg ccgccccttt gccagtggct cgcgaaaacg ctccggaaac    6540
tcgctcatgc ctaggctccc tggggtctgg cagcaggtca cgcccaccta gcccaagacc    6600
gtgagctgct gcgcgtagcc ctgatcggcg ccgaccaccg aggcgatcag cccctggttc    6660
acccggtcgt agagccgcag cgggccctgt cgggctgcct cactcgacga cgcgcatcgg    6720
gactagccgc ggctggtggc tccgctagtc ggggaccaag tgggccagca tctcggcgtc    6780
gcccgggaca gcccgacgga ggagggtgta gaccgggctt tcgagcagcc accacaggtg    6840
cgcgtgctcg gtcgcgggat tgatcgtcat cacggtcgga tcgggcagat ccgcgttacg    6900
cctcccacat ctggcccgaa agctcgtcgg tggtgtccac gcgcacgagc cagcgcccta    6960
actagcagta gtgccagcct agcccgtcta ggcgcaatgc tgcggcccac tgcgcctggt    7020
cgtcgtccac gtcgagcacc aagcccaacc tgatcgacgg ggtgcgggcc gcaatgtagc    7080
ggcgggtgag cgcctccgcg acgcgggtg acgcggacca gcagcaggtg cagctcgtgg    7140
ttcgggttgg actagctgcc ccacgcccgg cgttacatcg ccgcccactc gcggaggcgc    7200
cgcggctgcg gccactgccc gtcccggacg tagtcatccg tcgcgtgcgg gtatttgaac    7260
```

```
cgccagcggt ccaaccaggc gtcaacagca gcggtcatga gcgccgacgc cggtgacggg    7320
cagggcctgc atcagtaggc agcgcacgcc cataaacttg gcggtcgcca ggttggtccg    7380
cagttgtcgt cgccagtact ccgccaagct agggccggat ctgtaccgat cggggaggc    7440
gcgccgcaaa ttatttaaga gtctcgctag caaaccatgt caggtgttgc ggtgggttcc    7500
ggcggttcga tcccggccta gacatggcta gccccctccg cgcggcgttt aataaattct    7560
cagagcgatc gtttggtaca gtccacaacg ccacccaagg gggtaaacct ccacccgaat    7620
tatttaagag tctcgctagc taagccctat ctgatgctgc gcgggggggtc cttcgcactg    7680
aatctcaaag gtggccggct cccatttgga ggtgggctta ataaattctc agagcgatcg    7740
attcgggata gactacgacg cgcccccag gaagcgtgac ttagagtttc caccggccga    7800
gaatttcgtc gcgcgaaaac ctccctggac agttctggaa ttcagcaaga ggtgtgtctg    7860
aacttcggtg ttttttttggg gggtgactcc agcggggtgg cttaaagcag cgcgcttttg    7920
gagggacctg tcaagacctt aagtcgttct ccacacagac ttgaagccac aaaaaaaccc    7980
cccactgagg tcgccccacc gcacaacgcg aacagagacc ttgtgtgtac gacggcggga    8040
ggtaagtcgg gtacggctcg gactgcggta gagcaaccgt cgaatcgatt tcgagcagag    8100
cgtgttgcgc ttgtctctgg aacacacatg ctgccgccct ccattcagcc catgccgagc    8160
ctgacgccat ctcgttggca gcttagctaa agctcgtctc cgagcagagc aagatattcc    8220
aaaactccgg ggttcctcgg cggcctcccc cgtctgtttg ctcaaccgag ggagacctgg    8280
cggtcccgcg tttccggacg gctcgtctcg ttctataagg ttttgaggcc caaggagcc    8340
gccggagggg gcagacaaac gagttggctc cctctggacc gccagggcgc aaaggcctgc    8400
cgcgggaccg cctaccgctc gagagcggaa gagcatctag atgcattcgc gaggtaccca    8460
gcttttgttc cctttagtga gggttaattg cgcgcttggc gcgccctggc ggatggcgag    8520
ctctcgcctt ctcgtagatc tacgtaagcg ctccatgggt cgaaaacaag ggaaatcact    8580
cccaattaac gcgcgaaccg gtaatcatgg tcatagctgt ttcctgtgtg aaattgttat    8640
ccgctcacaa ttccacacaa catacgagcc ggaagcataa agtgtaaagc ctggggtgcc    8700
cattagtacc agtatcgaca aaggacacac tttaacaata ggcgagtgtt aaggtgtgtt    8760
gtatgctcgg ccttcgtatt tcacatttcg daccccacgg taatgagtga gctaactcac    8820
attaattgcg ttgcgctcac tgcccgcttt ccagtcggga aacctgtcgt gccagctgca    8880
ttaatgaatc ggccaacgcg attactcact cgattgagtg taattaacgc aacgcgagtg    8940
acgggcgaaa ggtcagccct ttggacagca cggtcgacgt aattacttag ccggttgcgc    9000
cggggagagg cggtttgcgt attgggcgca tgcataaaaa ctgttgtaat tcattaagca    9060
ttctgccgac atggaagcca tcacaaacgg catgatgaac gccctctcc gccaaacgca    9120
taacccgcgt acgtattttt gacaacatta agtaattcgt aagacggctg taccttcggt    9180
agtgtttgcc gtactacttg ctgaatcgcc agcggcatca gcaccttgtc gccttgcgta    9240
taatatttgc ccatgggggt gggcgaagaa ctccagcatg agatcccccgc gctggaggat    9300
gacttagcgg tcgccgtagt cgtggaacag cggaacgcat attataaacg ggtaccccca    9360
cccgcttctt gaggtcgtac tctaggggcg cgacctccta catccagccg gcgtcccgga    9420
aaacgattcc gaagcccaac cttttcataga aggcggcggt ggaatcgaaa tctcgtgatg    9480
gcaggttggg cgtcgcttgg gtaggtcggc cgcagggcct tttgctaagg cttcgggttg    9540
gaaagtatct tccgccgcca ccttagcttt agagcactac cgtccaaccc gcagcgaacc    9600
tcggtcattt cgaaccccag agtcccgctc agaagaactc gtcaagaagg cgatagaagg    9660
```

```
cgatgcgctg cgaatcggga gcggcgatac cgtaaagcac agccagtaaa gcttggggtc   9720
tcagggcgag tcttcttgag cagttcttcc gctatcttcc gctacgcgac gcttagccct   9780
cgccgctatg gcatttcgtg gaggaagcgg tcagcccatt cgccgccaag ctcttcagca   9840
atatcacggg tagccaacgc tatgtcctga tagcggtccg ccacacccag ccggccacag   9900
ctccttcgcc agtcgggtaa gcggcggttc gagaagtcgt tatagtgccc atcggttgcg   9960
atacaggact atcgccaggc ggtgtgggtc ggccggtgtc tcgatgaatc cagaaaagcg  10020
gccattttcc accatgatat tcggcaagca ggcatcgcca tgggtcacga cgagatcctc  10080
gccgtcgggc atgcgcgcct agctacttag gtcttttcgc cggtaaaagg tggtactata  10140
agccgttcgt ccgtagcggt acccagtgct gctctaggag cggcagcccg tacgcgcgga  10200
tgagcctggc gaacagttcg gctggcgcga gcccctgatg ctcttcgtcc agatcatcct  10260
gatcgacaag accggcttcc atccgagtac gtgctcgctc actcggaccg cttgtcaagc  10320
cgaccgcgct cggggactac gagaagcagg tctagtagga ctagctgttc tggccgaagg  10380
taggctcatg cacgagcgag gatgcgatgt ttcgcttggt ggtcgaatgg gcaggtagcc  10440
ggatcaagcg tatgcagccg ccgcattgca tcagccatga tggatacttt ctcggcagga  10500
ctacgctaca aagcgaacca ccagcttacc cgtccatcgg cctagttcgc atacgtcggc  10560
ggcgtaacgt agtcggtact acctatgaaa gagccgtcct gcaaggtgag atgacaggag  10620
atcctgcccc ggcacttcgc ccaatagcag ccagtcccct cccgcttcag tgacaacgtc  10680
gagcacagct cgcaaggaa cgttccactc tactgtcctc taggacgggg ccgtgaagcg  10740
ggttatcgtc ggtcagggaa gggcgaagtc actgttgcag ctcgtgtcga cgcgttcctt  10800
cgcccgtcgt ggccagccac gatagccgcg ctgcctcgtc ctgcagttca ttcagggcac  10860
cggacaggtc ggtcttgaca aaagaaccg gcgcccctg gcgggcagca ccggtcggtg  10920
ctatcggcgc gacggagcag gacgtcaagt aagtcccgtg gcctgtccag ccagaactgt  10980
ttttcttggc ccgcggggac cgctgacagc cggaacacgg cggcatcaga gcagccgatt  11040
gtctgttgtg cccagtcata gccgaatagc ctctccaccc aagcggccgg agaacctgcg  11100
gcgactgtcg gccttgtgcc gccgtagtct cgtcggctaa cagacaacac gggtcagtat  11160
cggcttatcg gagaggtggg ttcgccggcc tcttggacgc tgcaatccat cttgttcaat  11220
catgcgaaac gatcctcatc ctgtctcttg atcagatctt gatccctgc gccatcgat  11280 ccttggcggc aagaaagcca acgttaggta gaacaagtta gtacgctttg ctaggagtag  11340
gacagagaac tagtctagaa ctaggggacg cggtagtcta ggaaccgccg ttctttcggt  11400
tccagtttac tttgcagggc ttcccaacct taccagaggg cgccccagct ggcaattccg  11460
gttcgcttgc tgtccataaa accgcccagt ctagctatcg aggtcaaatg aaacgtcccg  11520
aagggttgga atggtctccc gcggggtcga ccgttaaggc caagcgaacg acaggtattt  11580
tggcgggtca gatcgatagc ccatgtaagc ccactgcaag ctacctgctt tctctttgcg  11640
cttgcgtttt cccttgtcca gatagcccag tagctgacat tcatcccagg tggcactttt  11700
ggtacattcg ggtgacgttc gatggacgaa agagaaacgc gaacgcaaaa gggaacaggt  11760
ctatcgggtc atcgactgta agtagggtcc accgtgaaaa cggggaaatg tgcgcgcccg  11820
cgttcctgct ggcgctgggc ctgtttctgg cgctggactt cccgctgttc cgtcagcagc  11880
ttttcgccca cggccttgat gcccctttac acgcgcgggc gcaaggacga ccgcgacccg  11940
gacaaagacc gcgacctgaa gggcgacaag gcagtcgtcg aaaagcgggt gccggaacta  12000
```

```
gatcgcggcg gccttggcct gcatatcccg attcaacggc cccagggcgt ccagaacggg    12060
cttcaggcgc tcccgaaggt ctcgggccgt ctcttgggct ctagcgccgc cggaaccgga    12120
cgtatagggc taagttgccg gggtcccgca ggtcttgccc gaagtccgcg agggcttcca    12180
gagcccggca gagaacccga tgatcggcct tcttgcgcat ctcacgcgct cctgcggcgg    12240
cctgtagggc aggctcatac ccctgccgaa ccgcttttgt cagccggtcg gccacggctt    12300
actagccgga agaacgcgta gagtgcgcga ggacgccgcc ggacatcccg tccgagtatg    12360
gggacggctt ggcgaaaaca gtcggccagc cggtgccgaa ccggcgtctc aacgcgcttt    12420
gagattccca gcttttcggc caatccctgc ggtgcatagg cgcgtggctc gaccgcttgc    12480
gggctgatgg tgacgtggcc ggccgcagag ttgcgcgaaa ctctaagggt cgaaaagccg    12540
gttagggacg ccacgtatcc gcgcaccgag ctggcgaacg cccgactacc actgcaccgg    12600
cactggtggc cgctccaggg cctcgtagaa cgcctgaatg cgcgtgtgac gtgccttgct    12660
gccctcgatg ccccgttgca gccctagatc ggccacagcg gtgaccaccg gcgaggtccc    12720
ggagcatctt gcggacttac gcgcacactg cacggaacga cgggagctac ggggcaacgt    12780
cgggatctag ccggtgtcgc gccgcaaacg tggtctggtc gcgggtcatc tgcgctttgt    12840
tgccgatgaa ctccttggcc gacagcctgc cgtcctgcgt cagcggcacc acgaacgcgg    12900
cggcgtttgc accagaccag cgcccagtag acgcgaaaca acggctactt gaggaaccgg    12960 ctgtcgacg gcaggacgca gtcgccgtgg tgcttgcgcc tcatgtgcgg gctggtttcg    13020
tcacggtgga tgctggccgt cacgatgcga tccgccccgt acttgtccgc cagccacttg    13080
tgcgccttct cgaagaacgc agtacacgcc cgaccaaagc agtgccacct acgaccggca    13140
gtgctacgct aggcggggca tgaacaggcg gtcggtgaac acgcggaaga gcttcttgcg    13200
cgcctgctgt tcttggctgg ccgacttcca ccattccggg ctggccgtca tgacgtactc    13260
gaccgccaac acagcgtcct tgcgccgctt ctctggcagc gcggacgaca agaaccgacc    13320
ggctgaaggt ggtaaggccc gaccggcagt actgcatgag ctggcggttg tgtcgcagga    13380
acgcggcgaa gagaccgtcg aactcgcgca gtcggcccat cgcttcatcg gtgctgctgg    13440
ccgcccagtg ctcgttctct ggcgtcctgc tggcgtcagc gttgggcgtc tcgcgctcgc    13500
ttgagcgcgt cagccgggta gcgaagtagc cacgacgacc ggcgggtcac gagcaagaga    13560
ccgcaggacg accgcagtcg caacccgcag agcgcgagcg ggtaggcgtg cttgagactg    13620
gccgccacgt tgcccatttt cgccagcttc ttgcatcgca tgatcgcgta tgccgccatg    13680 cctgccccctc ccttttggtg ccatccgcac gaactctgac cggcggtgca acgggtaaaa    13740
gcggtcgaag aacgtagcgt actagcgcat acggcggtac ggacggggag ggaaaaccac    13800
tccaaccggc tcgacggggg cagcgcaagg cggtgcctcc ggcgggccac tcaatgcttg    13860
agtatactca ctagactttg cttcgcaaag tcgtgaccgc aggttggccg agctgccccc    13920
gtcgcgttcc gccacggagg ccgcccggtg agttacgaac tcatatgagt gatctgaaac    13980
gaagcgtttc agcactggcg ctacggcggc tgcggcgccc tacgggcttg ctctccgggc    14040
ttcgccctgc gcggtcgctg cgctcccttg ccagcccgtg gatatgtgga cgatggccgc    14100
gatgccgccg acgccgcggg atgcccgaac gagaggcccg aagcgggacg cgccagcgac    14160
gcgagggaac ggtcgggcac ctatacacct gctaccggcg gagcggccac cggctggctc    14220
gcttcgctcg gcccgtggac aaccctgctg acaagctga tggacaggct gcgcctgccc    14280
acgagcttga ccacagggat ctcgccggtg gccgaccgag cgaagcgagc cgggcaccctg    14340 ttgggacgac ctgttcgact acctgtccga cgcggacggg tgctcgaact ggtgtcccta    14400
```

```
tgcccaccgg ctacccagcc ttcgaccaca tacccaccgg ctccaactgc gcggcctgcg    14460
gccttgcccc atcaattttt ttaattttct ctggggaaaa acgggtggcc gatgggtcgg    14520
aagctggtgt atgggtggcc gaggttgacg cgccggacgc cggaacgggg tagttaaaaa    14580
aattaaaaga gacccctttt gcctccggcc tgcggcctgc gcgcttcgct tgccggttgg    14640
acaccaagtg gaaggcgggt caaggctcgc gcagcgaccg cgcagcggct tggccttgac    14700
cggaggccgg acgccggacg cgcgaagcga acggccaacc tgtggttcac cttccgccca    14760
gttccgagcg cgtcgctggc gcgtcgccga accggaactg gcgcctggaa cgacccaagc    14820
ctatgcgagt gggggcagtc gaaggcgaag cccgcccgcc tgcccccga gcctcacggc    14880 ggcgagtgcg ggggttccaa cgcggacctt gctgggttcg gatacgctca cccccgtcag    14940
cttccgcttc gggcgggcgg acgggggggct cggagtgccg ccgctcacgc ccccaaggtt    15000
gggggcagcg ccaccttggg caaggccgaa ggccgcgcag tcgatcaaca agccccggag    15060
gggccacttt ttgccggagc ccccgtcgcg gtggaacccg ttccggcttc cggcgcgtca    15120
gctagttgtt cggggcctcc ccggtgaaaa acggcctc                           15158
```

<210> SEQ ID NO 5
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Pro Glu Leu Ala Val Arg Thr Glu Phe Asp Tyr Ser Ser Glu Ile
1               5                   10                  15

Tyr Lys Asp Ala Tyr Ser Arg Ile Asn Ala Ile Val Ile Glu Gly Glu
            20                  25                  30

Gln Glu Ala Tyr Ser Asn Tyr Leu Gln Met Ala Glu Leu Leu Pro Glu
        35                  40                  45

Asp Lys Glu Glu Leu Thr Arg Leu Ala Lys Met Glu Asn Arg His Lys
    50                  55                  60

Lys Gly Phe Gln Ala Cys Gly Asn Asn Leu Gln Val Asn Pro Asp Met
65                  70                  75                  80

Pro Tyr Ala Gln Glu Phe Phe Ala Gly Leu His Gly Asn Phe Gln His
                85                  90                  95

Ala Phe Ser Glu Gly Lys Val Val Thr Cys Leu Leu Ile Gln Ala Leu
            100                 105                 110

Ile Ile Glu Ala Phe Ala Ile Ala Ala Tyr Asn Ile Tyr Ile Pro Val
        115                 120                 125

Ala Asp Asp Phe Ala Arg Lys Ile Thr Glu Gly Val Val Lys Asp Glu
    130                 135                 140

Tyr Thr His Leu Asn Tyr Gly Glu Glu Trp Leu Lys Ala Asn Phe Ala
145                 150                 155                 160

Thr Ala Lys Glu Glu Leu Glu Gln Ala Asn Lys Glu Asn Leu Pro Leu
                165                 170                 175

Val Trp Lys Met Leu Asn Gln Val Gln Gly Asp Ala Lys Val Leu Gly
            180                 185                 190

Met Glu Lys Glu Ala Leu Val Glu Asp Phe Met Ile Ser Tyr Gly Glu
        195                 200                 205

Ala Leu Ser Asn Ile Gly Phe Ser Thr Arg Glu Ile Met Arg Met Ser
    210                 215                 220

```
Ser Tyr Gly Leu Ala Gly Val
225                 230

<210> SEQ ID NO 6
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Phe Gly Leu Ile Gly His Leu Thr Ser Leu Glu His Ala Gln Ala
1               5                   10                  15

Val Ala Glu Asp Leu Gly Tyr Pro Glu Tyr Ala Asn Gln Gly Leu Asp
                20                  25                  30

Phe Trp Cys Ser Ala Pro Pro Gln Val Val Asp Asn Phe Gln Val Lys
            35                  40                  45

Ser Val Thr Gly Gln Val Ile Glu Gly Lys Tyr Val Glu Ser Cys Phe
50                  55                  60

Leu Pro Glu Met Leu Thr Gln Arg Arg Ile Lys Ala Ala Ile Arg Lys
65                  70                  75                  80

Ile Leu Asn Ala Met Ala Leu Ala Gln Lys Val Gly Leu Asp Ile Thr
                85                  90                  95

Ala Leu Gly Gly Phe Ser Ser Ile Val Phe Glu Asn Phe Asn Leu Lys
                100                 105                 110

Gln Asn Asn Gln Val Arg Asn Val Glu Leu Asp Phe Gln Arg Phe Thr
            115                 120                 125

Thr Gly Asn Thr His Thr Ala Tyr Val Ile Cys Arg Gln Val Glu Ser
130                 135                 140

Gly Ala Lys Gln Leu Gly Ile Asp Leu Ser Gln Ala Thr Val Ala Val
145                 150                 155                 160

Cys Gly Ala Thr Gly Asp Ile Gly Ser Ala Val Cys Arg Trp Leu Asp
                165                 170                 175

Ser Lys His Gln Val Lys Glu Leu Leu Leu Ile Ala Arg Asn Arg Gln
            180                 185                 190

Arg Leu Glu Asn Leu Gln Glu Glu Leu Gly Arg Gly Lys Ile Met Asp
        195                 200                 205

Leu Glu Thr Ala Leu Pro Gln Ala Asp Ile Ile Val Trp Val Ala Ser
        210                 215                 220

Met Pro Lys Gly Val Glu Ile Ala Gly Glu Met Leu Lys Lys Pro Cys
225                 230                 235                 240

Leu Ile Val Asp Gly Gly Tyr Pro Lys Asn Leu Asp Thr Arg Val Lys
                245                 250                 255

Ala Asp Gly Val His Ile Leu Lys Gly Gly Ile Val Glu His Ser Leu
            260                 265                 270

Asp Ile Thr Trp Glu Ile Met Lys Ile Val Glu Met Asp Ile Pro Ser
        275                 280                 285

Arg Gln Met Phe Ala Cys Phe Ala Glu Ala Ile Leu Leu Glu Phe Glu
    290                 295                 300

Gly Trp Arg Thr Asn Phe Ser Trp Gly Arg Asn Gln Ile Ser Val Asn
305                 310                 315                 320

Lys Met Glu Ala Ile Gly Glu Ala Ser Val Lys His Gly Phe Cys Pro
                325                 330                 335

Leu Val Ala Leu
```

<210> SEQ ID NO 7
<211> LENGTH: 410
<212> TYPE: DNA
<213> ORGANISM: Unknown
<220> FEATURE:
<223> OTHER INFORMATION: Description of Unknown: Cyanobacterium Rubisco
      large subunit promoter polynucleotide

<400> SEQUENCE: 7

| | | | | | |
|---|---|---|---|---|---|
| cagtcaatgg | agagcattgc | cataagtaaa | ggcatcccct | gcgtgataag | attaccttca | 60 |
| gaaaacagat | agttgctggg | ttatcgcaga | tttttctcgc | gtcagttacc | tctcgtaacg | 120 |
| gtattcattt | ccgtagggga | cgcactattc | taatggaagt | cttttgtcta | tcaacgaccc | 180 |
| aatagcgtct | aaaaagagcg | aaccaaataa | ctgtaaataa | taactgtctc | tggggcgacg | 240 |
| gtaggcttta | tattgccaaa | tttcgcccgt | gggagaaagc | taggctattc | aatgtttatg | 300 |
| ttggtttatt | gacatttatt | attgacagag | accccgctgc | catccgaaat | ataacggttt | 360 |
| aaagcgggca | ccctctttcg | atccgataag | ttacaaatac | gaggactcct | | 410 |

<210> SEQ ID NO 8
<211> LENGTH: 2962
<212> TYPE: DNA
<213> ORGANISM: Rhodococcus opacus
<220> FEATURE:
<221> NAME/KEY: modified_base
<222> LOCATION: (1070)..(1070)
<223> OTHER INFORMATION: a, c, t or g
<220> FEATURE:
<221> NAME/KEY: modified_base
<222> LOCATION: (1170)..(1170)
<223> OTHER INFORMATION: a, c, t or g

<400> SEQUENCE: 8

| | | | | | |
|---|---|---|---|---|---|
| cctggctcag | gacgaacgct | ggcggcgtgc | ttaacacatg | caagtcgagc | ggtaaggccc | 60 |
| ttcggggtac | acgagcggcg | aacgggtgag | taacacgtgg | ggaccgagtc | ctgcttgcga | 120 |
| ccgccgcacg | aattgtgtac | gttcagctcg | ccattccggg | aagccccatg | tgctcgccgc | 180 |
| ttgcccactc | attgtgcacc | gtgatctgcc | ctgcacttcg | gataagcct | gggaaactgg | 240 |
| gtctaatacc | ggatatgacc | ttcggctgca | tggctgaggg | tggaaaggtt | tactggtgca | 300 |
| cactagacgg | gacgtgaagc | cctattcgga | ccctttgacc | cagattatgg | cctatactgg | 360 |
| aagccgacgt | accgactccc | acctttccaa | atgaccacgt | ggatgggccc | gcggcctatc | 420 |
| agcttgttgg | tggggtaatg | gcctaccaag | gcgacgacgg | gtagccgacc | tgagagggtg | 480 |
| accggccaca | ctgggactga | cctacccggg | cgccggatag | tcgaacaacc | accccattac | 540 |
| cggatggttc | cgctgctgcc | catcggctgg | actctcccac | tggccggtgt | gaccctgact | 600 |
| gacacggccc | agactcctac | gggaggcagc | agtgggaat | attgcacaat | gggcgaaagc | 660 |
| ctgatgcagc | gacgccgcgt | gagggatgac | ggccttcggg | ctgtgccggg | tctgaggatg | 720 |
| ccctccgtcg | tcaccccta | taacgtgtta | cccgctttcg | gactacgtcg | ctgcggcgca | 780 |
| ctccctactg | ccggaagccc | ttgtaaacct | ctttcagcag | ggacgaagcg | aaagtgacgg | 840 |
| tacctgcaga | agaagcaccg | gccaactacg | tgccagcagc | cgcggtaata | cgtagggtgc | 900 |
| aacatttgga | gaaagtcgtc | cctgcttcgc | tttcactgcc | atggacgtct | tcttcgtggc | 960 |
| cggttgatgc | acggtcgtcg | gcgccattat | gcatcccacg | aagcgttgtc | cggaattact | 1020 |
| gggcgtaaag | agctcgtagg | cggtttgtcg | cgtcgtctgt | gaaaactcan | agctcaacct | 1080 |

```
cgagcttgca ggcgatacgg ttcgcaacag gccttaatga cccgcatttc tcgagcatcc    1140
gccaaacagc gcagcagaca cttttgagtn tcgagttgga gctcgaacgt ccgctatgcc    1200
gcagacttga gtactgcagg ggagactgga attcctggtg tagcggtgaa atgcgcagat    1260
atcaggagga acaccggtgg cgaaggcggg tctctgggca cgtctgaact catgacgtcc    1320
cctctgacct aaggaccac atcgccactt tacgcgtcta tagtcctcct tgtggccacc    1380
gcttccgccc agagaccgt gtaactgacg ctgaggagcg aaagcgtggg tagcaaacag    1440
gattagatac cctggtagtc cacgccgtaa acggtgggcg ctaggtgtgg gtttccttcc    1500
cattgactgc gactcctcgc tttcgcaccc atcgtttgtc ctaatctatg ggaccatcag    1560
gtgcggcatt tgccacccgc gatccacacc caaaggaagg acgggatccg tgccgtagtt    1620
aacgcattaa gcgccccgcc tggggagtac ggccgcaagg ttaaaactca aaggaattga    1680
cgggggcccg cacaagcggc tgccctaggc acggcatcaa ttgcgtaatt cgcggggcgg    1740
acccctcatg ccggcgttcc aattttgagt ttccttaact gcccccgggc gtgttcgccg    1800
ggagcatgtg gattaattcg atgcaacgcg aagaaccta cctgggtttg acatataccg    1860
gaaagccgta gagataccgc cccccttgtg gtcggtatac cctcgtacac ctaattaagc    1920
tacgttgcgc ttcttggaat ggacccaaac tgtatatggc ctttcggcat ctctatggcg    1980 ggggaacac cagccatatg aggtggtgca tggctgtcgt cagctcgtgt cgtgagatgt    2040
tgggttaagt cccgcaacga gcgcaaccct tgtcttatgt tgccagcacg taatggtggg    2100
tccaccacgt accgacagca gtcgagcaca gcactctaca acccaattca gggcgttgct    2160
cgcgttggga acagaataca acggtcgtgc attaccaccc gactcgtaag agactgccgg    2220
ggtcaactcg gaggaaggtg gggacgacgt caagtcatca tgccccttat gtccagggct    2280
tcacacatgc tacaatggcc ctgagcattc tctgacggcc ccagttgagc tccttccac    2340 ccctgctgca gttcagtagt acggggaata caggtcccga agtgtgtacg atgttaccgg    2400
ggtacagagg gctgcgatac cgtgaggtgg agcgaatccc ttaaagccgg tctcagttcg    2460
gatcggggtc tgcaactcga ccccgtgaag tcggagtcgc ccatgtctcc cgacgctatg    2520
gcactccacc tcgcttaggg aatttcggcc agagtcaagc ctagccccag acgttgagct    2580
ggggcacttc agcctcagcg tagtaatcgc agatcagcaa cgctgcggtg aatacgttcc    2640
cgggccttgt acacaccgcc cgtcacgtca tgaaagtcgg taacacccga agccggtggc    2700
atcattagcg tctagtcgtt gcgacgccac ttatgcaagg gcccggaaca tgtgtggcgg    2760
gcagtgcagt actttcagcc attgtgggct tcggccaccg ctaaccccttt gtgggaggga    2820 gccgtcgaag gtgggatcgg cgattgggac gaagtcgtaa caaggtagcc gtaccggaag    2880
ggattgggga acaccctccc tcggcagctt ccaccctagc cgctaaccct gcttcagcat    2940
tgttccatcg gcatggcctt cc                                            2962

<210> SEQ ID NO 9
<211> LENGTH: 3042
<212> TYPE: DNA
<213> ORGANISM: Rhodococcus opacus

<400> SEQUENCE: 9
tcaacggaga gtttgatcct ggctcaggac gaacgctggc ggcgtgctta acacatgcaa     60
gtcgagcggt aaggcccttc ggggtacacg agcggcgaac agttgcctct caaactagga    120
ccgagtcctg cttgcgaccg ccgcacgaat tgtgtacgtt cagctcgcca ttccgggaag    180
ccccatgtgc tcgccgcttg gggtgagtaa cacgtgggtg atctgccctg cacttcggga    240
```

-continued

```
taagcctggg aaactgggtc taataccgga tatgaccttc ggctgcatgg ccgttggtgg    300
cccactcatt gtgcacccac tagacgggac gtgaagccct attcggaccc tttgacccag    360
attatggcct atactggaag ccgacgtacc ggcaaccacc aaaggtttac tggtgcagga    420
tgggcccgcg gcctatcagc ttgttggtgg ggtaatggcc taccaaggcg acgacgggta    480
gccgacctga gagggtgacc tttccaaatg accacgtcct acccgggcgc cggatagtcg    540
aacaaccacc ccattaccgg atggttccgc tgctgcccat cggctggact ctcccactgg    600
ggccacactg ggactgagac acggcccaga ctcctacggg aggcagcagt ggggaatatt    660
gcacaatggg cgaaagcctg atgcagcgac gccgcgtgag ccgtgtgac cctgactctg     720
tgccgggtct gaggatgccc tccgtcgtca ccccttataa cgtgttaccc gctttcggac    780
tacgtcgctg cggcgcactc ggatgacggc cttcgggttg taaacctctt tcagcaggga    840
cgaagcgaaa gtgacggtac ctgcagaaga agcaccggcc aactacgtgc cagcagccgc    900
cctactgccg gaagcccaac atttggagaa agtcgtccct gcttcgcttt cactgccatg    960
gacgtcttct tcgtggccgg ttgatgcacg gtcgtcggcg ggtaatacgt agggtgcaag   1020
cgttgtccgg aattactggg cgtaaagagc tcgtaggcgg tttgtcgcgt cgtctgtgaa   1080
aactcgaggc tcaacctcga ccattatgca tcccacgttc gcaacaggcc ttaatgaccc   1140
gcatttctcg agcatccgcc aaacagcgca gcagacactt ttgagctccg agttggagct   1200
gcttgcaggc gatacgggca gacttgagta ctgcaggga gactggaatt cctggtgtag    1260
cggtgaaatg cgcagatatc aggaggaaca ccggtggcga cgaacgtccg ctatgcccgt   1320
ctgaactcat gacgtcccct ctgaccttaa ggaccacatc gccactttac gcgtctatag   1380
tcctccttgt ggccaccgct aggcgggtct ctgggcagta actgacgctg aggagcgaaa   1440
gcgtgggtag cgaacaggat tagataccct ggtagtccac gccgtaaacg gtgggcgcta   1500
tccgcccaga gacccgtcat tgactgcgac tcctcgcttt cgcacccatc gcttgtccta   1560
atctatggga ccatcaggtg cggcatttgc cacccgcgat ggtgtgggtt tccttccacg   1620
ggatccgtgc cgtagctaac gcattaagcg ccccgcctgg ggagtacggc cgcaaggcta   1680
aaactcaaag gaattgacgg ccacacccaa aggaaggtgc cctaggcacg gcatcgattg   1740
cgtaattcgc ggggcggacc cctcatgccg gcgttccgat tttgagtttc cttaactgcc   1800
gggcccgcac aagcggcgga gcatgtggat taattcgatg caacgcgaag aaccttacct   1860
gggtttgaca tataccggaa agctgcagag atgtggcccc cccgggcgtg ttcgccgcct   1920
cgtacaccta attaagctac gttgcgcttc ttggaatgga cccaaactgt atatggcctt   1980
tcgacgtctc tacaccgggg ccttgtggtc ggtatacagg tggtgcatgg ctgtcgtcag   2040
ctcgtgtcgt gagatgttgg gttaagtccc gcaacgagcg caaccccttgt cttatgttgc   2100
ggaacaccag ccatatgtcc accacgtacc gacagcagtc gagcacagca ctctacaacc   2160
caattcaggg cgttgctcgc gttgggaaca gaatacaacg cagcacgtaa tggtggggac   2220
tcgtaagaga ctgccggggt caactcggag gaaggtgggg acgacgtcaa gtcatcatgc   2280
cccttatgtc cagggcttca gtcgtgcatt accaccctg agcattctct gacggcccca   2340
gttgagcctc cttccacccc tgctgcagtt cagtagtacg gggaatacag gtcccgaagt   2400
cacatgctac aatggccggt acagagggct gcgataccgt gaggtggagc gaatccctta   2460
aagccggtct cagttcggat cggggtctgc aactcgaccc gtgtacgatg ttaccggcca   2520
tgtctcccga cgctatggca ctccacctcg cttagggaat tcggccaga gtcaagccta    2580
```

| gccccagacg ttgagctggg cgtgaagtcg gagtcgctag taatcgcaga tcagcaacgc | 2640 |
| tgcggtgaat acgttcccgg gccttgtaca caccgcccgt cacgtcatga agtcggtaa | 2700 |
| gcacttcagc ctcagcgatc attagcgtct agtcgttgcg acgccactta tgcaagggcc | 2760 |
| cggaacatgt gtggcgggca gtgcagtact ttcagccatt cacccgaagc cggtggccta | 2820 |
| acccctcgtg ggagggagcc gtcgaaggtg ggatcggcga ttgggacgaa gtcgtaacaa | 2880 |
| ggtagccgta ccgaaggtg gtgggcttcg gccaccggat tggggagcac cctccctcgg | 2940 |
| cagcttccac cctagccgct aaccctgctt cagcattgtt ccatcggcat ggccttccac | 3000 |
| cggctggatc acctcctttc tgccgaccta gtggaggaaa ga | 3042 |

<210> SEQ ID NO 10
<211> LENGTH: 2924
<212> TYPE: DNA
<213> ORGANISM: Ralstonia sp.

<400> SEQUENCE: 10

| acgtggcggc atgccttaca catgcaagtc gaacggcagc gcggacttcg gtctggcggc | 60 |
| gagtggcgaa cgggtgagta atacatcgga acgtaccctg tgcaccgccg tacggaatgt | 120 |
| gtacgttcag cttgccgtcg cgcctgaagc cagaccgccg ctcaccgctt gcccactcat | 180 |
| tatgtagcct tgcatgggac ttgtggggga taactagtcg aaagattagc taataccgca | 240 |
| tacgacctga gggtgaaagt gggggaccgc aaggcctcac gcagcaggag cggccgatgt | 300 |
| aacacccccct attgatcagc tttctaatcg attatggcgt atgctggact cccactttca | 360 |
| cccccctggcg ttccggagtg cgtcgtcctc gccggctaca ctgattagct agttggtggg | 420 |
| gtaaaggccc accaaggcga cgatcagtag ctggtctgag aggacgatca gccacactgg | 480 |
| gactgagaca cggcccagac gactaatcga tcaaccaccc catttccggg tggttccgct | 540 |
| gctagtcatc gaccagactc tcctgctagt cggtgtgacc ctgactctgt gccgggtctg | 600 |
| tcctacggga ggcagcagtg gggaattttg gacaatgggg caaccctga tccagcaatg | 660 |
| ccgcgtgtgt gaagaaggcc ttcgggttgt aaagcacttt aggatgccct ccgtcgtcac | 720 |
| cccttaaaac ctgttacccc cgttgggact aggtcgttac ggcgcacaca cttcttccgg | 780 |
| aagcccaaca tttcgtgaaa tgtccggaaa gaaatcgcgc tggttaatac ctgcgtgatg | 840 |
| acggtaccgg aagaataagc accgctaac tacgtgccag cagccgcggt aatacgtagg | 900 |
| acaggccttt ctttagcgcg accaattatg gacgcactac tgccatggcc ttcttattcg | 960 |
| tggccgattg atgcacggtc gtcggcgcca ttatgcatcc gtgcgagcgt taatcggaat | 1020 |
| tactgggcgt aaagcgtgcg caggcggttt tgtaagacag gcgtgaaatc cccgggctta | 1080 |
| acctgggaat tgcgcttgtg cacgctcgca attagcctta atgacccgca tttcgcacgc | 1140 |
| gtccgccaaa acattctgtc cgcactttag gggcccgaat tggaccctta acgcgaacac | 1200 |
| actgcaaggc tagagtgcgt cagagggggg tagaattcca cgtgtagcag tgaaatgcgt | 1260 |
| agagatgtgg aggaataccg atggcgaagg cgagccccct tgacgttccg atctcacgca | 1320 |
| gtctccccc atcttaaggt gcacatcgtc actttacgca tctctacacc tccttatggc | 1380 |
| taccgcttcc gctcgggga ggaccttgac tgacgctcat gcacgaaagc gtggggagca | 1440 |
| aacaggatta gataccctgg tagtccacgc cctaaacgat gtcaactagt tgttgggatt | 1500 |
| cctggaactg actgcgagta cgtgctttcg caccccctcgt ttgtcctaat ctatgggacc | 1560 |
| atcaggtgcg ggatttgcta cagttgatca acaaccctaa catttttctca gtaacgtagc | 1620 |
| taacgcgtga agttgaccgc ctggggagta cggctgcaag attaaaactc aaaggaattg | 1680 |

```
acggggaccc gcacaagcgg gtaaaagagt cattgcatcg attgcgcact tcaactggcg    1740 gaccccctcat gccgacgttc taattttgag tttccttaac tgcccctggg cgtgttcgcc   1800
tggatgatgt ggattaattc gatgcaacgc gaaaaacctt acctacccctt gacatgccct   1860 aacgaagcag agatgcatta gtgcccgcaa agggaaagtg acctactaca cctaattaag    1920
ctacgttgcg cttttttggaa tggatgggaa ctgtacggga ttgcttcgtc tctacgtaat   1980
cacgggcgtt tcccttttcac ggacacaggt gctgcatggc tgtcgtcagc tcgtgtcgtg   2040
agatgttggg ttaagtcccg caacgagcgc aacccttgtc tctagttgcc tacgcaagag    2100
cctgtgtcca cgacgtaccg acagcagtcg agcacagcac tctacaaccc aattcagggc    2160
gttgctcgcg ttgggaacag agatcaacgg atgcgttctc cactctagag agactgccgg    2220
tgacaaaccg gaggaaggtg gggatgacgt caagtcctca tggcccttat gggtagggct    2280
tcacacgtca tacaatggtg gtgagatctc tctgacggcc actgtttggc ctccttccac    2340
ccctactgca gttcaggagt accgggaata cccatcccga agtgtgcagt atgttaccac    2400
cgtacagagg gttgccaacc cgcgaggggg agctaatccc agaaaacgca tcgtagtccg    2460
gatcgtagtc tgcaactcga ctacgtgaag ctggaatcgc gcatgtctcc caacggttgg   2520
gcgctccccc tcgattaggg tcttttgcgt agcatcaggc ctagcatcag acgttgagct    2580
gatgcacttc gaccttagcg tagtaatcgc ggatcagcat gccgcggtga atacgttccc    2640
gggtcttgta cacaccgccc gtcacaccat gggagtgggt tttgccagaa gtagttagcc    2700
atcattagcg cctagtcgta cggcgccact tatgcaaggg cccagaacat gtgtggcggg    2760
cagtgtggta ccctcaccca aaacggtctt catcaatcgg taaccgcaag gagggcgatt    2820
accacggcag ggttcatgac tggggtgaag tcgtaacaag gtattggcgt tcctcccgct    2880
aatggtgccg tcccaagtac tgaccccact tcagcattgt tcca                     2924
```

<210> SEQ ID NO 11
<211> LENGTH: 284
<212> TYPE: PRT
<213> ORGANISM: Rhodococcus opacus

<400> SEQUENCE: 11

```
Met Ala Ser Ile Glu Asp Ile Leu Glu Leu Glu Ala Leu Glu Lys Asp
1               5                   10                  15

Ile Phe Arg Gly Ala Val His Pro Ser Val Leu Lys Arg Thr Phe Gly
                20                  25                  30

Gly Gln Val Ala Gly Gln Ser Leu Val Ser Ala Val Arg Thr Val Asp
            35                  40                  45

Glu Arg Phe Glu Val His Ser Leu His Gly Tyr Phe Leu Arg Pro Gly
        50                  55                  60

Asn Pro Thr Glu Pro Thr Val Tyr Leu Val Asp Arg Ile Arg Asp Gly
65                  70                  75                  80

Arg Ser Phe Cys Thr Arg Arg Val Thr Gly Ile Gln Asp Gly Lys Ala
                85                  90                  95

Ile Phe Thr Met Ser Ala Ser Phe His Ser Gln Asp Glu Gly Ile Glu
            100                 105                 110

His Gln Asp Thr Met Pro Ser Val Pro Glu Pro Glu Gly Leu Val Asp
        115                 120                 125

Ala Gln Thr Val Glu Glu Met Ala Ala Thr Asp Leu Tyr Arg Glu Trp
    130                 135                 140

Lys Glu Trp Asp Val Arg Ile Val Pro Ala Gly Cys Thr Gly Lys Thr
```

```
                    145                 150                 155                 160
Pro Gly Ile Ala Ala Lys Gln Arg Val Trp Met Arg Tyr Arg Asn Lys
                165                 170                 175

Leu Pro Asp Asp Gln Val Phe His Ile Cys Thr Leu Ala Tyr Leu Ser
            180                 185                 190

Asp Met Thr Leu Leu Gly Ala Ser Lys Val Pro His Pro Gly Val Val
            195                 200                 205

Thr Gln Thr Ala Ser Leu Asp His Ala Met Trp Phe Leu Arg Pro Phe
        210                 215                 220

Arg Ala Asp Glu Trp Leu Leu Tyr Asp Gln Thr Ser Pro Ser Ala Gly
225                 230                 235                 240

Phe Gly Arg Ala Leu Thr Gln Gly Arg Met Phe Asp Arg Lys Gly Thr
                245                 250                 255

Met Val Ala Ala Val Val Gln Glu Gly Leu Thr Arg Ile Gln Arg Asp
            260                 265                 270

Gln Asp Gln Arg Asp Ile Glu Thr Gly Asn Met Ala
            275                 280
```

<210> SEQ ID NO 12
<211> LENGTH: 1460
<212> TYPE: DNA
<213> ORGANISM: Rhodococcus opacus
<220> FEATURE:
<221> NAME/KEY: modified_base
<222> LOCATION: (799)..(799)
<223> OTHER INFORMATION: a, c, t or g

<400> SEQUENCE: 12

```
ggcggcgtgc ttaacacatg caagtcgagc ggtaaggccc ttcggggtac acgagcggcg      60
aacgggtgag taacacgtgg gtgatctgcc ctgcacttcg ggataagcct gggaaactgg     120
gtctaatacc ggatatgacc ttcggctgca tggctgaggg tggaaaggtt tactggtgca     180
ggatgggccc gcggcctatc agcttgttgg tggggtaatg gcctaccaag gcgacgacgg     240
gtagccgacc tgagagggtg accggccaca ctgggactga gacacggccc agactcctac     300
gggaggcagc agtggggaat attgcacaat gggcgaaagc ctgatgcagc gacgccgcgt     360
gagggatgac ggccttcggg ttgtaaacct ctttcagcag gacgaagcg  aaagtgacgg     420 tacctgcaga agaagcaccg gccaactacg tgccagcagc cgcggtaata cgtagggtgc     480
aagcgttgtc cggaattact gggcgtaaag agctcgtagg cggtttgtcg cgtcgtctgt     540
gaaaactcac agctcaacct cgagcttgca ggcgatacgg gcagacttga gtactgcagg     600
ggagactgga attcctggtg tagcggtgaa atgcgcagat atcaggagga acaccggtgg     660
cgaaggcggg tctctgggca gtaactgacg ctgaggagcg aaagcgtggg tagcaaacag     720
gattagatac cctggtagtc cacgccgtaa acggtgggcg ctaggtgtgg gtttccttcc     780
acgggatccg tgccgtagnt aacgcattaa gcgccccgcc tggggagtac ggccgcaagg     840
ttaaaactca aaggaattga cggggggccc cacaagcggc ggagcatgtg gattaattcg     900
atgcaacgcg aagaacctta cctgggtttg acatataccg gaaagccgta gagataccgc     960
cccccttgtg gtcggtatac aggtggtgca tggctgtcgt cagctcgtgt cgtgagatgt    1020
tgggttaagt cccgcaacga gcgcaaccct tgtcttatgt tgccagcacg taatggtggg    1080
gactcgtaag agactgccgg ggtcaactcg gaggaaggtg gggacgacgt caagtcatca    1140
tgccccttat gtccagggct tcacacatgc tacaatggcc ggtacagagg ctgcgatac     1200 cgtgaggtgg agcgaatccc ttaaagccgg tctcagttcg gatcggggtc tgcaactcga    1260
```

```
cccgtgaag tcggagtcgc tagtaatcgc agatcagcaa cgctgcggtg aatacgttcc    1320
cgggccttgt acacaccgcc cgtcacgtca tgaaagtcgg taacacccga agccggtggc    1380 ctaaccccctt gtgggaggga gccgtcgaag gtgggatcgg cgattgggac gaagtcgtaa    1440
caaggtagcc gtaccggaag                                                 1460
```

<210> SEQ ID NO 13
<211> LENGTH: 1473
<212> TYPE: DNA
<213> ORGANISM: Rhodococcus opacus
<220> FEATURE:
<221> NAME/KEY: modified_base
<222> LOCATION: (562)..(562)
<223> OTHER INFORMATION: a, c, t or g

<400> SEQUENCE: 13

```
aggacgaacg ctggcggcgt gcttaacaca tgcaagtcga gcggtaaggc ccttcggggt      60
acacgagcgg cgaacgggtg agtaacacgt gggtgatctg ccctgcactt cgggataagc     120
ctgggaaact gggtctaata ccggatatga ccttcggctg catggctgag ggtggaaagg     180
tttactggtg caggatgggc ccgcggccta tcagcttgtt ggtggggtaa tggcctacca     240
agccgacgac gggtagccga cctgagaggg tgaccggcca cactgggact gagacacggc     300
ccagactcct acgggaggca gcagtgggga atattgcaca atgggcgaaa gcctgatgca     360
gcgacgccgc gtgagggatg acggccttcg ggttgtaaac ctctttcagc agggacgaag     420
cgaaagtgac ggtacctgca gaagaagcac cggccaacta cgtgccagca gccgcggtaa     480
tacgtagggt gcaagcgttg tccggaatta ctgggcgtaa agagctcgta ggcggtttgt     540
cgcgtcgtct gtgaaaactc anagctcaac ctcgagcttg caggcgatac gggcagactt     600
gagtactgca ggggagactg gaattcctgg tgtagcggtg aaatgcgcag atatcaggag     660
gaacaccggt ggcgaaggcg ggtctctggg cagtaactga cgctgaggag cgaaagcgtg     720
ggtagcaaac aggattagat accctggtag tccacgccgt aaacggtggg cgctaggtgt     780
gggtttcctt ccacgggatc cgtgccgtag ctaacgcatt aagcgccccg cctggggagt     840
acggccgcaa ggctaaaact caaaggaatt gacggggggcc cgcacaagcg gcggagcatg     900
tggattaatt cgatgcaacg cgaagaacct tacctgggtt tgacatatac cggaaagccg     960
tagagatacg gccccccttg tggtcggtat acaggtggtg catggctgtc gtcagctcgt    1020
gtcgtgagat gttgggttaa gtcccgcaac gagcgcaacc cttgtcttat gttgccagca    1080
cgtaatggtg gggactcgta agagactgcc gggtcaact cggaggaagg tggggacgac    1140
gtcaagtcat catgcccctt atgtccaggg cttcacacat gctacaatgg ccggtacaga    1200
gggctgcgat accgtgaggt ggagcgaatc ccttaaagcc ggtctcagtt cggatcgggg    1260
tctgcaactc gacccccgtga agtcggagtc gctagtaatc gcagatcagc aacgctgcgg    1320
tgaatacgtt cccgggcctt gtacacaccg cccgtcacgt catgaaagtc ggtaacaccc    1380
gaagccggtg gcctaacccc ttgtgggagg gagccgtcga aggtgggatc ggcgattggg    1440
acgaagtcgt aacaaggtag ccgtaccgga agg                                1473
```

<210> SEQ ID NO 14
<211> LENGTH: 1462
<212> TYPE: DNA
<213> ORGANISM: Cupriavidus necator

<400> SEQUENCE: 14

```
acgtggcggc atgccttaca catgcaagtc gaacggcagc gcggacttcg gtctggcggc    60
gagtggcgaa cgggtgagta atacatcgga acgtaccctg ttgtggggga taactagtcg   120
aaagattagc taataccgca tacgacctga gggtgaaagt gggggaccgc aaggcctcac   180
gcagcaggag cggccgatgt ctgattagct agttggtggg gtaaaggccc accaaggcga   240
cgatcagtag ctggtctgag aggacgatca gccacactgg gactgagaca cggcccagac   300
tcctacggga ggcagcagtg gggaattttg gacaatgggg gcaaccctga tccagcaatg   360
ccgcgtgtgt gaagaaggcc ttcgggttgt aaagcacttt tgtccggaaa gaaatcgcgc   420
tggttaatac ctgcgtgatg acggtaccgg aagaataagc accggctaac tacgtgccag   480
cagccgcggt aatacgtagg gtgcgagcgt taatcggaat tactgggcgt aaagcgtgcg   540
caggcggttt tgtaagacag gcgtgaaatc cccgggctta acctgggaat tgcgcttgtg   600
actgcaaggc tagagtgcgt cagagggggg tagaattcca cgtgtagcag tgaaatgcgt   660
agagatgtgg aggaataccg atggcgaagg cgagccccct ggaccttgac tgacgctcat   720
gcacgaaagc gtggggagca acaggatta gatacctgg tagtccacgc cctaaacgat   780
gtcaactagt tgttgggatt cattttctca gtaacgtagc taacgcgtga agttgaccgc   840
ctggggagta cggctgcaag attaaaactc aaaggaattg acgggacccc gcacaagcgg   900
tggatgatgt ggattaattc gatgcaacgc gaaaaacctt acctacccct gacatgccct   960
aacgaagcag agatgcatta gtgcccgcaa agggaaagtg gacacaggt gctgcatggc  1020
tgtcgtcagc tcgtgtcgtg agatgttggg ttaagtcccg caacgagcgc aacccttgtc  1080
tctagttgcc tacgcaagag cactctagag agactgccgg tgacaaaccg gaggaaggtg  1140
gggatgacgt caagtcctca tggcccttat gggtagggct tcacacgtca tacaatggtg  1200
cgtacagagg gttgccaacc cgcgaggggg agctaatccc agaaaacgca tcgtagtccg  1260
gatcgtagtc tgcaactcga ctacgtgaag ctggaatcgc tagtaatcgc ggatcagcat  1320
gccgcggtga atacgttccc gggtcttgta cacaccgccc gtcaccat gggagtgggt  1380
tttgccagaa gtagttagcc taaccgcaag gagggcgatt accacggcag ggttcatgac  1440
tggggtgaag tcgtaacaag gt                                          1462
```

<210> SEQ ID NO 15
<211> LENGTH: 1479
<212> TYPE: DNA
<213> ORGANISM: Ralstonia sp.

<400> SEQUENCE: 15

```
agtttgatcc tggctcagat tgaacgctgg cggcatgcct tacacatgca agtcgaacgg    60
cagcgcggac ttcggtctgg cggcgagtgg cgaacgggtg agtaatacat cggaacgtac   120
cctgttgtgg gggataacta gtcgaaagat tagctaatac cgcatacgac ctgagggtga   180
aagcggggga ccgtaaggcc tcgcgcagca ggagcggccg atgtctgatt agctagttgg   240
tggggtaaag gcccaccaag cgacgatca gtagctggtc tgagaggacg atcagccaca   300
ctgggactga gacacggccc agactcctac gggaggcagc agtggggaat tttggacaat   360
ggggcaacc ctgatccagc aatgccgcgt gtgtgaagaa ggccttcggg ttgtaaagca   420
cttttgtccg gaaagaaaac gctctggtta atacctggag tggatgacgg taccggaaga   480
ataagcaccg gctaactacg tgccagcagc cgcggtaata cgtagggtgc gagcgttaat   540
cggaattact gggcgtaaag cgtgcgcagg cggttttgta agacaggcgt gaaatccccg   600
agctcaactt gggaattgcg cttgtgactg caaggctaga gtatgtcaga ggggggtaga   660
```

```
attccacgtg tagcagtgaa atgcgtagag atgtggagga ataccgatgg cgaaggcagc      720
cccctgggac gtcactgacg ctcatgcacg aaagcgtggg gagcaaacag gattagatac      780
cctggtagtc cacgccctaa acgatgtcaa ctagttgttg gggattcatt tcttcagtaa      840
cgtagctaac gcgtgaagtt gaccgcctgg ggagtacggt cgcaagatta aaactcaaag      900
gaattgacgg ggacccgcac aagcggtgga tgatgtggat taattcgatg caacgcgaaa      960
aaccttacct acccttgaca tgccactaac gaagcagaga tgcatcaggt gcccgaaagg     1020
gaaagtggac acaggtgctg catggctgtc gtcagctcgt gtcgtgagat gttgggttaa     1080
gtcccgcaac gagcgcaacc cttatcttta gttgctacgc aagggcactc tagagagact     1140
gccggtgaca aaccggagga aggtggggat gacgtcaagt cctcatggcc cttatgggta     1200
gggcttcaca cgtcatacaa tggtcgctac agagggttgc caacccgcga ggggagcta    1260 atcccagaaa acgcatcgta gtccggatcg cagtctgcaa ctcgactgcg tgaagctgga     1320
atcgctagta atcgcggatc agcatgccgc ggtgaatacg ttcccgggtc ttgtacacac     1380
cgcccgtcac accatgggag tgggttttgc cagaagtagt tagcctaacc gcaaggaggg     1440
cgattaccac ggcagggttc atgactgggg tgaagtcgt                           1479

<210> SEQ ID NO 16
<211> LENGTH: 1486
<212> TYPE: DNA
<213> ORGANISM: Gordonia alkanivorans

<400> SEQUENCE: 16
gctcaggacg aacgctggcg gcgtgcttaa cacatgcaag tcgaacggaa aggcccagct       60
tgctgggtac tcgagtggcg aacgggtgag taacacgtgg gtgatctgcc ctgaactttg      120
ggataagcct gggaaactgg gtctaatacc ggatatgacc ttggagtgca tgctctgggg      180
tggaaagctt ttgcggttca ggatgggccc gcggcctatc agcttgttgg tggggtaatg      240
gcctaccaag gcgacgacgg gtagccgacc tgagagggtg atcggccaca ctgggactga      300
gacacggccc agactcctac gggaggcagc agtggggaat attgcacaat gggcgcaagc      360
ctgatgcagc gacgccgcgt gagggatgac ggccttcggg ttgtaaacct ctttcaccag      420
ggacgaagcg caagtgacgg tacctggaga agaagcaccg gccaactacg tgccagcagc      480
cgcggtaata cgtagggtgc gagcgttgtc cggaattact gggcgtaaag agctcgtagg      540
cggtttgtcg cgtcgtctgt gaaattctgc aactcaattg taggcgtgca ggcgatacgg      600
gcagacttga gtactacagg ggagactgga attcctggtg tagcggtgaa atgcgcagat      660
atcaggagga acaccggtgg cgaaggcggg tctctgggta gtaactgacg ctgaggagcg      720
aaagcgtggg tagcgaacag gattagatac cctggtagtc cacgccgtaa acggtgggta      780
ctaggtgtgg ggctcatttc acgagttccg tgccgtagct aacgcattaa gtaccccgcc      840
tggggagtac ggccgcaagg ctaaaactca aaggaattga cggggccccg cacaagcggc      900
ggagcatgtg gattaattcg atgcaacgcg aagaacctta cctgggtttg acatacacca      960
gacgcatgta gagatacatg ttcccttgtg gttggtgtac aggtggtgca tggctgtcgt     1020
cagctcgtgt cgtgagatgt tgggttaagt cccgcaacga gcgcaaccct tgtcctgtat     1080
tgccagcggg ttatgccggg gacttgcagg agactgccgg ggtcaactcg gaggaaggtg     1140
gggatgacgt caagtcatca tgccccttat gtccagggct tcacacatgc tacaatggct     1200
ggtacagagg gctgcgatac cgtgaggtgg agcgaatccc ttaaagccag tctcagttcg     1260
```

| gattggggtc tgcaactcga ccccatgaag tcggagtcgc tagtaatcgc agatcagcaa | 1320 |
| cgctgcggtg aatacgttcc cgggccttgt acacaccgcc cgtcacgtca tgaaagtcgg | 1380 |
| taacacccga agccggtggc ctaaccccctt gtgggaggga gctgtcgaag gtgggatcgg | 1440 |
| cgattgggac gaagtcgtaa caaggtagcc gtaccggaag gtgcgg | 1486 |

<210> SEQ ID NO 17
<211> LENGTH: 1491
<212> TYPE: DNA
<213> ORGANISM: Gordonia sp

<400> SEQUENCE: 17

| gatcatggct caggacgaac gctggcggcg tgcttaacac atgcaagtcg aacggaaagg | 60 |
| cccgcttgcg ggtactcgag tggcgaacgg gtgagtaaca cgtgggtgat ctgccctgga | 120 |
| ctctgggata agcctgggaa actgggtcta ataccggata tgaccttaca tcgcatggtg | 180 |
| tttggtggaa agcttttgcg gttcaggatg ggcccgcggc ctatcagctt gttggtgggg | 240 |
| taatggccta ccaaggcgac gacgggtagc cgacctgaga gggtgatcgg ccacactggg | 300 |
| actgagacac ggcccagact cctacggag gcagcagtgg ggaatattgc acaatgggcg | 360 |
| caagcctgat gcagcgacgc cgcgtgaggg atgacgccct tcgggttgta aacctctttc | 420 |
| accagggacg aagcgcaagt gacggtacct ggagaagaag caccggccaa ctacgtgcca | 480 |
| gcagccgcgg taatacgtag ggtgcgagcg ttgtccggaa ttactgggcg taaagagctc | 540 |
| gtaggcggtt tgtcgcgtcg tctgtgaaat tctgcaactc aattgtaggc gtgcaggcga | 600 |
| tacgggcaga cttgagtact acaggggaga ctggaattcc tggtgtagcg gtgaaatgcg | 660 |
| cagatatcag gaggaacacc ggtggcgaag gcgggtctct gggtagtaac tgacgctgag | 720 |
| gagcgaaagc gtgggtagcg aacaggatta gataccctgg tagtccacgc cgtaaacggt | 780 |
| gggtactagg tgtggggctc atttcacgag ttccgtgccg tagctaacgc attaagtacc | 840 |
| ccgcctgggg agtacggccg caaggctaaa actcaaagga attgacgggg cccgcacaa | 900 |
| gcggcggagc atgtggatta attcgatgca acgcgaagaa ccttacctgg gtttgacata | 960 |
| caccagaaag ctatagagat atagccccc ttgtggttgg tgtacaggtg gtgcatggct | 1020 |
| gtcgtcagct cgtgtcgtga tgttgggt taagtcccgc aacgagcgca acccttgtcc | 1080 |
| tgtattgcca gcgggttatg ccggggactt gcaggagact gccggggtca actcggagga | 1140 |
| aggtggggat gacgtcaagt catcatgccc cttatgtcca gggcttcaca catgctacaa | 1200 |
| tggctggtac agagggctgc gataccgtga ggtggagcga atcccttaaa gccagtctca | 1260 |
| gttcggattg ggtctgcaa ctcgaccccca tgaagtcgga gtcgctagta atcgcagatc | 1320 |
| agcaacgctg cggtgaatac gttcccgggc cttgtacaca ccgcccgtca cgtcatgaaa | 1380 |
| gtcggtaaca cccgaagccg gtggcctaac cccttgtggg agggagctgt cgaaggtggg | 1440 |
| atcggcgatt gggacgaagt cgtaacaagg tagccgtacc ggaaggtgcg g | 1491 |

<210> SEQ ID NO 18
<211> LENGTH: 1505
<212> TYPE: DNA
<213> ORGANISM: Mycobacterium fortuitum

<400> SEQUENCE: 18

| ttgatcctgg ctcaggacga acgctggcgg cgtgcttaac acatgcaagt cgaacggaaa | 60 |
| ggcccttcgg ggtactcgag tggcgaacgg gtgagtaaca cgtgggtgat ctgccctgca | 120 |
| ctttgggata agcctgggaa actgggtcta ataccgaata tgaccacgcg cttcatggtg | 180 |

```
tgtggtggaa agcttttgcg gtgtgggatg ggcccgcggc ctatcagctt gttggtgggg      240
taatggccta ccaaggcgac gacgggtagc cggcctgaga gggtgaccgg ccacactggg      300
actgagatac ggcccagact cctacgggag gcagcagtgg ggaatattgc acaatgggcg      360
caagcctgat gcagcgacgc cgcgtgaggg atgacggcct tcggttgta aacctctttc       420 aatagggacg aagcgcaagt gacggtacct atagaagaag gaccggccaa ctacgtgcca      480
gcagccgcgg taatacgtag ggtccgagcg ttgtccggaa ttactgggcg taaagagctc      540
gtaggtggtt tgtcgcgttg ttcgtgaaaa ctcacagctt aactgtgggc gtgcgggcga      600
tacgggcaga ctagagtact gcaggggaga ctggaattcc tggtgtagcg gtggaatgcg      660
cagatatcag gaggaacacc ggtggcgaag gcgggtctct gggcagtaac tgacgctgag      720
gagcgaaagc gtggggagcg aacaggatta gataccctgg tagtccacgc cgtaaacggt      780
gggtactagg tgtgggtttc cttccttggg atccgtgccg tagctaacgc attaagtacc      840
ccgcctgggg agtacggccg caaggctaaa actcaaagga attgacgggg cccgcacaa       900 gcggcggagc atgtggatta attcgatgca acgcgaagaa ccttacctgg gtttgacatg      960
cacaggacga ctgcagagat gtggtttccc ttgtggcctg tgtgcaggtg gtgcatggct     1020
gtcgtcagct cgtgtcgtga gatgttgggt taagtcccgc aacgagcgca acccttgtct     1080
catgttgcca gcacgttatg gtggggactc gtgagagact gccggggtca actcggagga     1140
aggtggggat gacgtcaagt catcatgccc cttatgtcca gggcttcaca catgctacaa     1200
tggccggtac aaagggctgc gatgccgtga ggtggagcga atcctttcaa gccggtctc      1260 agttcggatc ggggtctgca actcgacccc gtgaagtcgg agtcgctagt aatcgcagat     1320
cagcaacgct gcggtgaata cgttcccggg ccttgtacac accgcccgtc acgtcatgaa     1380
agtcggtaac acccgaagcc ggtggcctaa cccttgtgga gggagccgtc gaaggtggga     1440
tcggcgattg ggacgaagtc gtaacaaggt agccgtaccg gaaggtgcgg ctggatcacc     1500
tcctt                                                                 1505

<210> SEQ ID NO 19
<211> LENGTH: 1460
<212> TYPE: DNA
<213> ORGANISM: Mycobacterium parafortuitum

<400> SEQUENCE: 19
cgaacgctgg cggcgtgctt aacacatgca agtcgaacgg aaaggcccct cggggtactc       60
gagtggcgaa cgggtgagta acacgtgggt gatctgccct gcactttggg ataagcctgg      120
gaaactgggt ctaataccga atatgatcat tggcttcctg gctggtggtg aaagcttt        180 gcggtgtggg atgggcccgc ggcctatcag cttgttggtg gggtaatggc ctaccaaggc      240
gacgacgggt agccggcctg agagggtgac cggccacact gggactgaga tacggcccag      300
actcctacgg gaggcagcag tgggaatat tgcacaatgg gcgcaagcct gatgcagcga      360
cgccgcgtga gggatgacgg ccttcgggtt gtaaacctct ttcgccaggg acgaagcgca      420
agtgacggta cctggagaag aaggaccggc caactacgtg ccagcagccg cggtaatacg      480
tagggtccga gcgttgtccg gaattactgg gcgtaaagag ctcgtaggtg gtttgtcgcg      540
ttgttcgtga aaactcacag cttaactgtg gcgtgcggg cgatacgggc agactagagt       600
actgcagggg agactggaat tcctggtgta gcggtggaat gcgcagatat caggaggaac      660
accggtggcg aaggcgggtc tctgggcagt aactgacgct gaggagcgaa agcgtgggga      720
```

```
gcgaacagga ttagataccc tggtagtcca cgccgtaaac ggtgggtact aggtgtgggt    780
ttccttcctt gggatccgtg ccgtagctaa cgcattaagt accccgcctg ggagtacgg    840 ccgcaaggct aaaactcaaa gaaattgacg ggggcccgca caagcggcgg agcatgtgga    900
ttaattcgat gcaacgcgaa gaaccttacc tgggtttgac atgcacagga cgccggcaga    960
gatgtcggtt cccttgtggc ctgtgtgcag gtggtgcatg gctgtcgtca gctcgtgtcg   1020
tgagatgttg ggttaagtcc cgcaacgagc gcaacccttg tctcatgttg ccagcacgta   1080
atggtgggga ctcgtgagag actgccgggg tcaactcgga ggaaggtggg gatgacgtca   1140
agtcatcatg cccccttatgt ccagggcttc acacatgcta caatggccgg tacaaagggc   1200
tgcgatgccg tgaggtggag cgaatccttt caaagccggt ctcagttcgg atcgggtct   1260 gcaactcgac cccgtgaagt cggagtcgct agtaatcgca gatcagcaac gctgcggtga   1320
atacgttccc gggccttgta cacaccgccc gtcacgtcat gaaagtcggt aacacccgaa   1380
gccggtggcc taccccttg tgggagggag ccgtcgaagg tgggatcggc gattgggacg   1440
aagtcgtaac aaggtagccg                                               1460
```

<210> SEQ ID NO 20
<211> LENGTH: 1480
<212> TYPE: DNA
<213> ORGANISM: Mycobacterium sphagni

<400> SEQUENCE: 20

```
gagtttgatc ctggctcagg acgaacgctg gcggcgtgct taacacatgc aagtcgaacg     60
gaaaggccct tcggggtact cgagtggcga acgggtgagt aacacgtggg tgatctgccc    120
tgcactttgg gataagcctg ggaaactggg tctaataccg aataggaccg catgcttcat    180
ggtgtgtggt ggaaagcttt tgcggtgtgg gatgggcccg cggcctatca gcttgttggt    240
ggggtaatgg cctaccaagg cgacgacggg tagccggcct gagagggtgt ccggccacac    300
tgggactgag atacggccca gactcctacg ggaggcagca gtggggaata ttgcacaatg    360
ggcgcaagcc tgatgcagcg acgccgcgtg agggatgacg ccttcgggt tgtaaacctc    420 tttcagcagg gacgaagcgc aagtgacggt acctgtagaa gaagcaccgg ccaactacgt    480
gccagcagcc gcggtaatac gtagggtgcg agcgttgtcc ggaattactg ggcgtaaaga    540
gctcgtaggt ggtttgtcgc gttgttcgtg aaaactcaca gctcaactgt gggcgtgcgg    600
gcgatacggg cagacttgag tactgcaggg gagactggaa ttcctggtgt agcggtggaa    660
tgcgcagata tcaggaggaa caccggtggc gaaggcgggt ctctgggcag taactgacgc    720
tgaggagcga aagcgtgggg agcgaacagg attagatacc ctggtagtcc acgccgtaaa    780
cggtgggtac taggtgtggg tttccttcct tgggatccgt ccgtagcta acgcattaag    840 taccccgcct ggggagtacg gccgcaaggc taaaactcaa gaaattgac ggggcccgc    900 acaagcggcg gagcatgtgg attaattcga tgcaacgcga gaaccttac ctgggtttga    960 catgcacagg acgccggcag gatgtcggtt cccttgtgg cctgtgtgca ggtggtgcat   1020
ggctgtcgtc agctcgtgtc gtgagatgtt gggttaagtc ccgcaacgag cgcaacccctt   1080 gtctcatgtt gccagcacgt aatggtgggg actcgtgaga actgccgggg tcaactcgg    1140 aggaaggtgg ggatgacgtc aagtcatcat gccccttatg tccagggctt cacacatgct   1200
acaatggccg gtacaaaggg ctgcgatgcc gtgaggtgga gcgaatcctt tcaaagccgg   1260
tctcagttcg gatcgggtc tgcaactcga ccccgtgaag tcggagtcgc tagtaatcgc   1320
agatcagcaa cgctgcggtg aatacgttcc cgggccttgt acacaccgcc cgtcacgtca   1380
```

```
tgaaagtcgg taacacccga agccggtggc ctaaccccctt gtgggaggga gccgtcgaag    1440
gtgggatcgg cgattgggac gaagtcgtaa caaggtagcc                           1480

<210> SEQ ID NO 21
<211> LENGTH: 1494
<212> TYPE: DNA
<213> ORGANISM: Nocardia farcinica

<400> SEQUENCE: 21
gacgaacgct ggcggcgtgc ttaacacatg caagtcgagc ggtaaggccc ttcggggtac      60
acgagcggcg aacgggtgag taacacgtgg gtgatctgcc ctgtacttcg ggataagcct    120
gggaaactgg gtctaatacc ggatatgacc ttacatcgca tggtgtttgg tggaaagatt    180
tatcggtaca ggatgggccc gcggcctatc agcttgttgg tggggtaatg gcctaccaag    240
gcgacgacgg gtagccggcc tgagagggcg accggccaca ctgggactga gacacggccc    300
agactcctac gggaggcagc agtggggaat attgcacaat gggcgaaagc ctgatgcagc    360
gacgccgcgt gagggatgac ggccttcggg ttgtaaacct ctttcgacag gacgaagcg    420 caagtgacgg tacctgtaga agaagcaccg gccaactacg tgccagcagc cgcggtaata    480
cgtagggtgc gagcgttgtc cggaattact gggcgtaaag agcttgtagg cggtttgtcg    540
cgtcgtccgt gaaaacttgg ggctcaaccc caagcttgcg ggcgatacgg gcagacttga    600
gtactgcagg ggagactgga attcctggtg tagcggtgaa atgcgcagat atcaggagga    660
acaccggtgg cgaaggcggg tctctgggca gtaactgacg ctgaagaagcg aaagcgtggg    720 tagcgaacag gattagatac cctggtagtc cacgccgtaa acgtgggcg ctaggtgtgg    780 gtttccttcc acgggatccg tgccgtagct aacgcattaa gcgccccgcc tggggagtac    840
ggccgcaagg ctaaaactca aaggaattga cggggggcccg cacaagcggc ggagcatgtg    900
gattaattcg atgcaacgcg aagaacctta cctgggtttg acatacaccg gaaacctgca    960
gagatgtagg ccccccttgtg gtcggtgtac aggtggtgca tggctgtcgt cagctcgtgt   1020
cgtgagatgt tgggttaagt cccgcaacga gcgcaacccct tgtcctgtgt tgccagcgcg   1080
ttatggcggg gactcgcagg agactgccgg ggtcaactcg aggaaggtg gggacgacgt    1140 caagtcatca tgccccttat gtccagggct tcacacatgc tacaatggcc ggtacagagg   1200
gctgcgatac cgtgaggtgg agcgaatccc ttaaagccgg tctcagttcg gatcggggtc   1260
tgcaactcga ccccgtgaag ttggagtcgc tagtaatcgc agatcagcaa cgctgcggtg   1320
aatacgttcc cgggccttgt acacaccgcc cgtcacgtca tgaaagtcgg taacacccga   1380
agccggtggc ctaaccccctt gtgggaggga gccgtcgaag gtgggatcgg cgattgggac   1440
gaagtcgtaa caaggtagcc gtaccggaag gtgcggctgg atcacctcct ttct         1494

<210> SEQ ID NO 22
<211> LENGTH: 1513
<212> TYPE: DNA
<213> ORGANISM: Nocardia sp.

<400> SEQUENCE: 22
gagtttgatc ctggctcagg acgaacgctg gcggcgtgct taacacatgc aagtcgagcg      60
gtaaggccct tcggggtaca cgagcggcga acgggtgagt aacacgtggg tgatctgccc    120
tgtacttcgg gataagcctg ggaaactggg tctaataccg gatatgacct tacatcgcat    180
ggtgtttggt ggaaagattt atcggtacag gatgggcccg cggcctatca gcttgttggt    240
```

```
ggggtaatgg cctaccaagg cgacgacggg tagccggcct gagagggcga ccggccacac    300
tgggactgag acacggccca gactcctacg ggaggcagca gtggggaata ttgcacaatg    360
ggcgaaagcc tgatgcagcg acgccgcgtg agggatgacg ccttcgggt tgtaaacctc     420 tttcgacagg gacgaagcgc aagtgacggt acctgtagaa gaagcaccgg ccaactacgt    480
gccagcagcc gcggtaatac gtagggtgcg agcgttgtcc ggaattactg ggcgtaaaga    540
gcttgtaggc ggtttgtcgc gtcgtccgtg aaaacttggg gctcaacccc aagcttgcgg    600
gcgatacggg cagacttgag tactgcaggg gagactggaa ttcctggtgt agcggtgaaa    660
tgcgcagata tcaggaggaa caccggtggc gaaggcgggt ctctgggcag taaccgacgc    720
tgagaagcga aagcgtgggt agcgaacagg attagatacc ctggtagtcc acgccgtaaa   780
cggtgggcgc taggtgtggg tttccttcca cgggatccgt gccgtagcta acgcattaag    840
cgccccgcct ggggagtacg gccgcaaggc taaaactcaa aggaattgac ggggcccgc     900 acaagcggcg gagcatgtgg attaattcga tgcaacgcga agaaccttac ctgggtttga    960
catacaccgg aaacctgcag agatgtaggc ccccttgtgg tcggtgtaca ggtggtgcat   1020
ggccgtcgtc agctcgtgtc gtgagatgtt gggttaagtc ccgcaacgag cgcaaccctt   1080
gtcctgtgtt gccagcgcgt tatggcgggg actcgcagga gactgccggg gtcaactcgg   1140
aggaaggtgg ggacgacgtc aagtcatcat gccccttatg tccagggctt cacacatgct   1200 acaatgccg gtacagaggg ctgcgatacc gtgaggtgga cgaatccct taaagccggt     1260 ctcagttcgg atcggggtct gcaactcgac cccgtgaagt tggagtcgct agtaatcgca   1320
gatcagcaac gctgcggtga atacgttccc gggccttgta cacaccgccc gtcacgtcat   1380
gaaagtcggt aacacccgaa gccggtggcc taaccccttg tgggagggag ccgtcgaagg   1440
tgggatcggc gattgggacg aagtcgtaac aaggtagccg taccggaagg tgcggctgga   1500
tcacctcctt tct                                                      1513

<210> SEQ ID NO 23
<211> LENGTH: 1490
<212> TYPE: DNA
<213> ORGANISM: Rhodococcus rhodochrous

<400> SEQUENCE: 23
gagtttgaat ctggctcagg acgaacgctg gcggcgtgct taacacatgc aagtcgaacg     60
atgaagccca gcttgctggg tggattagtg gcgaacgggt gagtaacacg tgggtgatct    120 gcccctgcact ctgggataag cctgggaaac tgggtctaat accggatatg acctcttgct   180
gcatggcgag gggtggaaag ttttttcggtg caggatgagc ccgcggccta tcagcttgtt   240
ggtggggtaa tggcctacca aggcgacgac gggtagccgg cctgagaggg cgaccggcca   300
cactgggact gagacacggc ccagactcct acgggaggca gcagtgggga atattgcaca    360
atgggcgaaa gcctgatgca gcgacgccgc gtgagggatg acggccttcg ggttgtaaac    420
ctctttcagc agggacgaag cgaaagtgac ggtacctgca gaagaagcac cggccaacta    480
cgtgccagca gccgcggtaa tacgtagggt gcgagcgttg tccggaatta ctgggcgtaa    540
agagctcgta gccggtttgt cgcgtcgtct gtgaaatccc gcagctcaac tgcgggcttg   600
caggcgatac gggcagactc gagtactgca ggggagactg gaattcctgg tgtagcggtg   660
aaatgcgcag atatcaggag gaacaccggt ggcgaaggcg gtctctggg cagtaactga    720 cgctgaggag cgaaagcgtg ggtagcgaac aggattagat accctggtag tccacgccgt    780
aaacggtggg cgctaggtgt gggtttcctt ccacgggatc cgtgccgtag ccaacgcatt    840
```

```
aagcgccccg cctggggagt acggccgcaa ggctaaaact caaaggaatt gacggggcc      900
cgcacaagcg gcggagcatg tggattaatt cgatgcaacg cgaagaacct tacctgggtt      960
tgacatgtac cggacgactg cagagatgtg gtttcccttg tggccggtag acaggtggtg     1020
catggctgtc gtcagctcgt gtcgtgagat gttgggttaa gtcccgcaac gagcgcaacc     1080
cttgtcctgt gttgccagca cgtaatggtg gggactcgca ggagactgcc ggggtcaact     1140
cggaggaagg tggggacgac gtcaagtcat catgcccctt atgtccaggg cttcacacat     1200
gctacaatgg tcggtacaga gggctgcgat accgtgaggt ggagcgaatc ccttaaagcc     1260
ggtctcagtt cggatcgggg tctgcaactc gaccccgtga agtcggagtc gctagtaatc     1320
gcagatcagc aacgctgcgg tgaatacgtt cccgggcctt gtacacaccg cccgtcacgt     1380
catgaaagtc ggtaacaccc gaagccggtg gcctaaccc ttgtgggagg gagccgtcga     1440
aggtgggatc ggcgattggg acgaagtcgt aacaaggtag ccgtaccgga                1490
```

<210> SEQ ID NO 24
<211> LENGTH: 1481
<212> TYPE: DNA
<213> ORGANISM: Rhodococcus coprophilus

<400> SEQUENCE: 24

```
cctggctcag gacgaacgct ggcggcgtgc ttaacacatg caagtcgaac gatgatgccc       60
agcttgctgg gcggattagt ggcgaacggg tgagtaacac gtgggtgatc tgccctgcac      120
ttcgggataa gcctgggaaa ctgggtctaa taccggatat gaccatggga tgcatgtcct      180
gtggtggaaa ggtttactgg tgcaggatga gcccgcggcc tatcagcttg ttggtggggt      240
aatggcctac caaggcgacg acgggtagcc ggcctgagag ggcgaccggc cacactggga      300
ctgagacacg gcccagactc ctacggagg cagcagtggg gaatattgca caatgggcga      360
aagcctgatg cagcgacgcc gcgtgaggga tgacggcctt cgggttgtaa acctctttca      420
gcagggacga agcgcaagtg actgtacctg cagaagaagc accggctaac tacgtgccag      480
cagccgcggt aatacgtagg gtgcgagcgt tgtccggaat tactgggcgt aaagagttcg      540
taggcggttt gtcgcgtcgt gtgtgaaatc ccgcagctca actgcgggct tgcaggcgat      600
acggcagac ttgagtactg caggggagac tggaattcct ggtgtagcgg tgaaatgcgc      660
agatatcagg aggaacaccg gtggcgaagg cgggtctctg gcagtaact gacgctgagg      720
aacgaaagcg tgggtagcga acaggattag atacctggt agtccacgcc gtaaacggtg      780
ggcgctaggt gtgggtttcc ttccacggga tccgtgccgt agctaacgca ttaagcgccc      840
cgcctgggga gtacggccgc aaggctaaaa ctcaaaggaa ttgacgggg cccgcacaag      900
cggcggagca tgtggattaa ttcgatgcaa cgcgaagaac cttacctggg tttgacatat      960
accggacgac tgcagagatg tggtttccct tgtggtcggt atacaggtgg tgcatggctg     1020
tcgtcagctc gtgtcgtgag atgttgggtt aagtcccgca acgagcgcaa cccttgtctt     1080
atgttgccag cacgtaatgg ggggactcg taagagactg ccggggtcaa ctcggaggaa     1140
ggtggggacg acgtcaagtc atcatgcccc ttatgtccag gcttcacac atgctacaat     1200
ggtcggtaca gagggctgcg ataccgtgag gtggagcgaa tcccttaaag ccggtctcag     1260
ttcggatcgg gtctgcaac tcgaccccgt gaagtcggag tcgctagtaa tcgcagatca     1320
gcaacgctgc ggtgaatacg ttcccgggcc ttgtacacac cgcccgtcac gtcatgaaag     1380
tcggtaacac ccgaagccgg tggcctaacc ccttgtggga gggagccgtc gaaggtggga     1440
```
tcggcgattg ggacgaagtc gtaacaaggt agccgtaccg g         1481

<210> SEQ ID NO 25
<211> LENGTH: 1486
<212> TYPE: DNA
<213> ORGANISM: Rhodococcus triatomae

<400> SEQUENCE: 25

```
ggcggcgtgc ttaacacatg caagtcgagc ggtaaggcct tcggggtac acgagcggcg    60
aacgggtgag taacacgtgg gtgatctgcc ctgcactctg ggataagcct gggaaactgg   120
gtctaatacc ggatatgact accggctgca tggtctggtg gtggaaagat ttatcggtgc   180
aggatgggcc cgcggcctat cagcttgttg gtggggtaat ggcctaccaa ggcgacgacg   240
ggtagccgac ctgagagggt gaccggccac actgggactg agacacgcc cagactccta    300
cgggaggcag cagtggggaa tattgcacaa tgggcgaaag cctgatgcag cgacgccgcg   360
tgagggatga cggccttcgg gttgtaaacc tctttcaaca gggacgaagc gcaagtgacg   420
gtacctgtag aagaagcacc ggccaactac gtgccagcag ccgcggtaat acgtagggtg   480
cgagcgttgt ccggaattac tgggcgtaaa gagctcgtag gcggtttgtc gcgtcgtctg   540
tgaaaaccag cagctcaact gctggcttgc aggcgatacg ggcagacttg agtactgcag   600
gggagactgg aattcctggt gtagcggtga atgcgcaga tatcaggagg aacaccggtg    660
gcgaaggcgg gtctctgggc agtaactgac gctgaggagc gaaagcgtgg gtagcgaaca   720
ggattagata ccctggtagt ccacgccgta acggtgggc gctaggtgtg ggtttccttc    780
cacgggatcc gtgccgtagc taacgcatta agcgccccgc ctggggagta cggccgcaag   840
gctaaaactc aaaggaattg acggggccc gcacaagcgg cggagcatgt ggattaattc    900
gatgcaacgc gaagaacctt acctgggttt gacatacacc ggaaagccgt agagatacgg   960
cccccttgt ggtcggtgta caggtggtgc atggctgtcg tcagctcgtg tcgtgagatg    1020
ttgggttaag tcccgcaacg agcgcaaccc ttgtcctgtg ttgccagcac gtaatggtgg   1080
ggactcgcag gagactgccg gggtcaactc ggaggaaggt ggggacgacg tcaagtcatc   1140
atgcccctta tgtccagggc ttcacacatg ctacaatggc cggtacagag ggctgcgata   1200
ccgtgaggtg gagcgaatcc cttaaagccg gtctcagttc ggatcggggt ctgcaactcg   1260
accccgtgaa gtcggagtcg ctagtaatcg cagatcagca acgctgcggt gaatacgttc   1320
ccgggccttg tacaccgc cgtcacgtc atgaaagtcg gtaacacccg aagccggtgg     1380
cctaaccct tgtgggaggg agccgtcgaa ggtgggatcg cgattggga cgaagtcgta    1440
acaaggtagc cgtaccggaa ggtgcggctg gatcacttcc tttcta                  1486
```

<210> SEQ ID NO 26
<211> LENGTH: 1507
<212> TYPE: DNA
<213> ORGANISM: Nocardia coeliaca

<400> SEQUENCE: 26

```
tttgatcctg gctcaggacg aacgctggcg gcgtgcttaa cacatgcaag tcgagcggta    60
aggcctttcg gggtacacga gcggcgaacg ggtgagtaac acgtgggtga tctgccctgc   120
acttcgggat aagcctggga aactgggtct aataccggat atgacctcag gttgcatgac   180
ttggggtgga aagatttatc ggtgcaggat gggcccgcgg cctatcagct tgttggtggg   240
gtaatggcct accaaggcga cgacgggtag ccgacctgag agggtgaccg gccacactgg   300
gactgagaca cggcccagac tcctacggga ggcagcagtg gggaatattg cacaatgggc   360
```

```
gaaagcctga tgcagcgacg ccgcgtgagg gatgacggcc ttcgggttgt aaacctcttt      420
cagcagggac gaagcgcaag tgacggtacc tgcagaagaa gcaccggcta actacgtgcc      480
agcagccgcg gtaatacgta gggtgcaagc gttgtccgga attactgggc gtaaagagtt      540
cgtaggcggt ttgtcgcgtc gtttgtgaaa accagcagct caactgctgg cttgcaggcg      600
atacgggcag acttgagtac tgcaggggag actggaattc ctggtgtagc ggtgaaatgc      660
gcagatatca ggaggaacac cggtggcgaa ggcgggtctc tgggcagtaa ctgacgctga      720
ggaacgaaag cgtgggtagc gaacaggatt agataccctg gtagtccacg ccgtaaacgg      780
tgggcgctag gtgtgggttc cttccacgga atccgtgccg tagctaacgc attaagcgcc      840
ccgcctgggg agtacggccg caaggctaaa actcaaagga attgacgggg ccccgcacaa      900
gcggcggagc atgtggatta attcgatgca acgcgaagaa ccttacctgg gtttgacata      960
taccggaaag ctgcagagat gtggcccccc ttgtggtcgg tatacaggtg gtgcatggct     1020
gtcgtcagct cgtgtcgtga gatgttgggt taagtcccgc aacgagcgca acccctatct     1080
tatgttgcca gcacgttatg gtggggactc gtaagagact gccgggtca actcggagga     1140 aggtggggac gacgtcaagt catcatgccc cttatgtcca gggcttcaca catgctacaa     1200
tggccagtac agagggctgc gagaccgtga ggtggagcga atcccttaaa gctggtctca     1260
gttcggatcg ggtctgcaa ctcgaccccg tgaagtcgga gtcgctagta atcgcagatc     1320
agcaacgctg cggtgaatac gttcccgggc cttgtacaca ccgcccgtca cgtcatgaaa     1380
gtcggtaaca cccgaagccg gtggcttaac cccttgtggg agggagccgt cgaaggtggg     1440
atcggcgatt gggacgaagt cgtaacaagg tagccgtacc ggaaggtgcg gctggatcac     1500
ctcctttt                                                              1507
```

<210> SEQ ID NO 27
<211> LENGTH: 1507
<212> TYPE: DNA
<213> ORGANISM: Nocardia globerula

<400> SEQUENCE: 27

```
gtttgatcct ggctcaggac gaacgctggc ggcgtgctta acacatgcaa gtcgagcggt       60
aaggcctttc gggtacacg agcggcgaac gggtgagtaa cacgtgggtg atctgccctg      120
cacttcggga taagcctggg aaactgggtc taataccgga tatgacctcc tatcgcatgg      180
tgggtggtgg aaagatttat cggtgcagga tgggcccgcg gcctatcagc ttgttggtgg      240
ggtaatggcc taccaaggcg acgacgggta gccgacctga gaggtgacc ggccacactg      300 ggactgagac acggcccaga ctcctacggg aggcagcagt ggggaatatt gcacaatggg      360
cgaaagcctg atgcagcgac gccgcgtgag ggacgacggc cttcgggttg taaacctctt      420
tcagcaggga cgaagcgcaa gtgacggtac ctgcagaaga agcaccggct aactacgtgc      480
cagcagccgc ggtaatacgt agggtgcaag cgttgtccgg aattactggg cgtaaagagt      540
tcgtaggcgg tttgtcacgt cgtttgtgaa aactcacagc tcaactgtga gcctgcaggc      600
gatacgggca gacttgagta ctgcagggga gactggaatt cctggtgtag cggtgaaatg      660
cgcagatatc aggaggaaca ccggtggcga aggcgggtct ctgggcagta actgacgctg      720
aggaacgaaa gcgtgggtag cgaacaggat tagataccct ggtagtccac gccgtaaacg      780
gtgggcgcta ggtgtgggtt ccttccacgg aatccgtgcc gtagctaacg cattaagcgc      840
cccgcctggg gagtacggcc gcaaggctaa aactcaaagg aattgacggg ggcccgcaca      900
```

```
agcggcggag catgtggatt aattcgatgc aacgcgaaga accttacctg ggtttgacat      960
ataccggaaa gccgtagaga tacggcccccc cttgtggtcg gtatacaggt ggtgcatggc   1020
tgtcgtcagc tcgtgtcgtg agatgttggg ttaagtcccg caacgagcgc aaccccctatc   1080 ttatgttgcc agcacgttat ggtggggact cgtaagagac tgccggggtc aactcggagg   1140
aaggtgggga cgacgtcaag tcatcatgcc ccttatgtcc agggcttcac acatgctaca   1200
atggccagta cagagggctg cgagaccgtg aggtggagcg aatcccttaa agctggtctc   1260
agttcggatc ggggtctgca actcgacccc gtgaagtcgg agtcgctagt aatcgcagat   1320
cagcaacgct gcggtgaata cgttcccggg ccttgtacac accgcccgtc acgtcatgaa   1380
agtcggtaac acccgaagcc ggtggcttaa ccccttgtgg gagggagccg tcgaaggtgg   1440
gatcggcgat tgggacgaag tcgtaacaag gtagccgtac cggaaggtgc ggctggatca   1500
cctcctt                                                              1507

<210> SEQ ID NO 28
<211> LENGTH: 1508
<212> TYPE: DNA
<213> ORGANISM: Rhodococcus equi

<400> SEQUENCE: 28
gagtttgatc ctggctcagg acgaacgctg gcggcgtgct taacacatgc aagtcgagcg     60
gtagggccct tcgggtaca cgagcggcga acgggtgagt aacacgtggg tgatctgccc    120
tgcacttcgg gataagcttg ggaaactggg tctaataccg gatatgagcc tctactgcat    180
ggtggaggtt ggaaaggttt actggtgcag gatgggcccg cggcctatca gcttgttggt    240
ggggtaatgg cctaccaagg cgacgacggg tagccggcct gagagggcga ccggccacac    300
tgggactgag acacggccca gactcctacg ggaggcagca gtggggaata ttgcacaatg    360
ggcgaaagcc tgatgcagcg acgccgcgtg agggatgacg ccttcgggt tgtaaacctc    420 tttcagcagg gacgaagcga gagtgacggt acctgcagaa gaagcaccgg ccaactacgt    480
gccagcagcc gcggtaatac gtagggtgcg agcgttgtcc ggaattactg ggcgtaaaga    540
gctcgtaggc ggtttgtcgc gtcgtcggtg aaaaccagca gctcaactgc tggcttgcag    600
gcgatacggg cagacttgag tactgcaggg gagactggaa ttcctggtgt agcggtgaaa    660
tgcgcagata tcaggaggaa caccggtggc gaaggcgggt ctctgggcag taactgacgc    720
tgaggagcga aagcgtgggt agcgaacagg attagatacc ctggtagtcc acgccgtaaa    780
cggtgggcgc taggtgtggg tttccttcca cgggatccgt gccgtagcta acgcattaag    840
cgccccgcct ggggagtacg gccgcaaggc taaaactcaa aggaattgac ggggccccgc    900
acaagcggcg gagcatgtgg attaattcga tgcaacgcga gaaccttac ctgggtttga    960 catataccgg aaagccgtag agatacggcc ccccttgtgg tcggtataca ggtggtgcat   1020
ggctgtcgtc agctcgtgtc gtgagatgtt gggttaagtc ccgcaacgag cgcaacccct   1080
gtcctgtgtt gccagcacgt aatggtgggg actcgcagga accgccgggg tcaactcgg   1140 aggaaggtgg ggacgacgtc aagtcatcat gccccttatg tccagggctt cacacatgct   1200
acaatggccg gtacagaggg ctgcgatacc gtgaggtgga gcgaatccct taaagccggt   1260
ctcagttcgg atcggggtct gcaactcgac cccgtgaagt cggagtcgct agtaatcgca   1320
gatcagcaac gctgcggtga atacgttccc gggccttgta cacaccgccc gtcacgtcat   1380
gaaagtcggt aacacccgaa gccgtggcc taacccttgt ggagggagcc gtcgaaggtg   1440
ggatcggcga ttgggacgaa gtcgtaacaa ggtagccgta ccggaaggtg cggctggatc   1500
```

| acctcctt | 1508 |

<210> SEQ ID NO 29
<211> LENGTH: 1442
<212> TYPE: DNA
<213> ORGANISM: Rhodococcus sp.

<400> SEQUENCE: 29

| ctggctcagg acgaacgctg gcggcgtgct taacacatgc aagtcgagcg gtaaggccct | 60 |
| tcggggtaca cgagcggcga acgggtgagt aacacgtggg tgatctgccc tgcacttcgg | 120 |
| gataagcctg ggaaactggg tctaataccg gatatgacct tcggctgcat ggctgagggt | 180 |
| ggaaaggttt actggtgcag gatgagcccg cggcctatca gcttgttggt ggggtaatgg | 240 |
| cctaccaagg cgacgacggg tagccgacct gagagggtga ccggccacac tgggactgag | 300 |
| acacggccca gactcctacg ggaggcagca gtggggaata ttgcacaatg ggcgaaagcc | 360 |
| tgatgcagcg acgccgcgtg agggatgacg gccttcgggt tgtaaacctc tttcagcagg | 420 |
| gacgaagcga aagtgacggt acctgcagaa gaagcaccgg ctaactacgt gccagcagcc | 480 |
| gcggtaatac gtagggtgca agcgttgtcc ggaattactg ggcgtaaaga gttcgtaggc | 540 |
| ggtttgtcgc gtcgtctgtg aaaactcaca gctcaactgt gagcttgcag gcgatacggg | 600 |
| cagacttgag tactgcaggg gagactgaa ttcctggtgt agcggtgaaa tgcgcagata | 660 |
| tcaggaggaa caccggtggc gaaggcgggt ctctgggcag taactgacgc tgaggaacga | 720 |
| aagcgtgggt agcaaacagg attagatacc ctggtagtcc acgccgtaaa cggtgggcgc | 780 |
| taggtgtggg ttccttccac gggatctgtg ccgtagctaa cgcattaagc gccccgcctg | 840 |
| gggagtacgg ccgcaaggct aaaactcaaa ggaattgacg ggggcccgca caagcggcgg | 900 |
| agcatgtgga ttaattcgat gcaacgcgaa gaaccttacc tgggtttgac atataccgga | 960 |
| aagccgtaga gatacggccc cccttgtggt cggtatacag gtggtgcatg gctgtcgtca | 1020 |
| gctcgtgtcg tgagatgttg ggttaagtcc cgcaacgagc gcaacccttg tcttatgttg | 1080 |
| ccagcacgta atggtgggga ctcgtaagag actgccgggg tcaactcgga ggaaggtggg | 1140 |
| gacgacgtca agtcatcatg ccccttatgt ccagggcttc acacatgcta caatggccag | 1200 |
| tacagagggc tgcgaaccgt gaggtggagc gaatccctta aagcyggtct cagttcggat | 1260 |
| cggggtctgc aactcgaccc cgtgaagtcg gagtcgctag taatcgcaga tcagcaacgc | 1320 |
| tgcggtgaat acgttcccgg gccttgtaca caccgcccgt cacgtcatga aagtcggtaa | 1380 |
| cacccgaagc cggtggccta accccttgtg ggagggagcc gtcgaaggtg ggatcggcga | 1440 |
| tt | 1442 |

<210> SEQ ID NO 30
<211> LENGTH: 1474
<212> TYPE: DNA
<213> ORGANISM: Rhodococcus sp.

<400> SEQUENCE: 30

| agagtttgat cctggctcag gacgaacgct ggcggcgtgc ttaacacatg caagtcgagc | 60 |
| ggtaaggccc ttcggggtac acgagcggcg aacgggtgag taacacgtgg gtgatctgcc | 120 |
| ctgcacttcg ggataagcct gggaaactgg gtctaatacc ggatatgacc ttcggctgca | 180 |
| tggctgaggg tggaaaggtt tactggtgca ggatgggccc gcggcctatc agcttgttgg | 240 |
| tggggtaatg gcctaccaag gcgacgacgg gtagccgacc tgagagggtg accggccaca | 300 |

```
ctgggactga gacacggccc agactcctac gggaggcagc agtggggaat attgcacaat    360
gggcgaaagc ctgatgcagc gacgccgcgt gagggatgac ggccttcggg ttgtaaacct    420
cttcagcag ggacgaagcg aaagtgacgg tacctgcaga agaagcaccg gctaactacg     480
```

```
ctgggactga gacacggccc agactcctac gggaggcagc agtggggaat attgcacaat    360
gggcgaaagc ctgatgcagc gacgccgcgt gagggatgac ggccttcggg ttgtaaacct    420
ctttcagcag ggacgaagcg aaagtgacgg tacctgcaga agaagcaccg gctaactacg    480
tgccagcagc cgcggtaata cgtagggtgc aagcgttgtc cggaattact gggcgtaaag    540
agttcgtagg cggtttgtcg cgtcgtttgt gaaaactcam rgctcaactg tgagcttgca    600
ggcgatacgg gcagacttga gtactgcagg ggagactgga attcctggtg tagcggtgaa    660
atgcgcagat atcaggagga acaccggtgg cgaaggcggg tctctgggca gtaactgacg    720
ctgaggaacg aaagcgtggg tagcaaacag gattagatac cctggtagtc cacgccgtaa    780
acggtgggcg ctaggtgtgg gttccttcca cgggatctgt gccgtagcta acgcattaag    840
cgccccgcct ggggagtacg gccgcaaggc taaaactcaa aggaattgac ggggccccgc    900
acaagcggcg gagcatgtgg attaattcga tgcaacgcga agaaccttac ctgggtttga    960
catataccgg aaagccgtag agatacggcc cccttgtgg tcggtataca ggtggtgcat     1020
ggctgtcgtc agctcgtgtc gtgagatgtt gggttaagtc cgcaacgag cgcaaccctt     1080
gtcttatgtt gccagcacgt aatggtgggg actcgtaaga gactgccggg gtcaactcgg    1140
aggaaggtgg ggacgacgtc aagtcatcat gccccttatg tccagggctt cacacatgct    1200
acaatggcca gtacagaggg ctgcgagacc gtgaggtgga gcgaatccct aaagctggt     1260
ctcagttcgg atcggggtct gcaactcgac cccgtgaagt cggagtcgct agtaatcgca    1320
gatcagcaac gctgcggtga atacgttccc gggccttgta cacaccgccc gtcacgtcat    1380
gaaagtcggt aacacccgaa gccggtggcc taaccccttg tgggagggag ccgtcgaagg    1440
tgggatcggc gattgggacg aagtcgtaac aagg                                1474

<210> SEQ ID NO 31
<211> LENGTH: 1437
<212> TYPE: DNA
<213> ORGANISM: Rhodococcus jostii

<400> SEQUENCE: 31
aggacgaacg ctggcggcgt gcttaacaca tgcaagtcga gcggtaaggc ccttcggggt      60
acacgagcgg cgaacgggtg agtaacacgt gggtgatctg ccctgcactt cgggataagc    120
ctgggaaact gggtctaata ccggatatga ccttcggctg catggctgag ggtgaaagg     180
tttactggtg caggatgggc ccgcggccta tcagcttgtt ggtggggtaa tggcctacca    240
aggcgacgac gggtagccga cctgagaggg tgaccggcca cactgggact gagacacggc    300
ccagactcct acgggaggca gcagtgggga atattgcaca atgggcgaaa gcctgatgca    360
gcgacgccgc gtgagggatg acggccttcg ggttgtaaac ctctttcagc agggacgaag    420
cgaaagtgac ggtacctgca gaagaagcac cggctaacta cgtgccagca gccgcggtaa    480
tacgtagggt gcaagcgttg tccggaatta ctgggcgtaa agagttcgta ggcggttgt     540
cgcgtcgttt gtgaaaactc acagctcaac tgtgagcctg caggcgatac gggcagactt    600
gagtactgca ggggagactg gaattcctgg tgtagcggtg aaatgcgcag atatcaggag    660
gaacaccggt ggcgaaggcg gtctctggg cagtaactga cgctgaggaa cgaaagcgtg     720
ggtagcaaac aggattagat accctggtag tccacgccgt aaacggtggg cgctaggtgt    780
gggttccttc acgggatct gtgccgtagc taacgcatta agcgcccgc ctggggagta      840
cggccgcaag gctaaaactc aaaggaattg acggggcccc gcacaagcgg cggagcatgt    900
ggattaattc gatgcaacgc gaagaacctt acctgggttt gacatatacc ggaaagccgt    960
```

-continued

| | |
|---|---|
| agagatacgg cccccttgt ggtcggtata caggtggtgc atggctgtcg tcagctcgtg | 1020 |
| tcgtgagatg ttgggttaag tcccgcaacg agcgcaaccc ttgtcttatg ttgccagcac | 1080 |
| gtaatggtgg ggactcgtaa gagactgccg gggtcaactc ggaggaaggt ggggacgacg | 1140 |
| tcaagtcatc atgcccctta tgtccagggc ttcacacatg ctacaatggc cagtacagag | 1200 |
| ggctgcgaga ccgtgaggtg gagcgaatcc cttaaagctg gtctcagttc ggatcggggt | 1260 |
| ctgcaactcg accccgtgaa gtcggagtcg ctagtaatcg cagatcagca acgctgcggt | 1320 |
| gaatacgttc ccgggccttg tacacaccgc ccgtcacgtc atgaaagtcg gtaacacccg | 1380 |
| aagccggtgg cctaaccct tgtgggaggg agccgtcgaa ggtgggatcg gcgattg | 1437 |

<210> SEQ ID NO 32
<211> LENGTH: 1485
<212> TYPE: DNA
<213> ORGANISM: Rhodococcus opacus
<220> FEATURE:
<221> NAME/KEY: modified_base
<222> LOCATION: (812)..(812)
<223> OTHER INFORMATION: a, c, t or g

<400> SEQUENCE: 32

| | |
|---|---|
| gatcctggct caggacgaac gctggcggcg tgcttaacac atgcaagtcg agcggtaagg | 60 |
| cccttcgggg tacacgagcg cgaacgggtg agtaacacg tgggtgatct gccctgcact | 120 |
| tcgggataag cctgggaaac tgggtctaat accggatatg accttcggct gcatggctga | 180 |
| gggtggaaag gtttactggt gcaggatggg cccgcggcct atcagcttgt tggtggggta | 240 |
| atggcctacc aaggcgacga cgggtagccg acctgagagg gtgaccggcc acactgggac | 300 |
| tgagacacgg cccagactcc tacgggaggc agcagtgggg aatattgcac aatgggcgaa | 360 |
| agcctgatgc agcgacgccg cgtgagggat gacggccttc gggttgtaaa cctctttcag | 420 |
| cagggacgaa gcgaaagtga cggtacctgc agaagaagca ccggccaact acgtgccagc | 480 |
| agccgcggta atacgtaggg tgcaagcgtt gtccggaatt actgggcgta aagagttcgt | 540 |
| aggcggtttg tcgcgtcgtc tgtgaaaact caaagctcaa cctcgagcct gcaggcgata | 600 |
| cgggcagact tgagtactgc aggggagact ggaattcctg gtgtagcggt gaaatgcgca | 660 |
| gatatcagga ggaacaccgg tggcgaaggc gggtctctgg gcagtaactg acgctgagga | 720 |
| acgaaagcgt gggtagcgaa caggattaga taccctggta gtccacgccg taaacggtgg | 780 |
| gcgctaggtg tgggtttcct tccacgggat cngtgccgta gctaacgcat aagcgcccc | 840 |
| gcctggggag tacggccgca aggctaaaac tcaaaggaat tgacggggc ccgcacaagc | 900 |
| ggcggagcat gtggattaat tcgatgcaac gcgaagaacc ttacctgggt ttgacatata | 960 |
| ccggaaagcc gtagagatac ggcccccctt gtggtcggta tacaggtggt gcatggctgt | 1020 |
| cgtcagctcg tgtcgtgaga tgttgggtta agtcccgcaa cgagcgcaac ccttgtctta | 1080 |
| tgttgccagc acgtaatggt ggggactcgt aagagactgc cggggtcaac tcggaggaag | 1140 |
| gtggggacga cgtcaagtca tcatgcccct tatgtccagg gcttcacaca tgctacaatg | 1200 |
| gccggtacag agggctgcga taccgtgagg tggagcgaat cccttaaagc tggtctcagt | 1260 |
| tcggatcggg gtctgcaact cgaccccgtg aagtcggagt cgctagtaat cgcagatcag | 1320 |
| caacgctgcg gtgaatacgt tcccgggcct tgtacacacc gcccgtcacg tcatgaaagt | 1380 |
| cggtaacacc cgaagccggt ggcctaaccc cttgtgggag ggagccgtcg aaggtgggat | 1440 |
| cggcgattgg gacgaagtcg taacaaggta gccgtaccgg aaggt | 1485 |

<210> SEQ ID NO 33
<211> LENGTH: 1510
<212> TYPE: DNA
<213> ORGANISM: Rhodococcus imtechensis

<400> SEQUENCE: 33

```
ttgatcctgg ctcaggacga acgctggcgg cgtgcttaac acatgcaagt cgagcggtaa      60
ggcccttcgg ggtacacgag cggcgaacgg gtgagtaaca cgtgggtgat ctgccctgca     120
cttcgggata agcctgggaa actgggtcta ataccggata tgaccttcgg ctgcatggct     180
gagggtggaa aggtttactg gtgcaggatg ggcccgcggc ctatcagctt gttggtgggg     240
taatggccta ccaaggcgac gacgggtagc cgacctgaga gggtgaccgg ccacactggg     300
actgagacac ggcccagact cctacgggag gcagcagtgg ggaatattgc acaatgggcg     360
aaagcctgat gcagcgacgc cgcgtgaggg atgacggcct tcggttgta  aacctctttc     420
agcagggacg aagcgaaagt gacggtacct gcagaagaag caccggccaa ctacgtgcca     480
tcagccgcgg taatacgtag ggtgcaagcg ttgtccggaa ttactgggcg taaagagctc     540
gtaggcggtt tgtcgtgtcg tctgtgaaaa ctcgaggctc aacctcgagc ttgcaggcga     600
tacgggcaga cttgagtact gcaggggaga ctggaattcc tggtgtagcg gtgaaatgcg     660
cagatatcag gaggaacacc ggtggcgaag gcgggtctct gggcagtaac tgacgctgag     720
gagcgaaagc gtggaaaccg aacaggatta gataccctgg tagtccacgc cgtaaacggt     780
gggcgctagg tgtgggtttc cttccacggg atccgtgccg tagctaacgc attaagcgcc     840
ccgcctgggg agtacggccg caaggctaaa actcaaagga attgacgggg gcccgcacaa     900
gcggcggagc atgtggatta attcgatgca acgcgaagaa ccttacctgg gtttgacata     960
taccggaaag ccgtagagat acggcccccc ttgtggtcgg tatacaggtg gtgcatggct    1020
gtcgtcagct cgtgtcgtaa gatgttgggt taagtcccgc aacgagcgca accttgtct    1080
tatgttgcca gcacgtaatg gtggggactc gtaagagact gccggggtca actcggagga    1140
aggtggggac gacgtcaagt catcatgccc cttatgtcca gggcttcaca catgctacaa    1200
tggccagtac agagggctgc gagaccgtga ggtggagcga atcccttaaa gctggtctca    1260
gttcggatcg gggtctgcaa ctcgacccccg tgaagtcgga gtcgctagta atcgcagatc    1320
agcaacgctg cggtgaatac gttcccaggc cttgtacaca ccgcccgtca cgtcatgaaa    1380
gtcggtaaca cccgaagccg gtggcctaac cccttgtggg agggagccgt cgaaggtggg    1440
atcggcgatt gggacgaagt cgtaacaagg tagccgtacc ggaaggtgcg gctggaaact    1500
gccgaggggg                                                           1510
```

<210> SEQ ID NO 34
<211> LENGTH: 1473
<212> TYPE: DNA
<213> ORGANISM: Rhodococcus koreensis

<400> SEQUENCE: 34

```
gacgaacgct ggcggcgtgc ttaacacatg caagtcgagc ggtaaggccc ttcggggtac      60
acgagcggcg aacgggtgag taacacgtgg gtgatctgcc ctgcacttcg ggataagcct     120
gggaaactgg gtctaatacc ggatatgacc aaggactgca tggttttttgg tggaaaggtt     180
tactggtgca ggatgggccc gcggcctatc agcttgttgg tggggtaatg gcctaccaag     240
gcgacgacgg gtagccgacc tgagagggtg accggccaca ctgggactga cacggccc     300
agactcctac gggaggcagc agtggggaat attgcacaat gggcgaaagc ctgatgcagc     360
```

```
gacgccgcgt gagggatgac ggccttcggg ttgtaaacct ctttcagcag ggacgaagcg      420
agagtgacgg tacctgcaga agaagcaccg gccaactacg tgccagcagc cgcggtaata      480
cgtagggtgc aagcgttgtc cggaattact gggcgtaaag agctcgtagg cggtttgtcg      540
cgtcgtctgt gaaaactcga ggctcaacct cgagcttgca ggcgatacgg gcagacttga      600
gtactgcagg ggagactgga attcctggtg tagcggtgaa atgcgcagat atcaggagga      660
acaccggtgg cgaaggcggg tctctgggca gtaactgacg ctgaggagcg aaagcgtggg      720
tagcgaacag gattagatac cctggtagtc cacgccgtaa acggtgggcg ctaggtgtgg      780
gttccttcca cgggatccgt gccgtagcta acgcattaag cgccccgcct ggggagtacg      840
gccgcaaggc taaaactcaa aggaattgac ggggccccgc acaagcggcg gagcatgtgg      900
attaattcga tgcaacgcga agaaccttac ctgggtttga catataccgg aaagccgtag      960
agatacggcc cccttgtggt cggtataca ggtggtgcat ggctgtcgtc agctcgtgtc      1020
gtgagatgtt gggttaagtc ccgcaacgag cgcaacccct tgtcttatgt tgccagcacgt   1080 aatggtgggg actcgtaaga gactgccggg gtcaactcgg aggaaggtgg ggacgacgtc    1140
aagtcatcat gccccttatg tccagggctt cacacatgct acaatggcca gtacagaggg    1200
ctgcgagacc gtgaggtgga gcgaatccct aaagctggt ctcagttcgg atcggggtct    1260
gcaactcgac cccgtgaagt cggagtcgct agtaatcgca gatcagcaac gctgcggtga   1320
atacgttccc gggccttgta cacaccgccc gtcacgtcat gaaagtcggt aacacccgaa    1380
gccggtggcc taaccccttg tgggagggag ccgtcgaagg tgggatcggc gattgggacg    1440
aagtcgtaac aaggtagccg taccggaagg tgc                                 1473

<210> SEQ ID NO 35
<211> LENGTH: 1450
<212> TYPE: DNA
<213> ORGANISM: Rhodococcus sp.

<400> SEQUENCE: 35
tcctggctca ggacgaacgc tggcggcgtg cttaacacat gcaagtcgag cggtaaggcc      60
cttcggggta cacgagcggc gaacgggtga gtaacacgtg ggtgatctgc cctgcacttc     120
gggataagcc tgggaaactg ggtctaatac cggatatgac cttcggctgc atggctgttg    180
gtggaaaggt ttactggtgc aggatgggcc cgcggcctat cagcttgttg gtggggtaat    240
ggcctaccaa ggcgacgacg ggtagccgac ctgagagggt gaccggccac actgggactg    300
agacacggcc cagactccta cgggaggcag cagtggggaa tattgcacaa tgggcgaaag    360
cctgatgcag cgacgccgcg tgagggatga cggccttcgg ttgtaaaccc tctttcagca    420
gggacgaagc gagagtgacg gtacctgcag aagaagcacc ggccaactac gtgccagcag    480
ccgcggtaat acgtagggtg caagcgttgt ccggaattac tgggcgtaaa gagctcgtag    540
gcggtttgtc gcgtcgtctg tgaaaactcg aggctcaacc tcgagcttgc aggcgatacg    600
ggcagacttg agtactgcag gggagactgg aattcctggt gtagcggtga atgcgcaga    660 tatcaggagg aacaccggtg gcgaaggcgg gtctctgggc agtaactgac gctgaggagc    720
gaaagcgtgg gtagcgaaca ggattagata ccctggtagt ccacgccgta acggtgggc    780 gctaggtgtg gtttccttc acgggatcc gtgccgtagc taacgcatta agcgccccgc    840
ctggggagta cggccgcaag gctaaaactc aaaggaattg acggggcccc gcacaagcgg    900
cggagcatgt ggattaattc gatgcaacgc gaagaacctt acctgggttt gacatatacc    960
```

-continued

```
ggaaagccgt agagatacgg cccccttgt ggtcggtata caggtggtgc atggctgtcg    1020
tcagctcgtg tcgtgagatg tgggttaag tcccgcaacg agcgcaaccc ttgtcttatg    1080
ttgccagcac gtaatggtgg ggactcgtaa gagactgccg gggtcaactc ggaggaaggt    1140
ggggacgacg tcaagtcatc atgcccctta tgtccagggc ttcacacatg ctacaatggc    1200
cggtacagag ggctgcgata ccgtgaggtg gagcgaatcc cttaaagccg gtctcagttc    1260
ggatcggggt ctgcaactcg accccgtgaa gtcggagtcg ctagtaatcg cagatcagca    1320
acgctgcggt gaatacgttc ccgggccttg tacacaccgc ccgtcacgtc atgaaagtcg    1380
gtaacacccg aagccggtgg cctaaccct cgtgggaggg agccgtcgaa ggtgggatcg    1440
gcgattggga                                                          1450
```

<210> SEQ ID NO 36
<211> LENGTH: 1471
<212> TYPE: DNA
<213> ORGANISM: Rhodococcus opacus

<400> SEQUENCE: 36

```
gacgaacgct ggcggcgtgc ttaacacatg caagtcgagc ggtaaggccc ttcggggtac      60
acgagcggcg aacgggtgag taacacgtgg gtgatctgcc ctgcacttcg ggataagcct    120
gggaaactgg gtctaatacc ggatatgacc ttcggctgca tggctgaggg tggaaaggtt    180
tactggtgca ggatgggccc gcggcctatc agcttgttgg tggggtaatg gcctaccaag    240
gcgacgacgg gtagccgacc tgagagggtg accggccaca ctgggactga cacggccc     300 agactcctac gggaggcagc agtggggaat attgcacaat gggcgaaagc ctgatgcagc    360
gacgccgcgt gagggatgac ggccttcggg ttgtaaacct ctttcagcag gacgaagcg    420 agagtgacgg tacctgcaga agaagcaccg gccaactacg tgccagcagc cgcggtaata    480
cgtagggtgc aagcgttgtc cggaattact gggcgtaaag agctcgtagg cggtttgtcg    540
cgtcgtctgt gaaaactcga ggctcaacct cgagcttgca ggcgatacgg gcagacttga    600
gtactgcagg ggagactgga attcctggtg tagcggtgaa atgcgcagat atcaggagga    660
acaccggtgg cgaaggcggg tctctgggca gtaactgacg ctgaggagcg aaagcgtggg    720
tagcgaacag gattagatac cctggtagtc cacgccgtaa acggtgggcg ctaggtgtgg    780 gttccttcc acgggatccg tgccgtagct aacgcattaa gcgccccgcc tggggagtac    840
ggccgcaagg ctaaaactca aaggaattga cgggggcccg cacaagcggc ggagcatgtg    900
gattaattcg atgcaacgcg aagaaccta cctgggtttg acatataccg gaaagccgta    960
gagatacggc cccccttgtg gtcggtatac aggtggtgca tggctgtcgt cagctcgtgt   1020
cgtgagatgt gggttaagt cccgcaacga gcgcaaccct tgtcttatgt tgccagcacg   1080
taatggtggg gactcgtaag agactgccgg ggtcaactcg gaggaaggtg gggacgacgt   1140
caagtcatca tgccccttat gtccagggct tcacacatgc tacaatggcc ggtacagagg   1200
gctgcgatac cgtgaggtgg agcgaatccc ttaaagccgg tctcagttcg gatcgggtc   1260 tgcaactcga ccccgtgaag tcggagtcgc tagtaatcgc agatcagcaa cgctgcggtg   1320
aatacgttcc cgggccttgt acacaccgcc cgtcacgtca tgaaagtcgg taacacccga   1380
agccggtggc ctaaccctc gtgggaggga gccgtcgaag gtgggatcgg cgattgggac   1440
gaagtcgtaa caaggtagcc gtaccggaag g                                 1471
```

<210> SEQ ID NO 37
<211> LENGTH: 1482

```
<212> TYPE: DNA
<213> ORGANISM: Rhodococcus sp.

<400> SEQUENCE: 37
gagtttgatc ctggctcagg acgaacgctg gcggcgtgct taacacatgc aagtcgagcg      60
gtaaggccct tcggggtaca cgagcggcga acgggtgagt aacacgtggg tgatctgccc     120
tgcacttcgg gataagcctg ggaaactggg tctaataccg gatatgacct tcggctgcat     180
ggctgagggt ggaaaggttt actggtgcag gatgggcccg cggcctatca gcttgttggt     240
ggggtaatgg cctaccaagg cgacgacggg tagccgacct gagagggtga ccggccacac     300
tgggactgag acacggccca gactcctacg ggaggcagca gtgggaata ttgcacaatg      360 ggcgaaagcc tgatgcagcg acgccgcgtg agggatgacg ccttcgggt tgtaaacctc      420 tttcagcagg gacgaagcga aagtgacggt acctgcagaa gaagcaccgg ccaactacgt     480
gccagcagcc gcggtaatac gtagggtgca agcgttgtcc ggaattactg ggcgtaaaga    540
gctcgtaggc ggtttgtcgc gtcgtctgtg aaaactcgag gctcaacctc gagcttgcag    600
gcgatacggg cagacttgag tactgcaggg gagactggaa ttcctggtgt agcggtgaaa    660
tgcgcagata tcaggaggaa caccggtggc gaaggcgggt ctctgggcag taactgacgc    720
tgaggagcga aagcgtgggt agcgaacagg attagatacc ctggtagtcc acgccgtaaa    780
cggtgggcgc taggtgtggg tttccttcca cgggatccgt gccgtagcta acgcattaag    840
cgccccgcct ggggagtacg gccgcaaggc taaaactcaa aggaattgac ggggcccgc     900 acaagcggcg gagcatgtgg attaattcga tgcaacgcga agaaccttac ctgggtttga    960
catataccgg aaagccgtag agatacggcc cccttgtgg tcggtataca ggtggtgcat    1020
ggctgtcgtc agctcgtgtc gtgagatgtt gggttaagtc cgcaacgag cgcaaccctt    1080 gtcttatgtt gccagcacgt aatggtgggg actcgtaaga gactgccggg gtcaactcgg    1140
aggaaggtgg ggacgacgtc aagtcatcat gccccttatg tccagggctt cacacatgct    1200
acaatggccg gtacagaggg ctgcgatacc gtgaggtgga gcgaatccct taaagccggt    1260
ctcagttcgg atcggggtct gcaactcgac cccgtgaagt cggagtcgct agtaatcgca    1320
gatcagcaac gctgcggtga atacgttccc gggccttgta cacaccgccc gtcacgtcat    1380
gaaagtcggt aacacccgaa gccggtggcc taacccttg tgggagggag ccgtcgaagg    1440
tgggatcggc gattgggacg aagtcgtaac aaggtagccg ta                      1482

<210> SEQ ID NO 38
<211> LENGTH: 1446
<212> TYPE: DNA
<213> ORGANISM: Rhodococcus sp.

<400> SEQUENCE: 38
gcggcgtgct taacacatgc aagtcgagcg gtaaggccct tcggggtaca cgagcggcga      60
acgggtgagt aacacgtggg tgatctgccc tgcacttcgg gataagcctg ggaaactggg    120
tctaataccg gatatgacct tcggctgcat ggctgagggt ggaaaggttt actggtgcag    180
gatgggcccg cggcctatca gcttgttggt ggggtaatgg cctaccaagg cgacgacggg    240
tagccgacct gagagggtga ccggccacac tgggactgag acacggccca gactcctacg    300
ggaggcagca gtgggaata ttgcacaatg ggcgaaagcc tgatgcagcg acgccgcgtg     360
agggatgacg ccttcgggt tgtaaacctc tttcagcagg gacgaagcga aagtgacggt     420
acctgcagaa gaagcaccgg ccaactacgt gccagcagcc gcggtaatac gtagggtgca    480
```

```
agcgttgtcc ggaattactg ggcgtaaaga gctcgtaggc ggtttgtcgc gtcgtctgtg      540
aaaactcgag gctcaacctc gagcttgcag gcgatacggg cagacttgag tactgcaggg      600
gagactggaa ttcctggtgt agcggtgaaa tgcgcagata tcaggaggaa caccggtggc      660
gaaggcgggt ctctgggcag taactgacgc tgaggggcga aagcgtgggt agcgaacagg      720
attagatacc ctggtagtcc acgccgtaaa cggtgggcgc taggtgtggg tttccttcca      780
cgggatccgt gccgtagcta acgcattaag cgccccgcct ggggagtacg gccgcaaggc      840
taaaactcaa aggaattgac ggggcccgc acaagcggcg gagcatgtgg attaattcga      900
tgcaacgcga agaaccttac ctgggtttga catataccgg aaagccgtag agatacggcc      960
ccccttgtgg tcggtataca ggtggtgcat ggctgtcgtc agctcgtgtc gtgagatgtt     1020
gggttaagtc ccgcaacgag cgcaacccctt gtcttatgtt gccagcacgt aatggtgggg     1080
actcgtaaga gactgccggg gtcaactcgg aggaaggtgg ggacgacgtc aagtcatcat     1140
gccccttatg tccagggctt cacacatgct acaatggccg gtacagaggg ctgcgatacc     1200
gtgaggtgga gcgaatccct aaagccggt ctcagttcgg atcggggtct gcaactcgac     1260
cccgtgaagt cggagtcgct agtaatcgca gatcagcaac gctgcggtga atacgttccc     1320
gggccttgta cacaccgccc gtcacgtcat gaaagtcggt aacacccgaa gccagtggcc     1380
taaccccttg tgggagggag ccgtcgaagg tgggatcggc gattgggacg aagtcgtaac     1440
aaggta                                                                1446

<210> SEQ ID NO 39
<211> LENGTH: 1497
<212> TYPE: DNA
<213> ORGANISM: Rhodococcus wratislaviensis

<400> SEQUENCE: 39
cctggctcag gacgaacgct ggcggcgtgc ttaacacatg caagtcgagc ggtaaggccc       60
ttcggggtac acgagcggcg aacgggtgag taacacgtgg gtgatctgcc ctgcacttcg      120
ggataagcct gggaaactgg gtctaatacc ggatatgacc ttcggctgca tggctgaggg      180
tggaaaggtt tactggtgca ggatgggccc gcggcctatc agcttgttgg tggggtaatg      240
gcctaccaag gcgacgacgg gtagccgacc tgagagggtg accggccaca ctgggactga      300
gacacggccc agactcctac gggaggcagc agtggggaat attgcacaat gggcgaaagc      360
ctgatgcagc gacgccgcgt gagggatgac ggccttcggg ttgtaaacct ctttcagcag      420
ggacgaagcg aaagtgacgg tacctgcaga agaagcaccg gccaactacg tgccagcagc      480
cgcggtaata cgtagggtgc aagcgttgtc cggaattact gggcgtaaag agctcgtagg      540
cggtttgtcg cgtcgtctgt gaaaactcga ggctcaacct cgagcttgca ggcgatacgg      600
gcagacttga gtactgcagg ggagactgga attcctggtg tagcggtgaa atgcgcagat      660
atcaggagga acaccggtgg cgaaggcggg tctctgggca gtaactgacg ctgaggagcg      720
aaagcgtggg tagcgaacag gattagatac cctggtagtc cacgccgtaa acggtgggcg      780
ctaggtgtgg gtttccttcc acgggatccg tgccgtagct aacgcattaa gcgccccgcc      840
tggggagtac ggccgcaagg ctaaaactca aaggaattga cggggcccg cacaagcggc      900 ggagcatgtg gattaattcg atgcaacgcg aagaacctta cctgggtttg acatataccg      960
gaaagccgta gagatacggc ccccttgtg tcggtatac aggtggtgca tggctgtcgt     1020
cagctcgtgt cgtgagatgt tgggttaagt cccgcaacga gcgcaaccct tgtcttatgt     1080
tgccagcacg taatggtggg gactcgtaag agactgccgg ggtcaactcg gaggaaggtg     1140
```

```
gggacgacgt caagtcatca tgcccttat gtccagggct tcacacatgc tacaatggcc    1200
ggtacagagg gctgcgatac cgtgaggtgg agcgaatccc ttaaagccgg tctcagttcg   1260
gatcggggtc tgcaactcga ccccgtgaag tcggagtcgc tagtaatcgc agatcagcaa   1320
cgctgcggtg aatacgttcc cgggccttgt acacaccgcc cgtcacgtca tgaaagtcgg   1380
taacacccga agccggtggc ctaacccctt gtgggaggga gccgtcgaag gtgggatcgg   1440
cgattgggac gaagtcgtaa caaggtagcc gtaccggaag gtgcggctgg atcacct     1497
```

<210> SEQ ID NO 40
<211> LENGTH: 1481
<212> TYPE: DNA
<213> ORGANISM: Rhodococcus opacus
<220> FEATURE:
<221> NAME/KEY: modified_base
<222> LOCATION: (570)..(570)
<223> OTHER INFORMATION: a, c, t, g, unknown or other

<400> SEQUENCE: 40

```
cctggctcag gacgaacgct ggcggcgtgc ttaacacatg caagtcgagc ggtaaggccc      60
ttcggggtac acgagcggcg aacgggtgag taacacgtgg gtgatctgcc ctgcacttcg    120
ggataagcct gggaaactgg gtctaatacc ggatatgacc ttcggctgca tggctgaggg    180
tggaaaggtt tactggtgca ggatgggccc gcggcctatc agcttgttgg tggggtaatg    240
gcctaccaag gcgacgacgg gtagccgacc tgagagggtg accggccaca ctgggactga    300
gacacggccc agactcctac gggaggcagc agtggggaat attgcacaat gggcgaaagc    360
ctgatgcagc gacgccgcgt gagggatgac ggccttcggg ttgtaaacct ctttcagcag    420
ggacgaagcg aaagtgacgg tacctgcaga agaagcaccg gccaactacg tgccagcagc    480
cgcggtaata cgtagggtgc aagcgttgtc cggaattact gggcgtaaag agctcgtagg    540
cggtttgtcg cgtcgtctgt gaaaactcan agctcaacct cgagcttgca ggcgatacgg    600
gcagacttga gtactgcagg ggagactgga attcctggtg tagcggtgaa atgcgcagat    660
atcaggagga acaccggtgg cgaaggcggg tctctgggca gtaactgacg ctgaggagcg    720
aaagcgtggg tagcaaacag gattagatac cctggtagtc cacgccgtaa acggtgggcg    780
ctaggtgtgg gtttccttcc acgggatccg tgccgtagtt aacgcattaa gcgccccgcc    840
tggggagtac ggccgcaagg ttaaaactca aaggaattga cgggggcccg cacaagcggc    900
ggagcatgtg gattaattcg atgcaacgcg aagaaccta cctgggtttg acatataccg    960
gaaagccgta gagataccgc cccttgtg gtcggtatac aggtggtgca tggctgtcgt     1020
cagctcgtgt cgtgagatgt tgggttaagt cccgcaacga gcgcaaccct tgtcttatgt   1080
tgccagcacg taatggtggg gactcgtaag agactgccgg ggtcaactcg gaggaaggtg   1140
gggacgacgt caagtcatca tgcccttat gtccagggct tcacacatgc tacaatggcc    1200
ggtacagagg gctgcgatac cgtgaggtgg agcgaatccc ttaaagccgg tctcagttcg   1260
gatcggggtc tgcaactcga ccccgtgaag tcggagtcgc tagtaatcgc agatcagcaa   1320
cgctgcggtg aatacgttcc cgggccttgt acacaccgcc cgtcacgtca tgaaagtcgg   1380
taacacccga agccggtggc ctaacccctt gtgggaggga gccgtcgaag gtgggatcgg   1440
cgattgggac gaagtcgtaa caaggtagcc gtaccggaag g                       1481
```

<210> SEQ ID NO 41
<211> LENGTH: 1521
<212> TYPE: DNA

-continued

```
<213> ORGANISM: Rhodococcus opacus

<400> SEQUENCE: 41
tcaacggaga gtttgatcct ggctcaggac gaacgctggc ggcgtgctta acacatgcaa      60
gtcgagcggt aaggcccttc ggggtacacg agcggcgaac gggtgagtaa cacgtgggtg     120
atctgccctg cacttcggga taagcctggg aaactgggtc taataccgga tatgaccttc     180
ggctgcatgg ccgttggtgg aaaggtttac tggtgcagga tgggcccgcg gcctatcagc     240
ttgttggtgg ggtaatggcc taccaaggcg acgacgggta gccgacctga gagggtgacc     300
ggccacactg ggactgagac acggcccaga ctcctacggg aggcagcagt ggggaatatt     360
gcacaatggg cgaaagcctg atgcagcgac gccgcgtgag ggatgacggc cttcggttg      420 taaacctctt tcagcaggga cgaagcgaaa gtgacggtac ctgcagaaga agcaccggcc     480
aactacgtgc cagcagccgc ggtaatacgt agggtgcaag cgttgtccgg aattactggg     540
cgtaaagagc tcgtaggcgg tttgtcgcgt cgtctgtgaa aactcgaggc tcaacctcga     600
gcttgcaggc gatacgggca gacttgagta ctgcagggga gactggaatt cctggtgtag     660
cggtgaaatg cgcagatatc aggaggaaca ccggtggcga aggcgggtct ctgggcagta     720
actgacgctg aggagcgaaa gcgtgggtag cgaacaggat tagataccct ggtagtccac     780
gccgtaaacg gtgggcgcta ggtgtgggtt tccttccacg ggatccgtgc cgtagctaac     840
gcattaagcg ccccgcctgg ggagtacggc cgcaaggcta aaactcaaag gaattgacgg     900
gggcccgcac aagcggcgga gcatgtggat taattcgatg caacgcgaag aaccttacct     960
gggtttgaca tataccggaa agctgcagag atgtggcccc ccttgtggtc ggtatacagg    1020
tggtgcatgg ctgtcgtcag ctcgtgtcgt gagatgttgg gttaagtccc gcaacgagcg    1080 caaccttgt cttatgttgc cagcacgtaa tggtggggac tcgtaagaga ctgccggggt     1140
caactcggag gaaggtgggg acgacgtcaa gtcatcatgc cccttatgtc cagggcttca    1200
cacatgctac aatggccggt acagagggct gcgataccgt gaggtggagc gaatccctta    1260
aagccggtct cagttcggat cggggtctgc aactcgaccc cgtgaagtcg gagtcgctag    1320
taatcgcaga tcagcaacgc tgcggtgaat acgttcccgg gccttgtaca caccgcccgt    1380
cacgtcatga aagtcggtaa cacccgaagc cggtggccta acccctcgtg ggagggagcc    1440
gtcgaaggtg ggatcggcga ttgggacgaa gtcgtaacaa ggtagccgta ccggaaggtg    1500
cggctggatc acctcctttc t                                              1521
```